US009896443B2

(12) United States Patent
Spicer et al.

(10) Patent No.: US 9,896,443 B2
(45) Date of Patent: Feb. 20, 2018

(54) PERFORIN INHIBITING BENZENESULFONAMIDE COMPOUNDS, PREPARATION AND USES THEREOF

(71) Applicant: Peter MacCallum Cancer Institute, East Melbourne, Victoria (AU)

(72) Inventors: Julie Ann Spicer, Auckland (NZ); William Alexander Denny, Auckland (NZ); Christian Karl Miller, Auckland (NZ); Patrick David O'Connor, Auckland (NZ); Kristiina Huttunen, Kuopio (FI); Joseph A. Trapani, Camberwell (AU); Geoff Hill, Herston (AU); Kylie Alexander, Herston (AU)

(73) Assignee: Peter MacCallum Cancer Institute, East Melbourne, Victoria (AU)

( * ) Notice: Subject to any disclaimer, the term of this patent is extended or adjusted under 35 U.S.C. 154(b) by 0 days.

(21) Appl. No.: 14/422,498

(22) PCT Filed: Aug. 21, 2013

(86) PCT No.: PCT/AU2013/000925
§ 371 (c)(1),
(2) Date: Feb. 19, 2015

(87) PCT Pub. No.: WO2014/028968
PCT Pub. Date: Feb. 27, 2014

(65) Prior Publication Data

US 2015/0218150 A1 Aug. 6, 2015

Related U.S. Application Data

(60) Provisional application No. 61/691,652, filed on Aug. 21, 2012.

(51) Int. Cl.
*C07D 409/04* (2006.01)
*C07D 417/14* (2006.01)
(Continued)

(52) U.S. Cl.
CPC .......... *C07D 417/14* (2013.01); *A61K 31/404* (2013.01); *A61K 31/4035* (2013.01);
(Continued)

(58) Field of Classification Search
CPC .................................................... C07D 409/04
(Continued)

(56) References Cited

FOREIGN PATENT DOCUMENTS

WO WO-2008/150827 A1 12/2008
WO WO-2011/075784 A1 6/2011

OTHER PUBLICATIONS

Jordan "Tamoxifen . . . " Nature Rev. v.2, p. 205-213 (2003).*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Braga et al., "Making crystals from . . . " J. Royal Soc. Chem. Commun. p. 3635-3645 (2005).*
(Continued)

*Primary Examiner* — Patricia L Morris
(74) *Attorney, Agent, or Firm* — Choate, Hall & Stewart LLP; Charles E. Lyon

(57) ABSTRACT

Compounds of formula (1a) and pharmaceutically acceptable salts, solvates, and hydrates thereof and related methods of modulatin perforin activity on a cell: wherein Ring A is selected from a 6-10 membered aryl, 5-6 membered cycloalkyi, 5-6 membered heteroaryl or 5-6 membered heterocyclyl, wherein the heteroaryl and heterocyclyl rings comprise at least one heteroatom selected from N, O or S; and wherein the aryl, cycloalkyi, heteroaryl or heterocyclyl rings are optionally substituted with 1 to 3 substituents selected from halo, nitro, —$C_1$-Cealkyl, —$C_1$-Ceamino-alkyl, —$C_1$-$C_6$hydroxyalkyl, -halo$C_1$-$C_6$alkyl, —$C_1$-$C_6$alkoxyl, -halo$C_1$—C<alkoxyl, heteroaryl, aryl, hydroxyl, —C(0)Ci-C6alkyl, —OC(0)Ci-$C_6$alkyl, —$CH_2$OC(O) CrC$_6$alkyl, —C(O)OC$_1$, —$C_6$alkyI, —NHC(O)C$_1$, —C6alkyl, —NHS$(O)_2C_1$-$C_6$alkyl, —S$(O)_2C_1$-$C_6$alkyl, —S$(O)_2NH_2$, and —C(O)NJJ; Ring B is a 6-10 membered arylene or a 5-6 membered heteroarylene comprising at least one heteroatom selected from N, 0 or S; and wherein the aryl or heteroaryl is optionally, substituted with one or more substituents selected from —NJJ, —OJ, halo, $C_1$-$C_6$alkyl, -halo$C_1$-C6alkyl, —$C_1$-$C_6$alkoxy, -halo$C_1$-$C_6$alkoxyl, and —C(0)NJJ; Ring C is selected from a 5-10 membered heteroarylene or a 5-10 membered heterocyclene, each comprising at least one heteroatom selected from N, S and O; Ring D is an optionally substituted benzofused 9-11 membered heterocyclyl or optionally substituted ben2ofused 9-11 membered heteroaryl comprising at least one heteroatom selected from N or O; L is a linker selected from branched and unbranched C1-C4 alkylene, —S(0)2-NH—, —C(0)-NH—, —NH—C(0)-NH—, —S(0)2-NH—C(0)-NH—, —S(0)2-NH—C(0)- and —CH═CH—; wherein Rings B and C, and Rings C and D, are connected to each other via a C—C bond at any of the available C atoms on each respective ring; and J in each occurrence is independently selected from H, optionally substituted $C_1$-$C_6$alkyl or optionally substituted halo$C_1$-$C_6$alkyl.

formula (Ia)

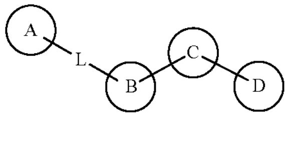

8 Claims, 2 Drawing Sheets

(51) Int. Cl.
*A61K 31/4035* (2006.01)
*A61K 31/404* (2006.01)
*A61K 31/4439* (2006.01)
*C07D 409/14* (2006.01)
*C07D 401/14* (2006.01)
*C07D 413/14* (2006.01)

(52) U.S. Cl.
CPC ........ *A61K 31/4439* (2013.01); *C07D 401/14* (2013.01); *C07D 409/04* (2013.01); *C07D 409/14* (2013.01); *C07D 413/14* (2013.01)

(58) Field of Classification Search
USPC ........................................ 546/277.1; 514/339
See application file for complete search history.

(56) References Cited

OTHER PUBLICATIONS

Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Ivanisevic et al. "Use of X-ray . . . " Pharm. Sci. Encycl. p. 1-42 (2010).*
Seddon "Pseudopolymorph . . . " Crystal Growth & design v.4(6) p. 1087 (2004) (2 pages from internet).*
Jain et al., "Polymorphism in Pharmacy", Indian Drugs, 1986, 23(6) 315-329.*
CAS registry No. 342627-74-1, STN entry date Jun. 20, 2001.
CAS registry No. 924792-05-2, STN entry date Mar. 5, 2007.
CAS registry No. 924805-71-0, STN entry date Mar. 5, 2007.
Lena, G. et al., Dihydrofuro[3,4-c]pyridinones as Inhibitors of the Cytolytic Effects of the Pore-Forming Glycoprotein Perforin, J. Med. Chem., 51(23): 7614-7624 (2008).
Lyons, D.M. et al., Inhibition of the cellular function of perf orin by l-amino-2,4-dicyanopyrido[l,2-a]benzimidazoles, Bioorg. Med. Chem., 19(13): 4091-4100 (2011).
International Preliminary Report on Patentability for PCT/AU2013/000925, 7 pages (dated Feb. 24, 2015).
International Search Report for PCT/AU2013/000925, 4 pages (dated Oct. 22, 2013).
Written Opinion for PCT/AU2013/000925, 5 pages (dated Oct. 22, 2013).
Spicer, J. A., et al., Inhibition of the pore-forming protein perforin by a series of aryl-substituted isobenzofuran-1(3H)-ones, Bioorganic & Medicinal Chemistry, 20: 1319-1336 (2012).

* cited by examiner

PERFORIN INHIBITING BENZENESULFONAMIDE COMPOUNDS, PREPARATION AND USES THEREOF

FIELD

The present invention relates generally to compounds capable of modulating perforin activity, more particularly to compounds capable of inhibiting perforin activity, and uses thereof. More specifically, the present invention relates to benzenesulfonamides and related compounds and analogues thereof, to their preparation, and to their use as tools for biological studies or as agents or drugs for immunosuppressive therapies, whether they are used alone or in combination with other treatment modalities.

BACKGROUND

Cytotoxic T lymphocytes (CTL) and natural killer (NK) cells perform tumour surveillance and provide a defense against viral infection and intracellular pathogens, by inducing apoptosis of virus-infected or transformed cells. A major component of this defense is the glycoprotein perforin. Upon stable conjugation of the CTL or NK cell with a target cell, perforin is released, binds calcium and assembles into aggregates of 12-18 molecules that form trans-membrane pores in the plasma membrane. This allows leakage of cell contents and the entry of secreted serine proteases (granzymes) which promote apoptosis.

Stimulation of CTL and NK cells, leading to abnormal cellular destruction, occurs in several autoimmune diseases (e.g., insulin-dependent diabetes) and in therapy-induced conditions (e.g., allograft rejection, graft-versus-host disease). In this context, small-molecule inhibitors of perforin function are of potential interest as a new class of therapeutic immunosuppressive agents.

To date, the only reported direct inhibitors of perforin function are those published by the present inventors (Lena et al, J. Med. Chem., 51(23), 7614-7624, 2008; Lyons et al, Bioorganic & Medicinal Chemistry, 19, 4091-4100, 2011; Spicer et al, Bioorganic & Medicinal Chemistry, 20, 1319-1336, 2012). Other reported inhibitors of perforin function are non-selective, complex natural products, primarily concanamycin A and other V-ATPase inhibitors such as bafilomycin A and prodigiosin 25-Cs that inhibit acidification. Other reported non-selective perforin inhibitors include cytochalasin D (an inhibitor of actin polymerisation), antimycin A and oligomycin A (inhibitors of cell respiration) and some protein kinase inhibitors (calphostin C, herbimycin A, staurosporine). However, such non-selective compounds display a broad spectrum of biological effects that generally make them undesirable for use in the treatment or prevention of conditions associated with aberrant perforin expression and/or activity.

In one or more aspects, the present invention may advantageously provide a class of compounds and their analogues as drugs for immunosuppressive therapies, or to at least provide a useful alternative to existing treatment modalities.

SUMMARY OF THE INVENTION

In one aspect of the present invention provides a method of modulating perforin activity, on a cell, said method including the step of exposing the cell to a compound of the formula (I):

formula (I)

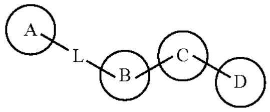

wherein

Ring A is selected from a 6-10 membered aryl, 5-6 membered cycloalkyl, 5-6 membered heteroaryl or 5-6 membered heterocyclyl, wherein the heteroaryl and heterocyclyl rings comprise at least one heteroatom selected from N, O or S; and wherein the aryl, cycloalkyl, heteroaryl or heterocyclyl rings are optionally substituted with 1 to 3 substituents selected from halo, nitro, cyano, —$C_1$-$C_6$alkyl, —$C_1$-$C_6$aminoalkyl, —$C_1$-$C_6$hydroxyalkyl, -halo$C_1$-$C_6$alkyl, —$C_1$-$C_6$alkoxyl, -halo$C_1$-$C_6$alkoxyl, heteroaryl, aryl, hydroxyl, —C(O)$C_1$-$C_6$alkyl, —OC(O)$C_1$-$C_6$alkyl, —$CH_2$OC(O)$C_1$-$C_6$alkyl, —C(O)O$C_1$-$C_6$alkyl, —NHC(O)$C_1$-$C_6$alkyl, —NHS$(O)_2$ $C_1$-$C_6$alkyl, —S$(O)_2C_1$-$C_6$, —S$(O)_2NH_2$, and —C(O)NJJ;

Ring B is a 6-10 membered arylene or a 5-6 membered heteroarylene comprising at least one heteroatom selected from N, O or S; and wherein the aryl or heteroaryl is optionally substituted with one or more substituents selected from —NJJ, —OJ, halo, —$C_1$-$C_6$alkyl, -halo$C_1$-$C_6$alkyl, —$C_1$-$C_6$alkoxy, -halo$C_1$-$C_6$alkoxy, and —C(O)NJJ;

Ring C is selected from a 5-10 membered heteroarylene or a 5-10 membered heterocyclene, each comprising at least one heteroatom selected from N, S and O;

Ring D is an optionally substituted 6-11 membered heterocyclyl or optionally substituted 6-11 membered heteroaryl comprising at least one heteroatom selected from N or O;

L is a linker selected from branched or unbranched $C_1$-$C_4$ alkylene, —S$(O)_2$—NH—, —C(O)—NH—, —NH—C(O)—NH—, —S$(O)_2$—NH—C(O)—NH—, —S$(O)_2$—NH—C(O)—, —C(O)—NH—C(S)—NH— and —CH═CH—;

wherein Rings B and C, and Rings C and D, are connected to each other via a C—C bond at any of the available C atoms on each respective ring; and J in each occurrence is independently selected from H, optionally substituted $C_1$-$C_6$alkyl or optionally substituted halo$C_1$-$C_6$alkyl;

and pharmaceutically acceptable salts, solvates, and hydrates thereof.

The present invention also relates to a method of modulating the activity of a perforin molecule, or a fragment or variant thereof, on a cell. The said method comprises exposing the cell to a compound of formula (I) or a pharmaceutically acceptable salt, solvate, or hydrate thereof or a salt thereof. The exposure could take place both in vivo, for example, by administering to a patient in need thereof a compound of formula (I), or ex vivo exposure, for instance, contacting the cell with a compound of formula (I) in an experimental assay.

In another aspect of the present invention, there is provided a method of inhibiting activity of a perforin molecule, or a fragment or variant thereof, on a cell, said method comprising exposing the cell to a compound of formula (I), or a pharmaceutically acceptable salt, solvate, or hydrate thereof, as herein described.

In yet a further aspect of the present invention, there is provided a prophylactic or therapeutic method of treating a subject at risk of or susceptible to a disease or disorder, or having a disease or disorder associated with undesirable perforin activity, said method comprising administering to said subject a compound of formula (I), or a pharmaceutically acceptable salt or a pharmaceutically acceptable salt, solvate, or hydrate thereof, as herein described. In some embodiments the disease or disorder is an autoimmune or inflammatory disease or disorder, such as juvenile diabetes mellitus (type 1 or insulin dependent), crohns disease, colitis and inflammatory bowel disease, fibrosis and fibrotic disorders, Guillain-Barre syndrome, lupus erythematosus, psoriasis, pancreatitis, rheumatoid arthritis, sepsis, vasculitis and Wegener's granulmatosis, as well as other conditions including but not limited to graft-versus-host disease, chronic or acute allograft rejection, infectious diseases, including mosquito-borne diseases of the *Plasmodium* genus, such as malaria, in particular cerebral malaria, and conditions associated with cytotoxic T lymphocyte- or natural killer cell-mediated immune pathology.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

DETAILED DESCRIPTION OF THE INVENTION

Figure 1:
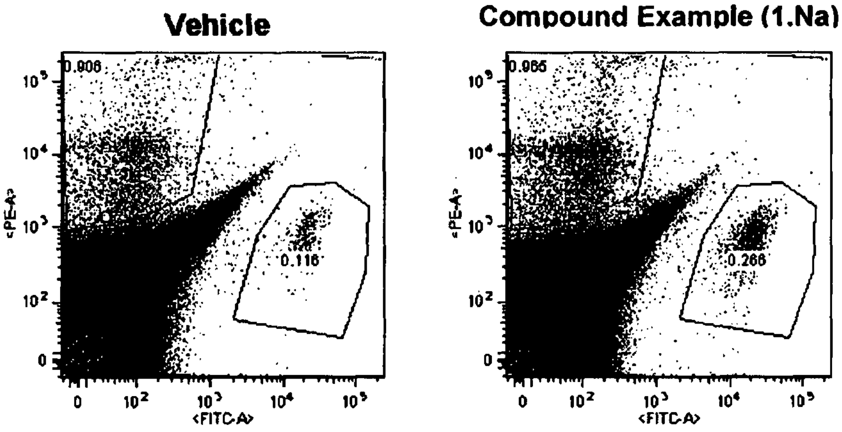
FIG. 1: In vivo cytotoxicity assay results comparing the ratio of recipient (CD45.1+) versus donor cells (CFSE+).

Despite evidence of its apparent role in the aforementioned pathophysiologies, the biological function of perforin remains poorly understood at the molecular and cellular levels. This lack of substantial progress has been mostly attributed to a lack of cell lines capable of synthesising and storing this toxic protein for the purposes of further investigation. In this regard, the present inventors have previously provided a method of expressing sufficient quantities of recombinant perforin in a cell, or fragment or variants thereof, which avoid the undesirable effects attributed to perforin's inherent cytotoxicity (see WO 2005/083098, the entire contents of which are incorporated herein by reference). By utilising this methodology, the present inventors have, for the first time, been able to isolate recombinant perforin in sufficient quantities that allow for the screening of compounds that modulate perforin expression and/or activity. Using such screening methods, the present inventors have now identified compounds that are capable of modulating perforin activity, such as inhibiting perforin activity, providing a means of treating or preventing diseases or disorders associated with aberrant perforin expression and/or activity, or disorders where CTL, NK cells or other lymphocytes pathologically target tissues through the use of perforin or perforin-dependent pathways.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, hydroxyl, amino, alkylamino, alkenylamino, cycloalkylamino, cycloalkenylamino, arylamino, heteroaryl, heteroarylamino, heterocyclylamino, aminoarylamino, aminoheteroarylamino, aminoheterocyclylamino, tetrahydropyridinylamino, azetidinyl, pyrrolidinyl, piperidinyl, piperazinyl, morpholinyl, azetidinylamino, pyrrolidinylamino, piperidinylamino, piperazinylamino, azetidinylcarbonylamino, pyrrolidinylcarbonylamino, piperidinylcarbonylamino, piperazinylcarbonylamino, alkoxy, alkenyloxy, alkynyloxy, cycloalkoxy, cycloalkenyloxy, aryloxy, heteroaryloxy, heterocyclyloxy, aminoalkoxy, aminoalkenyloxy, aminoalkynyloxy, aminocycloalkoxy, aminocycloalkenyloxy, aminoaryloxy, aminoheteroaryloxy, azetidinyloxy, pyrrolidinyloxy, piperidinyloxy, or piperazinyloxy "Acyl" means an R—C(═O)— group in which the R group may be an alkyl, cycloalkyl, heterocycloalkyl, aryl or heteroaryl group as defined herein. Examples of acyl include acetyl and benzoyl.

"Alkyl" as a group or part of a group refers to a straight or branched aliphatic hydrocarbon group, preferably a $C_1$-$C_{10}$alkyl, more preferably a $C_1$-$C_8$alkyl, most preferably $C_1$-$C_6$alkyl unless otherwise noted. Examples of suitable straight and branched $C_1$-$C_6$alkyl substituents include methyl, ethyl, n-propyl, 2-propyl, n-butyl, sec-butyl, t-butyl, hexyl, and the like.

"Alkylene" refers to divalent alkyl groups preferably having from 1 to 10 carbon atoms and more preferably 1 to 6 carbon atoms, and even more preferably 1 to 3 carbon atoms. Examples of such alkylene groups include methylene ($—CH_2—$), ethylene ($—CH_2CH_2—$), and the propylene isomers (e.g., $—CH_2CH_2CH_2—$ and $—CH(CH_3)CH_2—$), and the like.

"Alkenyl" means an aliphatic hydrocarbon group containing at least one carbon-carbon double bond and which may be straight or branched, preferably a $C_2$-$C_{10}$alkenyl, more preferably a $C_2$-$C_8$alkenyl, most preferably $C_2$-$C_6$alkenyl. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl.

"Alkynyl" means an aliphatic hydrocarbon group containing a carbon-carbon triple bond and which may be straight or branched, preferably a $C_2$-$C_{10}$alkynyl, more preferably a $C_2$-$C_8$alkynyl, most preferably $C_2$-$C_6$alkynyl.

"Alkylamino" includes both mono-alkylamino and dialkylamino, unless specified. "Mono-alkylamino" means an alkyl-NH— group, in which alkyl is as defined herein. "N,N-dialkylamino" means a $(alkyl)_2N—$ group, in which each alkyl may be the same or different and are each as defined herein for alkyl. The alkyl group is preferably a $C_1$-$C_{10}$alkyl group. The group is bonded to the remainder of the molecule through the nitrogen atom.

"Alkenylamino" includes both mono-alkenylamino and dialkenylamino, unless specified. "Mono-alkenylamino"

means an alkenyl-NH— group, in which alkenyl is as, defined herein. The alkenyl group is preferably a $C_2$-$C_{10}$alkenyl group. The group is bonded to the remainder of the molecule through the nitrogen atom.

"Alkoxy" as a group or part of a group refers to an alkyl-O— group in which alkyl is as defined herein. Preferably the alkoxy is a $C_1$-$C_{10}$alkoxy. Examples include, but are not limited to, methoxy and ethoxy.

"Aminoalkoxy" refers to an alkoxy group as defined herein, further substituted with at least one amine. Preferred aminoalkoxy groups are $C_1$-$C_{10}$aminoalkoxy groups.

"Alkenyloxy" refers to an alkenyl-O— group in which alkenyl is as defined herein. Preferred alkenyloxy groups are $C_2$-$C_{10}$alkenyloxy groups.

"Aminoalkenyloxy" refers to an alkenyl-O— group as defined herein, further substituted with at least one amine. Preferred aminoalkenyloxy groups are $C_2$-$C_{10}$aminoalkenyloxy groups.

"Alkynyloxy" refers to an alkynyl-O— group in which alkynyl is as defined herein. Preferred alkynyloxy groups are $C_2$-$C_{10}$alkynyloxy groups.

"Aminoalkynyloxy" refers to an alkynyl-O— group as defined herein, further substituted with at least one amine. Preferred aminoalkynyloxy groups are $C_2$-$C_{10}$aminoalkynyloxy groups.

"Aryl" refers to an unsaturated aromatic carbocyclic group having a single ring (eg., phenyl) or multiple condensed rings (eg., naphthyl or anthryl), preferably having from 6 to 14 carbon atoms. Examples of aryl groups include phenyl, naphthyl and the like.

"Arylamino" includes both mono-arylamino and di-arylamino unless specified. Mono-arylamino means a group of formula aryl-NH—, in which aryl is as defined herein. "N,N-diarylamino" means a group of formula $(aryl)_2N$— where each aryl may be the same or different and are each as defined herein for aryl.

"Aminoarylamino" refers to a group of formula $(NH_2)_n$-aryl-NH—, in which arylamino is as defined herein, further substituted with at least one amine at the ortho-, meta- or para position.

"Aryloxy" refers to an aryl-O— group in which the aryl is as defined herein. Preferably the aryloxy is a $C_6$-$C_{10}$aryloxy.

"Aminoaryloxy" refers to a group of formula $(NH_2)_n$-aryl-O—, in which aryloxy is as defined herein, further substituted with at least one amine at the ortho-, meta- or para position.

"Cycloalkyl" refers to a saturated monocyclic or fused or spiro polycyclic, carbocycle preferably containing from 3 to 10 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane.

"Cycloalkenyl" refers to a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

"Cycloalkylamino" refers to a cycloalkyl-NH— group in which cycloalkyl is as defined herein. Preferably the cycloalkylamino is a $C_3$-$C_{10}$cycloalkylamino.

"Cycloalkenylamino" refers to a cycloalkenyl-NH— group in which the cycloalkenyl is as defined herein. Preferably the cycloalkenylamino is a $C_3$-$C_{10}$cycloalkenylamino.

"Cycloalkoxy" refers to a cycloalkyl-O— group in which cycloalkyl is as defined herein. Preferably the cycloalkoxy is a $C_3$-$C_{10}$cycloalkoxy. Examples include, but are not limited to, cyclopropanoxy and cyclobutanoxy.

"Aminocycloalkoxy" refers to a cycloalkoxy group is as defined herein, further substituted on one or more of the available carbon atoms with at least one amine. Preferably the aminocycloalkoxy is a $C_3$-$C_{10}$aminocycloalkoxy. The group is bonded to the remainder of the molecule through the oxygen atom.

"Cycloalkenyloxy" refers to a cycloalkoxy group defined herein containing at least one carbon-carbon double bond.

"Aminocycloalkenyloxy" refers to an aminocycloalkloxy group defined herein containing at least one carbon-carbon double bond.

"Heteroaryl" either alone or part of a group refers to groups containing an aromatic ring (preferably a 5, 6, 9, 10 or 11 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl, and includes benzofused heteroaryl, such as benzothiophene, benzofuran, benzimidazole, benzoxazole, benzothiazole, benzisothiazole, and naphtho[2,3-b]thiophene.

"Heteroarylamino" refers to a heteroaryl-NH— group in which the heteroaryl is as defined herein. Preferably the heteroarylamino is a $C_2$-$C_{10}$heteroarylamino.

"Aminoheteroarylamino" refers to a $(NH_2)_n$-heteroaryl-NH— group in which the heteroarylamino is as defined herein, further substituted at one or more of the ring members with at least one amine. Preferably the aminoheteroarylamino is a $C_2$-$C_{10}$aminoheteroarylamino.

"Heteroaryloxy" refers to a heteroaryl-O— group in which the heteroaryl is as defined herein.

"Aminoheteroaryloxy" refers to a $(NH_2)_n$-heteroaryl-O— group in which the heteroaryloxy is as defined herein, further substituted at one or more of the ring members with at least one amine.

"Heteroarylcarbonylamino" refers to a heteroaryl-C(O)—NH— group in which the heteroaryl is as defined herein.

"Heterocyclyl" or "heterocyclic" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 11 membered, more preferably 4 to 7 membered or 9-11 membered. Examples of suitable heterocyclyl substituents include aziridinyl, oxiranyl, thiiranyl, azetidinyl, oxetanyl, thistanyl, pyrrolinyl, pyrrolidinyl, pyrazolidinyl, imidazolidinyl, tetrahydrofuryl, tetrahydrothiofuranyl, piperidinyl, thiazolidinyl, piperazinyl, tetrahydropyridinyl, morpholino, thiomorpholinyl, 1,3-diazapane, 1,4-diazapane, 1,4-oxazepane, and 1,4-oxathiapane, and includes benzofused compounds such as inddinyl, isoindolinyl, oxoisoindolinyl, isoquinolinyl, and quinolinyl.

"Heterocyclyloxy" refers to a heterocyclyl-O— group in which the heterocycloalkyl is as defined herein.

"Heterocyclylamino" refers to a heterocyclyl-NH— group in which the heterocycloalkyl is as defined herein.

"Aminoheterocyclylamino" refers to a $NH_2$-heterocyclyl-NH— group in which the heterocycloalkylamino is as defined herein, further substituted with an amine at one of the ring members.

"Heterocyclylcarbonylamino" refers to a heterocyclyl-C(O)—NH— group in which the heterocyclyl is as defined herein. Examples of suitable heterocyclylcarbonylamino substituents include azetidinylcarbonylamino, piperidinylcarbonylamino and piperazinylcarbonylamino.

"Alkylheterocyclyl" refers to an alkyl-heterocyclyl-group in which alkyl and heterocyclyl groups are as defined herein. Preferably the alkyl is a $C_1$-$C_6$alkyl group bound to the heterocyclyl group via either a carbon or heteroatom. The heterocyclic ring is preferably from 5 to 11 membered.

It is understood that included in the family of compounds of formula (I) and related formulae are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, formula (I), and related formulae, is intended to cover, where applicable, solvated as well as unsolvated forms of the compounds. Thus, each formula includes compounds having the indicated structure, including the hydrated as well as the non-hydrated forms.

In a further aspect the invention provides compounds which are useful for modulating perforin activity on a cell.

Accordingly, in a further aspect the invention provides compounds of formula (Ia):

formula (Ia)

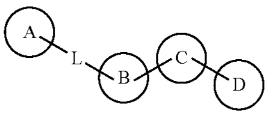

wherein

Ring A is selected from a 6-10 membered aryl, 5-6 membered cycloalkyl, 5-6 membered heteroaryl or 5-6 membered heterocyclyl, wherein the heteroaryl and heterocyclyl rings comprise at least one heteroatom selected from N, O or S; and wherein the aryl, cycloalkyl, heteroaryl or heterocyclyl rings are optionally substituted with 1 to 3 substituents selected from halo, nitro, cyano, —$C_1$-$C_6$alkyl, —$C_1$-$C_6$aminoalkyl, —$C_1$-$C_6$hydroxyalkyl, -halo$C_1$-$C_6$alkyl, —$C_1$-$C_6$alkoxyl, -halo$C_1$-$C_6$alkoxyl, heteroaryl, aryl, hydroxyl, —C(O)$C_1$-$C_6$alkyl, —OC(O)$C_1$-$C_6$alkyl, —$CH_2$OC(O)$C_1$-$C_6$alkyl, —C(O)O$C_1$-$C_6$alkyl, —NHC(O)$C_1$-$C_6$alkyl, —NHS$(O)_2$ $C_1$-$C_6$alkyl, —S$(O)_2$$C_1$-$C_6$alkyl, —S$(O)_2$$NH_2$, and —C(O)NJJ;

Ring B is a 6-10 membered arylene or a 5-6 membered heteroarylene comprising at least one heteroatom selected from N, O or S; and wherein the aryl or heteroaryl is optionally substituted with one or more substituents selected from —NJJ, —OJ, halo, —$C_1$-$C_6$alkyl, -halo$C_1$-$C_6$alkyl, —$C_1$-$C_6$alkoxy, -halo$C_1$-$C_6$alkoxyl, and —C(O)NJJ;

Ring C is selected from a 5-10 membered heteroarylene or a 5-10 membered heterocyclene, each comprising at least one heteroatom selected from N, S and O;

Ring D is an optionally substituted benzofused 9-11 membered heterocyclyl or optionally substituted benzofused 9-11 membered heteroaryl comprising at least one heteroatom selected from N or O;

L is a linker selected from branched and unbranched $C_1$-$C_4$ alkylene, —S$(O)_2$—NH—, —C(O)—NH—, —NH—C(O)—NH—, —S$(O)_2$—NH—C(O)—NH—, —S$(O)_2$—NH—C(O)—, —C(O)—NH—C(S)—NH— and —CH═CH—;

wherein Rings B and C, and Rings C and D, are connected to each other via a C—C bond at any of the available C atoms on each respective ring; and J in each occurrence is independently selected from H, optionally substituted $C_1$-$C_6$alkyl or optionally substituted halo$C_1$-$C_6$alkyl;

and pharmaceutically acceptable salts, solvates, and hydrates thereof.

In some embodiments of the invention, and with reference to the general formula (Ia), one or more of the following definitions may apply:

In an embodiment Ring D is an optionally substituted benzofused 9-11 membered heterocyclyl group.

In an embodiment Ring D is an optionally substituted benzofused 9-11 membered heterocyclyl of the formula (i) or (i')

(i)

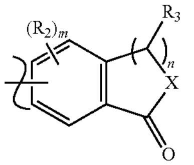

(i')

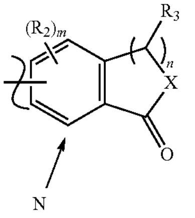

where X is N—$R_1$ or O;

$R_1$ is H or optionally substituted $C_1$-$C_6$ alkyl;

$R_2$ is halo, nitro, —$C_1$-$C_6$alkyl, —$C_1$-$C_6$aminoalkyl, —$C_1$-$C_6$hydroxyalkyl, —$C_1$-$C_6$haloalkyl, —$C_1$-$C_6$alkoxyl, -halo-$C_1$-$C_6$alkoxyl, heteroaryl, aryl, hydroxyl, —C(O)$C_1$-$C_6$alkyl, —OC(O)$C_1$-$C_6$alkyl, —$CH_2$OC(O)$C_1$-$C_6$alkyl, —C(O)O$C_1$-$C_3$alkyl, —NHC(O)$C_1$-$C_6$alkyl, —NHS$(O)_2$$C_1$-$C_6$alkyl, —S$(O)_2$$C_1$-$C_6$alkyl, —S$(O)_2$$NH_2$, or —C(O)NJJ, wherein each J is independently hydrogen or $C_1$-$C_3$ alkyl;

$R_3$ in each occurrence is independently H or optionally substituted $C_1$-$C_6$ alkyl;

n is 1-3; and m is 0-2;

wherein in formula (i') the arrow indicates that the heterocyclic N within the benzene ring can be located at any of the available positions.

In an embodiment Ring D is a benzofused 9-11 membered heterocyclyl selected from one of the following:

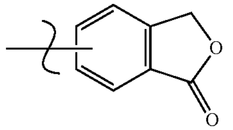
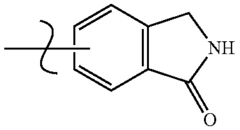
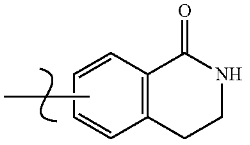
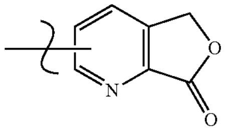
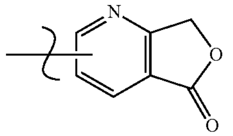
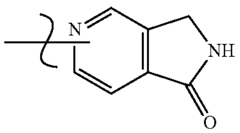
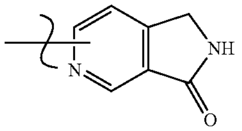
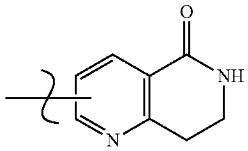
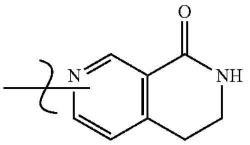
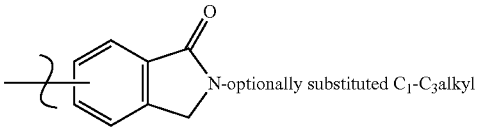
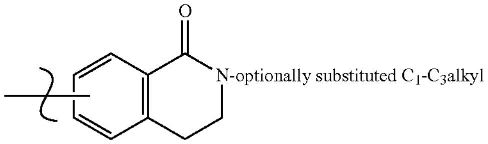

In an embodiment Ring D is a benzofused 9-11 membered heterocyclyl selected from one of the following:

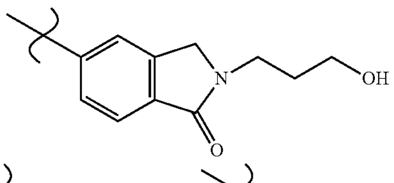
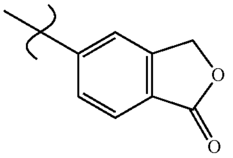
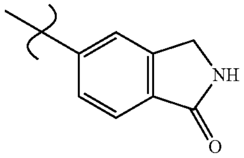
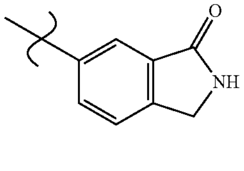
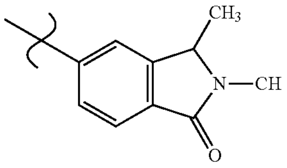

-continued

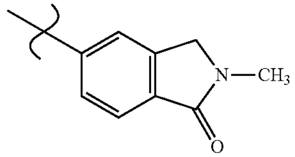
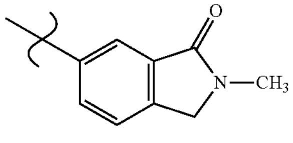
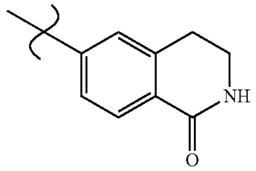
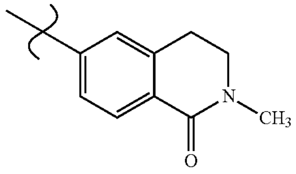
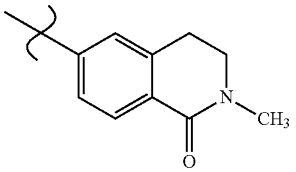
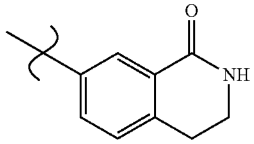
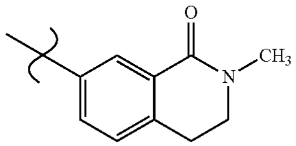

In an embodiment Ring D is an optionally substituted benzofused 9-11 membered heterocyclyl of formula (ii):

(ii)

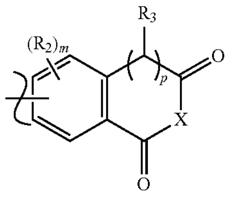

where X is N—$R_1$;

$R_1$ is H or optionally substituted $C_1$-$C_6$ alkyl;

$R_2$ is halo, nitro, —$C_1$-$C_6$alkyl, —$C_1$-$C_6$aminoalkyl, —$C_1$-$C_6$hydroxyalkyl, —$C_1$-$C_6$haloalkyl, —$C_1$-$C_6$alkoxyl, -halo-$C_1$-$C_6$alkoxyl, heteroaryl, aryl, hydroxyl, —C(O)$C_1$-$C_6$alkyl, acetyl, —$CH_2OC(O)C_1$-$C_6$alkyl, —C(O)O$C_1$-$C_3$alkyl, —NHC(O)$C_1$-$C_6$alkyl, —NHS$(O)_2C_1$-$C_6$alkyl, —S$(O)_2C_1$-$C_6$alkyl, —S$(O)_2$ $NH_2$, or —C(O)NJJ, wherein each J is independently hydrogen or $C_1$-$C_3$ alkyl;

$R_3$ in each occurrence is independently H or optionally substituted $C_1$-$C_6$ alkyl;

p is 0-2; and m is 0-2.

In an embodiment Ring D is a benzofused 9-11 membered heteroaryl.

In an embodiment Ring D is a benzofused 9-11 membered heteroaryl comprising at least one N heteroatom.

In an embodiment Ring D is a benzofused 9 membered heteroaryl of formula (iii):

(iii)

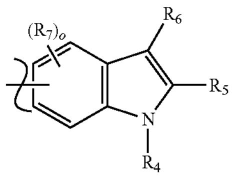

where $R_4$ is H or optionally substituted $C_1$-$C_6$ alkyl;

$R_5$ is H or optionally substituted $C_1$-$C_6$ alkyl;

$R_6$ is H, optionally substituted $C_1$-$C_6$ alkyl or aryl;

$R_7$ is halo, nitro, —$C_1$-$C_6$alkyl, —$C_1$-$C_6$aminoalkyl, —$C_1$-$C_6$hydroxyalkyl, —$C_1$-$C_6$haloalkyl, —$C_1$-$C_6$alkoxyl, -halo-$C_1$-$C_6$alkoxyl, heteroaryl, aryl, hydroxyl, —C(O)$C_1$-$C_6$alkyl, —OC(O)$C_1$-$C_6$alkyl, —$CH_2$OC(O)$C_1$-$C_6$alkyl, —C(O)O$C_1$-$C_3$alkyl, —NHC(O)$C_1$-$C_6$alkyl, —NHS$(O)_2C_1$-$C_6$alkyl, —S$(O)_2C_1$-$C_6$alkyl, —S$(O)_2NH_2$, or —C(O)NJJ, wherein each J is independently hydrogen or $C_1$-$C_3$ alkyl; and o is 0-2.

In an embodiment Ring D is a benzofused 9 membered heteroaryl of the formula:

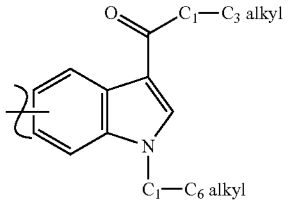

In another embodiment Ring D is:

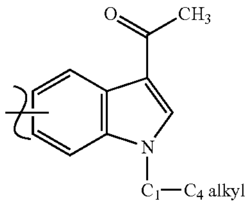

In another embodiment Ring D is:

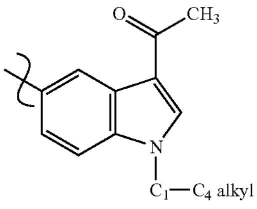

In an embodiment Ring C is a 9 or 10 membered fused bicyclic heteroarylene preferably a benzofused 9 or 10 membered heteroarylene.

In an embodiment Ring C is a 9 or 10 membered fused bicyclic heterocyclene, preferably a benzofused 9 or 10 membered heterocyclene.

In an embodiment Ring C is a 5 or 6 membered heterocyclene.

In an embodiment Ring C is a 5 or 6-membered heteroarylene.

In an embodiment Ring C is a 5 or 6-membered heteroarylene selected from thiophenylene, pyridinylene, furanylene, pyrrolylene, oxazolylene, isoxazolylene, thiazolylene, tetrazolylene, 1,2,3-oxadizolylene or triazolylene.

In an embodiment Ring C is selected from thiophenylene or pyridinylene.

In an embodiment Ring C is selected from:

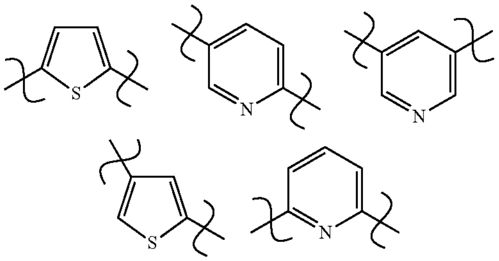

In an embodiment Ring C is thiophenylene, preferably

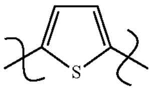

In an embodiment Ring C is a benzofused 9-10 membered heteroarylene group.

In an embodiment Ring C is a benzofused 9-10 membered heteroarylene group selected from:

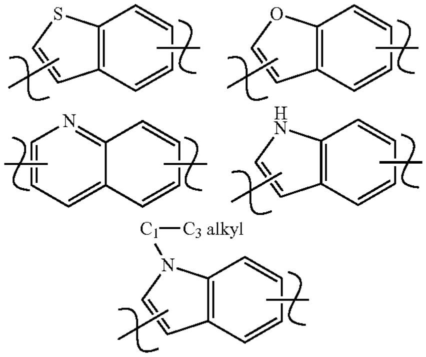

In an embodiment Ring C is a benzofused 9-10 membered heteroarylene group selected from:

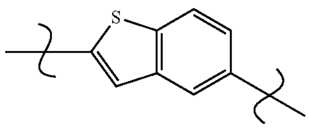

-continued

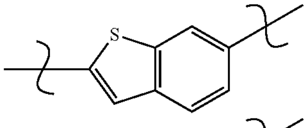

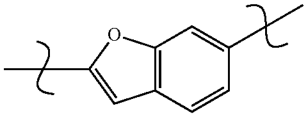

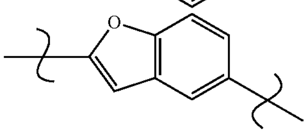

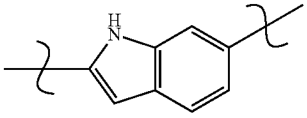

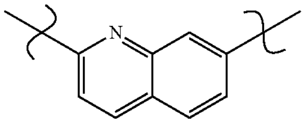

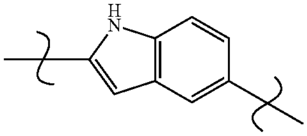

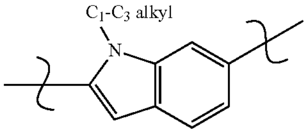

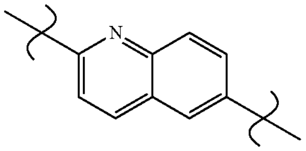

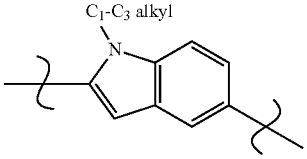

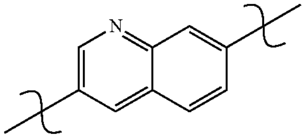

In an embodiment Ring D is a heterocyclylene group of formula (i) or a heteroaryl group of formula (iii), and Ring C is a thiophenylene moiety.

Accordingly, in a further aspect the invention provides compounds of formulae (II) and (III):

(II)

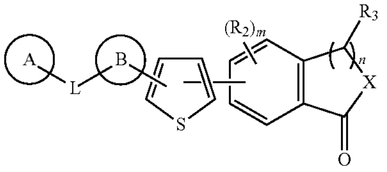

-continued (III)

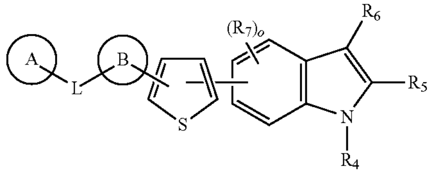

where Ring A, L, Ring B, and variables X, $R_2$-$R_7$, m, n and o are as defined herein.

In an embodiment the compounds of the invention are represented by formula (II).

In a further embodiment the invention provides compounds of formulae (IIa) and (IIIa):

(IIa)

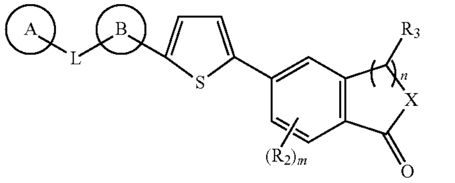

(IIIa)

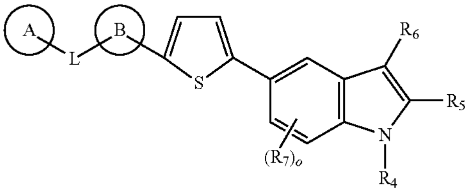

where Ring A, L, Ring B, and variables X, $R_2$-$R_7$, m, n and o are as defined herein.

With reference to formulae (Ia), (II), (IIa), (III) or (IIIa) the following further definitions may apply.

In an embodiment Ring B is an optionally substituted phenylene or an optionally substituted 6-membered heteroarylene containing a N-heteroatom.

In an embodiment Ring B is a 5-6 membered optionally substituted heteroarylene ring.

In another embodiment Ring B is a 6-membered optionally substituted heteroarylene ring.

In an embodiment Ring B is a 6-membered optionally substituted heteroarylene ring selected from pyridinylene, pyrazinylene, pyrimidylene, or pyridazinylene.

In an embodiment Ring B is an optionally substituted phenylene or an optionally substituted 6-membered heteroarylene containing a N-heteroatom of formula (iv):

(iv)

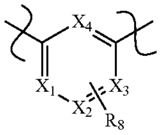

wherein $X_1$-$X_4$ are independently CH or N, and when $X_1$ is CH, $X_2$ is N, $X_3$ is CH, and $X_4$ is CH; or when $X_1$ is N, $X_2$ to $X_4$ are CH; or when $X_1$ to $X_3$ is CH and $X_4$ is N; or when $X_1$ is CH, $X_2$ is CH, $X_3$ is N, and $X_4$ is CH; or $X_1$ to $X_4$ are CH, and $R_8$ is an optional substituent attached to a ring C atom selected from Cl, F, $CF_3$, $OCF_3$, $C_1$-$C_3$alkyl, $C_1$-$C_3$alkoxy, or NJJ, wherein each J is independently selected from hydrogen or $C_1$-$C_3$alkyl.

In an embodiment the moiety (iv) is represented by formula (iva)

(iva)

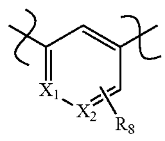

wherein $X_1$ and $X_2$ are independently CH or N, and when $X_1$ is CH, $X_2$ is N; or when $X_1$ is N, $X_2$ is CH; or $X_1$ and $X_2$ are CH, and $R_8$ is an optional substituent attached to a C atom selected from Cl, F, $CF_3$, $OCF_3$, $C_1$-$C_3$alkyl, $C_1$-$C_3$alkoxy, or NJJ, wherein each J is independently selected from hydrogen or $C_1$-$C_3$alkyl.

Accordingly in another aspect the invention provides compounds of formula (II') or (III'):

(II')

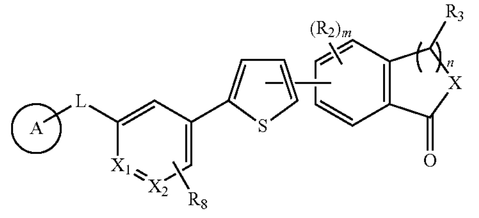

(III')

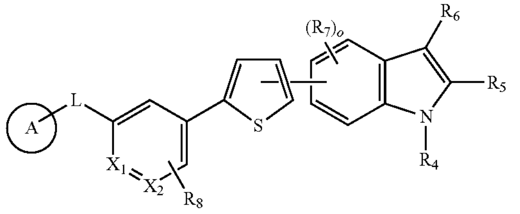

wherein Ring A, L, and variables X, $X_1$, $X_2$, $R_2$-$R_8$, m, n and o are as defined herein.

In another aspect the invention provides compounds of formula (IIa') or (IIIa'):

(IIa')

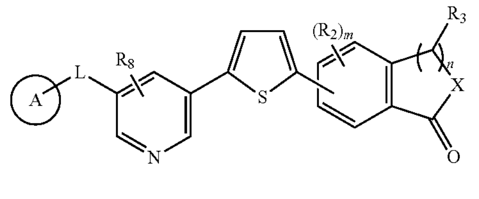

-continued (IIIa')

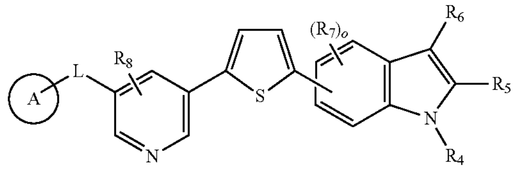

wherein Ring A, L, and variables X, $R_2$-$R_7$, m, n and o are as defined above, and wherein $R_8$ is selected from hydrogen, Cl, F, $CF_3$, $OCF_3$, $C_1$-$C_3$alkyl, $C_1$-$C_3$alkoxy, or NJJ, wherein each J is independently selected from hydrogen or $C_1$-$C_3$alkyl.

In an embodiment the compounds of the invention are represented by formula (IIa').

In a further embodiment the invention provides compounds of formulae (IIb'), (IIc'), (IIIb') and (IIIc'):

(IIb')

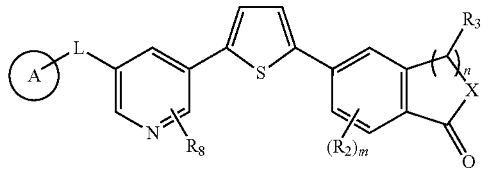

(IIc')

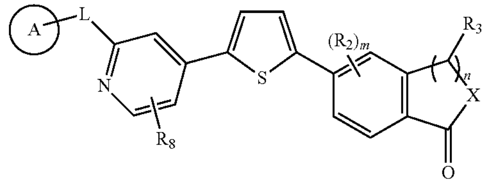

(IIIb')

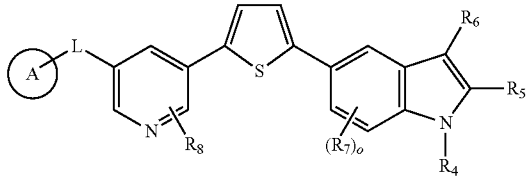

(IIIc')

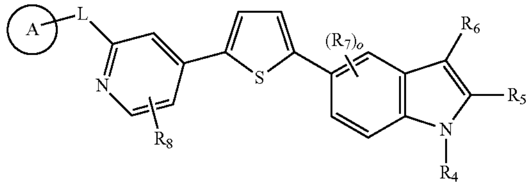

wherein Ring A, L, and variables X, $R_2$-$R_8$, m, n and o are as defined herein.

In another embodiment Ring B is an optionally substituted arylene group.

In another embodiment Ring B is an optionally substituted phenylene group.

In an embodiment Ring B is a phenylene group optionally substituted 1 or 2 times with a group selected from halo, nitro, —$C_1$-$C_6$alkyl, —$C_1$-$C_6$aminoalkyl, —$C_1$-$C_6$hydroxyalkyl, —$C_1$-$C_6$haloalkyl, —$C_1$-$C_6$alkoxyl, -halo-$C_1$-$C_6$alkoxyl, heteroaryl, aryl, hydroxyl, —C(O)$C_1$-$C_6$alkyl, —OC(O)$C_1$-$C_6$alkyl, —$CH_2$OC(O)$C_1$-$C_6$alkyl, —C(O)OC$_1$-C$_3$alkyl, —NHC(O)C$_1$-C$_6$alkyl, —NHS(O)$_2$ C$_1$-C$_6$alkyl, —S(O)$_2$C$_1$-C$_6$alkyl, —S(O)$_2$NH$_2$, and —C(O) NJJ. Preferably the substituent group(s) may be selected from F, Cl, Br, CN, NO$_2$, C$_1$-C$_4$ alkyl, —C(O)C$_1$-C$_4$alkyl, C$_1$-C$_4$ alkoxy, halo C$_1$-C$_4$ alkyl or halo C$_1$-C$_4$ alkyloxy.

Accordingly, in another aspect the invention provides compounds of formula (II") or (III"):

(II")

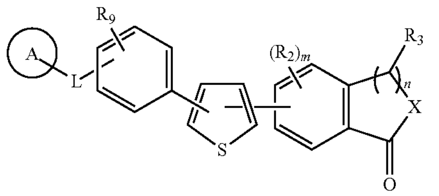

(III")

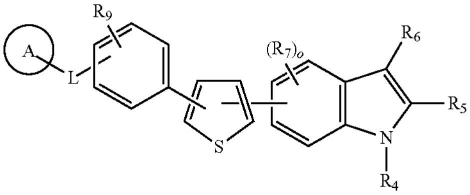

wherein Ring A, L, and variables X, R$_2$-R$_7$, m, n and o are as defined above, and wherein R$_9$ is selected from hydrogen, Cl, F, CF$_3$, OCF$_3$, C$_1$-C$_3$alkoxy, or NJJ, wherein each J is independently selected from hydrogen or C$_1$-C$_3$alkyl.

In an embodiment the compounds of the invention are represented by formula (II").

In a further embodiment the invention provides compounds of formulae (IIa") and (IIIa"):

(IIa")

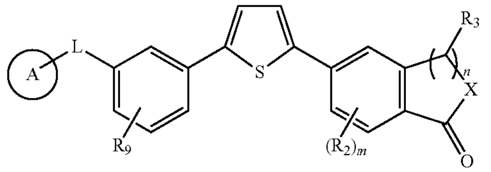

(IIIa")

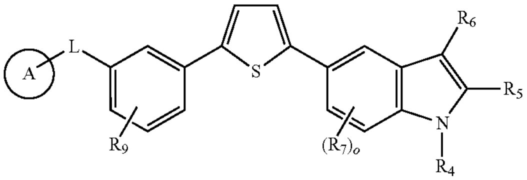

wherein Ring A, L, and variables X, R$_2$-R$_7$ and R$_9$, m, n and o are as defined herein.

With reference to compounds of formulae (Ia), (II), (IIa), (II'), (IIa'), (IIb'), (IIc'), (II"), (IIa"), (III), (IIIa), (III'), (IIIa'), (IIIb'), (IIIc'), (III") and (IIIa"), L is preferably selected from —NHS(O)$_2$—, —N(C$_1$-C$_6$ alkyl)S(O)$_2$—, —NHC(O)—, or —N(C$_1$-C$_6$ alkyl)C(O)—.

In an embodiment L is —NHS(O)$_2$— (which includes the reverse sulphonamide linkage arrangement —S(O)$_2$NH$_2$—).

In an embodiment L is —NHC(O)— (which includes the reverse amide linkage arrangement —C(O)—NH—).

With reference to compounds of formulae (Ia), (II), (IIa), (II'), (IIa'), (IIb'), (IIc'), (II"), (IIa"), (III), (IIIa), (III'), (IIIa'), (IIIb'), (IIIc'), (III") and (IIIa"), Ring A is preferably selected from a 6-membered optionally substituted aryl or a 5- or 6-membered heteroaryl group.

In an embodiment Ring A is a 6-membered optionally substituted phenyl group.

In an embodiment Ring A is a phenyl group optionally substituted 1 to 3 times with a group selected from halo, nitro, —C$_1$-C$_6$alkyl, —C$_1$-C$_6$aminoalkyl, —C$_1$-C$_6$hydroxyalkyl, —C$_1$-C$_6$haloalkyl, —C$_1$-C$_6$alkoxyl, -halo-C$_1$-C$_6$alkoxyl, heteroaryl, aryl, hydroxyl, —C(O)C$_1$-C$_6$alkyl, —OC(O)C$_1$-C$_6$alkyl, —CH$_2$OC(O)C$_1$-C$_6$alkyl, —C(O)OC$_1$-C$_3$alkyl, —NHC(O)C$_1$-C$_6$alkyl, —NHS(O)$_2$ C$_1$-C$_6$alkyl, —S(O)$_2$C$_1$-C$_6$alkyl, —S(O)$_2$NH$_2$, and —C(O) NJJ, where each J is independently hydrogen or C$_1$-C$_4$alkyl. Preferably the substituent group(s) may be selected from F, Cl, Br, CN, NO$_2$, OCF$_3$, C$_1$-C$_4$ alkyl, halo C$_1$-C$_4$ alkyl or C$_1$-C$_4$ alkyloxy.

In an embodiment Ring A is a 6-membered optionally substituted heteroaryl group.

In an embodiment Ring A is an optionally substituted pyridyl group.

In an embodiment Ring A is a pyridyl group optionally substituted 1 or 2 times with a group selected from halo, nitro, cyano, —C$_1$-C$_6$alkyl, —C$_1$-C$_6$aminoalkyl, —C$_1$-C$_6$hydroxyalkyl, —C$_1$-C$_6$haloalkyl, —C$_1$-C$_6$alkoxyl, -halo-C$_1$-C$_6$alkoxyl, heteroaryl, aryl, hydroxyl, —C(O)C$_1$-C$_6$alkyl, —OC(O)C$_1$-C$_6$alkyl, —CH$_2$OC(O)C$_1$-C$_6$alkyl, —C(O)OC$_1$-C$_3$alkyl, —NHC(O)C$_1$-C$_6$alkyl, —NHS(O)$_2$ C$_1$-C$_6$alkyl, —S(O)$_2$C$_1$-C$_6$alkyl, —S(O)$_2$NH$_2$, and —C(O) NJJ, where each J is independently hydrogen or C$_1$-C$_4$alkyl. Preferably the substituent group(s) may be selected from F, Cl, Br, CN, NO$_2$, OCF$_3$, C$_1$-C$_4$ alkyl, C$_1$-C$_4$ alkoxy, —C(O) C$_1$-C$_4$alkyl, halo C$_1$-C$_4$ alkyl or C$_1$-C$_4$ alkyloxy.

Exemplary compounds of the present invention include but are not limited to the group consisting of:

(1)

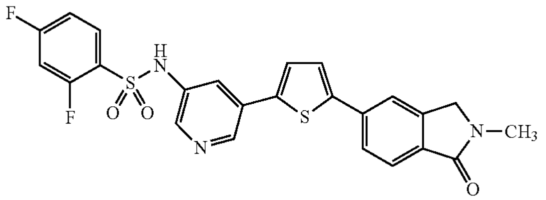

(2)

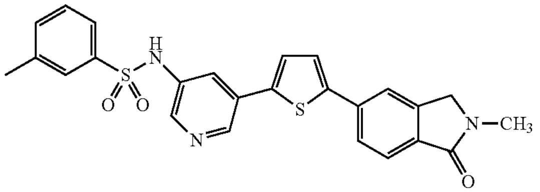

-continued
(3)
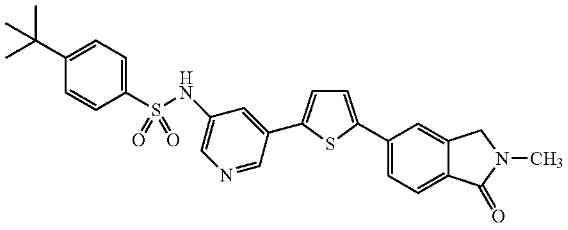
(4)
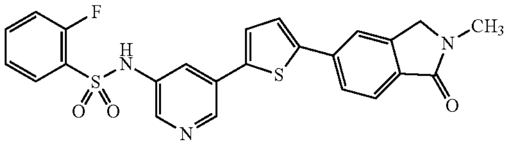
(5)
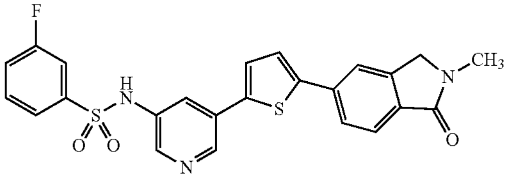
(6)
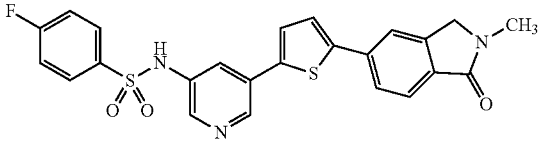
(7)
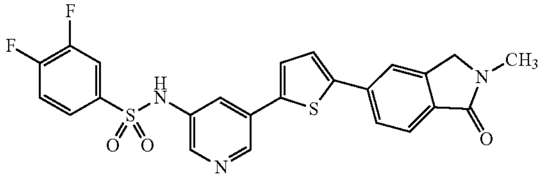
(8)
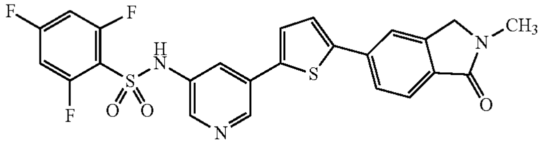
(9)
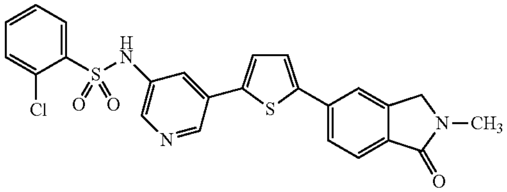
(10)
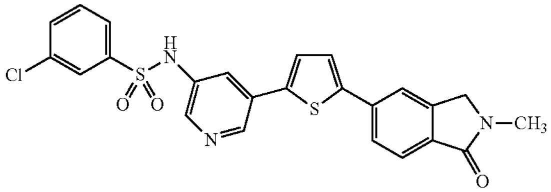
(11)
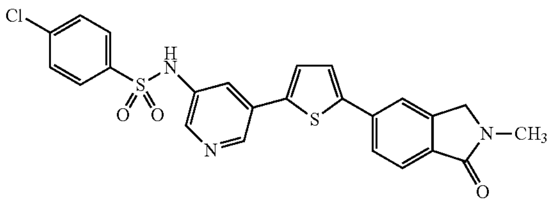
(12)
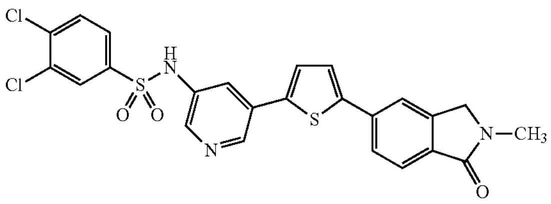
(13)
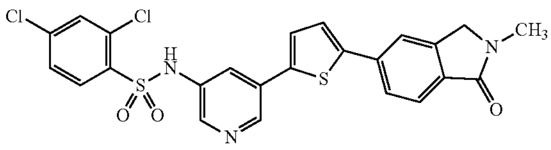
(14)
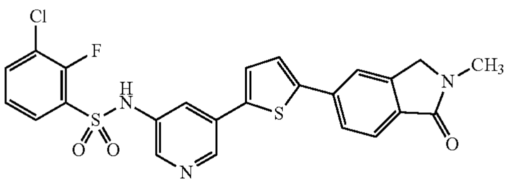
(15)
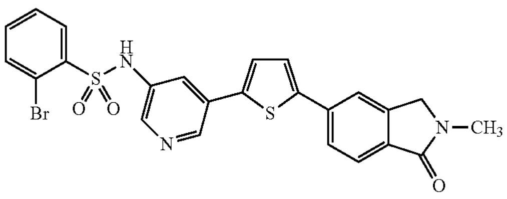
(16)
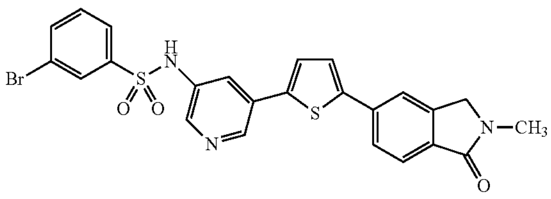

-continued
(17)
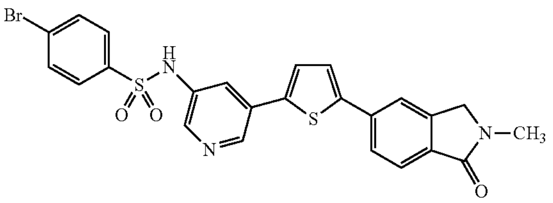
(18)
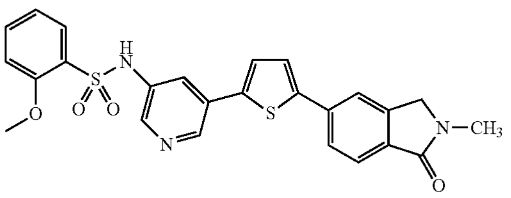
(19)
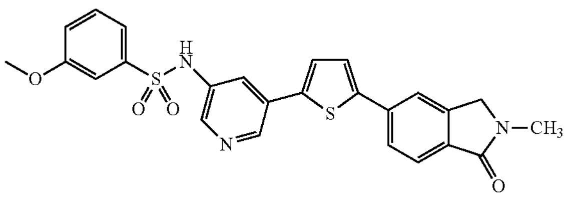
(20)
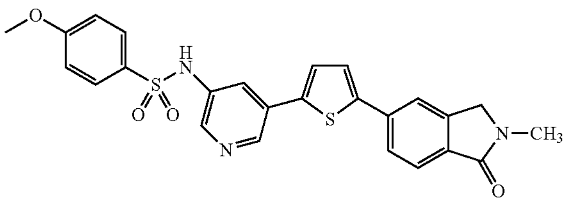
(21)
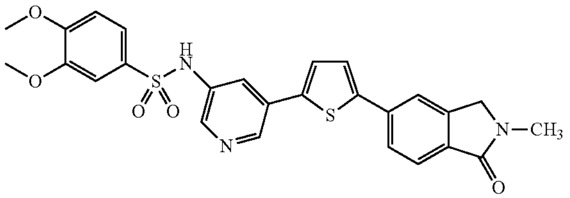
(22)
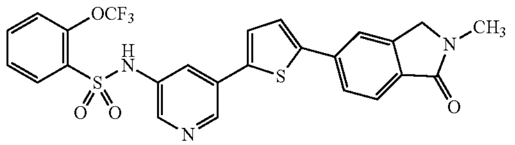
(23)
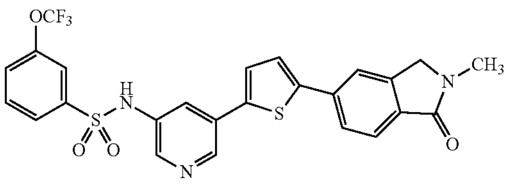
(24)
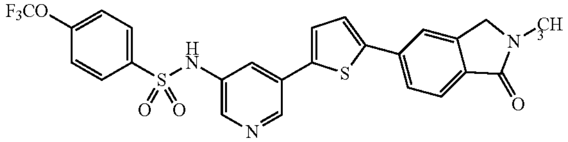
(25)
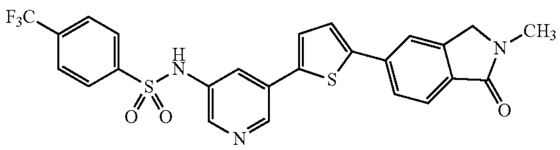
(26)
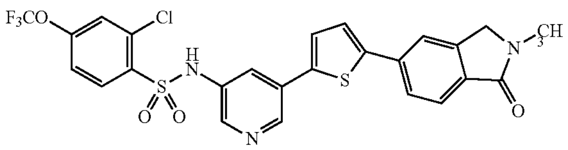
(27)
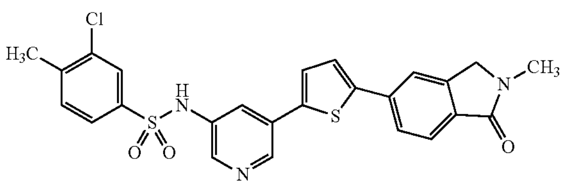
(28)
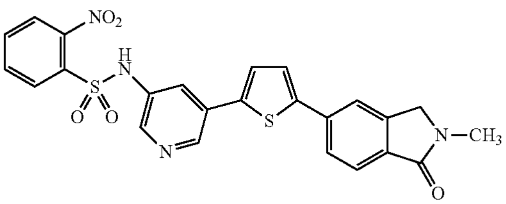
(29)
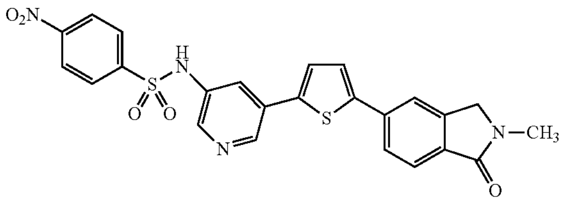
(30)
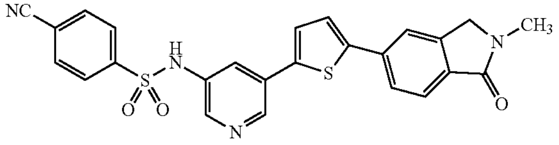

-continued
(31)
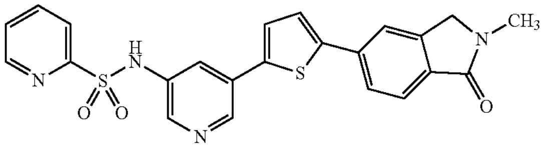
(32)
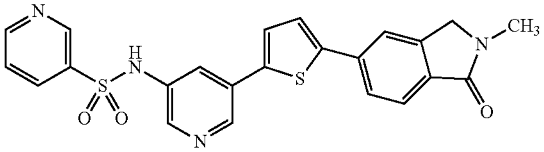
(33)
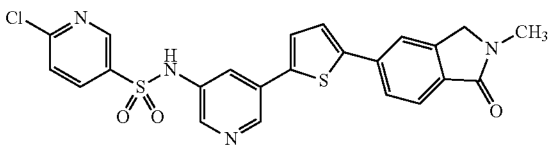
(34)
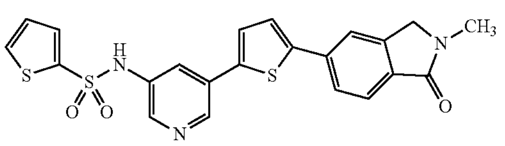
(35)
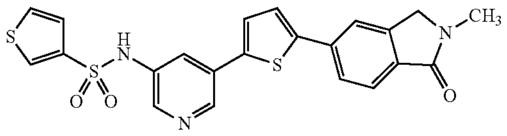
(36)
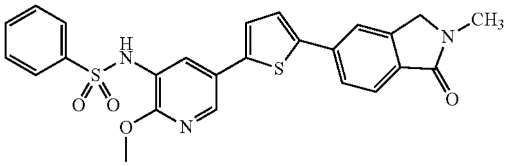
(37)
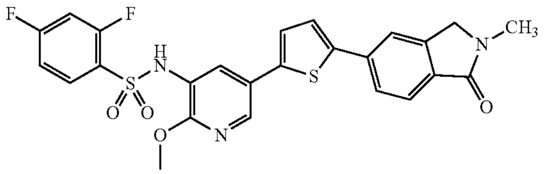
(38)
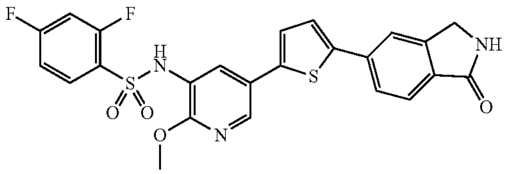
(39)
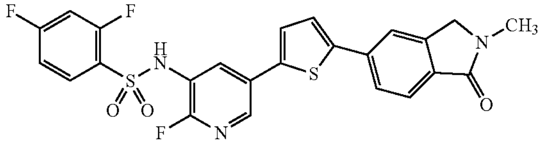
(40)
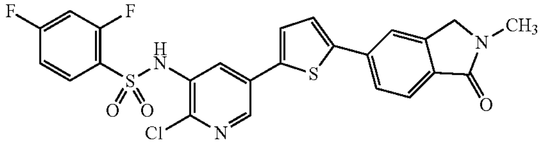
(41)
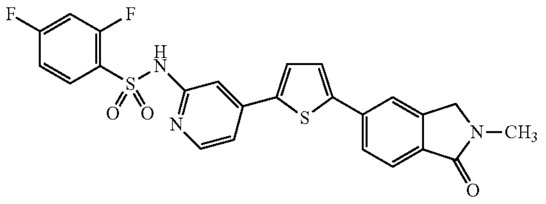
(42)
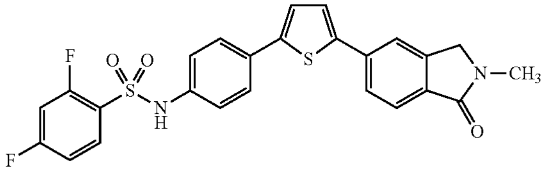
(43)
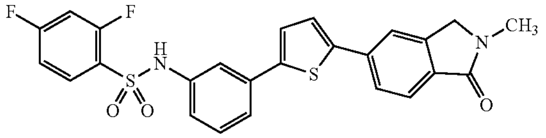
(44)
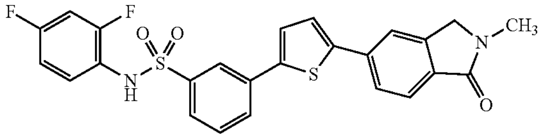
(45)
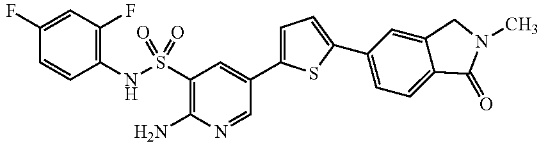
(46)
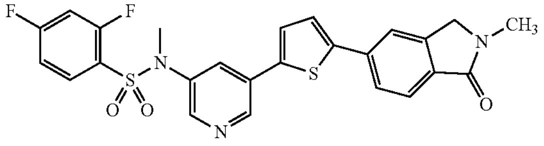
(47)
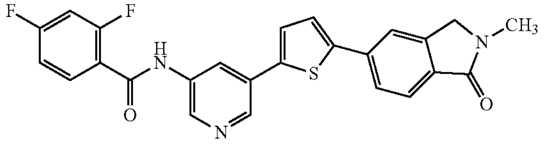
(48)
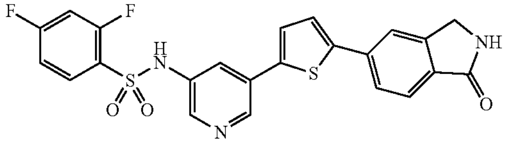

-continued
(49)
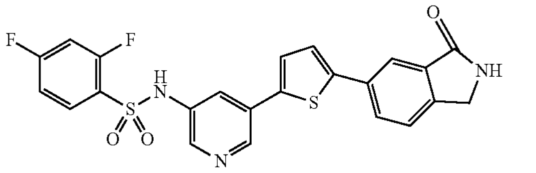
(50)
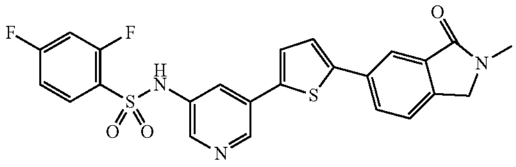
(51)
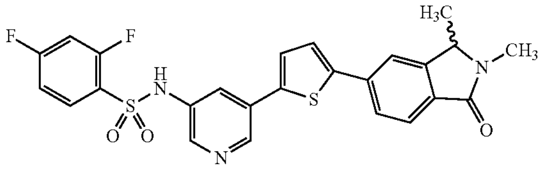
(52)
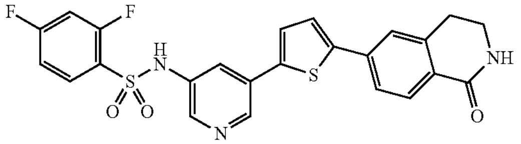
(53)
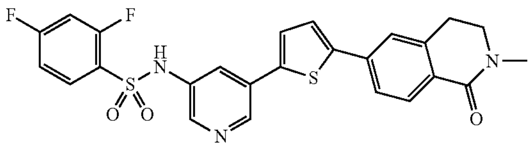
(54)
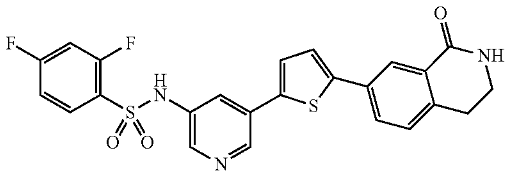
(55)
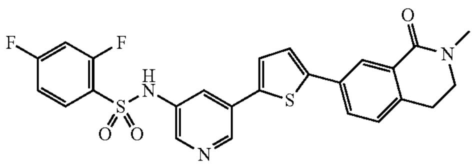
(56)
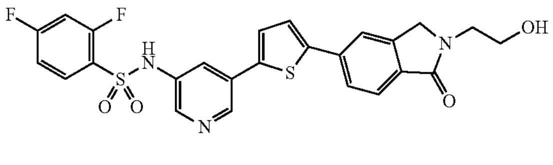
(57)
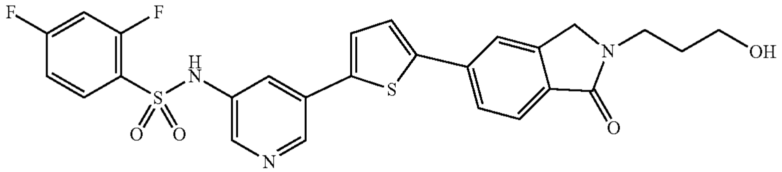
(58)
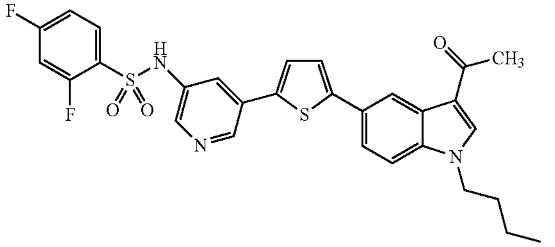
(59)
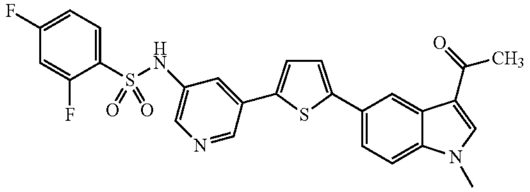
(60)
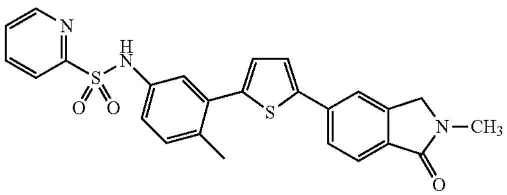
(61)
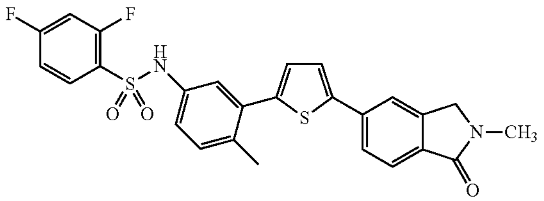
(62)
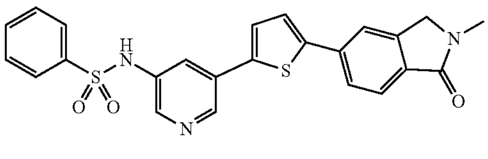
(63)
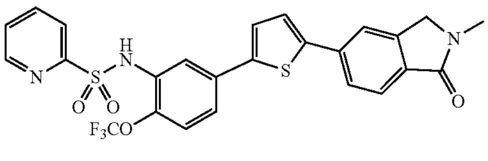

-continued
(64)
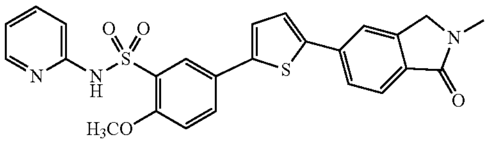
(65)
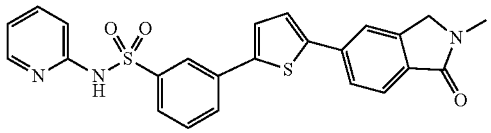
(66)
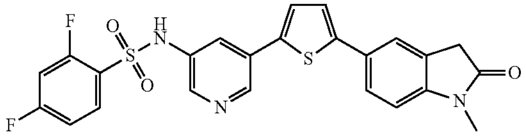
(67)
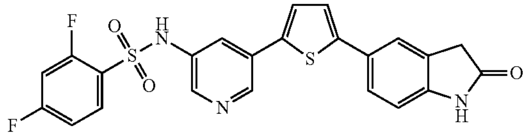
(68)
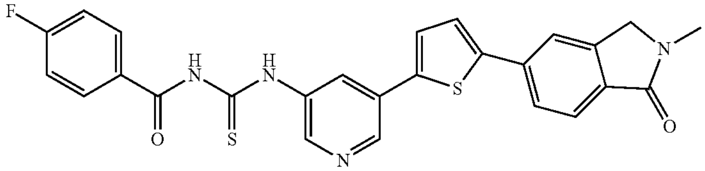
(69)
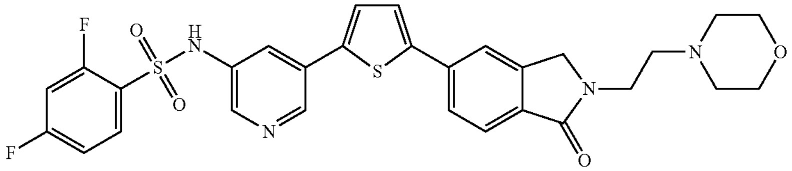
(70)
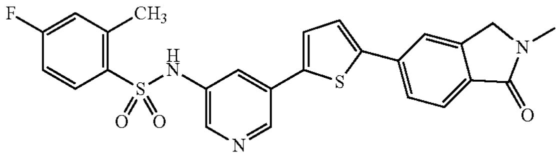
(71)
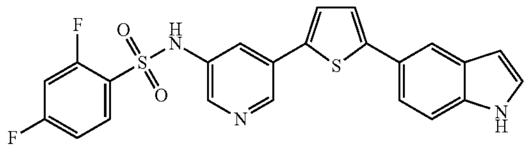
(72)
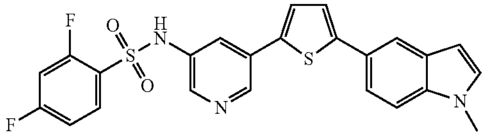
(73)
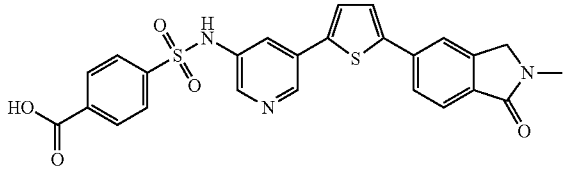
(74)
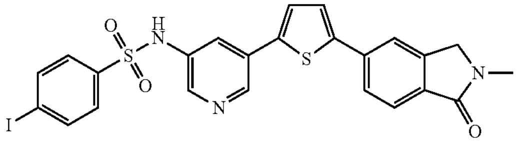
(75)
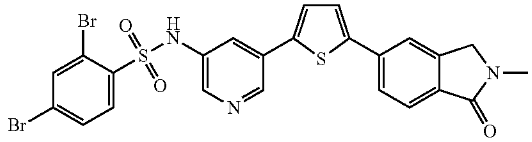
(76)
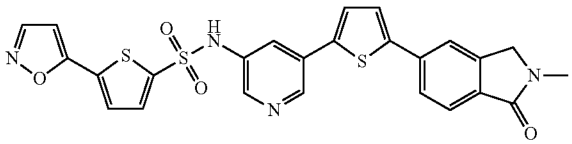
(77)
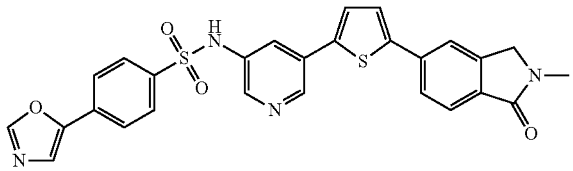
(78)
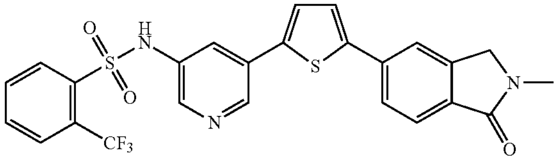
(79)
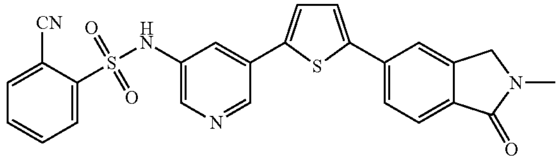

-continued (80)

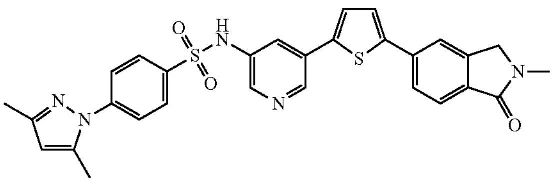

(81)

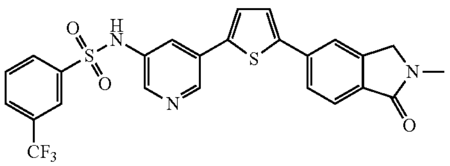

(82)

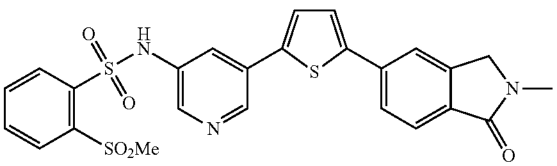

(83)

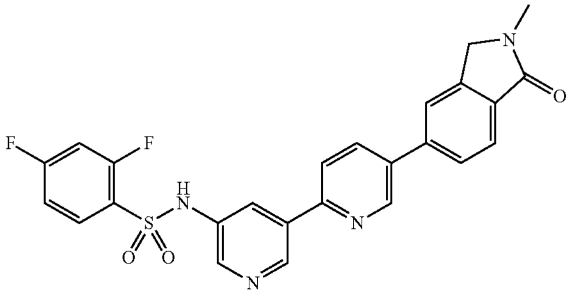

(84)

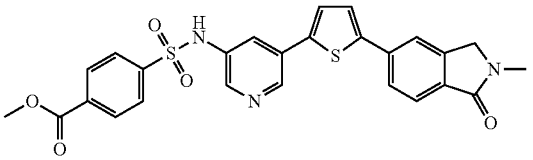

(85)

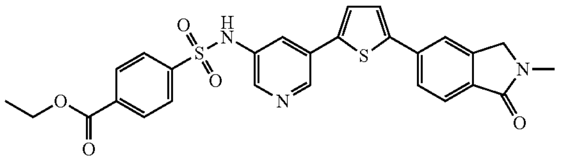

(86)

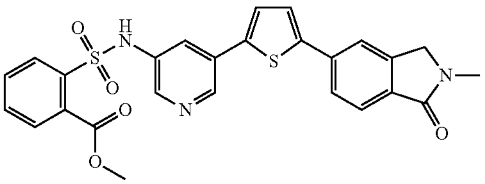

(87)

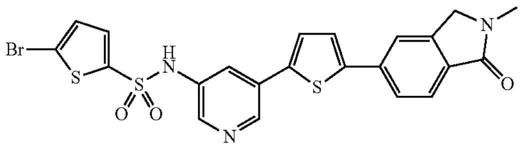

(88)

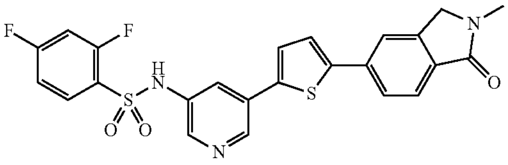

(89)

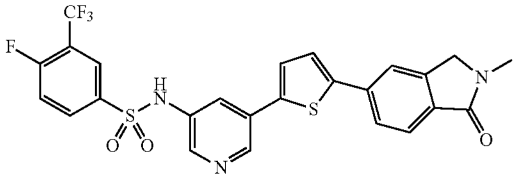

(90)

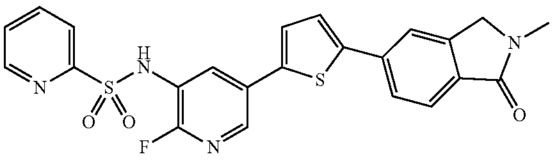

(91)

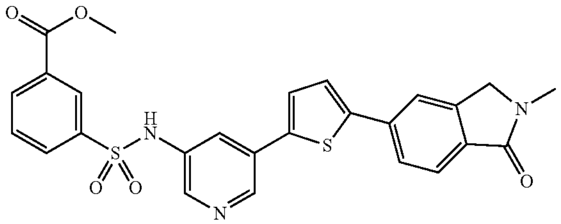

In another aspect of the present invention, there is provided a pharmaceutical composition including the compound of the present invention, as herein described and a pharmaceutically acceptable carrier, excipient, diluent and/or adjuvant.

In some embodiments, the compounds of the present invention inhibit the activity of a perforin molecule, or a fragment or variant thereof, by binding the perforin molecule, or a fragment or variant thereof, and preventing the perforin molecule from contacting a target cell.

Alternatively, and without being limited by theory, the inhibitor may act in other ways including but not limited to preventing calcium binding by perforin molecules, preventing normal folding of perforin into an active configuration, preventing perforin from polymerising into a form capable of forming a transmembrane pore, or preventing perforin from effectively delivering other granule contents such as granzymes to induce apoptosis.

Without being limited by theory, the compounds of the present invention may also inhibit the activity of a perforin molecule, or a fragment or variant thereof, by modulating a target cell, a receptor on the target cell or an interacting molecule such as a ligand on the surface of the target cell to which perforin is targeted such that the cell is modified to be less responsive to the perforin molecule.

The compounds of the present invention have been identified by the screening methods previously described in WO 2005/083098, the entire contents of which are incorporated herein by reference, and show an ability to inhibit the cytolytic activity of mouse and human perforin. Given the degree of sequence homology of native perforin from different species, and the fact that the compounds identified by the present inventors are capable of inhibiting the cytolytic activity of human and mouse perforin, it is contemplated that the compounds of the present invention will also demonstrate an ability to inhibit the cytolytic activity of perforin from other species.

The terms "perforin", "cytolysin", "pore-forming protein (pfp)" and "C9-like protein" are used interchangeably herein and encompass perforin polypeptides and fragments thereof in various forms, including naturally occurring or synthetic variants. Examples of perforins encompassed by the present invention include human perforin. Also encompassed by the present invention are mouse and rat perforin isoforms, although perforins derived from other species, including those that may be made by lower organisms such as bacteria, are also envisaged.

As used herein, the term "native perforin" refers to a perforin polypeptide molecule having an amino acid sequence that occurs in nature (e.g., a natural protein). Native perforin, or naturally occurring perforin, may be identified as one of the main constituents of cytocidal granules, is found to migrate with a molecular mass of approximately 66 kDa upon reduction and SDS-polyacrylamide gel electrophoresis, and migrates more slowly under non-reducing conditions (70-75 kDa), suggestive of a tightly disulphide-bonded structure in its native form. In the presence of calcium ions ($Ca^{2+}$), perforin monomers aggregate into tubular structures that span the lipid bilayer, producing circular lesions (varying between 6 and 20 nm in diameter) that are thought to grow in diameter through the progressive recruitment of additional monomers.

Variants of perforin may exhibit amino acid sequences that are at least 80% identical to a native perforin polypeptide or fragment thereof. Also contemplated are embodiments in which a variant comprises an amino acid sequence that is at least 90% identical. It is envisaged that the invention will encompass embodiments in which a variant comprises an amino acid sequence that is at least 95% identical. In one embodiment the amino acid sequence will be at least 98% identical, in further embodiments it will be at least 99% identical. Amino acid sequences that are at least 99.9% identical to the native perforin polypeptide or fragment thereof are also encompassed in the present invention. Percent identity may be determined by visual inspection and mathematical calculation. Among the naturally occurring variants and fragments thereof provided are variants of native perforin that retain native biological activity or a substantial equivalent thereof. Also provided herein are naturally occurring variants that have enhanced biological activity as compared to a native perforin molecule.

Variants of perforin include polypeptides that are substantially homologous to the native form of perforin, but which have an amino acid sequence different from that of the native form because of one or more deletions, insertions or substitutions. Particular embodiments include polypeptides that comprise from one to ten deletions, insertions or substitutions of amino acid residues when compared to a native sequence. A given sequence may be replaced, for example, by a residue having similar physiochemical characteristics. Examples of conservative substitution of one aliphatic residue for another, such as Ile, Val, Leu or Ala for one another; substitution of one polar residue for another, such as between Lys and Arg, Glu and Asp, or Gin and Asn; or substitutions of one aromatic residue for another, such as Phe, Trp or Tyr for one another. Other conservative substitutions, e.g., involving substitutions of entire regions having similar hydrophobicity characteristics, are well known in the art. Variants may also be defined by the truncation of a native perforin polypeptide. Further variants encompassed by the present invention include, but are not limited to, deglycosylated perforin polypeptides, or fragments thereof, or those polypeptides demonstrating increased glycosylation when compared to native perforin. Also encompassed are perforin polypeptide variants with increased hydration. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, an amino acid residue of a perforin polypeptide is preferably replaced with another amino acid residue from the same side chain family. Mutations may occur along all or part of a perforin coding sequence and the resultant mutants can be screened for perforin activity to identify variants that demonstrate the same or increased perforin activity in comparison to a native perforin molecule.

As used herein, the terms "perforin activity", "biological activity of perforin" and the like refer to the cytolytic activity of a perforin polypeptide; that is, its ability to bind to a target cell membrane and polymerise into pore-like transmembrane channels leading to cell lysis. The activity also includes the capacity to synergise with other toxins such as granule toxins and other molecules to induce apoptosis. The target cell can be any cell that is capable of being lysed by native perforin.

The biological activity of perforin can be assessed by the skilled addressee by any number of means known in the art including, but not limited to, the measurement of target cell lysis, the delivery of granzyme B molecules into the target cell, the measurement of target cell membrane disruption (such as by changes in ion transport), the induction of apoptosis in the target cell, the modification of vesicular trafficking and the general assessment of target cell death. The target cell may be a red blood cell (RBC) and hence a common means of measuring perforin activity is by a RBC lysis test. It may also be any nucleated cell.

As used herein, the term "fragment" refers to a portion of a perforin polypeptide, or a variant thereof. Such fragments would retain biological activity as compared to a native perforin molecule.

In a further embodiment, a fragment of a perforin polypeptide may consist of the biologically active C-terminal domain. Such fragments may generally be identified using techniques well known to those skilled in the art in identifying perforin activity, as herein described. Perforin polypeptide fragments may also be identified by screening fragments for their ability to react with perforin-specific antibodies and/or antisera. Antisera and antibodies are "perforin-specific" if they specifically bind to a perforin polypeptide or a variant or fragment thereof (i.e., they react with a perforin in an enzyme-linked immunosorbent assay [ELISA] or other immunoassay, and do not react detectably with unrelated polypeptides). Such antisera and antibodies may be prepared as described herein, and using well-known techniques (see, for example, Harlow and Lane, *Antibodies: A Laboratory Manual*, Cold Spring Harbor Laboratory, 1988).

It would be understood by one skilled in the art that the present invention is applicable to any species, including, but not limited to, human, rat, mouse, bird, horse, and lower organisms such as bacteria.

The compounds of the present invention have been identified by their ability to inhibit perforin activity, and as such, may be referred to herein as "inhibitors", "perforin inhibitors", "inhibitors of perforin activity", and the like.

Pharmaceutically Acceptable Salts

The term "pharmaceutically acceptable" as applied to salts of the present invention and/or used in methods of the present invention refers to salts which are, within the scope of sound medical judgment, suitable for use in contact with the tissues of humans and lower animals without undue toxicity, irritation, allergic, or a like negative response that exceeds a reasonable risk/therapeutic benefit ratio. One skilled in the art will understand that a pharmaceutically acceptable salt is a salt that is suitable for administration to a patient. Accordingly, the present invention also extends to a pharmaceutically acceptable salt of any one of the compounds of the present invention.

Pharmaceutically acceptable salts are generally known in the art, and in the case of the present invention, include relatively non-toxic, organic or inorganic salts of the compounds of the present invention. Examples of such salts include, but are not limited to, acid addition salts such as hydrochloride salts, sulfate salts, bisulfate salts, borate salts, nitrate salts, acetate salts, phosphate salts, hydrobromide salts, laurylsulfonate salts, glucoheptonate salts, oxalate salts, oleate salts, laurate salts, stearate salts, palmitate salts, valerate salts, benzoate salts, naphthylate salts, mesylate salts, tosylate salts, citrate salts, lactate salts, maleate salts, succinate salts, tartrate salts, fumarate salts, and the like (see, for example, Berge et al., *J. Pharm. Sci.* 1977, 66:1-19). In addition, pharmaceutically acceptable salts also include basic salts such as alkali metal salts, alkaline earth salts, and ammonium salts. For example, pharmaceutically acceptable basic salts include salts of aluminum, calcium, lithium, magnesium, potassium, sodium, zinc, and the like. In addition, organic salts may also be used including, e.g., salts of lysine, N,N'-dibenzylethylenediamine, chloroprocaine, choline, diethanolamine, ethylenediamine, meglumine (N-methylglucamine), procaine and tris. The basic nitrogen-containing groups in the compounds of the present invention can be quaternized with various organic agents including, e.g., alkyl halides (such as lower alkyl halide including methyl, ethyl, propyl, and butyl chlorides, bromides and iodides), long chain halides (e.g., decyl, lauryl, myristyl and stearyl chlorides, bromides and iodides), aralkyl halides (e.g., benzyl and phenethyl bromides), dialkyl sulfates (e.g., dimethyl, diethyl, dibutyl and diamyl sulfates).

In some embodiments the pharmaceutically acceptable salts will be sodium salts of the compounds disclosed herein. Sodium salts of the compounds disclosed herein will be denoted by the term "Na" adjacent to the compound number, for example, compound (1.Na).

The pharmaceutically acceptable salts of the compounds of the present invention also can exist in the form of solvates, e.g., with water, methanol, ethanol, dimethylformamide, ethyl acetate, and the like, and mixtures thereof.

Derivatives

The present invention also provides derivatives of the natural or synthetic compounds of the present invention through modification by conventional chemical, physical and biochemical means (see, e.g., Blondelle et al., 1996, *Trends in Biotech.* 14:60), or subjected to directed or random chemical modifications, such as acylation, alkylation, esterification, amidification, and the resultant analogs can be screened for their ability to modulate perforin activity, as herein described.

In a particular embodiment, a derivative of the present invention is an ester, amide or hydrate of any one of the compounds of the present invention and/or used in methods of the invention. The term "pharmaceutically acceptable" refers to esters, amides, or hydrates which are, within the scope of sound medical judgment, suitable for use in contact with the tissues of humans and lower animals without undue toxicity, irritation, allergic, or a like negative response that exceeds a reasonable risk/therapeutic benefit ratio. One skilled in the art will appreciate that the encompassed pharmaceutically acceptable esters, amides, hydrates are esters, amides, hydrates suitable for administration to a patient.

Pharmaceutically acceptable esters can be made by reacting a hydroxyl group in the compounds of the present invention with a pharmaceutically acceptable organic acid, or by reacting a carboxylic acid group in the compounds with a pharmaceutically acceptable alcohol such as methanol, ethanol, propanol, etc. The organic acids used to form acid addition salts described above can all be useful.

Pharmaceutically acceptable amides can be prepared by reacting an amino functional group of the compounds of the above formulas with a pharmaceutically acceptable organic acid, as will be apparent to skilled artisans.

The compounds of the present invention may also be amended by adding one or more protected amino and/or hydroxyl groups by methods known to the skilled addressee. If the protective groups present are different from one another, in many cases they can be removed selectively.

The term "amino protective group" is generally known to those skilled in the art and relates to groups which are suitable for protecting (for blocking) an amino group from chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the protective groups are removed after the desired reaction (or reaction sequence), their nature and size is otherwise uncritical. Those having 1-20, in particular 1-8 C atoms are preferred. The expression "acyl group" is to be interpreted in the widest sense in connection with the present process. It includes acyl groups derived from aliphatic, araliphatic, aromatic or heterocyclic carboxylic acids or sulfonic acids and also, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxy-alkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxy-benzyloxycarbonyl, FMOC; arylsulfonyl such as Mtr Pbf or Pmc. Preferred amino protective groups are BOC and Mtr, additionally CBZ, Fmoc, benzyl and acetyl.

The term "hydroxyl protective group" is likewise generally known and relates to groups which are suitable for protecting a hydroxyl group from chemical reactions, but which are easily removable after the desired chemical reaction has been carried out at other positions in the molecule. Typical groups of this type are the abovementioned unsubstituted or substituted aryl, aralkyl or acyl groups and additionally also alkyl groups. The nature and size of the hydroxyl protective groups is not critical, since they are removed again after the desired chemical reaction or reaction sequence; groups containing 1-20, in particular 1-10, C atoms are preferred. Examples of hydroxyl protective groups are, inter alia, benzyl, p-nitro-benzyl, p-toluenesulfonyl, tert-butyl and acetyl, benzyl and tert-butyl being particularly preferred. The COOH groups in aspartic acid and glutamic acid are preferably protected in the form of their tert-butyl esters (e.g. Asp(OtBu)).

The ability of the derivatives of the present invention to inhibit the cytolytic activity of perforin can be assessed by any number of means available to the skilled addressee, as taught, for example, in WO 2005/083098.

The present invention also provides compositions comprising a complex of a perforin inhibitor, or a pharmaceutically acceptable salt or a derivative thereof, as herein described, bound to a targeting molecule that is capable of enhancing delivery of the compound by providing for increased specificity, efficiency and duration of therapeutic action. Such targeting molecules comprise immunoconjugates, fusion proteins, and liposomes, microparticles, bioerodable polymers, gels, and foams. The targeting molecule may also comprise a targeting receptor molecule which enhancing the delivery of the perforin inhibitor to a cell or tissue, particularly to a cell or tissue which expresses a ligand to that receptor. The receptor may be derived from natural sources, or it may be synthesized by methods known in the art. In these compositions, the compounds of the present invention may remain substantially inactive or unavailable in the absence of a targeted receptor molecule to which they specifically bound.

The term "ligand" refers to a specific binding partner of a receptor and includes, without limitation, receptor agonists, partial agonists, mixed agonists, antagonists, drugs, hormones, transmitters, autocoids, growth factors, cytokines, prosthetic groups, coenzymes, cofactors, regulatory factors, antigens, haptens, vitamins, nucleic acids and synthetic heteropolymers comprising amino acids, nucleotides, carbohydrates or nonbiologic monomers, including analogs and derivatives thereof, and conjugates or complexes formed by attaching or binding any of these molecules to a second molecule.

The term "receptor" refers to a specific binding partner of a ligand and includes, without limitation, membrane receptors, soluble receptors, cloned receptors, recombinant receptors, hormone receptors, drug receptors, transmitter receptors, autocoid receptors, cytokine receptors, antibodies, antibody fragments, engineered antibodies, antibody mimics, molecular recognition units, adhesion molecules, agglutinins, integrins, selectins, nucleic acids and synthetic heteropolymers comprising amino acids, nucleotides, carbohydrates or nonbiologic monomers, including analogs and derivatives thereof, and conjugates or complexes formed by attaching or binding any of these molecules to a second molecule.

"Prodrug derivatives" are also included in the scope of the present invention, wherein the perforin inhibitor, or a derivative thereof, is further modified with, for example, alkyl or acyl groups, sugars or oligopeptides, which are rapidly cleaved in the body to give the active compounds according to the invention. That is, the term "prodrug" refers to a precursor or modified compound of the present invention that is not fully active or available until converted in vivo to its therapeutically active or available form.

The term "synthetic receptor" refers to any naturally occurring, recombinant, biologically produced or synthetic ligand or receptor which is designed, selected or engineered to specifically bind a drug. The terms "therapeutic receptor" and "pathophysiologic receptor" refer to the molecular site of drug action. The term "therapeutic target" refers to an object of therapeutic intervention, including any physiologic or pathologic entity comprising therapeutic receptors, such as a specified organ, tissue or type of cell, platelet, corpuscle, microorganism, molecular complex or molecule.

General Synthetic Protocols

The compounds of the present invention may be prepared according to the following general schemes:

Scheme A

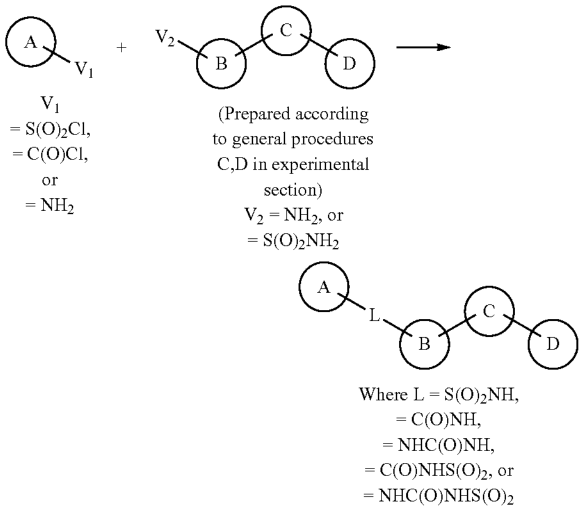

Where subunit A is highly reactive, it is possible to assemble the B-C-D ring moieties using methods already described in the experimental section and subsequently react or couple such moieties with subunit A in the final step. This affords the linkers, L, as shown above in Scheme A.

Scheme B

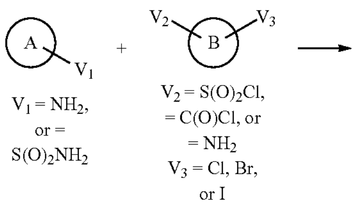

-continued

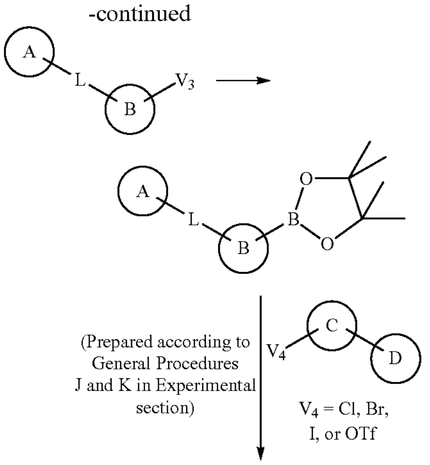

-continued

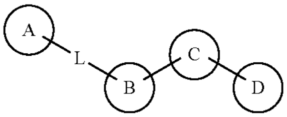

Where L = $NHS(O)_2$,
= NHC(O),
= $S(O)_2NHC(O)$, or
= $S(O)_2NHC(O)NH$

Where subunit B is the highly reactive component, it is preferable to assemble the A-L-B ring moiety first, then form a boronate (or other organometallic, in situ, or isolated), followed by reaction with a reactive/functionalised C-D ring moiety using methods already described in the experimental section as described herein.

Scheme C

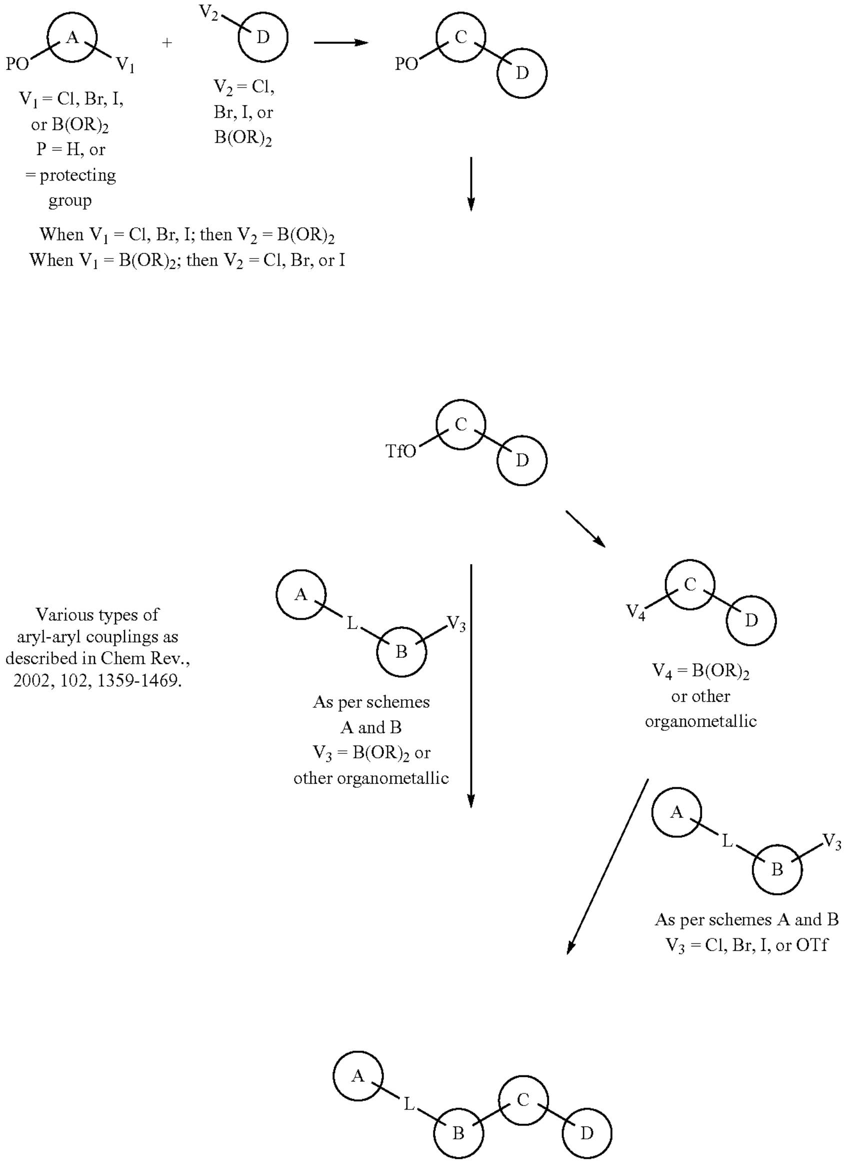

When the C ring subunit is other than thiophene the chemistry involves the formation of two aryl-aryl (C—C) bonds to the C ring subunit in different steps. This may be achieved by introducing orthogonal functionality to facilitate this step (i.e., to eliminate the homo-coupling which would otherwise occur). The D ring subunit may be introduced in a Suzuki reaction as already described in the experimental section; the halide and boronate can be on either side of the reactive intermediate. A hydroxyl substituent (protected if necessary) can be carried through this step to provide a handle which can be converted to the C-D ring triflate intermediate. This C-D ring triflate intermediate can then be reacted with various organometallic A-L-B ring subunits, or alternatively, converted to organometallic substituents and reacted with halides or triflate on the C-D subunit. Applicable reactions for these two steps would include Suzuki, Stille, Negishi, Grignard and others, all described in Hassan, et al., Chem Rev., 102, 1359-1469, 2002.

Other compounds of the present invention can be prepared by the addition, removal or modification of existing substituents. This could be achieved by using standard techniques for functional group inter-conversion that are well known in the industry, such as those described in "Comprehensive organic transformations: a guide to functional group preparations" by Larock R. C., New York, VCH Publishers, Inc. 1989.

Examples of functional group inter-conversions are: —C(O)NR*R** from —$CO_2CH_3$ by heating with or without catalytic metal cyanide, e.g. NaCN, and HNR*R** in $CH_3OH$; —OC(O)R from —OH with e.g., ClC(O)R in pyridine; —NC(S)NR*R** from —NHR with an alkylisothiocyanate or thiocyanic acid; —NRC(O)OR* from —NHR with alkyl chloroformate; —NRC(O)NR*R** from —NHR by treatment with an isocyanate, e.g. HN═C═O or RN═C═O; —NRC(O)R* from —NHR by treatment with ClC(O)R* in pyridine; —C(═NR)NR*R** from —C(NR*R**)SR with $H_3NR^+OAc^-$ by heating in alcohol; —C(NR*R**)SR from —C(S)NR*R** with R—I in an inert solvent, e.g. acetone; —C(S)NR*R** (where R* or R** is not hydrogen) from —C(S)$NH_2$ with HNR*R**; —C(═NCN)—NR*R** from —C(═NR*R**)—SR with $NH_2CN$ by heating in anhydrous alcohol, alternatively from —C(═NH)—NR*R** by treatment with BrCN and NaOEt in EtOH; —NR—C(═NCN)SR from —NHR* by treatment with $(RS)_2C$═NCN; —NR**$SO_2R$ from —NHR* by treatment with $ClSO_2R$ by heating in pyridine; —NR*C(S)R from —NR*C(O)R by treatment with Lawesson's reagent [2,4-bis(4-methoxyphenyl)-1,3,2,4-dithiadiphosphetane-2,4-disulfide]; —$NRSO_2CF_3$ from —NHR with triflic anhydride and base, —CH($NH_2$)CHO from —CH($NH_2$)C(O)OR* with Na(Hg) and HCl/EtOH; —$CH_2$C(O)OH from —C(O)OH by treatment with $SOCl_2$ then $CH_2N_2$ then $H_2O$/$Ag_2O$; —C(O)OH from —$CH_2$C(O)$OCH_3$ by treatment with PhMgX/HX then acetic anhydride then $CrO_3$; R—OC(O)R* from RC(O)R* by R**$CO_3$H; —$CCH_2OH$ from —C(O)OR* with Na/R*OH; —$CHCH_2$ from —$CH_2CH_2OH$ by the Chugaev reaction; —$NH_2$ from —C(O)OH by the Curtius reaction; —$NH_2$ from —C(O)NHOH with TsCl/base then $H_2O$; —CHC(O)CHR from —CHCHOHCHR by using the Dess-Martin Periodinane regent or $CrO_3$/aq$H_2SO_4$/acetone; —$C_6H_5CHO$ from —$C_6H_5CH_3$ with $CrO_2Cl_2$; —CHO from —CN with $SnCl_2$/HCl; —CN from —C(O)NHR with $PCl_5$; —$CH_2R$ from —C(O)R with $N_2H_4$/KOH.

During the reactions described above a number of the moieties may need to be protected. Suitable protecting groups are well known in industry and have been described in many references such as Protecting Groups in Organic Synthesis, Greene T W, Wiley-Interscience, New York, 1981.

Pharmaceutical Compositions

In yet another aspect of the present invention there is provided a pharmaceutical composition including a compound of the present invention, or a pharmaceutically acceptable salt or a derivative thereof, as herein described (also referred to herein as an "active compound"). In some embodiments, the pharmaceutical composition may comprise a pharmaceutically acceptable carrier, excipient, diluent and/or adjuvant.

Pharmaceutical compositions of the present invention may be employed alone or in conjunction with other compounds, such as therapeutic compounds.

As used herein, the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is generally formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL.™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, or liquid polyetheylene glycol, and the like), and suitable mixtures thereof. The proper fluidity can be maintained, for example, by the use of a coating such as lecithin, by the maintenance of the required particle size in the case of a dispersion or by the use of surfactants. Prevention of the action of microorganisms can be achieved by incorporation of various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, or sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof.

Oral compositions generally comprise an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or orange flavouring.

For administration by inhalation, the compounds are delivered in the form of an aerosol spray from a pressurised container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished with nasal sprays or suppositories. The compounds can be prepared in the form of suppositories (e.g., with conventional suppository bases such as cocoa butter and other glycerides) or retention enemas for rectal delivery.

For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosages for use in humans. The dosage lies within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate perforin activity is used as a template, or "imprinting molecule", to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be seen in Ansell, R. J. et al. (1996) *Current Opinion in Biotechnology* 7:89-94 and in Shea, K. J. (1994) *Trends in Polymer Science* 2:166-173. Such "imprinted" affinity matrices are amenable to ligand-binding assays, whereby the immobilized monoclonal antibody component is replaced by an appropriately imprinted matrix. An example of the use of such matrices in this way can be seen in Vlatakis, G. et al. (1993) *Nature* 361:645-647. Through the use of isotope-labeling, the "free" concentration of compound which modulates the expression or activity of perforin can be readily monitored and used in calculations of $IC_{50}$. Such "imprinted" affinity matrices can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al. (1995) *Analytical Chemistry* 67:2142-2144.

The skilled artisan will appreciate that certain factors may influence the dosage and timing required to effectively treat a subject, including the activity of the specific compound employed, the age, body weight, general health, gender, and diet of the subject, the time of administration, the route of administration, the rate of excretion, any drug combination, the degree of expression or activity to be modulated, the severity of the disease or disorder, previous treatments and other diseases present.

The pharmaceutical compositions according to the present invention can be included in a container, pack, or dispenser together with instructions for administration.

Uses

It is another aspect of the present invention to provide a method of inhibiting activity of a perforin molecule, or a fragment or variant thereof, on a cell, said method comprising exposing the cell to a compound, or a pharmaceutically acceptable salt or a derivative thereof, as herein described. The cell may be a target cell (as herein described), or alternatively, it may be a CTL and/or NK cell that express perforin. The exposing of the cell to the compound, or a pharmaceutically acceptable salt or a derivative thereof (as herein described), may occur in vitro, ex vivo or in vivo.

Where the exposing of a cell to the compound occurs in vitro or ex vivo, for example, the method of the present invention may be used as a diagnostic tool to determine the efficacy of certain compounds (alone or in combination) for inhibiting perforin activity in a patient. For example, a CTL and/or NK cell that expresses perforin may be removed from a patient and exposed to one or more compounds of the present invention (or pharmaceutically acceptable salts or derivatives thereof) in the presence of a suitable target cell (as herein described). The target cell may, though need not be, from the same patient. In another example, a target cell may be removed from a patient and exposed to one or more compounds of the present invention (or pharmaceutically acceptable salts or derivatives thereof) in the presence of perforin. The ability of the compound (or compounds) to inhibit the activity of perforin can be assessed by measuring the degree of target cell lysis by any method known to one skilled in the art. Thus, one may be able to ascertain whether a certain compound is more efficacious than another and tailor a specific treatment regime to that patient.

In some embodiments, the exposing of the cell to the compound, or a pharmaceutically acceptable salt or a derivative thereof, as herein described is in vivo.

Accordingly, in one embodiment the present invention provides the use of a compound of the present invention, or a pharmaceutically acceptable salt, solvate, and hydrate thereof, for treating or preventing a disease or disorder associated with undesirable perforin activity.

In another embodiment, the present invention provides the use of a compound of the present invention, or a pharmaceutically acceptable salt, solvate, and hydrate thereof, in the manufacture of a medicament for treating or preventing a disease or disorder associated with undesirable perforin activity.

Methods of Treatment

In yet a further aspect of the present invention there is provided a prophylactic or therapeutic method of treating a subject at risk of or susceptible to a disease or disorder, or having a disease or disorder, associated with aberrant perforin expression and/or activity. Such disease or disorder will generally be associated with either an increase in levels of perforin molecules, an increase in perforin activity as compared to a healthy population, or a pathological attack of the subject's tissues or by CTL, NK cells or other lymphocytes that utilise the perforin pathway.

In one embodiment, the prophylactic or therapeutic method comprises the steps of administering a compound according to the present invention, or a pharmaceutically acceptable salt or a derivative thereof (as herein described), to a subject who has a disease or disorder, a symptom of disease or disorder, or predisposition toward a disease or disorder associated with undesired perforin activity as herein described, for the purpose to cure, heal alleviate, relieve, alter, remedy, ameliorate, improve, or affect the disease or disorder, the symptoms of the disease or disorder, or the predisposition towards the disease or disorder. Compounds of the present invention will be administered in a therapeutically effective amount.

As used herein, the term "effective amount" refers to an amount of compound which, when administered according to a desired dosing regimen, provides the desired therapeutic activity. Dosing may occur once, or at intervals of minutes or hours, or continuously over any one of these periods. Suitable dosages may lie within the range of about 0.1 ng per kg of body weight to 1 g per kg of body weight per dosage. A typical dosage is in the range of 1 μg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

The prophylactic or therapeutic methods of the present invention may also comprise the administering of a combination of the compounds according to the present invention, or pharmaceutically acceptable salts or derivatives thereof (as herein described), to a subject who has a disease or disorder, a symptom of disease or disorder, or predisposition toward a disease or disorder associated with undesired perforin activity as herein described, for the purpose to cure, heal alleviate, relieve, alter, remedy, ameliorate, improve, or affect the disease or disorder, the symptoms of the disease or disorder, or the predisposition towards the disease or disorder. It is envisaged that certain combinations of compounds of the present invention (or pharmaceutically acceptable salts or derivatives thereof) may provide enhanced inhibition of perforin activity in comparison to prophylactic or therapeutic methods that utilise only one of the compounds of the present invention (or pharmaceutically acceptable salts or derivatives thereof).

It would also be appreciated by one skilled in the art that the prophylactic or therapeutic methods as herein described could be used in any number of combinations with other treatment modalities currently employed in the art.

Conditions in which perforin expression and/or activity is increased, and where it is desirable to reduce said activity, may be identified by those skilled in the art by any or a combination of diagnostic or prognostic assays known in the art. For example, a biological sample obtained from a subject (e.g. blood, serum, plasma, urine, saliva, and/or cells derived therefrom) may be analysed for perforin expression and/or activity or the presence of CTL, NK cells or other lymphocytes capable of using perforin to induce tissue damage, as hereinbefore described. Such conditions include, but are not limited to, juvenile diabetes mellitus (type 1 or insulin dependent), graft-versus-host disease, chronic or acute allograft rejection, malaria and any other conditions associated with cytotoxic T lymphocyte- or natural killer cell-mediated immune pathology.

Thus, in one embodiment of the present invention, the prophylactic and therapeutic methods of treatment are applicable to the treatment and/or prevention of immune mediated conditions or inflammatory diseases and disorders such as, but not limited to, autoimmune or inflammatory diseases and disorders including juvenile diabetes mellitus (type 1 or insulin dependent), crohns disease, colitis and inflammatory bowel disease, fibrosis and fibrotic disorders, Guillain-Barre syndrome, lupus erythematosus, psoriasis, pancreatitis, rheumatoid arthritis, sepsis, vasculitis and Wegener's granulmatosis, as well as other conditions including but not limited to graft-versus-host disease, chronic or acute allograft rejection, infectious diseases, including mosquito-borne diseases of the *Plasmodium* genus, such as malaria, in particular cerebral malaria, and conditions associated with cytotoxic T lymphocyte- or natural killer cell-mediated immune pathology.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. The term also refers to the study of how a patient's genes determine his or her response to a drug (e.g., a patient's "drug response phenotype", or "drug response genotype"). Thus, another aspect of the present invention provides methods for tailoring an individual's prophylactic or therapeutic treatment with either the perforin molecules of the present invention or agents that modulate perforin expression and/or activity (such as those identified by screening assays as herein described), according to that individual's drug response genotype. Pharmacogenomics allows a clinician or physician to target prophylactic or therapeutic treatments to patients who will most benefit from the treatment and to avoid treatment of patients who will experience toxic drug-related side effects.

It is considered that the above methods are suitable for the prophylactic and therapeutic treatment of any species, including, but not limited to, all mammals including humans, cannines, felines, cattle, horses, rats and mice, as well as birds, reptiles and lower organisms such as bacteria.

For the above mentioned indications, the appropriate dosage will vary depending on, e.g. the compound employed, the age, sex, weight and general physical condition of the subject, the mode of administration, the nature and/or severity of the condition or the desired effect. By balancing these features it is well within the general skill of a medical practitioner to determine appropriate dosages.

To assist in modifying those cells that may be targeted for lysis by perforin, the compounds employed in the prophylactic or therapeutics methods of the present invention may be attached to an identifying moiety such as an antibody so that the moiety identifies and targets the compound to those cells which require the modification of perforin activity. In conjunction with the treatment of diseases or disorders associated with undesired perforin expression and/or activity, pharmacogenomics (i.e., the study of the relationship between an individual's genotype and that individual's response to a foreign compound or drug) may also be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent to modulate perforin expression and/or activity, as well as tailoring the dosage and/or therapeutic regimen of such treatment.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms.

One pharmacogenomic approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process; however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug's target is known (i.e., perforin), all common variants of that gene can be fairly easily identified in the population and it can be determined if having one version of the gene versus another is associated with a particular drug response.

Alternatively, a method termed the "gene expression profiling" can be utilized to identify genes that predict drug response. For example, the gene expression of an animal dosed with a drug (e.g., a compound according to the present invention) can give an indication whether gene pathways related to toxicity have been turned on.

Information generated from more than one of the above pharmacogenomic approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a therapeutic agent as hereinbefore described.

Monitoring the influence of agents (e.g., drugs) on the activity of perforin can be applied in clinical trials. For example, the effectiveness of a compound of the present invention to inhibit perforin activity or the lytic or pro-apoptotic activity of CTL or NK cells can be monitored in clinical trials of subjects exhibiting enhanced perforin, CTL or NK cell activity as compared to a healthy population. In such clinical trials, the activity of perforin, and possibly, other genes that have been implicated in, for example, conditions associated with undesired perforin expression and/or activity (i.e. surrogate markers) can be used as a "read out" or markers of the phenotype of a particular cell.

Examples of the procedures used in the present invention will now be more fully described. It should be understood, however, that the following description is illustrative only and should not be taken in any way as a restriction on the generality of the invention described above.

EXAMPLES

Methods for Preparing Compounds of Formula (I) of the Invention

The following examples are representative of the present invention, and provide detailed methods for preparing exemplary compounds of the present invention.

NMR spectra were obtained on a Bruker Avance-400 spectrometer at 400 MHz for $^{1}H$ and 100 MHz for $^{13}C$ spectra, referenced to $Me_4Si$. Low resolution mass spectra were obtained on a Thermo Finnigan Surveyor MSQ. High resolution mass spectra were recorded on a Varian VG 7070 spectrometer at nominal 5000 resolution. Analyses were performed by the Microchemical Laboratory, University of Otago, Dunedin, NZ. Melting points were determined using an Electrothermal Model 9200 or Gallenkamp digital melting point apparatus, and are as read. Column chromatography was carried out on silica gel, (Merck 230-400 mesh) unless otherwise stated.

The compounds of the present invention can be prepared via general procedures A to F as set out in Scheme 1 below.

Scheme 1

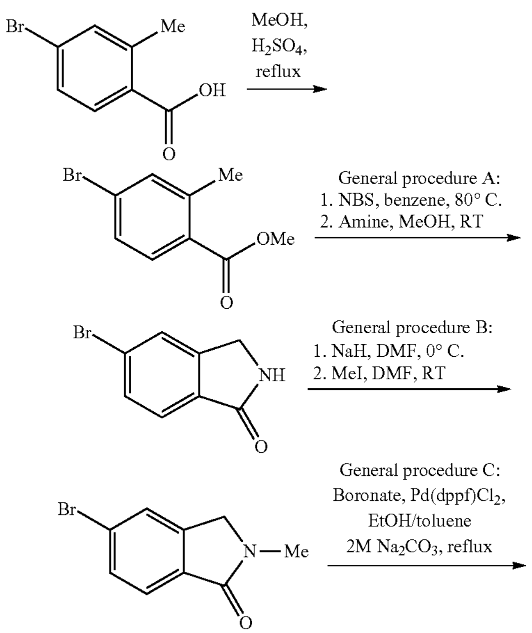

-continued

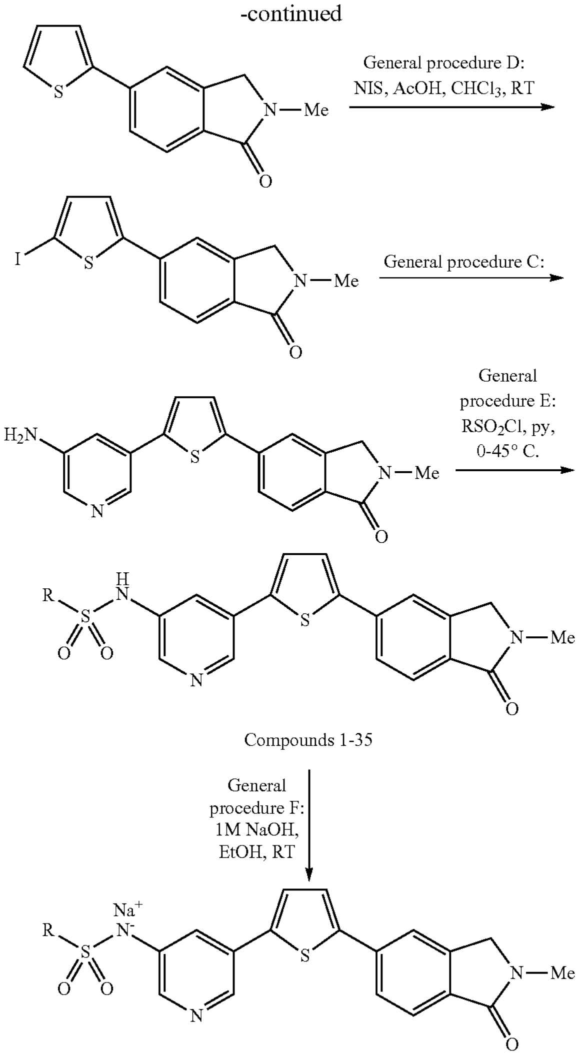

Example 1

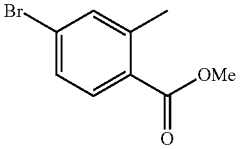

Methyl 4-bromo-2-methylbenzoate (Scheme 1)

4-Bromo-2-methylbenzoic acid (20.0 g, 93.1 mmol) was suspended in dry MeOH (200 mL), to which was added c.$H_2SO_4$ (1 mL). This mixture was heated at reflux for 72 h. Upon cooling, all solvent was removed under reduced pressure and the resulting oil dissolved in EtOAc (500 mL) then washed with sat. $NaHCO_3$ (3×100 mL), brine (100 mL) and dried ($Na_2SO_4$). The solution was filtered and the solvent removed under reduced pressure to afford the title compound as a pale yellow oil (19.92 g, 93%). $^{1}H$ NMR [400 MHz, $(CD_3)_2SO$] δ 7.77 (d, J=8.4 Hz, 1H), 7.40-7.42 (m, 1H), 7.35-7.39 (m, 1H), 3.88 (s, 3H), 2.57 (s, 3H).

Example 2

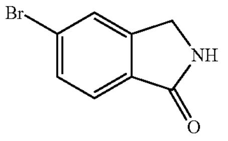 [SMILES: O=C1NCc2cc(Br)ccc21]

General Procedure A: 5-Bromoisoindolin-1-one (Scheme 1)

Methyl 4-bromo-2-methylbenzoate (19.90 g, 86.9 mmol) was dissolved in benzene (200 mL), to which was added N-bromosuccinimide (18.56 g, 100 mmol) and 2,2'-azobis (2-methylpropionitrile) (1.43 g, 8.69 mmol). This mixture was heated at 80° C. overnight then upon cooling, filtered and the filtrate diluted with $Et_2O$ (300 mL). This solution was washed with sat. sodium metabisulphite solution (which was also back-extracted with 2×50 mL $Et_2O$), then all $Et_2O$ fractions combined and washed with brine (150 mL), dried ($Na_2SO_4$) and filtered. The solvent was removed under reduced pressure to yield an oil which was purified by filtration through a plug of silica (5% EtOAc/hexanes as eluant), giving an oil which solidified to a white solid under vacuum. $^1H$ NMR shows this material to be 93% the desired bromide, along with 7% unreacted starting material and a trace of dibromide (total of 26.7 g). This solid was dissolved in MeOH (500 mL) and $NH_3$ (g) bubbled through the solution until saturated. This mixture was stirred overnight at room temperature then all solvent removed under reduced pressure. The resulting solid was suspended and stirred in $Et_2O$ (200 mL), then collected by filtration. This procedure was repeated, but using water and the solid again collected by filtration and dried under vacuum. The title compound was isolated as a crystalline cream solid (13.30 g, 72%). $^1H$ NMR [400 MHz, $(CD_3)_2SO$] δ 8.59 (br s, 1H), 7.83 (dd, J=1.5, 0.6 Hz, 1H), 7.66 (dd, J=8.0, 1.7 Hz, 1H), 7.59 (d, J=8.1 Hz, 1H), 4.37 (s, 2H). LRMS ($APCI^+$) calcd for $C_8H_6BrNO$ 212, 214 ($MH^+$). found 212, 214.

Example 3

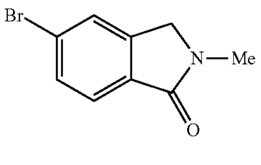 [SMILES: CN1Cc2cc(Br)ccc2C1=O]

General Procedure B: 5-Bromo-2-methylisoindolin-1-one (Scheme 1)

5-Bromoisoindolin-1-one (2.0 g, 9.43 mmol) was dissolved with warming in DMF (150 mL), then cooled to 0° C. NaH (415 mg, 10.4 mmol) was added and the mixture stirred under $N_2$ at 0° C. for 0.5 h. Methyl iodide (0.65 mL, 10.4 mmol) was added dropwise and the reaction allowed to warm to room temperature and stir for another 1 h. A small quantity of water was added to quench the reaction then the DMF removed under reduced pressure to give an oily yellow residue which was dissolved in EtOAc (150 mL). This solution was washed with water (3×100 mL), brine (100 mL) and dried ($Na_2SO_4$). Removal of the solvent under reduced pressure gave a solid which was purified by filtration through a plug of silica gel (10% acetone/$CH_2Cl_2$ as eluant). The title compound was isolated as a very pale yellow crystalline solid (1.64 g, 80%). $^1H$ NMR [400 MHz, $(CD_3)_2SO$] δ 7.85 (dd, J=1.5, 0.6 Hz, 1H), 7.66 (dd, J=8.0, 1.7 Hz, 1H), 7.59 (d, J=8.0 Hz, 1H), 4.46 (s, 2H), 3.05 (s, 3H). LRMS ($APCI^+$) calcd for $C_9H_8BrNO$ 226, 228 ($MH^+$). found 226, 228.

Example 4

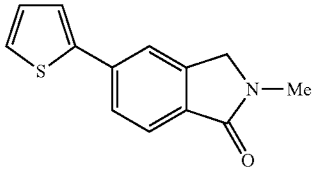 [SMILES: CN1Cc2cc(-c3cccs3)ccc2C1=O]

General Procedure C: 2-Methyl-5-(thiophen-2-yl) isoindolin-1-one (Scheme 1)

5-Bromo-2-methylisoindolin-1-one (520 mg, 2.30 mmol) and thiophene-2-boronic acid (442 mg, 3.45 mmol) were dissolved in a mixture of toluene (12 mL) and EtOH (6 mL). A solution of 2 M $Na_2CO_3$ (3 mL) and Pd(dppf)$Cl_2$ (94 mg, 0.12 mmol) were added and the entire mixture heated at reflux under $N_2$ for 2 h. Additional thiophene-2-boronic acid (294 mg, 2.30 mmol) was added and reflux continued under $N_2$ overnight. Upon cooling, the mixture was diluted with water (100 mL) and extracted with $CH_2Cl_2$ (6×50 mL). The combined organic fractions were dried ($Na_2SO_4$), filtered, and the solvent removed under reduced pressure to give a crude solid which was purified by flash column chromatography on silica gel (EtOAc as eluant). The title compound was isolated as a light-brown solid (510 mg, 97%). $^1H$ NMR [400 MHz, $(CD_3)_2SO$] δ 7.87 (s, 1H), 7.77 (dd, J=7.9, 1.6 Hz, 1H), 7.67 (dd, J=7.9, 0.3 Hz, 1H), 7.61-7.66 (m, 2H), 7.18 (dd, J=5.0, 1.4 Hz, 1H), 4.49 (s, 2H), 3.08 (s, 3H). LRMS ($APCI^+$) calcd for $C_{13}H_{12}NOS$ 230 ($MH^+$). found 230.

Example 5

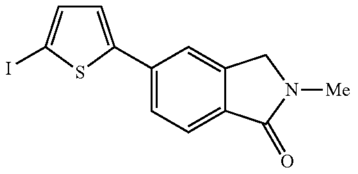 [SMILES: CN1Cc2cc(-c3ccc(I)s3)ccc2C1=O]

General Procedure D: 5-(5-Iodothiophen-2-yl)-2-methylisoindolin-1-one (Scheme 1)

2-Methyl-5-(thiophen-2-yl)isoindolin-1-one (510 mg, 2.22 mmol) was dissolved in a mixture of $CHCl_3$/AcOH (3:1, 16 mL) and N-iodosuccinimide (500 mg, 2.22 mmol) added. This mixture was stirred at room temperature for 2 h., then additional N-iodosuccinimide (500 mg, 2.22 mmol) added and stirring continued overnight. The reaction mixture was diluted with water (100 mL) and extracted with $CH_2Cl_2$ (3×50 mL). The combined $CH_2Cl_2$ fractions were washed with sat. $NaHCO_3$ (2×50 mL), 1 M $Na_2S_2O_5$ solution (50 mL), dried ($Na_2SO_4$) and filtered. The solvent was removed under reduced pressure to afford a solid which was triturated with $Et_2O$ and collected by filtration to give the title compound as a pale brown crystalline solid (693 mg, 88%). $^1H$ NMR [400 MHz, $(CD_3)_2SO$] δ 7.82 (br s, 1H), 7.71 (br d, J=8.0 Hz, 1H), 7.67 (d, J=8.0 Hz, 1H), 7.41 (d, J=3.8 Hz, 1H), 7.37 (d, J=3.8 Hz, 1H), 4.49 (s, 2H), 3.07 (s, 3H). LRMS ($APCI^+$) calcd for $C_{13}H_{11}INOS$ 356 ($MH^+$). found 356.

Example 6

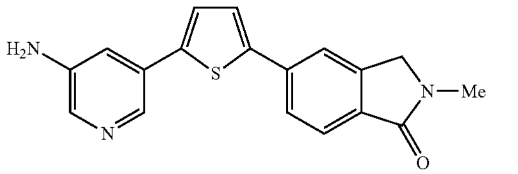 [SMILES: CN1Cc2cc(-c3ccc(-c4cncc(N)c4)s3)ccc2C1=O]

5-(5-(5-Aminopyridin-3-yl)thiophen-2-yl)-2-methylisoindolin-1-one 5-(5-Iodothiophen-2-yl)-2-methylisoindolin-1-one was reacted with 5-(4,4,5,5-tetramethyl-1,3,2-dioxaborolan-2-yl)pyridin-3-amine (1.2 equivalents) according to general procedure C. The desired product was collected by filtration from the cooled reaction mixture and washed with $H_2O$, MeOH and $CH_2Cl_2$. No further purification was required and the title compound was isolated as a green solid (84%), mp ($MeOH/CH_2Cl_2$) 244-248° C. $^1H$ NMR [400 MHz, $(CD_3)_2SO$] δ 8.12 (d, J=2.0 Hz, 1H), 7.92 (s, 1H), 7.90 (d, J=2.5 Hz, 1H), 7.80 (dd, J=8.0, 1.3 Hz, 1H), 7.70 (d, J=4.3 Hz, 1H), 7.68 (s, 1H), 7.54 (d, J=3.8 Hz, 1H), 7.16 (t, J=2.2 Hz, 1H), 5.51 (br s, 2H), 4.51 (s, 2H), 3.09 (s, 3H). Anal. ($C_{16}H_{10}N_2O_3S_2.0.25H_2O$) C, H, N.

Example 7

(1)

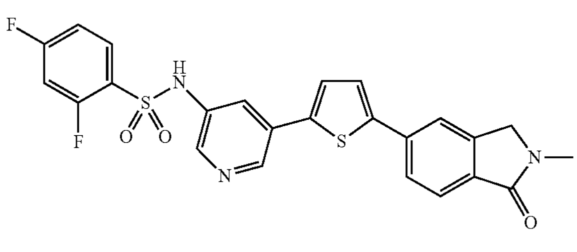

General Procedure E: 2,4-Difluoro-N-(5-(5-(2-methyl-1-oxoisoindolin-5-yl)thiophen-2-yl)pyridin-3-yl)benzenesulfonamide (1) (Scheme 1)

To 5-(5-(5-Aminopyridin-3-yl)thiophen-2-yl)-2-methylisoindolin-1-one (225 mg, 0.79 mmol) in dry pyridine (23 mL) under $N_2$ at RT, was added dropwise, 2,4-difluorobenzenesulphonyl chloride (336 mg, 1.58 mmol) in $CH_2Cl_2$ (3 mL) over 5 min. The suspension was heated to 45° C. under $N_2$ for 4 h., at which point another portion of 2,4-difluorobenzenesulphonyl chloride (169 mg, 0.79 mmol) in $CH_2Cl_2$ (2 mL) was added. The whole mixture was left to stir for at 45° C. under $N_2$ for 16 h., then the solvent removed under reduced pressure. The resulting residue was suspended in acetone (10 mL), 1 M HCl (20 mL) added, and the entire mixture stirred for 10 minutes. The solid was then collected by filtration, washed well with 1 M HCl and water, dried, and purified by chromatography as described below.

In cases where the bis-sulphonamide was also formed, a second step was introduced where the crude product above was treated with a 1:1 mixture of 1,4-dioxane and 2 M NaOH. The crude sulphomamide resulting from subsequent acidification of the reaction mixture was isolated by filtration, washed well with water, and dried. Purification was carried out by flash column chromatography (2% MeOH/$CH_2Cl_2$ as eluant), giving the title compound (1) as a pale yellow solid (211 mg, 54%), mp ($MeOH/CH_2Cl_2$) 266-269° C. $^1H$ NMR [400 MHz, $(CD_3)_2SO$] δ 11.15 (br s, 1H), 8.69 (d, J=2.0 Hz, 1H), 8.25 (d, J=2.4 Hz, 1H), 8.01 (dt, J=8.7, 6.3 Hz, 1H), 7.95 (s, 1H), 7.83 (dd, J=8.0, 1.5 Hz, 1H), 7.68-7.75 (m, 3H), 7.65 (d, J=3.9 Hz, 1H), 7.58 (dt, J=8.9, 2.4 Hz, 1H), 7.30 (dt, J=8.2, 2.0 Hz, 1H), 4.52 (s, 2H), 3.09 (s, 3H). Anal. ($C_{24}H_{17}F_2N_3O_3S_2$) C, H, N.

Example 8

(1)

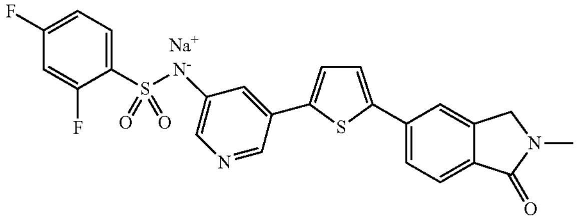

(sodium salt)

General Procedure F: 2,4-Difluoro-N-(5-(5-(2-methyl-1-oxoisoindolin-5-yl)thiophen-2-yl)pyridin-3-yl)benzenesulfonamide, sodium salt (1.Na) (Scheme 1)

2,4-Difluoro-N-(5-(5-(2-methyl-1-oxoisoindolin-5-yl)thiophen-2-yl)pyridin-3-yl)benzenesulfonamide (1) (940 mg, 1.89 mmol) was suspended in EtOH (100 mL), then an aqueous solution of 1 M NaOH (1.89 mL) added. After stirring for 2 h. at room temperature, the solution was filtered through a pad of celite to remove minor insoluble impurities, washing well with EtOH. The resulting combined filtrates were combined and concentrated to ca 20 mL, then diluted with an equal volume of $Et_2O$ which resulted in crystallization of the title compound (1.Na) as a pale yellow solid (919 mg, 94%). $^1H$ NMR [400 MHz, $(CD_3)_2SO$] δ 8.07 (d, J=2.1 Hz, 1H), 7.91 (m, 2H), 7.78-7.88 (m, 2H), 7.68 (d, J=7.9 Hz, 1H), 7.65 (d, J=3.8 Hz, 1H), 7.40-7.43 (m, 2H), 7.18 (ddd, J=9.7, 2.5 Hz, 1H), 7.04-7.11 (m, 1H), 4.51 (s, 2H), 3.08 (s, 3H). Anal. ($C_{24}H_{16}F_2N_3NaO_3S_2.H_2O$) C, H, N.

Example 9

(2)

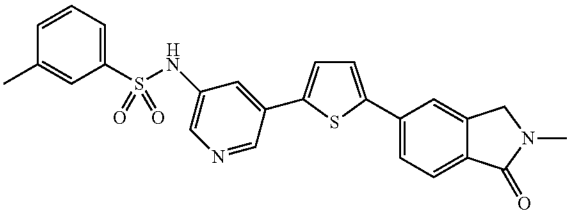

3-Methyl-N-(5-(5-(2-methyl-1-oxoisoindolin-5-yl)thiophen-2-yl)pyridin-3-yl)benzenesulfonamide (2)

5-(5-(5-Aminopyridin-3-yl)thiophen-2-yl)-2-methylisoindolin-1-one was reacted with 3-toluenesulfonyl chloride according to general procedure E, and the resulting crude product purified by flash column chromatography (1-5% $MeOH/CH_2Cl_2$ as eluant) to give the title compound (2) as a yellow solid (23%), mp ($MeOH/CH_2Cl_2$) 281-284° C. $^1H$ NMR [400 MHz, $(CD_3)_2SO$] δ 10.74 (bs, 1H), 8.66 (d, J=2.0 Hz, 1H), 8.21 (d, J=2.4 Hz, 1H), 7.94 (d, J=0.7 Hz, 1H), 7.83 (dd, J=8.0, 1.5 Hz, 1H), 7.60-7.74 (m, 6H), 7.44-7.49 (m, 2H), 4.52 (s, 2H), 3.09 (s, 3H), 2.36 (s, 3H). LRMS ($APCI^-$) calcd for $C_{21}H_{20}N_3O_3S_2$ 475 (M-H). found 475. Anal. ($C_{25}H_{21}N_3O_3S_2$) C, H, N.

Example 10

(3)

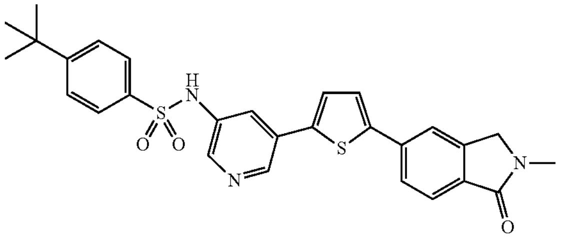

4-(tert-Butyl)-N-(5-(5-(2-methyl-1-oxoisoindolin-5-yl)thiophen-2-yl)pyridin-3-yl)benzenesulfonamide (3)

5-(5-(5-Aminopyridin-3-yl)thiophen-2-yl)-2-methylisoindolin-1-one was reacted with 4-tert-butylbenzenesulfonyl chloride according to general procedure E, and the resulting crude product purified by flash column chromatography (1-8% $MeOH/CH_2Cl_2$ as eluant) to give the title compound (3) as a yellow solid (31%), mp ($MeOH/CH_2Cl_2$) 285-288° C. $^1H$ NMR [400 MHz, $(CD_3)_2SO$] δ 10.73 (bs, 1H), 8.66 (d, J=2.0 Hz, 1H), 8.23 (d, J=2.3 Hz, 1H), 7.93 (d, J=0.7 Hz, 1H), 7.83 (dd, J=7.9, 1.5 Hz, 1H), 7.76 (d, J=8.6 Hz, 2H), 7.68-7.73 (m, 3H), 7.63 (d, J=3.9 Hz, 1H), 7.62 (d, J=8.6 Hz, 2H), 4.52 (s, 2H), 3.09 (s, 3H), 1.25 (s, 9H). LRMS ($APCI^-$) calcd for $C_{28}H_{26}N_3O_3S_2$ 517 (M-H). found 517. Anal. ($C_{28}H_{27}N_3O_3S_2.0.10H_2O$) C, H, N.

Example 11

(4)

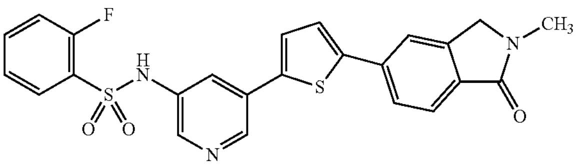

2-Fluoro-N-(5-(5-(2-methyl-1-oxoisoindolin-5-yl)thiophen-2-yl)pyridin-3-yl)benzene-sulfonamide (4)

5-(5-(5-Aminopyridin-3-yl)thiophen-2-yl)-2-methylisoindolin-1-one was reacted with 2-fluorobenzenesulphonyl chloride according to general procedure E to give the title compound (4) as a beige solid (82%); mp ($CH_2Cl_2$/MeOH) 289-292° C. $^1H$ MR [400 MHz, $(CD_3)_2SO$] δ 11.11 (br s, 1H), 8.67 (d, J=2.0 Hz, 1H), 8.25 (d, J=2.4 Hz, 1H), 7.95 (dt, J=7.4, 1.7 Hz, 2H), 7.83 (dd, J=8.0, 1.5 Hz, 1H), 7.68-7.76 (m, 4H), 7.63 (d, J=3.8 Hz, 1H), 7.38-7.49 (m, 2H), 4.52 (s, 2H), 3.09 (s, 3H). LRMS ($APCI^-$) calcd for $C_{24}H_{18}N_3O_3FS_2$ 479 (M-H). found 479. Anal. ($C_{24}H_{18}FN_3O_3S_2$) C, H, N.

Example 12

(5)

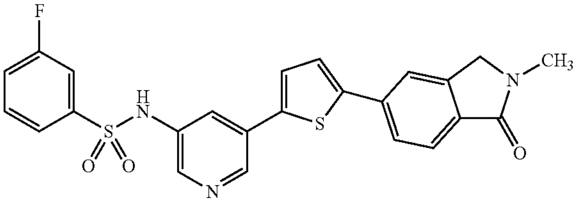

3-Fluoro-N-(5-(5-(2-methyl-1-oxoisoindolin-5-yl)thiophen-2-yl)pyridin-3-yl)benzene-sulfonamide (5)

5-(5-(5-Aminopyridin-3-yl)thiophen-2-yl)-2-methylisoindolin-1-one was reacted with 3-fluorobenzenesulphonyl chloride according to general procedure E to give the title compound (5) as a beige solid (56%); mp ($CH_2Cl_2$/MeOH) 292-294° C. $^1H$ NMR [400 MHz, $(CD_3)_2SO$] δ 10.88 (br s, 1H), 8.70 (d, J=2.0 Hz, 1H), 8.22 (d, J=2.3 Hz, 1H), 7.94 (s, 1H), 7.83 (dd, J=7.9, 1.5 Hz, 1H), 7.69-7.75 (m, 3H), 7.61-7.68 (m, 4H), 7.50-7.58 (m, 1H), 4.52 (s, 2H), 3.09 (s, 3H). Anal. ($C_{24}H_{18}FN_3O_3S_2$) C, H, N.

Example 13

(6)

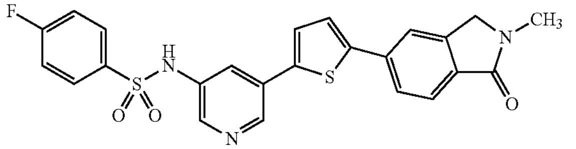

4-Fluoro-N-(5-(5-(2-methyl-1-oxoisoindolin-5-yl)thiophen-2-yl)pyridin-3-yl)benzene-sulfonamide (6)

5-(5-(5-Aminopyridin-3-yl)thiophen-2-yl)-2-methyl-isoindolin-1-one was reacted with 4-fluorobenzenesulphonyl chloride according to general procedure E, and the title compound (6) isolated as a yellow solid (86%); mp ($CH_2Cl_2$/MeOH) 272-274° C. $^1$H NMR [400 MHz, $(CD_3)_2SO$] δ 10.79 (br s, 1H), 8.69 (d, J=2.0 Hz, 1H), 8.21 (d, J=2.3 Hz, 1H), 7.94 (s, 1H), 7.85-7.92 (m, 2H), 7.83 (dd, J=7.9, 1.5 Hz, 1H), 7.68-7.75 (m, 3H), 7.66 (d, J=3.9 Hz, 1H), 7.40-7.48 (m, 2H), 4.52 (s, 2H), 3.09 (s, 3H).

In this case the product was converted to its sodium salt according to general procedure F to give the desired product as a yellow solid (90%). $^1$H NMR [400 MHz, $(CD_3)_2SO$] δ 8.03 (d, J=2.1 Hz, 1H), 7.90 (s, 1H), 7.88 (d, J=2.5 Hz, 1H), 7.73-7.84 (m, 3H), 7.68 (d, J=7.9 Hz, 1H), 7.64 (d, J=3.8 Hz, 1H), 7.37-7.42 (m, 2H), 7.15-7.23 (m, 2H), 4.51 (s, 2H) 3.08 (s, 3H). Anal. ($C_{24}H_{17}FN_3NaO_3S_2.3H_2O$) C, H, N.

Example 14

(7)

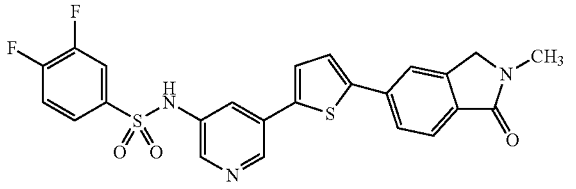

3,4-Difluoro-N-(5-(5-(2-methyl-1-oxoisoindolin-5-yl)thiophen-2-yl)pyridin-3-yl)benzene-sulfonamide (7)

5-(5-(5-Aminopyridin-3-yl)thiophen-2-yl)-2-methyl-isoindolin-1-one was reacted with 3,4-difluorobenzenesulphonyl chloride according to general procedure E to give the title compound (7) as a yellow solid (18%); mp ($CH_2Cl_2$/MeOH) 282-285° C. $^1$H NMR [400 MHz, $(CD_3)_2SO$] δ 10.88 (br s, 1H), 8.72 (d, J=1.4 Hz, 1H), 8.23 (d, J=2.3 Hz, 1H), 7.95 (s, 1H), 7.90 (d, J=8.3 Hz, 1H), 7.83 (d, J=8.0 Hz, 1H), 7.66-7.76 (m, 6H), 4.52 (s, 2H), 3.09 (s, 3H). Anal. ($C_{24}H_{17}F_2N_3O_3S_2$) C, H, N.

Example 15

(8)

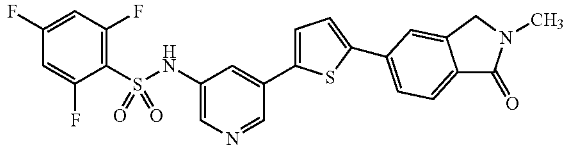

2,4,6-Trifluoro-N-(5-(5-(2-methyl-1-oxoisoindolin-5-yl)thiophen-2-yl)pyridin-3-yl)benzene-sulfonamide (8)

5-(5-(5-Aminopyridin-3-yl)thiophen-2-yl)-2-methyl-isoindolin-1-one was reacted with 2,4,6-trifluorobenzenesulphonyl chloride according to general procedure E to give the title compound (8) as a beige solid (16%); mp ($CH_2Cl_2$/MeOH) 272-275° C. $^1$H NMR [400 MHz, $(CD_3)_2SO$] δ 11.43 (br s, 1H), 8.28 (d, J=2.3 Hz, 1H), 7.95 (s, 1H), 7.83 (dd, J=7.9, 1.5 Hz, 1H), 7.79 (t, J=2.2 Hz, 1H), 7.73 (d, J=3.9 Hz, 1H), 7.71 (d, J=7.9 Hz, 1H), 7.65 (d, J=3.9 Hz, 1H), 7.47 (br t, J=9.4 Hz, 2H), 4.52 (s, 2H), 3.09 (s, 3H). Anal. ($C_{24}H_{16}F_3N_3O_3S_2$) C, H, N.

Example 16

(9)

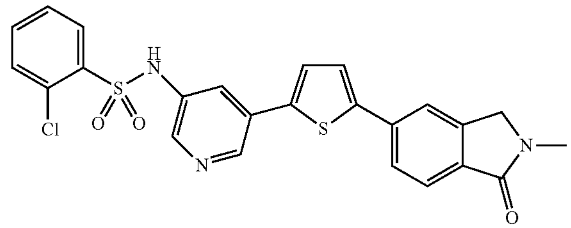

2-Chloro-N-(5-(5-(2-methyl-1-oxoisoindolin-5-yl)thiophen-2-yl)pyridin-3-yl)benzenesulfonamide (9)

5-(5-(5-Aminopyridin-3-yl)thiophen-2-yl)-2-methyl-isoindolin-1-one was reacted with 2-chlorobenzenesulfonyl chloride according to general procedure E, and the resulting crude product purified by flash column chromatography (1-8% MeOH/$CH_2Cl_2$ as eluant) to give the title compound (9) as a yellow solid (29%), mp (MeOH/$CH_2Cl_2$) 299-303° C. $^1$H NMR [400 MHz, $(CD_3)_2SO$] δ 11.14 (bs, 1H), 8.64 (d, J=1.9 Hz, 1H), 8.26 (d, J=2.3 Hz, 1H), 8.17 (dd, J=7.3, 1.2 Hz, 1H), 7.94 (s, 1H), 7.83 (dd, J=7.9, 1.5 Hz, 1H), 7.55-7.73 (m, 7H), 4.52 (s, 2H), 3.09 (s, 3H). LRMS ($APCI^-$) calcd for $C_{24}H_{17}ClN_3O_3S_2$ 495 (M-H). found 495. Anal. ($C_{24}H_{18}ClN_3O_3S_2.0.1CH_2Cl_2$) C, H, N.

Example 17

(10)

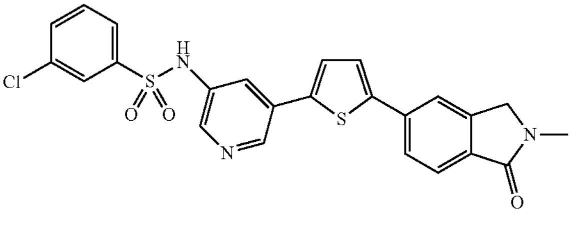

3-Chloro-N-(5-(5-(2-methyl-1-oxoisoindolin-5-yl)thiophen-2-yl)pyridin-3-yl)benzenesulfonamide (10)

5-(5-(5-Aminopyridin-3-yl)thiophen-2-yl)-2-methyl-isoindolin-1-one was reacted with 3-chlorobenzenesulfonyl chloride according to general procedure E, and the resulting crude product purified by flash column chromatography (1-5% MeOH/$CH_2Cl_2$ as eluant) to give the title compound (10) as an orange solid (49%), mp (MeOH/$CH_2Cl_2$) 291-295° C. $^1$H NMR [400 MHz, $(CD_3)_2SO$] δ 10.88 (bs, 1H), 8.71 (d, J=2.0 Hz, 1H), 8.22 (d, J=2.4 Hz, 1H), 7.95 (d, J=0.7 Hz, 1H), 7.81-7.86 (m, 2H), 7.69-7.79 (m, 5H), 7.67 (d, J=3.9 Hz, 1H), 7.63 (t, J=7.9 Hz, 1H), 4.52 (s, 2H), 3.09 (s, 3H). LRMS ($APCI^-$) calcd for $C_{24}H_{17}ClN_3O_3S_2$ 495 (M-H). found 495. Anal. ($C_{24}H_{18}ClN_3O_3S_2.0.2H_2O$) C, H, N.

(11)

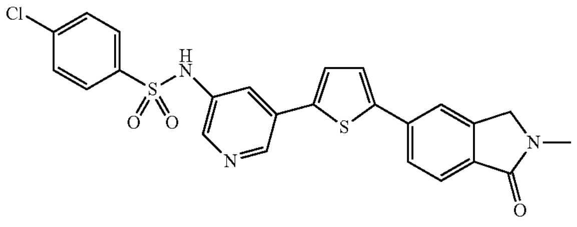

Example 18

4-Chloro-N-(5-(5-(2-methyl-1-oxoisoindolin-5-yl)thiophen-2-yl)pyridin-3-yl)benzenesulfonamide (11)

5-(5-(5-Aminopyridin-3-yl)thiophen-2-yl)-2-methyl-isoindolin-1-one was reacted with 4-chlorobenzenesulfonyl chloride according to general procedure E, and the resulting crude product purified by flash column chromatography (1-5% $MeOH/CH_2Cl_2$ as eluant) to give the title compound (11) as a yellow solid (59%), mp (($MeOH/CH_2Cl_2$) 281-284° C. $^1$H NMR [400 MHz, $(CD_3)_2SO$] δ 10.84 (bs, 1H), 8.70 (d, J=2.0 Hz, 1H), 8.21 (d, J=2.3 Hz, 1H), 7.94 (s, 1H), 7.79-7.85 (m, 3H), 7.65-7.74 (m, 6H), 4.52 (s, 2H), 3.09 (s, 3H). LRMS ($APCI^-$) calcd for $C_{24}H_{17}ClN_3O_3S_2$ 495 (M-H). found 495. Anal. ($C_{24}H_{18}ClN_3O_3S_2$) C, H, N.

In this case the product was converted to its sodium salt according to general procedure F to give the desired product as a yellow solid (77%), mp (EtOH) 240-244° C. $^1$H NMR [400 MHz, $(CD_3)_2SO$] δ 8.04 (d, J=2.1 Hz, 1H), 7.91 (d, J=0.8 Hz, 1H), 7.89 (d, J=2.4 Hz, 1H), 7.80 (dd, J=7.9, 1.5 Hz, 1H), 7.73 (d, J=8.6 Hz, 2H), 7.68 (d, J=7.8 Hz, 1H), 7.64 (d, J=3.8 Hz, 1H), 7.43 (d, J=8.6 Hz, 2H), 7.41 (d, J=3.8 Hz, 1H), 7.39 (t, J=2.3 Hz, 1H), 4.51 (s, 2H), 3.08 (s, 3H). Anal. ($C_{24}H_{17}ClN_3O_3S_2Na.2H_2O$) C, H, N.

Example 19

(12)

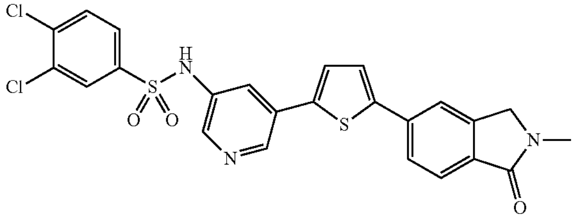

3,4-Dichloro-N-(5-(5-(2-methyl-1-oxoisoindolin-5-yl)thiophen-2-yl)pyridin-3-yl)benzenesulfonamide (12)

5-(5-(5-Aminopyridin-3-yl)thiophen-2-yl)-2-methyl-isoindolin-1-one was reacted with 3,4-dichlorobenzenesulfonyl chloride according to general procedure E, and the resulting crude product purified by flash column chromatography (1-5% $MeOH/CH_2Cl_2$ as eluant) to give the title compound (12) as an orange-brown solid (15%), mp ($MeOH/CH_2Cl_2$) 256-259° C. $^1$H NMR [400 MHz, $(CD_3)_2SO$] δ 10.92 (bs, 1H), 8.72 (d, J=2.0 Hz, 1H), 8.23 (d, J=2.4 Hz, 1H), 8.03 (d, J=2.2 Hz, 1H), 7.94 (s, 1H), 7.89 (d, J=8.5 Hz, 1H), 7.83 (dd, J=8.0, 1.6 Hz, 1H), 7.70-7.77 (m, 4H), 7.69 (d, J=3.9 Hz, 1H), 4.52 (s, 2H), 3.09 (s, 3H). HRMS (ESI) calcd for $C_{24}H_{16}Cl_2N_3O_3S_2$ 528.0016 (M-H). found 528.0048.

Example 20

(13)

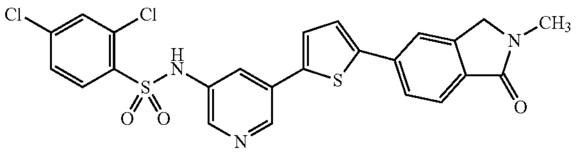

2,4-Dichloro-N-(5-(5-(2-methyl-1-oxoisoindolin-5-yl)thiophen-2-yl)pyridin-3-yl)benzene-sulfonamide (13)

5-(5-(5-Aminopyridin-3-yl)thiophen-2-yl)-2-methyl-isoindolin-1-one was reacted with 2,4-dichlorobenzenesulphonyl chloride according to general procedure E to give the title compound (13) as a yellow solid (55%); mp ($CH_2Cl_2$/MeOH) 282-285° C. $^1$H NMR [400 MHz, $(CD_3)_2SO$] δ 11.2 (br s, 1H), 8.67 (d, J=2.0 Hz, 1H), 8.26 (d, J=2.4 Hz, 1H), 8.14 (d, J=8.6 Hz, 1H), 7.96 (s, 1H), 7.91 (d, J=2.0 Hz, 1H), 7.83 (dd, J=8.0, 1.5 Hz, 1H), 7.65-7.74 (m, 4H), 7.64 (d, J=3.9 Hz, 1H), 4.52 (s, 2H), 3.09 (s, 3H).

In this case the product was converted to its sodium salt according to general procedure F to give the desired product as a beige solid (89%). $^1$H NMR [400 MHz, $(CD_3)_2SO$] δ 8.08 (d, J=2.1 Hz, 1H), 8.01 (d, J=8.4 Hz, 1H), 7.88-7.92 (m, 2H), 7.80 (dd, J=7.9, 1.5 Hz, 1H), 7.68 (d, J=8.0, 1H), 7.64 (d, J=3.8, 1H), 7.54 (d, J=2.1, 1H), 7.46 (dd, J=8.4, 2.2 Hz, 1H), 7.41 (d, J=3.8 Hz, 1H), 7.37 (t, J=2.3 Hz, 1H), 4.51 (s, 2H), 3.08 (s, 3H). Anal. ($C_{24}H_{16}Cl_2N_3NaO_3S_2.0.9CH_2Cl_2$) C, H, N.

Example 21

(14)

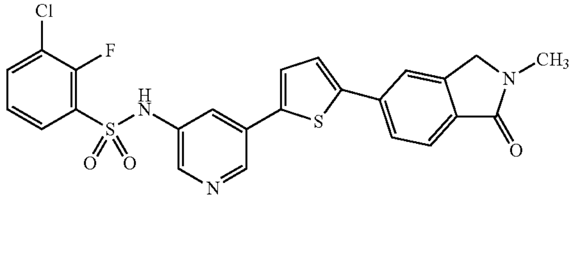

3-Chloro-2-fluoro-N-(5-(5-(2-methyl-1-oxoisoindolin-5-yl)thiophen-2-yl)pyridin-3-yl)benzenesulfonamide (14)

5-(5-(5-Aminopyridin-3-yl)thiophen-2-yl)-2-methylisoindolin-1-one was reacted with 3-chloro-2-fluorobenzenesulphonyl chloride according to general procedure E, to give the title compound (14) as a pale yellow solid (63%); mp ($CH_2Cl_2$/MeOH) 269-272° C. $^1$H NMR [400 MHz, $(CD_3)_2SO$] δ 11.30 (br s, 1H), 8.71 (d, J=1.9 Hz, 1H), 8.27 (d, J=2.3 Hz, 1H), 7.87-7.98 (m, 3H), 7.83 (dd, J=7.9, 1.2 Hz, 1H), 7.68-7.76 (m, 3H), 7.66 (d, J=3.9 Hz, 1H), 7.45 (t, J=8.0 Hz, 1H), 4.52 (s, 2H), 3.09 (s, 3H). Anal. ($C_{24}H_{17}ClN_3O_3S_2$.0.1$H_2O$) C, H, N.

Example 22

(15)

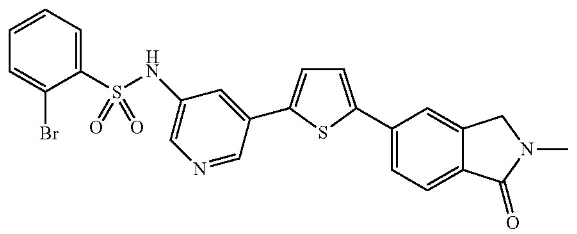

2-Bromo-N-(5-(5-(2-methyl-1-oxoisoindolin-5-yl)thiophen-2-yl)pyridin-3-yl)benzenesulfonamide (15)

5-(5-(5-Aminopyridin-3-yl)thiophen-2-yl)-2-methylisoindolin-1-one was reacted with 2-bromobenzenesulfonyl chloride according to general procedure E, and the resulting crude product purified by flash column chromatography (1-6% MeOH/$CH_2Cl_2$ as eluant) to give the title compound (15) as an orange solid (30%), mp (MeOH/$CH_2Cl_2$) 289-293° C. $^1$H NMR [400 MHz, $(CD_3)_2SO$] δ 11.15 (bs, 1H), 8.63 (s, 1H), 8.26 (d, J=2.3 Hz, 1H), 8.20 (dd, J=7.9, 1.7 Hz, 1H), 7.94 (s, 1H), 7.80-7.88 (m, 2H), 7.68-7.74 (m, 2H), 7.67 (t, J=2.2 Hz, 1H), 7.59-7.65 (m, 2H), 7.54 (dt, J=7.6, 1.7 Hz, 1H), 4.52 (s, 2H), 3.09 (s, 3H). LRMS (APCI$^-$) calcd for $C_{24}H_{17}BrN_3O_3S_2$ 539 (M-H). found 539. Anal. ($C_{24}H_{18}BrN_3O_3S_2$.0.3$CH_2Cl_2$) C, H, N.

Example 23

(16)

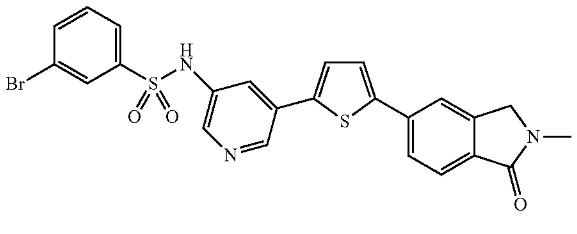

3-Bromo-N-(5-(5-(2-methyl-1-oxoisoindolin-5-yl)thiophen-2-yl)pyridin-3-yl)benzenesulfonamide (16)

5-(5-(5-Aminopyridin-3-yl)thiophen-2-yl)-2-methylisoindolin-1-one was reacted with 3-bromobenzenesulfonyl chloride according to general procedure E, and the resulting crude product purified by flash column chromatography (1-4% MeOH/$CH_2Cl_2$ as eluant) to give the title compound (16) as a yellow-orange solid (30%), mp (MeOH/$CH_2Cl_2$) 303-307° C. $^1$H NMR [400 MHz, $(CD_3)_2SO$] δ 10.87 (bs, 1H), 8.71 (d, J=1.9 Hz, 1H), 8.21 (d, J=2.3 Hz, 1H), 7.98 (t, J=1.8 Hz, 1H), 7.95 (d, J=0.7 Hz, 1H), 7.78-7.90 (m, 3H), 7.69-7.75 (m, 3H), 7.67 (d, J=3.9 Hz, 1H), 7.56 (t, J=8.0 Hz, 1H), 4.52 (s, 2H), 3.09 (s, 3H). HRMS (ESI$^+$) calcd for $C_{24}H_{18}BrN_3O_3S_2Na$, 561.9865 (M+Na$^+$). found 561.9862. Anal. ($C_{24}H_{18}BrN_3O_3S_2$) C, H, N.

Example 24

(17)

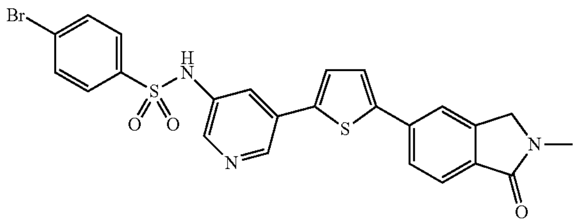

4-Bromo-N-(5-(5-(2-methyl-1-oxoisoindolin-5-yl)thiophen-2-yl)pyridin-3-yl)benzenesulfonamide (17)

5-(5-(5-Aminopyridin-3-yl)thiophen-2-yl)-2-methylisoindolin-1-one was reacted with 4-bromobenzenesulfonyl chloride according to general procedure E, and the resulting crude product purified by flash column chromatography (1-6% MeOH/$CH_2C_2$ as eluant) to give the title compound (17) as a yellow solid (60%), mp (MeOH/$CH_2Cl_2$) 276-279° C. $^1$H NMR [400 MHz, $(CD_3)_2SO$] δ 10.84 (bs, 1H), 8.69 (d, J=2.0 Hz, 1H), 8.21 (d, J=2.4 Hz, 1H), 7.94 (d, J=0.8 Hz, 1H), 7.80-7.86 (m, 3H), 7.69-7.76 (m, 5H), 7.66 (d, J=3.9 Hz, 1H), 4.52 (s, 2H), 3.09 (s, 3H). LRMS (APCI$^-$) calcd for $C_{24}H_{17}BrN_3O_3S_2$ 539 (M-H). found 539. Anal. ($C_{24}H_{18}BrN_3O_3S_2$.0.1$C_3H_6O$) C, H, N.

Example 25

(18)

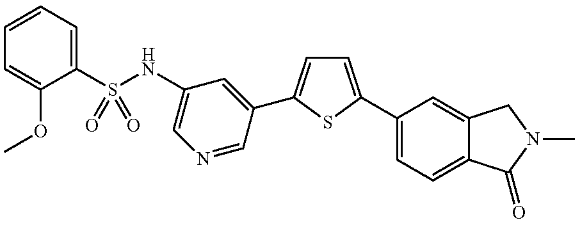

2-Methoxy-N-(5-(5-(2-methyl-1-oxoisoindolin-5-yl)thiophen-2-yl)pyridin-3-yl)benzenesulfonamide (18)

5-(5-(5-Aminopyridin-3-yl)thiophen-2-yl)-2-methylisoindolin-1-one was reacted with 2-methoxybenzenesulfonyl chloride according to general procedure E, and the resulting crude product purified by flash column chromatography (1-5% $MeOH/CH_2Cl_2$ as eluant) to give the title compound (18) as a yellow solid (26%), mp ($MeOH/CH_2Cl_2$) 273-276° C. $^1H$ NMR [400 MHz, $(CD_3)_2SO$] δ 10.49 (bs, 1H), 8.61 (d, J=2.0 Hz, 1H), 8.24 (d, J=2.4 Hz, 1H), 7.94 (s, 1H), 7.86 (dd, J=7.9, 1.7 Hz, 1H), 7.82 (dd, J=8.0, 1.6 Hz, 1H), 7.67-7.73 (m, 3H), 7.56-7.62 (m, 2H), 7.19 (d, J=7.9 Hz, 1H), 7.08 (dd, J=7.6, 0.7 Hz, 1H), 4.52 (s, 2H), 3.88 (s, 3H), 3.09 (s, 3H). LRMS ($APCI^-$) calcd for $C_{25}H_{20}N_3O_4S_2$ 491 (M-H). found 491. Anal. ($C_{25}H_{21}N_3O_4S_2$) C, H, N.

Example 26

(19)

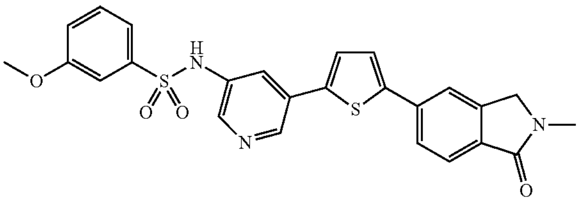

3-Methoxy-N-(5-(5-(2-methyl-1-oxoisoindolin-5-yl)thiophen-2-yl)pyridin-3-yl)benzenesulfonamide (19)

5-(5-(5-Aminopyridin-3-yl)thiophen-2-yl)-2-methylisoindolin-1-one was reacted with 3-methoxybenzenesulfonyl chloride according to general procedure E, and the resulting crude product purified by flash column chromatography (1-4% $MeOH/CH_2Cl_2$ as eluant) to give the title compound (19) as a pale yellow solid (33%), mp ($MeOH/CH_2Cl_2$) 278-280° C. $^1H$ NMR [400 MHz, $(CD_3)_2SO$] δ 10.76 (bs, 1H), 8.67 (d, J=2.0 Hz, 1H), 8.21 (d, J=2.3 Hz, 1H), 7.94 (d, J=0.7 Hz, 1H), 7.83 (dd, J=8.0, 1.5 Hz, 1H), 7.68-7.75 (m, 3H), 7.65 (d, J=3.9 Hz, 1H), 7.51 (t, J=8.0 Hz, 1H), 7.36-7.41 (m, 1H), 7.32 (t, J=2.1 Hz, 1H), 7.21 (ddd, J=8.3, 2.6, 0.8 Hz, 1H), 4.52 (s, 2H), 3.79 (s, 3H), 3.09 (s, 3H). HRMS ($ESI^+$) calcd for $C_{25}H_{22}N_3O_4S_2$ 492.1046 ($MH^+$). found 492.1033. Anal. ($C_{25}H_{21}N_3O_4S_2$) C, H, N.

Example 27

(20)

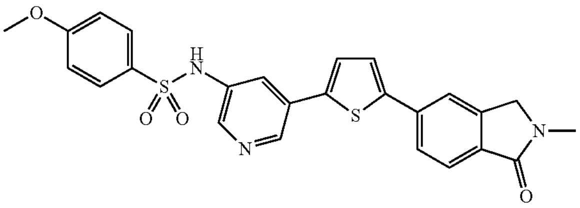

4-Methoxy-N-(5-(5-(2-methyl-1-oxoisoindolin-5-yl)thiophen-2-yl)pyridin-3-yl)benzenesulfonamide (20)

5-(5-(5-Aminopyridin-3-yl)thiophen-2-yl)-2-methylisoindolin-1-one was reacted with 4-methoxybenzenesulfonyl chloride according to general procedure E to give the title compound (20) as a dark yellow solid (37%), mp ($MeOH/CH_2Cl_2$) 254-258° C. $^1H$ NMR [400 MHz, $(CD_3)_2SO$] δ 10.62 (bs, 1H), 8.66 (d, J=1.8 Hz, 1H), 8.20 (d, J=2.2 Hz, 1H), 7.94 (s, 1H), 7.83 (d, J=8.3 Hz, 1H), 7.76 (d, J=8.9 Hz, 2H), 7.67-7.74 (m, 3H), 7.64 (d, J=3.8 Hz, 1H), 7.10 (d, J=8.9 Hz, 2H), 4.52 (s, 2H), 3.79 (s, 3H), 3.09 (s, 3H). HRMS ($ESI^+$) calcd for $C_{25}H_{22}N_3O_4S_2$ 492.1046 ($MH^+$). found 492.1033.

Example 28

(21.Na)

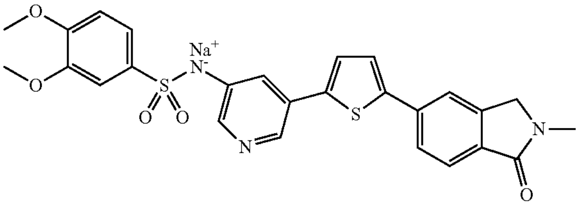

3,4-Dimethoxy-N-(5-(5-(2-methyl-1-oxoisoindolin-5-yl)thiophen-2-yl)pyridin-3-yl)benzenesulfonamide, sodium salt (21.Na)

5-(5-(5-Aminopyridin-3-yl)thiophen-2-yl)-2-methylisoindolin-1-one was reacted with 3,4-dimethoxybenzenesulfonyl chloride according to general procedure E, and the resulting crude product purified by flash column chromatography (1-5% $MeOH/CH_2Cl_2$ as eluant) to give the compound (21) as a pale orange solid (31%). $^1H$ NMR [400 MHz, $(CD_3)_2SO$] δ 10.57 (bs, 1H), 8.66 (d, J=2.0 Hz, 1H), 8.21 (d, J=2.4 Hz, 1H), 7.94 (d, J=0.7 Hz, 1H), 7.83 (dd, J=7.9, 1.5 Hz, 1H), 7.69-7.75 (m, 3H), 7.65 (d, J=3.9 Hz, 1H), 7.39 (dd, J=8.5, 2.2 Hz, 1H), 7.32 (d, J=2.2 Hz, 1H), 7.10 (d, J=8.6 Hz, 1H), 4.52 (s, 2H), 3.79 (s, 3H), 3.78 (s, 3H), 3.09 (s, 3H). LRMS ($APCI^-$) calcd for $C_{26}H_{22}N_3O_5S_2$ 521 (M-H). found 521.

In this case, the whole batch was converted to the corresponding sodium salt according to general procedure F, to give the title compound as a yellow solid (96%), mp (EtOH) 240-244° C. $^1H$ NMR [400 MHz, $(CD_3)_2SO$] δ 8.00 (d, J=2.1 Hz, 1H), 7.89 (d, J=0.8 Hz, 1H), 7.86 (d, J=2.5 Hz, 1H), 7.79 (dd, J=8.0, 1.6 Hz, 1H), 7.68 (d, J=7.9 Hz, 1H), 7.64 (d, J=3.8 Hz, 1H), 7.37-7.41 (m, 2H), 7.28-7.32 (m, 2H), 6.92 (d, J=8.1 Hz, 1H), 4.51 (s, 2H), 3.76 (s, 3H), 3.73 (s, 3H), 3.08 (s, 3H). Anal. ($C_{26}H_{22}N_3O_5S_2Na.1.2H_2O$) C, H, N.

Example 29

(22)

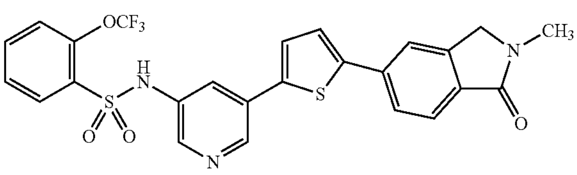

N-(5-(5-(2-Methyl-1-oxoisoindolin-5-yl)thiophen-2-yl)pyridin-3-yl)-2-(trifluoromethoxy)benzenesulfonamide (22)

5-(5-(5-Aminopyridin-3-yl)thiophen-2-yl)-2-methylisoindolin-1-one was reacted with 2-trifluoromethoxybenzenesulphonyl chloride according to general procedure E to give the title compound (22) as a pale yellow solid (42%); mp ($CH_2Cl_2$/MeOH) 251-254° C. $^1$H NMR [400 MHz, $(CD_3)_2SO$] δ 11.03 (br s, 1H), 8.67 (d, J=1.7 Hz, 1H), 8.23 (d, J=2.3 Hz, 1H), 8.09 (dd, J=7.8, 1.6 Hz, 1H), 7.94 (s, 1H), 7.75-7.85 (m, 2H), 7.68-7.74 (m, 3H), 7.63 (d, J=3.8 Hz, 1H), 7.55-7.62 (m, 2H), 4.52 (s, 2H), 3.09 (s, 3H). Anal. ($C_{25}H_{18}F_3N_3O_4S_2$.0.2$H_2O$) C, H, N.

Example 30

(23)

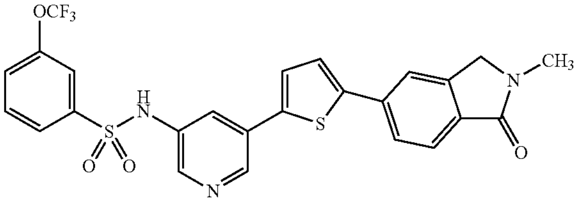

N-(5-(5-(2-Methyl-1-oxoisoindolin-5-yl)thiophen-2-yl)pyridin-3-yl)-3-(trifluoromethoxy)benzenesulfonamide (23)

5-(5-(5-Aminopyridin-3-yl)thiophen-2-yl)-2-methylisoindolin-1-one was reacted with 3-trifluoromethoxybenzenesulphonyl chloride according to general procedure B to give the title compound (23) as a light brown solid (22%); mp 230-232° C. $^1$H NMR [400 MHz, $(CD_3)_2SO$] δ 10.90 (br s, 1H), 8.70 (d, J=2.0 Hz, 1H), 8.20 (d, J=2.3 Hz, 1H), 7.94 (s, 1H), 7.80-7.87 (m, 2H), 7.67-7.79 (m, 6H), 7.65 (d, J=3.8 Hz, 1H), 4.52 (s, 2H), 3.09 (s, 3H). HRMS ($APCI^+$) calcd for $C_{25}H_{18}F_3N_3O_4S_2$ 546.0764 ($MH^+$). found 546.0747.

Example 31

(24)

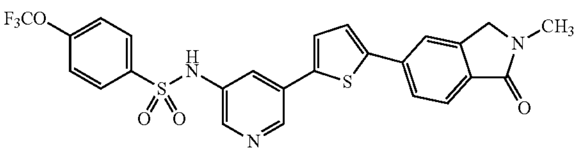

N-(5-(5-(2-Methyl-1-oxoisoindolin-5-yl)thiophen-2-yl)pyridin-3-yl)-4-(trifluoromethoxy)benzenesulfonamide (24)

5-(5-(5-Aminopyridin-3-yl)thiophen-2-yl)-2-methylisoindolin-1-one was reacted with 4-trifluoromethoxybenzenesulphonyl chloride according to general procedure E to give the title compound (24) as a pale yellow solid (41%); mp ($CH_2Cl_2$/MeOH) 293-296° C. $^1$H NMR [400 MHz, $(CD_3)_2SO$] δ 10.88 (br s, 1H), 8.70 (d, J=2.0 Hz, 1H), 8.22 (d, J=2.3 Hz, 1H), 7.92-7.98 (m, 3H), 7.82 (dd, J=8.0, 1.5 Hz, 1H), 7.72 (m, 3H), 7.66 (d, J=3.9 Hz, 1H), 7.57-7.63 (m, 2H), 4.52 (s, 2H), 3.09 (s, 3H). Anal. ($C_{25}H_{18}F_3N_3O_4S_2$) C, H, N.

Example 32

(25)

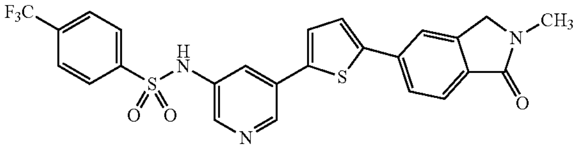

N-(5-(5-(2-Methyl-1-oxoisoindolin-5-yl)thiophen-2-yl)pyridin-3-yl)-4-(trifluoromethyl)benzenesulfonamide (25)

5-(5-(5-Aminopyridin-3-yl)thiophen-2-yl)-2-methylisoindolin-1-one was reacted with 4-trifluoromethylbenzenesulphonyl chloride according to general procedure E to give the title (25) compound as a pink solid (55%); mp ($CH_2Cl_2$/MeOH) 282-284° C. $^1$H NMR [400 MHz, $(CD_3)_2SO$] δ 10.99 (br s, 1H), 8.72 (d, J=2.0 Hz, 1H), 8.22 (d, J=2.3 Hz, 1H), 7.97-8.07 (m, 4H), 7.94 (s, 1H), 7.83 (dd, J=8.0, 1.6 Hz, 1H), 7.68-7.76 (m, 3H), 7.67 (d, J=3.9 Hz, 1H), 4.52 (s, 2H), 3.09 (s, 3H). Anal. ($C_{25}H_{18}F_3N_3O_3S_2$) C, H, N.

Example 33

(26)

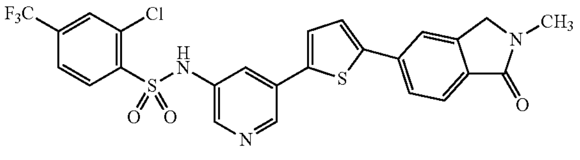

2-Chloro-N-(5-(5-(2-methyl-1-oxoisoindolin-5-yl) thiophen-2-yl)pyridin-3-yl)-4-(trifluoromethyl)benzenesulfonamide (26)

5-(5-(5-Aminopyridin-3-yl)thiophen-2-yl)-2-methyl isoindolin-1-one was reacted with 2-chloro-4-trifluoromethylbenzenesulphonyl chloride according to general procedure E to give the title compound (26) as a beige solid (61%); mp ($CH_2Cl_2$/MeOH) 292-295° C. $^1$H NMR [400 MHz, $(CD_3)_2$SO] δ 11.39 (br s, 1H), 8.68 (d, J=2.0 Hz, 1H), 8.35 (d, J=5.0 Hz, 1H), 8.28 (d, J=2.4 Hz, 1H), 8.17-(s, 1H), 7.97 (dd, J=8.4, 1.2 Hz, 1H), 7.93 (s, 1H), 7.82 (dd, J=7.9, 1.4 Hz, 1H), 7.67-7.75 (m, 1H), 7.64 (d, J=3.9 Hz, 1H), 4.52 (s, 2H), 3.09 (s, 3H). Anal. ($C_{25}H_{17}ClF_3N_3O_3S_2$) C, H, N.

Example 34

(27)

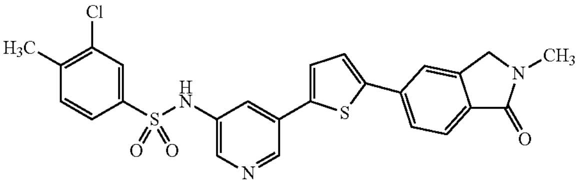

3-Chloro-4-methyl-N-(5-(5-(2-methyl-1-oxoisoindolin-5-yl)thiophen-2-yl)pyridin-3-yl)benzenesulfonamide (27)

5-(5-(5-Aminopyridin-3-yl)thiophen-2-yl)-2-methylisoindolin-1-one was reacted with 3-chloro-4-methylbenzenesulphonyl chloride according to general procedure E to give the title compound (27) as an off-white solid (50%); mp ($CH_2Cl_2$/MeOH) 277-279° C. $^1$H NMR [400 MHz, $(CD_3)_2$SO] δ 10.81 (br s, 1H), 8.70 (d, J=2.0 Hz, 1H), 8.22 (d, J=2.3 Hz, 1H), 7.94 (s, 1H), 7.80-7.86 (m, 2H), 7.64-7.75 (m, 5H), 7.58 (d, J=8.2 Hz, 1H), 4.52 (s, 2H), 3.09 (s, 3H), 2.36 (s, 3H). Anal. ($C_{25}H_{20}ClN_3O_3S_2$) C, H, N.

Example 35

(28)

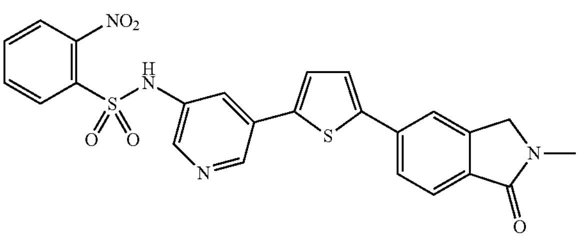

N-(5-(5-(2-Methyl-1-oxoisoindolin-5-yl)thiophen-2-yl)pyridin-3-yl)-2-nitrobenzenesulfonamide (28)

5-(5-(5-Aminopyridin-3-yl)thiophen-2-yl)-2-methylisoindolin-1-one was reacted with 2-nitrobenzenesulfonyl chloride according to general procedure E, and the resulting crude product purified by flash column chromatography (1-5% MeOH/$CH_2Cl_2$ as eluant) to give the title compound (28) as a yellow solid (32%), mp (MeOH/$CH_2Cl_2$) 270-273° C. $^1$H NMR [400 MHz, $(CD_3)_2$SO] δ 11.21 (bs, 1H), 8.71 (d, J=1.9 Hz, 1H), 8.26 (d, J=2.4 Hz, 1H), 8.06-8.10 (m, 1H), 7.98-8.01 (m, 1H), 7.94 (d, J=0.8 Hz, 1H), 7.86-7.90 (m, 2H), 7.83 (dd, J=8.0, 1.6 Hz, 1H), 7.72-7.75 (m, 2H), 7.71 (d, J=8.0 Hz, 1H), 7.66 (d, J=3.9 Hz, 1H), 4.52 (s, 2H), 3.09 (s, 3H). LRMS ($APCI^-$) calcd for $C_{24}H_{17}N_4O_5S_2$ 506 (M-H). found 506. Anal. ($C_{24}H_{18}N_4O_5S_2$) C, H, N.

Example 36

(29)

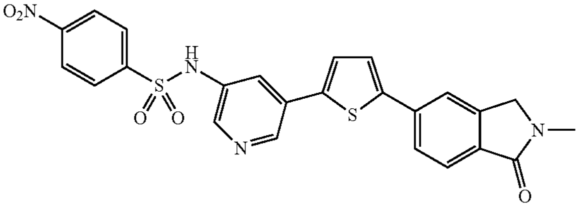

N-(5-(5-(2-Methyl-1-oxoisoindolin-5-yl)thiophen-2-yl)pyridin-3-yl)-4-nitrobenzenesulfonamide (29)

5-(5-(5-aminopyridin-3-yl)thiophen-2-yl)-2-methylisoindolin-1-one was reacted with 4-nitrobenzenesulfonyl chloride according to general procedure E, and the resulting crude product, purified by flash column chromatography (1-5% MeOH/$CH_2Cl_2$ as eluant) to give the title compound (29) as a pale yellow solid (56%); mp 272-275° C. $^1$H NMR [400 MHz, $(CD_3)_2$SO] δ 11.09 (br s, 1H), 8.71 (d, J=1.9 Hz, 1H), 8.40 (dq, J=9.0, 5.0 Hz, 2H), 8.22 (d, J=2.3 Hz, 1H), 8.07 (dq, J=8.9, 5.0 Hz, 2H), 7.95 (s, 1H), 7.83 (dd, J=7.9, 1.4 Hz, 1H), 7.76 (t, J=2.2 Hz, 1H), 7.73 (d, J=4.0 Hz, 1H), 7.71 (d, J=8.0 Hz, 1H), 7.68 (d, J=3.9 Hz, 1H), 4.52 (s, 2H), 3.09 (s, 3H). LRMS ($APCI^-$) calcd for $C_{24}H_{17}N_4O_5S_2$ 506 (M-H). found 506. HRMS ($APCI^+$) calcd for $C_{24}H_{18}N_4O_5S_2$ 507.0791 ($MH^+$). found 507.0792.

In this case the product was converted to its sodium salt according to general procedure F to give the desired product as an orange solid (89%). $^1$H NMR [400 MHz, $(CD_3)_2$SO] δ 8.24 (d, J=8.8 Hz, 2H), 8.11 (d, J=1.6 Hz, 1H), 7.96 (d, J=8.8 Hz, 2H), 7.94 (d, J=2.4 Hz, 1H), 7.91 (s, 1H), 7.81 (dd, J=8.0, 1.4 Hz, 1H), 7.68 (d, J=8.0 Hz, 1H), 7.65 (d, J=3.9 Hz, 1H), 7.47 (t, J=2.2 Hz, 1H), 7.45 (d, J=3.8 Hz, 1H), 4.51 (s, 2H), 3.08 (s, 3H).

Example 37

(30)

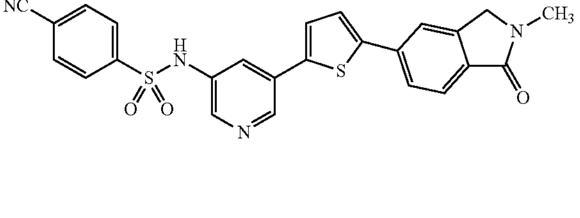

4-Cyano-N-(5-(5-(2-methyl-1-oxoisoindolin-5-yl)thiophen-2-yl)pyridin-3-yl)benzenesulfonamide (30)

5-(5-(5-Aminopyridin-3-yl)thiophen-2-yl)-2-methylisoindolin-1-one was reacted with 4-cyanobenzenesulphonyl chloride according to general procedure E to give the title compound (30) as a yellow solid (10%); mp ($CH_2Cl_2$/MeOH) 282-285° C. $^1$H NMR [400 MHz, $(CD_3)_2SO$] δ 11.02 (br s, 1H), 8.71 (d, J=2.0 Hz, 1H), 8.21 (d, J=2.4 Hz, 1H), 8.08 (d, J=8.6 Hz, 2H), 7.98 (d, J=8.6 Hz, 2H), 7.95 (s, 1H), 7.83 (dd, J=8.0, 1.6 Hz, 1H), 7.74 (d, J=4.0 Hz, 1H), 7.72 (s, 1H), 7.71 (d, J=8.4 Hz, 1H), 7.68 (d, J=3.9 Hz, 1H), 4.52 (s, 2H), 3.09 (s, 3H). Anal. ($C_{25}H_{18}N_4O_3S_2$.0.1$H_2O$) C, H, N.

Example 38

(31)

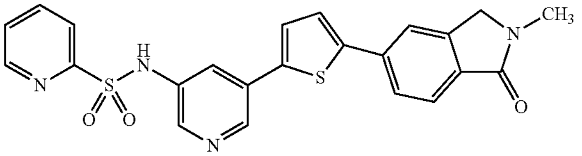

N-(5-(5-(2-Methyl-1-oxoisoindolin-5-yl)thiophen-2-yl)pyridin-3-yl)pyridine-2-sulfonamide (31)

5-(5-(5-Aminopyridin-3-yl)thiophen-2-yl)-2-methylisoindolin-1-one was reacted with pyridine-2-sulphonyl chloride according to general procedure B to give the title compound (31) as a cream solid (20%); mp 272-275° C. $^1$H NMR [400 MHz, $(CD_3)_2SO$] δ 11.01 (br s, 1H), 8.73-8.78 (m, 1H), 8.66 (d, J=2.0, Hz, 1H), 8.30 (d, J=2.4 Hz, 1H), 8.11 (td, J=7.8, 1.7 Hz, 1H), 8.60 (dt, J=7.6, 1.0 Hz, 1H), 7.94 (s, 1H), 7.81-7.87 (m, 2H), 7.73 (d, J=3.9 Hz, 1H), 7.71 (d, J=8.1 Hz, 1H), 7.66-7.70 (m, 1H), 7.64 (d, J=3.8 Hz, 1H), 4.52 (s, 2H), 3.09 (s, 3H).

In this case the product was converted to its sodium salt according to general procedure F to give the desired product as a light-brown solid (89%). $^1$H NMR [400 MHz, $(CD_3)_2SO$] δ 8.53 (td, J=4.7, 1.4 Hz, 1H), 8.04 (d, J=2.1 Hz, 1H), 7.93 (d, J=2.4 Hz, 1H), 7.91 (s, 1H), 7.83-7.87 (m, 2H), 7.80 (dd, J=8.0, 1.5 Hz, 1H), 7.68 (d, J=7.9 Hz, 1H), 7.65 (d, J=3.8 Hz, 1H), 7.60 (t, J=2.2 Hz, 1H), 7.41 (d, J=3.8 Hz, 1H), 7.32-7.38 (m, 1H), 4.51 (s, 2H), 3.08 (s, 3H). HRMS ($APCI^+$) calcd for $C_{23}H_{17}N_4NaO_3S_2$ 485.0713 ($MH^+$). found 485.0710.

Example 39

(32)

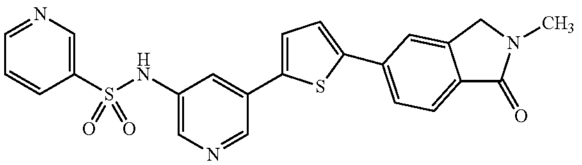

N-(5-(5-(2-Methyl-1-oxoisoindolin-5-yl)thiophen-2-yl)pyridin-3-yl)pyridine-3-sulfonamide (32)

5-(5-(5-Aminopyridin-3-yl)thiophen-2-yl)-2-methylisoindolin-1-one was reacted with pyridine-3-sulphonyl chloride according to general procedure E to give the title compound (32) as a light brown solid (45%); mp ($CH_2Cl_2$/MeOH) 283-286° C. $^1$H NMR [400 MHz, $(CD_3)_2SO$] δ 10.98 (br s, 1H), 8.97 (d, J=2.0 Hz, 1H), 8.83 (dd, J=4.8, 1.4 Hz, 1H), 8.70 (d, J=1.9 Hz, 1H), 8.22 (d, J=2.2 Hz, 1H), 8.20 (dt, J=8.1, 1.8 Hz, 1H), 7.94 (s, 1H), 7.84 (d, J=7.9 Hz, 1H), 7.75 (t, J=2.2 Hz, 1H), 7.73 (d, J=3.9 Hz, 1H), 7.71 (d, J=8.0 Hz, 1H), 7.69 (d, J=3.9 Hz, 1H), 7.65 (dd, J=5.2, 2.8 Hz, 1H), 4.52 (s, 2H), 3.09 (s, 3H). HRMS ($APCI^+$) calcd for $C_{23}H_{18}N_4O_3S_2$ 463.0893 ($MH^+$). found 463.0891.

Example 40

(33)

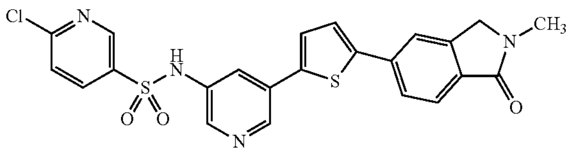

6-Chloro-N-(5-(5-(2-methyl-1-oxoisoindolin-5-yl)thiophen-2-yl)pyridin-3-yl)pyridine-3-sulfonamide (33)

5-(5-(5-Aminopyridin-3-yl)thiophen-2-yl)-2-methylisoindolin-1-one was reacted with 6-chloropyridine-3-sulphonyl chloride according to general procedure E. Purification by preparative HPLC, eluting with a gradient composed of mobile phases A (0.1% TFA/$H_2O$) and B (90% MeCN/$H_2O$) gave the title compound (33) as a pink solid (11%); mp ($CH_2Cl_2$/MeOH) 260-265° C. $^1$H NMR [400 MHz, $(CD_3)_2SO$] δ 11.04 (br s, 1H), 8.81 (d, J=2.3 Hz, 1H), 8.71 (d, J=1.9 Hz, 1H), 8.23 (d, J=2.3 Hz, 1H), 8.20 (dd, J=8.5, 2.6 Hz, 1H), 7.95 (s, 1H), 7.83 (dd, J=7.9, 1.4 Hz, 1H), 4.52 (s, 2H), 3.09 (s, 3H). Anal. ($C_{23}H_{17}ClN_4O_3S_2$) C, H, N.

Example 41

(34)

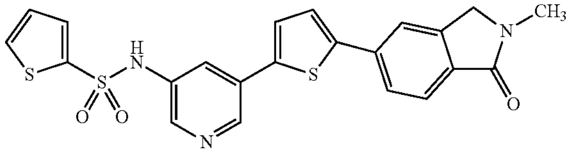

N-(5-(5-(2-Methyl-1-oxoisoindolin-5-yl)thiophen-2-yl)pyridin-3-yl)thiophene-2-sulfonamide (34)

5-(5-(5-Aminopyridin-3-yl)thiophen-2-yl)-2-methylisoindolin-1-one was reacted with thiophene-2-sulphonyl chloride according to general procedure E to give the title compound (34) as a cream solid (71%); mp ($CH_2Cl_2$/MeOH) 300-304° C. $^1$H NMR [400 MHz, $(CD_3)_2SO$] δ

10.91 (br s, 1H), 8.72 (d, J=2.0, Hz, 1H), 8.24 (d, J=2.3 Hz, 1H), 7.93-7.98 (m, 2H), 7.83 (dd, J=8.0, 1.5 Hz, 1H), 7.78 (t, J=2.2 Hz, 1H), 7.74 (d, J=3.9 Hz, 1H), 7.68 (d, J=3.9 Hz, 1H), 7.65 (dd, J=3.8, 1.3 Hz, 2H), 7.15 (dd, J=4.9, 3.8 Hz, 1H), 4.52 (s, 2H), 3.09 (s, 3H).

In this case the product was converted to its sodium salt according to general procedure F to give the desired product as a pale-yellow solid (90%). $^1H$ NMR [400 MHz, $(CD_3)_2SO$] δ 8.08 (d, J=2.1, Hz, 1H), 7.92 (d, J=2.4 Hz, 1H), 7.90 (s, 1H), 7.80 (dd, J=7.9, 1.5 Hz, 1H), 7.68 (d, J=8.0 Hz, 1H), 7.65 (d, J=3.8 Hz, 1H), 7.46-7.53 (m, 2H), 7.42 (d, J=3.9 Hz, 1H), 7.27 (dd, J=3.6, 1.3 Hz, 1H), 6.93 (dd, J=5.0, 3.6 Hz, 1H), 4.51 (s, 2H), 3.08 (s, 3H). Anal. ($C_{22}H_{16}N_3NaO_3S_3$.2.1$H_2O$) C, H, N.

Example 42

(35)

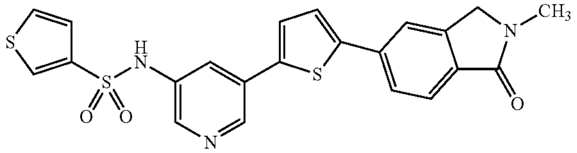

N-(5-(5-(2-Methyl-1-oxoisoindolin-5-yl)thiophen-2-yl)pyridin-3-yl)thiophene-3-sulfonamide (35)

5-(5-(5-Aminopyridin-3-yl)thiophen-2-yl)-2-methyl-isoindolin-1-one was reacted with thiophene-3-sulphonyl chloride according to general procedure E to give the title compound (35) as a yellow solid. $^1H$ NMR [400 MHz, $(CD_3)_2SO$] δ 10.72 (br s, 1H), 8.68 (d, J=1.9, Hz, 1H), 8.31 (q, J=1.3 Hz, 1H), 8.24 (d, J=2.3 Hz, 1H), 7.95 (s, 1H), 7.83 (dd, J=8.0, 1.4 Hz, 1H), 7.73-7.78 (m, 3H), 7.70 (d, J=8.0 Hz, 1H), 7.66 (d, J=3.9 Hz, 1H), 7.32 (dd, J=5.2, 1.4 Hz, 1H), 4.52 (s, 2H), 3.09 (s, 3H). Anal. ($C_{22}H_{17}N_3O_3S_3$) C, H, N.

Other compounds of the invention can be prepared via general procedures G and H as set out in Scheme 2 below:

Scheme 2

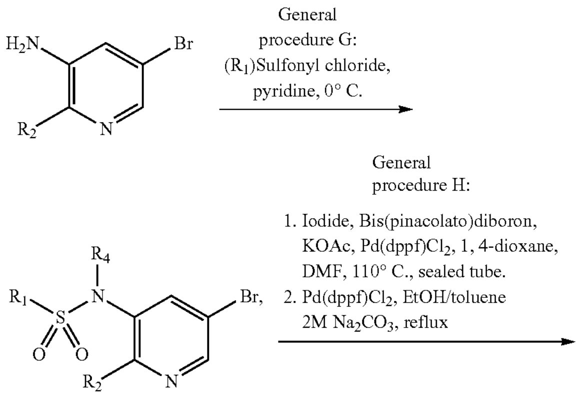

-continued

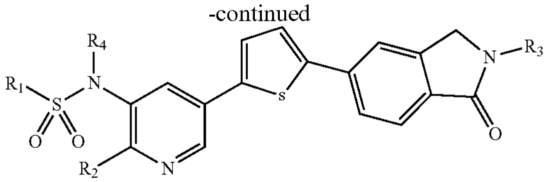

Compounds 36-47

Example 43

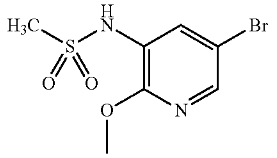

General Procedure G: N-(5-Bromo-2-methoxypyridin-3-yl)methanesulphonamide (Scheme 2)

To a solution of 5-bromo-2-methoxypyridin-3-amine (500 mg, 2.46 mmol) in dry pyridine (5 mL) at 0° C., was added methanesulphonyl chloride (0.48 mL, 6.15 mmol) in dry $CH_2Cl_2$ (2 mL) over 4 mins. After continuous stirring at room temperature for 16 h., the reaction mixture was diluted with citric acid, extracted into $CH_2Cl_2$ (3×25 mL), and the combined organic extracts concentrated in vacuo. If bis-sulphonamide is seen by LRMS/TLC at this stage, then the hydrolysis conditions described in general procedure E, were employed. Further purification by flash column chromatography on silica gel (1-5% MeOH/$CH_2Cl_2$) gave the title compound as a pale-pink fluffy solid (522 mg, 40%). $^1H$ NMR [400 MHz, $(CD_3)_2SO$] δ 9.47 (br s, 1H), 8.09 (d, J=2.3 Hz, 1H), 7.77 (d, J=2.3 Hz, 1H), 3.91 (s, 3H), 3.10 (s, 3H). LRMS ($APCI^+$) calcd for $C_7H_9BrN_2O_3S$, 282 ($MH^+$). found 282.

Example 44

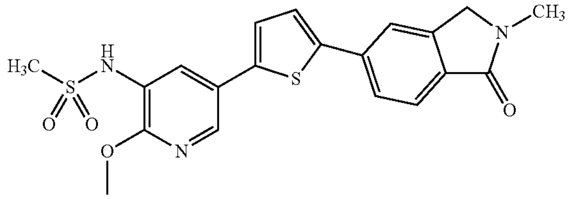

General Procedure H. N-(2-Methoxy-5-(5-(2-methyl-1-oxoisoindolin-5-yl)thiophen-2-yl)pyridin-3-yl)methanesulphonamide (Scheme 2)

The following is based on a modified literature procedure (Knight S. D. et al., *ACS Med. Chem. Lett.*, 2010, 1, 39-43 and WO2008150827). To N-(5-bromo-2-methoxypyridin-3-yl)methanesulphonamide (350 mg, 1.24 mmol) in dry 1,4-dioxane (9 mL)/dry DMF (1 mL) in a sealed tube was added, bis(pinacolato)diboron (347 mg, 1.37 mmol), KOAc (366 mg, 3.73 mmol), and the whole mixture was degassed and purged with $N_2$. $Pd(dppf)Cl_2.CH_2Cl_2$ (52 mg, 0.06 mmol) was then added with vigorous stirring and the mixture heated to 110° C. for 2 h. The disappearance of the starting bromide was monitored by LRMS. This mixture was then allowed to cool to room temperature and used in situ without further purification. LRMS ($APCI^+$) calcd for $C_{13}H_{21}BN_2O_5S$, 330 ($MH^+$). found 330 (boronate ester).

To the above mixture at room temperature was added, 5-(5-iodothiophen-2-yl)-2-methylisoindolin-1-one (220 mg, 0.62 mmol), 2 M $Na_2CO_3$ (1.3 mL, 2.49 mmol), and $Pd(dppf)Cl_2.CH_2Cl_2$ (52 mg, 0.06 mmol), and the whole mixture was degassed, purged with $N_2$, and heated to 105° C. for 16 h. The disappearance of 5-(5-iodothiophen-2-yl)-2-methylisoindolin-1-one was monitored by LRMS. The reaction mixture was then cooled to room temperature, diluted with $H_2O$ (50 mL), and extracted with 5% MeOH/$CH_2Cl_2$ (3×50 mL) and $CH_2Cl_2$ (2×50 mL). The combined organic extracts were washed with brine (1×100 mL), dried ($Na_2SO_4$), filtered, and concentrated in vacuo. The crude residue was dried onto silica gel and purified by flash column chromatography (1-5% MeOH/$CH_2Cl_2$) to give the title compound as a yellow solid (34%); mp ($CH_2Cl_2$/MeOH) 232-235° C. $^1H$ NMR [400 MHz, $(CD_3)_2SO$] δ 9.40 (br s, 1H), 8.35 (d, J=2.3 Hz, 1H), 7.92 (s, 1H), 7.88 (d, J=2.3 Hz, 1H), 7.81 (dd, J=8.0, 1.5 Hz, 1H), 7.66-7.73 (m, 2H), 7.55 (d, J=3.8 Hz, 1H), 4.51 (s, 2H), 3.96 (s, 3H), 3.09 (s, 3H), 3.08 (s, 3H). Anal. ($C_{20}H_{19}N_3O_4S_2$) C, H, N.

Example 45

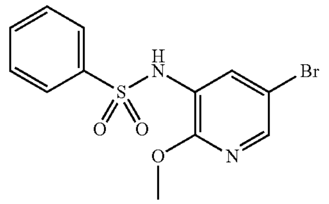 [SMILES: COc1ncc(Br)cc1NS(=O)(=O)c1ccccc1]

N-(5-Bromo-2-methoxypyridin-3-yl)benzenesulphonamide

5-Bromo-2-methoxypyridin-3-amine was reacted with benzenesulphonyl chloride according to general procedure G, and the title compound was given as a white solid (61%). $^1H$ NMR [400 MHz, $(CD_3)_2SO$] δ 10.15 (br s, 1H), 8.05 (d, J=2.2 Hz, 1H), 7.76 (d, J=7.3 Hz, 2H), 7.69 (d, J=2.2 Hz, 1H), 7.64 (d, J=7.3 Hz, 1H), 7.58 (d, J=7.8 Hz, 2H), 3.62 (s, 3H). LRMS ($APCI^+$) calcd for $C_{12}H_{11}BrN_2O_3S$, 344 ($MH^+$). found 344.

Example 46

(36)

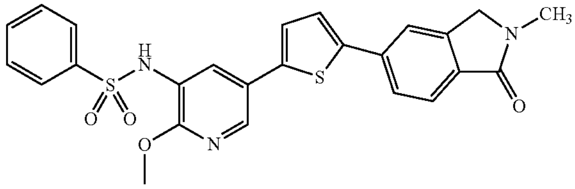

N-(2-Methoxy-5-(5-(2-methyl-1-oxoisoindolin-5-yl)thiophen-2-yl)pyridin-3-yl)benzenesulphonamide (36)

N-(5-Bromo-2-methoxypyridin-3-yl)benzenesulphonamide was reacted with bis(pinacolato)diboron and subsequently coupled to 5-(5-iodothiophen-2-yl)-2-methylisoindolin-1-one in situ according to general procedure H, to give the title compound (36) as a pale-yellow solid (35%); mp ($CH_2Cl_2$/MeOH) 280-283° C. $^1H$ NMR [400 MHz, $(CD_3)_2SO$] δ 10.57 (br s, 1H), 8.29 (d, J=2.1 Hz, 1H), 7.92 (s, 1H), 7.76-7.84 (m, 4H), 7.70 (d, J=7.8 Hz, 1H), 7.68 (d, J=3.8 Hz, 1H), 7.54-7.67 (m, 3H), 7.49 (d, J=3.9 Hz, 1H), 4.52 (s, 2H), 3.67 (s, 3H), 3.09 (s, 3H). Anal. ($C_{25}H_{21}N_3O_4S_2$) C, H, N.

Example 47

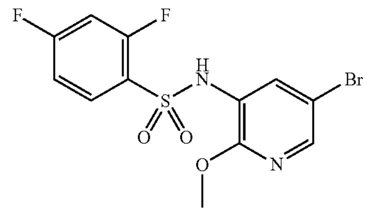 [SMILES: COc1ncc(Br)cc1NS(=O)(=O)c1ccc(F)cc1F]

N-(5-Bromo-2-methoxypyridin-3-yl)-2,4-difluorobenzenesulphonamide

5-Bromo-2-methoxypyridin-3-amine was reacted with 2,4-difluorobenzenesulphonyl chloride according to general procedure G, and the title compound was given as an ivory solid (45%). $^1H$ NMR [400 MHz, $(CD_3)_2SO$] δ 10.44 (br s, 1H), 8.12 (d, J=2.3 Hz, 1H), 7.72-7.81 (m, 1H), 7.75 (d, J=2.3 Hz, 1H), 7.52-7.61 (m, 1H), 7.18-7.27 (m, 1H), 3.61 (s, 3H). LRMS ($APCI^+$) calcd for $C_{12}H_9BrF_2N_2O_3S$, 380 ($MH^+$). found 380.

Example 48

(37)

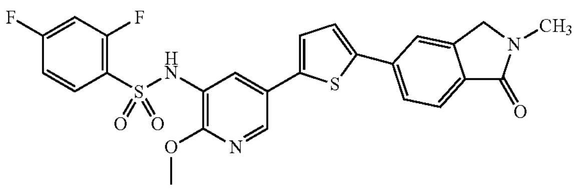

2,4-Difluoro-N-(2-methoxy-5-(5-(2-methyl-1-oxoisoindolin-5-yl)thiophen-2-yl)pyridin-3-yl)benzenesulphonamide (37)

N-(5-Bromo-2-methoxypyridin-3-yl)-2,4-difluorobenzenesulphonamide was reacted with bis(pinacolato)diboron and subsequently coupled to 5-(5-iodothiophen-2-yl)-2-methylisoindolin-1-one in situ according to general procedure H, to give the title compound (37) as a yellow powder (42%); mp (MeOH/$CH_2Cl_2$) 224-227° C. $^1H$ NMR [400 MHz, $(CD_3)_2SO$] δ 10.35 (br s, 1H), 8.35 (s, 1H), 7.92 (s, 1H), 7.85 (d, J=2.2 Hz, 1H), 7.82 (dd, J=8.0, 1.5 Hz, 1H), 7.74-7.83 (m, 1H), 7.70 (d, J=7.3 Hz, 1H), 7.69 (d, J=4.0 Hz, 1H), 7.51-7.61 (m, 1H), 7.54 (d, J=3.7 Hz, 1H), 7.22 (dt, J=8.3, 2.3 Hz, 1H), 4.51 (s, 2H), 3.66 (s, 3H), 3.09 (s, 3H). Anal. ($C_{25}H_{19}F_2N_3O_4S_2$) C, H, N.

Example 49

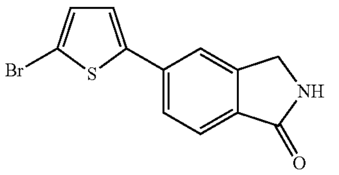 [SMILES: O=C1NCc2cc(-c3ccc(Br)s3)ccc21]

5-(5-Bromothiophen-2-yl)isoindolin-1-one

Reaction of thiophene-2-boronic acid and 5-iodoisoindolin-1-one according to general procedure C gave a crude product which was purified by flash column chromatography on silica gel (5% MeOH/$CH_2Cl_2$ as eluant) to give the title compound as a beige solid (60%), m.p. ($CH_2Cl_2$) 251-253° C. $^1$H NMR [400 MHz, $(CD_3)_2SO$] δ 8.55 (br s, 1H), 7.82 (br s, 1H), 7.73 (dd, J=7.9, 1.5 Hz, 1H), 7.68 (d, J=7.9 Hz, 1H), 7.49 (d, J=3.9 Hz, 1H), 7.31 (d, J=3.9 Hz, 1H), 4.41 (s, 2H). LRMS (APCI$^+$) calcd for $C_{12}H_9BrNOS$ 294, 296 (MH$^+$). found 294, 296. Anal. ($C_{12}H_8BrNOS$) C, H, N.

Example 50

(38)

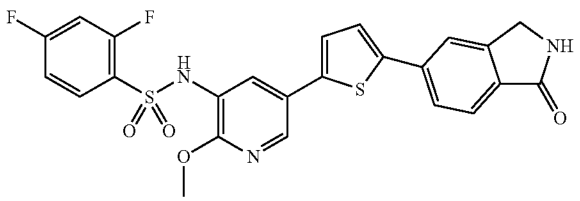

2,4-Difluoro-N-(2-methoxy-5-(5-(1-oxoisoindolin-5-yl)thiophen-2-yl)pyridin-3-yl)benzene sulphonamide (38)

N-(5-Bromo-2-methoxypyridin-3-yl)-2,4-difluorobenzenesulphonamide was reacted with bis(pinacolato)diboron and subsequently coupled to 5-(5-bromothiophen-2-yl) isoindolin-1-one in situ according to general procedure H, to give the title compound (38) as a green solid (35%); mp (MeOH/$CH_2Cl_2$) 266-270° C. $^1$H NMR [400 MHz, $(CD_3)_2SO$] δ 10.35 (s, 1H), 8.58 (br s, 1H), 8.37 (d, J=2.2 Hz, 1H), 7.91 (s, 1H), 7.87 (d, J=2.3 Hz, 1H), 7.73-7.84 (m, 2H), 7.71 (d, J=7.2 Hz, 1H), 7.69 (d, J=3.7 Hz, 1H), 7.54-7.63 (m, 1H), 7.55 (d, J=3.8 Hz, 1H), 7.58 (dt, J=8.4, 2.2 Hz, 1H), 4.53 (s, 2H), 3.66 (s, 3H). HRMS (APCI$^+$) calcd for $C_{24}H_{17}F_2N_3O_4S_2$ 514.0701 (MH$^+$). found 514.0710.

Example 51

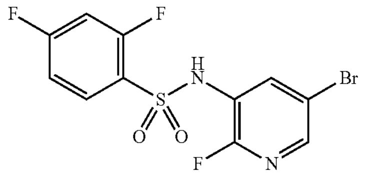 [SMILES: O=S(=O)(Nc1cc(Br)cnc1F)c1ccc(F)cc1F]

N-(5-Bromo-2-fluoropyridin-3-yl)-2,4-difluorobenzenesulphonamide

5-Bromo-2-fluoropyridin-3-amine was reacted with 2,4-difluorobenzenesulphonyl chloride according to general procedure G, and the title compound was given as a brown solid (17%). $^1$H NMR [400 MHz, $(CD_3)_2SO$] δ 11.13 (br s, 1H), 8.18 (s, 1H), 8.01 (dd, J=8.6, 2.3 Hz, 1H), 7.81-7.92 (m, 1H), 7.53-7.64 (m, 1H), 7.22-7.32 (m, 1H). LRMS (APCI$^+$) calcd for $C_{11}H_6BrF_3N_2O_2S$, 368 (MH$^+$). found 368.

Example 52

(39)

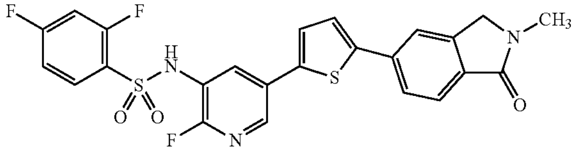

2,4-Difluoro-N-(2-fluoro-5-(5-(2-methyl-1-oxoisoindolin-5-yl)thiophen-2-yl)pyridin-3-yl)benzenesulphonamide (39)

N-(5-Bromo-2-fluoropyridin-3-yl)-2,4-difluorobenzenesulphonamide was reacted with bis(pinacolato)diboron and subsequently coupled to 5-(5-iodothiophen-2-yl)-2-methylisoindolin-1-one in situ according to general procedure H to give the title compound (39) as a pale green solid (32%); mp (MeOH/$CH_2Cl_2$) 237-239° C. $^1$H NMR [400 MHz, $(CD_3)_2SO$] δ 11.04 (br s, 1H), 8.42 (s, 1H), 8.06 (dd, J=9.1, 2.3 Hz, 1H), 7.94 (s, 1H), 7.84-7.92 (m, 1H), 7.82 (dd, J=7.9, 1.5 Hz, 1H), 7.74 (d, J=3.9 Hz, 1H), 7.72 (d, J=8.0 Hz, 1H), 7.68 (d, J=3.9 Hz, 1H), 7.57-7.65 (m, 1H), 7.28 (dt, J=8.9, 2.4 Hz, 1H), 4.52 (s, 2H), 3.09 (s, 3H).

In this case the product was converted to its sodium salt according to general procedure F to give the desired product as a light-green solid (89%). $^1$H NMR [400 MHz, $(CD_3)_2SO$] δ 7.91 (s, 1H), 7.83-7.90 (m, 1H), 7.79 (dd, J=7.9, 1.5 Hz, 1H), 7.71 (d, J=2.3 Hz, 1H), 7.67 (d, J=7.3 Hz, 1H), 7.60-7.65 (m, 2H), 7.33 (d, J=3.8 Hz, 1H), 7.22 (dt, J=9.7, 2.5 Hz, 1H), 7.11 (dt, J=8.3, 2.5 Hz, 1H), 4.51 (s, 2H), 3.08 (s, 3H). Anal. ($C_{24}H_{15}F_3N_3NaO_3S_2.1.9H_2O$) C, H, N.

Example 53

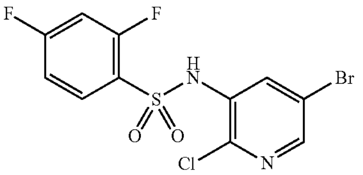 [SMILES: O=S(=O)(Nc1cc(Br)cnc1Cl)c1ccc(F)cc1F]

N-(5-Bromo-2-chloropyridin-3-yl)-2,4-difluorobenzenesulphonamide

5-Bromo-2-chloropyridin-3-amine was reacted with 2,4-difluorobenzenesulphonyl chloride according to general procedure G, and the title compound was given as an off-white solid (32%). $^1H$ NMR [400 MHz, $(CD_3)_2SO$] δ 11.03 (br s, 1H), 8.47 (d, J=2.3 Hz, 1H), 8.04 (d, J=2.3 Hz, 1H), 7.75-7.85 (m, 1H), 7.53-7.63 (m, 1H), 7.20-7.29 (m, 1H). LRMS (APCI$^+$) calcd for $C_{11}H_6BrF_2ClN_2O_2S$, 385 (MH$^+$). found 385.

Example 54

(40)

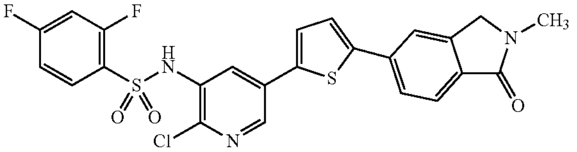

2,4-Difluoro-N-(2-chloro-5-(5-(2-methyl-1-oxoisoindolin-5-yl)thiophen-2-yl)pyridin-3-yl)benzenesulphonamide (40)

N-(5-Bromo-2-chloropyridin-3-yl)-2,4-difluorobenzenesulphonamide was reacted with bis(pinacolato)diboron and subsequently coupled to 5-(5-iodothiophen-2-yl)-2-methylisoindolin-1-one in situ according to general procedure H to give the title compound (40) as a yellow solid (12%); mp ($CH_2Cl_2$/MeOH) 238-240° C. $^1H$ NMR [400 MHz, $(CD_3)_2SO$] δ 10.92 (br s, 1H), 8.68 (d, J=1.8 Hz, 1H), 8.02 (d, J=2.4 Hz, 1H), 7.96 (s, 1H), 7.84 (dd, J=8.2, 1.8 Hz, 1H), 7.74-7.85 (m, 3H), 7.71 (d, J=8.0 Hz, 1H), 7.55-7.65 (m, 1H), 7.26 (dt, J=8.5, 2.0 Hz, 1H), 4.52 (s, 2H), 3.09 (s, 3H). Anal. ($C_{24}H_{16}ClF_2N_3O_3S_2$) C, H, N.

Example 55

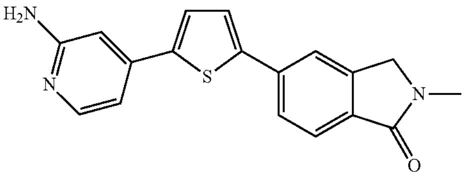 [SMILES: CN1Cc2cc(-c3ccc(-c4ccnc(N)c4)s3)ccc2C1=O]

5-(5-(2-Aminopyridin-4-yl)thiophen-2-yl)-2-methylisoindolin-1-one (scheme 1)

Reaction of 5-(5-iodothiophen-2-yl)-2-methylisoindolin-1-one with 4-(4,4,5,5-tetramethyl-1,3,2-dioxaborolan-2-yl)pyridin-2-amine according to general procedure C gave the title compound as a green-yellow solid (72%), mp ($CH_2Cl_2$/MeOH) 302-306° C. $^1H$ NMR [400 MHz, $(CD_3)_2SO$] δ 7.90-7.97 (m, 2H), 7.82 (d, J=7.1 Hz, 1H), 7.67-7.73 (m, 2H), 7.65 (d, J=3.4 Hz, 1H), 6.83 (d, J=4.0 Hz, 1H), 6.69 (s, 1H), 6.05 (bs, 2H) 4.52 (s, 2H), 3.09 (s, 3H). HRMS (ESI$^+$) calcd for $C_{18}H_{16}N_3OS$, 322.1009 (MH$^+$). found 322.1002.

Example 56

(41)

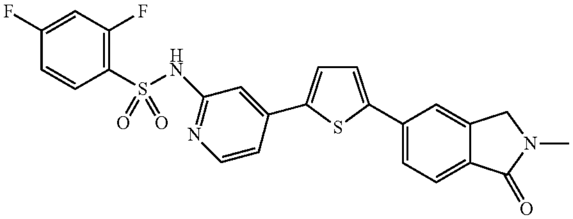

2,4-Difluoro-N-(4-(5-(2-methyl-1-oxoisoindolin-5-yl)thiophen-2-yl)pyridin-2-yl)benzenesulfonamide (41)

5-(5-(2-Aminopyridin-4-yl)thiophen-2-yl)-2-methylisoindolin-1-one was reacted with 2,4-difluorobenzenesulfonyl chloride according to general procedure E to give the title compound (41) as a pale brown solid (26%), mp ($CH_2Cl_2$/MeOH) 235-239° C. $^1H$ NMR [400 MHz, $(CD_3)_2SO$] δ 13.27 (bs, 1H), 7.99-8.09 (m, 2H), 7.85-7.98 (m, 3H), 7.80 (d, J=3.8 Hz, 1H), 7.72 (d, J=7.9 Hz, 1H), 7.38-7.51 (m, 2H), 7.19-7.32 (m, 2H) 4.53 (s, 2H), 3.09 (s, 3H). HRMS (ESI$^+$) calcd for $C_{24}H_{18}N_3O_3S_2F_2$ 498.0752 (MH$^+$). found 498.0754. Anal. ($C_{24}H_{17}N_3O_3S_2F_2$.0.20$H_2O$) C, H, N.

Example 57

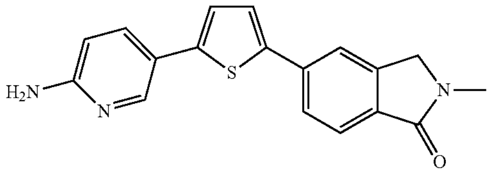 [SMILES: CN1Cc2cc(-c3ccc(-c4ccc(N)nc4)s3)ccc2C1=O]

5-(5-(6-Aminopyridin-3-yl)thiophen-2-yl)-2-methylisoindolin-1-one 5-(5-Iodothiophen-2-yl)-2-methylisoindolin-1-one was reacted with 5-(4,4,5,5-tetramethyl-1,3,2-dioxaborolan-2-yl)pyridin-2-amine according to general procedure C to give the title compound as a green-yellow solid (72%), mp (MeOH/$CH_2Cl_2$) 252-254° C. $^1H$ NMR [400 MHz, $(CD_3)_2SO$] δ 8.28 (dd, J=2.6, 0.6 Hz, 1H), 7.86 (s, 1H), 7.76 (dd, J=8.0, 1.5 Hz, 1H), 7.70 (dd, J=8.6, 2.6 Hz, 1H), 7.67 (d, J=7.9 Hz, 1H), 7.62 (d, J=3.8 Hz, 1H), 6.35 (d, J=3.8 Hz, 1H), 6.51 (dd, J=8.6, 0.6 Hz, 1H), 6.25 (bs, 2H) 4.49 (s, 2H), 3.08 (s, 3H). HRMS (ESI+) calcd for $C_{18}H_{16}N_3OS$, 322.1009 ($MH^+$). found 322.1007.

Example 58

(42)

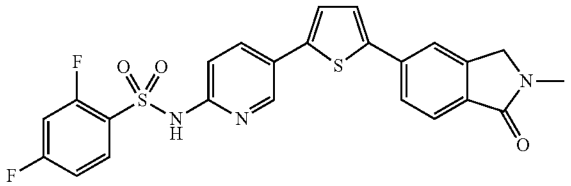

2,4-Difluoro-N-(5-(5-(2-methyl-1-oxoisoindolin-5-yl)thiophen-2-yl)pyridin-2-yl)benzenesulfonamide (42)

5-(5-(6-Aminopyridin-3-yl)thiophen-2-yl)-2-methylisoindolin-1-one was reacted with 2,4-difluorobenzenesulfonyl chloride according to general procedure E to give the title compound (42) as a pale brown solid (65%), mp ($CH_2Cl_2$/MeOH) 269-272° C. $^1$H NMR [400 MHz, $(CD_3)_2SO$] δ 12.00 (bs, 1H), 8.39 (bs, 1H), 7.99-8.10 (m, 2H), 7.89 (s, 1H), 7.78 (dd, J=8.0, 1.3 Hz, 1H), 7.69 (d, J=4.2 Hz, 1H), 7.68 (d, J=8.1 Hz, 1H), 7.57 (d, J=3.9 Hz, 1H), 7.44-7.53 (m, 1H), 7.26-7.33 (m, 1H), 7.16-7.26 (m, 1H) 4.50 (s, 2H), 3.07 (s, 3H). HRMS (ESI+) calcd for $C_{24}H_{18}N_3O_3S_2F_2$ 498.0752 ($MH^+$). found 498.0746. Anal. ($C_{24}H_{17}N_3O_3S_2F_2$.0.10$C_5H_5N$) C, H, N.

Example 59

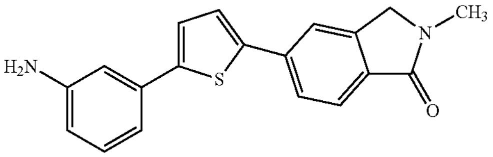 [SMILES: CN1Cc2cc(-c3ccc(-c4cccc(N)c4)s3)ccc2C1=O]

5-(5-(3-Aminophenyl)thiophen-2-yl)-2-methylisoindolin-1-one (scheme 1)

5-(5-Iodothiophen-2-yl)-2-methylisoindolin-1-one was reacted with (3-aminophenyl)boronic acid according to general procedure C to give the title compound as a green solid (69%), mp ($CH_2Cl_2$/MeOH) 244-247° C. $^1$H NMR [400 MHz, $(CD_3)_2SO$] δ 7.89 (s, 1H), 7.77 (dd, J=7.9, 1.3 Hz, 1H), 7.68 (d, J=8.0 Hz, 1H), 7.63 (d, J=3.8 Hz, 1H), 7.41 (d, J=3.8 Hz, 1H), 7.08 (t, J=7.72 Hz, 1H), 6.82-6.91 (m, 2H), 6.55 (dd, J=7.9, 1.3 Hz, 1H), 5.25 (br s, 2H), 4.50 (s, 2H), 3.08 (s, 3H).

Example 60

(43)

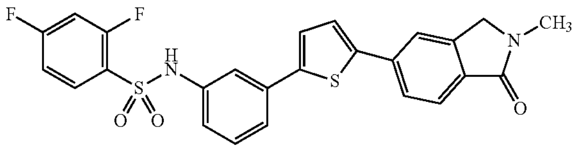

2,4-Difluoro-N-(3-(5-(2-methyl-1-oxoisoindolin-5-yl)thiophen-2-yl)phenyl)benzene sulphonamide (43)

5-(5-(3-Aminophenyl)thiophen-2-yl)-2-methylisoindolin-1-one was reacted with 2,4-difluorobenzenesulphonyl chloride according to general procedure E to give the title compound (43) as a yellow solid (62%), mp ($CH_2Cl_2$/MeOH) 260-262° C. $^1$H NMR [400 MHz, $(CD_3)_2SO$] δ 10.84 (br s, 1H), 7.93-8.02 (m, 1H), 7.91 (s, 1H), 7.81 (dd, J=8.0, 1.3 Hz, 1H), 7.70 (d, J=8.0 Hz, 1H), 7.67 (d, J=3.8 Hz, 1H), 7.55 (dt, J=8.5, 2.5 Hz, 1H), 7.47 (d, J=3.8 Hz, 1H), 7.38-7.45 (m, 2H), 7.25-7.36 (m, 2H), 7.05 (d, J=7.4 Hz, 1H), 4.51 (s, 2H), 3.09 (s, 3H). Anal. ($C_{25}H_{18}F_2N_2O_3S_2$.0.2$C_6H_{14}$) C, H, N.

Example 61

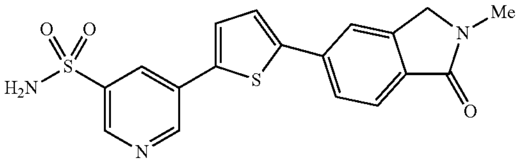 [SMILES: CN1Cc2cc(-c3ccc(-c4cncc(S(N)(=O)=O)c4)s3)ccc2C1=O]

5-(5-(2-Methyl-1-oxoisoindolin-5-yl)thiophen-2-yl) pyridine-3-sulphonamide (scheme 2)

5-Bromo pyridine-3-sulphonamide was reacted with bis (pinacolato)diboron and subsequently coupled to 5-(5-iodothiophen-2-yl)-2-methylisoindolin-1-one in situ according to general procedure H, to give the title compound as a yellow powder (11%), mp ($CH_2Cl_2$/MeOH) 248-250° C. $^1$H NMR [400 MHz, $(CD_3)_2SO$] δ 9.20 (d, J=2.2 Hz, 1H), 8.90 (d, J=2.0 Hz, 1H), 8.40 (t, J=2.2 Hz, 1H), 7.97 (s, 1H), 7.82-7.89 (m, 2H), 7.80 (d, J=3.9 Hz, 1H), 7.72 (d, J=8.1 Hz, 1H), 7.70 (br s, 2H), 4.52 (s, 2H), 3.09 (s, 3H). HRMS (FAB+) calcd for $C_{18}H_{15}N_3NaO_3S_2$ 408.0447 (M+Na+). found 408.0456.

Example 62

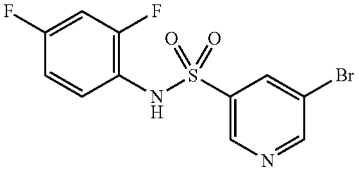 [SMILES: O=S(=O)(Nc1ccc(F)cc1F)c1cncc(Br)c1]

5-Bromo-N-(2,4-difluorophenyl)pyridine-3-sulphonamide

To a stirred solution of 2,4-difluoroaniline (0.42 mL, 4.10 mmol) in dry pyridine (10 mL) at 0° C. under $N_2$, was added 5-bromopyridine-3-sulphonyl chloride hydrogen chloride (600 mg, 2.05 mmol) portionwise over 5 mins. The reaction mixture was left to stir at 0° C. for 15 mins and allowed to warm to room temperature and stirred for a further 30 mins. The reaction mixture was then concentrated in vacuo and the residue dissolved in EtOAc (50 mL) and diluted with 2 M $Na_2CO_3$ (25 mL). The layers were separated and the organic layer washed further with $H_2O$ (25 mL), brine (25 mL), dried ($Na_2SO_4$), filtered and concentrated in vacuo. The crude material was recrystallised from 5% MeOH/$CH_2Cl_2$ and hexanes, and triturated with EtOAc to give the title compound as an ivory solid (370 mg, 56%). $^1$H NMR [400 MHz, $(CD_3)_2SO$] δ 10.52 (br s, 1H), 9.20 (d, J=2.2 Hz, 1H), 8.77 (d, J=2.0 Hz, 1H), 8.26 (t, J=2.1 Hz, 1H), 7.22-7.35 (m, 2H), 7.02-7.15 (m, 1H). LRMS (APCI$^+$) calcd for $C_{11}H_7BrF_2N_2O_2S$, 350 (MH$^+$). found 350.

Example 63

(44)

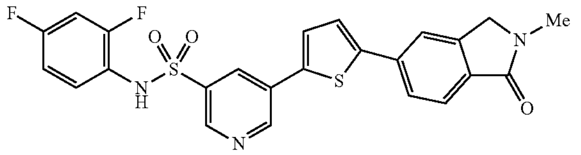

N-(2,4-Difluorophenyl)-5-(5-(2-methyl-1-oxoisoindolin-5-yl)thiophen-2-yl)pyridine-3-sulphonamide (44)

5-Bromo-N-(2,4-difluorophenyl)pyridine-3-sulphonamide was reacted with bis(pinacolato)diboron and subsequently coupled to 5-(5-iodothiophen-2-yl)-2-methylisoindolin-1-one in situ according to general procedure H, to give the title compound (44) as a yellow solid (23%); mp ($CH_2Cl_2$/MeOH) 221-224° C. $^1$H NMR [400 MHz, $(CD_3)_2SO$] δ 10.50 (br s, 1H), 9.23 (d, J=2.2 Hz, 1H), 8.71 (d, J=2.1 Hz, 1H), 8.21 (t, J=2.2 Hz, 1H), 7.96 (s, 1H), 7.81-7.88 (m, 2H), 7.78 (d, J=3.9 Hz, 1H), 7.72 (d, J=8.0 Hz, 1H), 7.23-7.35 (m, 2H), 7.09 (ddt, J=9.2, 1.4 Hz, 1H), 4.52 (s, 2H), 3.09 (s, 3H). Anal. ($C_{24}H_{17}F_2N_3O_3S_2$.0.1$H_2O$) C, H, N.

Example 64

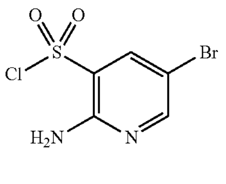 [SMILES: Nc1ncc(Br)cc1S(=O)(=O)Cl]

2-Amino-5-bromopyridine-3-sulphonyl chloride

The title compound was prepared using a modified literature procedure (see WO2008150827). 5-Bromopyridin-2-amine (7.5 g, 43.3 mmol) was added portionwise to a solution of chlorosulphonic acid (29 mL) at 0° C. The reaction mixture was then heated to reflux for 4 h., and upon cooling to room temperature, was poured over ice (50 g) with vigorous stirring. The yellow precipitate formed was quickly filtered, washed with cold $H_2O$ and hexanes, and dried under high-vacuum to yield a pale-yellow solid (7.1 g, 61%). LRMS (APCI$^+$) calcd for $C_5H_4BrClN_2O_2S$, 273 (MH$^+$). found 273. This was used without further purification in the next step.

Example 65

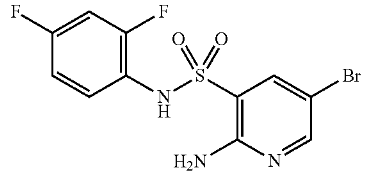 [SMILES: Nc1ncc(Br)cc1S(=O)(=O)Nc1ccc(F)cc1F]

2-Amino-5-bromo-N-(2,4-difluorophenyl)pyridine-3-sulphonamide 2,4-Difluoroaniline was reacted with 2-amino-5-bromopyridine-3-sulphonyl chloride according to general procedure G to give the title compound as a cream solid (78%). $^1$H NMR [400 MHz, $(CD_3)_2SO$] δ 7.97 (d, J=2.5 Hz, 1H), 7.79 (d, J=2.5 Hz, 1H), 7.00-7.10 (m, 1H), 6.80-6.90 (m, 1H), 6.71 (br s, 2H), 7.49 (ddt, J=8.9, 1.5 Hz, 1H). NB: N $\underline{H}SO_2$ is not observed in $(CD_3)_2SO$. LRMS (APCI$^+$) calcd for $C_{11}H_8BrF_2N_3O_2S$, 365 (MH$^+$). found 365.

Example 66

(45)

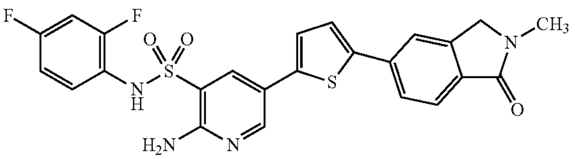

2-Amino-N-(2,4-difluorophenyl)-5-(5-(2-methyl-1-oxoisoindolin-5-yl)thiophen-2-yl)pyridine-3-sulphonamide (45)

2-Amino-5-bromo-N-(2,4-difluorophenyl)pyridine-3-sulphonamide was reacted with bis(pinacolato)diboron and subsequently coupled to 5-(5-iodothiophen-2-yl)-2-methylisoindolin-1-one in situ according to general procedure H, to give the title compound (45) as a yellow solid (10%), mp ($CH_2Cl_2$/MeOH) 278-279° C. $^1$H NMR [400 MHz, $(CD_3)_2SO$] δ 10.35 (br s, 1H), 8.61 (d, J=2.4 Hz, 1H), 7.88 (s, 1H), 7.84 (d, J=2.4 Hz, 1H), 7.77 (dd, J=8.0, 1.6 Hz, 1H), 7.67 (d, J=8.0 Hz, 1H), 7.64 (d, J=3.8 Hz, 1H), 7.43 (d, J=3.8 Hz, 1H), 7.24-7.38 (m, 2H), 7.08 (ddt, J=9.2, 1.4 Hz, 1H), 6.94 (br s, 2H), 4.49 (s, 2H), 3.08 (s, 3H). Anal. ($C_{24}H_{18}F_2N_4O_3S_2$.0.1$H_2O$) C, H, N.

Example 67

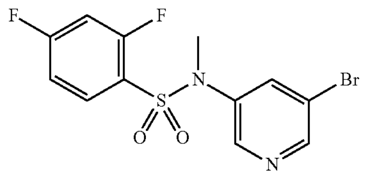 [SMILES: CN(c1cncc(Br)c1)S(=O)(=O)c1ccc(F)cc1F]

N-(5-Bromopyridin-3-yl)-2,4-difluoro-N-methylbenzenesulphonamide

N-(5-Bromopyridin-3-yl)-2,4-difluorobenzenesulphonamide was alkylated with methyl iodide according to general procedure B, followed by flash column chromatography (1-3% $MeOH/CH_2Cl_2$ as eluant) to yield the title compound as a brown solid (57%). $^1H$ NMR [400 MHz, $(CD_3)_2SO$] δ 8.65 (d, J=2.0 Hz, 1H), 8.51 (d, J=2.2 Hz, 1H), 8.04 (t, J=2.2 Hz, 1H), 7.72-7.83 (m, 1H), 7.57-7.68 (m, 1H), 7.32 (dt, J=8.2, 2.4 Hz, 1H), 3.26 (s, 3H). LRMS ($APCI^+$) calcd for $C_{12}H_9BrF_2N_2O_2S$, 364 ($MH^+$). found 364.

Example 68

(46)

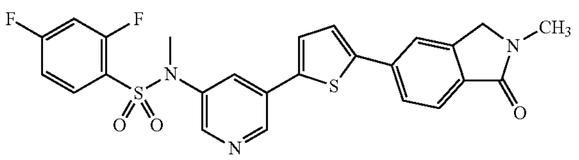

2,4-Difluoro-N-methyl-N-(5-(5-(2-methyl-1-oxoisoindolin-5-yl)thiophen-2-yl)pyridin-3-yl)benzenesulphonamide (46)

N-(5-Bromopyridin-3-yl)-2,4-difluoro-N-methylbenzenesulphonamide was reacted with bis(pinacolato)diboron and subsequently coupled to 5-(5-iodothiophen-2-yl)-2-methylisoindolin-1-one in situ according to general procedure H, to give the title compound (46) as a cream solid (52%); mp ($CH_2Cl_2$/MeOH) 200-202° C. $^1H$ NMR [400 MHz, $(CD_3)_2SO$] δ 8.87 (d, J=2.0 Hz, 1H), 8.43 (d, J=2.3 Hz, 1H), 7.96 (t, J=2.2 Hz, 1H), 7.94 (s, 1H), 7.83 (dd, J=7.8, 1.4 Hz, 1H), 7.73-7.81 (m, 3H), 7.71 (d, J=7.9 Hz, 1H), 7.63 (m, 1H), 7.32 (dt, J=8.1, 2.0 Hz, 1H), 4.52 (s, 2H), 3.34 (s, 3H), 3.09 (s, 3H). Anal. ($C_{25}H_{19}F_2N_3O_3S_2$) C, H, N.

Example 69

(47)

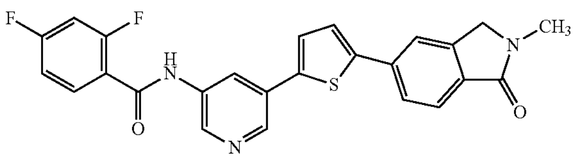

2,4-Difluoro-N-(5-(5-(2-methyl-1-oxoisoindolin-5-yl)thiophen-2-yl)pyridin-3-yl)benzamide (47)

To 2,4-difluorobenzoic acid (99 mg, 0.62 mmol) in dry $CH_2Cl_2$ (2 mL) was added oxalylchloride (193 mg, 1.52 mmol) and 1 drop of dry DMF. The whole mixture was refluxed for 2 h., cooled to room temperature and concentrated in vacuo to give 2,4-difluorobenzoic acid chloride. This was used directly in the next step without further purification.

To 5-(5-(5-aminopyridin-3-yl)thiophen-2-yl)-2-methylisoindolin-1-one (100 mg, 0.31 mmol) in dry pyridine (10 mL) at 0° C. under $N_2$ was added 2,4-difluorobenzoic acid chloride (110 mg, 0.62 mmol) in dry $CH_2Cl_2$ (2 mL) dropwise over 4 mins. The mixture was then left to stir at 45° C. for 16 h., quenched with $H_2O$ and concentrated in vacuo. The residue was taken up in citric acid, sonicated for 5 mins, and the precipitate formed was filtered and washed thoroughly with $H_2O$, MeOH, diethyl ether and dried on to silica gel. The crude material was chromatographed (1-3% $MeOH/CH_2Cl_2$) to give the title compound (47) as a yellow solid (52 mg, 36%); mp 267-269° C. $^1H$ NMR [400 MHz, $(CD_3)_2SO$] δ 10.76 (br s, 1H), 8.77 (t, J=2.9 Hz, 2H), 8.52 (t, J=2.0 Hz, 1H), 7.96 (s, 1H), 7.81-7.88 (m, 2H), 7.75 (d, J=3.9 Hz, 1H), 7.71 (d, J=3.8 Hz, 1H), 7.70 (s, 1H), 7.49 (dt, J=9.4, 2.5 Hz, 1H), 7.28 (dt, J=8.6, 2.2 Hz, 1H) 4.52 (s, 2H), 3.09 (s, 3H). LRMS ($APCI^+$) calcd for $C_{25}H_{17}N_3O_2F_2S$, 462.5 ($MH^+$). found 462.8. Anal. ($C_{25}H_{17}F_2N_3O_2S.0.5H_2O$) C, H, N.

Example 70

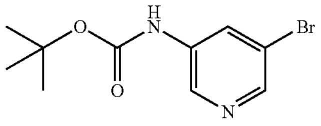

tert-Butyl (5-bromopyridin-3-yl)carbamate

3-Amino-5-bromopyridine (2.0 g, 11.6 mmol), di-tert-butyl-dicarbonate (3.03 g, 13.9 mmol), triethylamine (2.42 mL, 17.3 mmol) and 4-dimethylaminopyridine (142 mg, 1.16 mmol) were dissolved in dry DMF (20 mL) and heated at 90° C. overnight. Upon cooling, the reaction mixture was diluted with water (100 mL) and the resulting solid extracted into EtOAc (3×80 mL). The combined EtOAc fractions were washed with water (3×100 mL), brine (2×100 mL), dried ($Na_2SO_4$) and filtered. The solvent was removed under reduced pressure to afford a crude solid which was purified by filtration through a plug of flash silica gel (20% EtOAc/hexanes as eluent). The title compound was isolated as a white solid (2.22 g, 70%). $^1H$ NMR [400 MHz, $(CD_3)_2SO$] δ 8.33 (br d, J=1.5 Hz, 1H), 8.24 (br s, 2H), 6.62 (br s, 1H), 1.53 (s, 9H). LRMS ($APCI^+$) calcd for $C_{10}H_{13}BrN_2O_2$ 273, 275 ($MH^+$). found 273, 275.

Compounds of the invention can also be prepared via general procedures I, C, J, and E as set out in Scheme 3 below:

Scheme 3

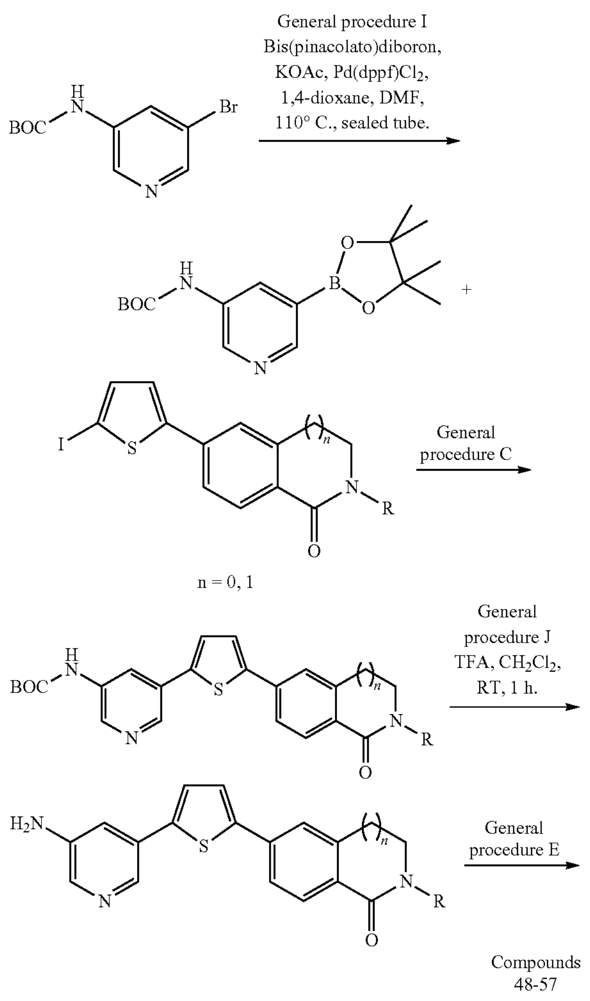

Example 71

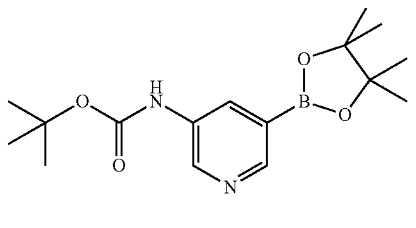 [SMILES: CC(C)(C)OC(=O)Nc1cncc(B2OC(C)(C)C(C)(C)O2)c1]

General Procedure J: tert-Butyl (5-(4,4,5,5-tetramethyl-1,3,2-dioxaborolan-2-yl)pyridin-3-yl)carbamate (scheme 3)

tert-Butyl (5-bromopyridin-3-yl)carbamate (5.0 g; 18.3 mmol) was placed in an oven-dried pressure tube, followed by bis(pinacolato)diboron (5.11 g, 20.1 mmol), KOAc (5.38 g, 54.9 mmol), Pd(dppf)$Cl_2$ (750 mg, 0.92 mmol) and 1,4-dioxane (50 mL). The tube was sealed under $N_2$ and the mixture heated with stirring at 100° C. for 20 h. Upon cooling, the reaction mixture was diluted with $CH_2Cl_2$ (200 mL), filtered through celite, and washed well with $CH_2Cl_2$. All solvent was removed from the filtrate under reduced pressure to give a black-brown viscous oil, which was purified by filtration through a plug of silica gel (EtOAc as eluent). The title compound was isolated as a foam, which upon trituration with 10% $Et_2O$ in hexanes, gave a pale brown crystalline solid (4.09 g, 70%). $^1H$ NMR [400 MHz, $(CD_3)_2SO$] δ 8.62 (d, J=1.4 Hz, 1H), 8.58 (d, J=2.8 Hz, 1H), 8.20 (br s, 1H), 6.49 (br s, 1H), 1.69 (s, 9H), 1.34 (s, 12H). LRMS ($APCI^+$) calcd for $C_{16}H_{26}BN_2O_4$ 321 ($MH^+$). found 321.

Example 72

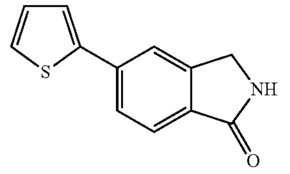 [SMILES: O=C1NCc2cc(-c3cccs3)ccc21]

5-(Thiophen-2-yl)isoindolin-1-one

5-Bromoisoindolin-1-one and thiophene-2-boronic acid were reacted according to general procedure C. The title compound was isolated as a glossy cream solid (63%). $^1H$ NMR [400 MHz, $(CD_3)_2SO$] δ 8.51 (br s, 1H), 7.77 (dd, J=7.9, 1.5 Hz, 1H), 7.68 (d, J=8.0 Hz, 1H), 7.61-7.65 (m, 3H), 7.19 (dd, J=5.1, 3.7 Hz, 1H), 4.41 (s, 2H). LRMS ($APCI^+$) calcd for $C_{12}H_{10}NOS$, 216 ($MH^+$). found 216.

Example 73

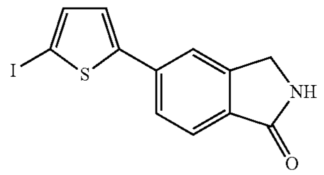 [SMILES: O=C1NCc2cc(-c3ccc(I)s3)ccc21]

5-(5-Iodothiophen-2-yl)isoindolin-1-one

Iodination of 5-(thiophen-2-yl)isoindolin-1-one with N-iodosuccinimide according to general procedure D gave the title compound as a fluffy cream solid (84%). $^1H$ NMR [400 MHz, $(CD_3)_2SO$] δ 8.54 (br s, 1H), 7.80 (s, 1H), 7.72 (dd, J=7.9, 1.3 Hz, 1H), 7.67 (d, J=7.9 Hz, 1H), 7.41 (d, J=3.8 Hz, 1H), 7.36 (d, J=3.8 Hz, 1H), 4.40 (s, 2H). LRMS ($APCI^+$) calcd for $C_{12}H_9INOS$, 342 ($MH^+$). found 342.

Example 74

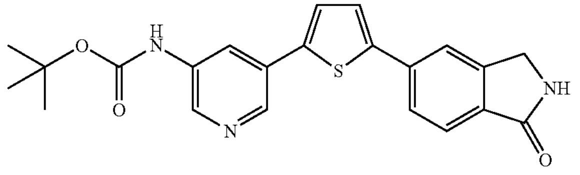 [SMILES: CC(C)(C)OC(=O)Nc1cncc(-c2ccc(-c3ccc4c(c3)CNC4=O)s2)c1]

tert-Butyl (5-(5-(1-oxoisoindolin-5-yl)thiophen-2-yl)pyridin-3-yl)carbamate 5-(5-Iodothiophen-2-yl)isoindolin-1-one was reacted with tert-butyl (5-(4,4,5,5-tetramethyl-1,3,2-dioxaborolan-2-yl)pyridin-3-yl)carbamate according to general procedure C to give the title compound as a pale yellow solid (93%). $^1$H NMR [400 MHz, $(CD_3)_2SO$] δ 9.75 (br s, 1H), 8.60 (d, J=2.1 Hz, 1H), 8.59 (br s, 1H), 8.25 (br s, 1H), 7.93 (br s, 1H), 7.84 (dd, J=7.9, 1.4 Hz, 1H), 7.69-7.74 (m, 3H), 7.65 (d, J=3.9 Hz, 1H), 4.43 (s, 2H), 1.51 (s, 9H). LRMS ($APCI^+$) calcd for $C_{22}H_{22}N_3O_3S$, 408 ($MH^+$). found 408.

Example 75

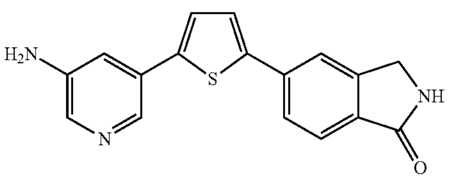 [SMILES: Nc1cncc(-c2ccc(-c3ccc4c(c3)CNC4=O)s2)c1]

General Procedure J: 5-(5-(5-Aminopyridin-3-yl)thiophen-2-yl)isoindolin-1-one tert-Butyl (5-(5-(1-oxoisoindolin-5-yl)thiophen-2-yl)pyridin-3-yl)carbamate (555 mg, 1.36 mmol) was dissolved in a mixture of $CH_2Cl_2$ (5 mL) and trifluoroacetic acid (5 mL) and stirred at room temperature for 1 h. The solvent was removed under reduced pressure, then the resulting solid suspended in acetone (12 mL) and stirred until homogenous. An equal volume of sat. $NaHCO_3$ was carefully added and the resulting suspension collected by filtration, washed well with water and dried under vacuum. The title compound was isolated as a pale green solid (408 mg, 97%). $^1$H NMR [400 MHz, $(CD_3)_2SO$] δ 8.57 (br s, 1H), 8.12 (d, J=2.0 Hz, 1H), 7.88-7.92 (m, 2H), 7.84 (dd, J=8.0, 1.5 Hz, 1H), 7.72 (d, J=8.2 Hz, 1H), 7.69 (d, J=3.8 Hz, 1H), 7.54 (d, J=3.8 Hz, 1H), 7.16 (t, J=2.3 Hz, 1H), 5.51 (br s, 2H), 4.43 (s, 2H). LRMS ($APCI^+$) calcd for $C_{17}H_{14}N_3OS$, 308 ($MH^+$). found 308.

Example 76

(48)

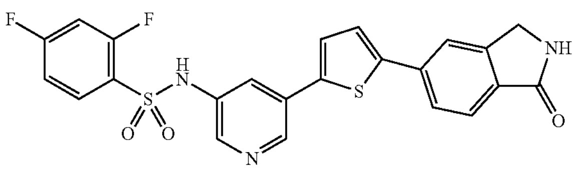

2,4-Difluoro-N-(5-(5-(1-oxoisoindolin-5-yl)thiophen-2-yl)pyridin-3-yl)benzenesulfonamide (48)

5-(5-(5-Aminopyridin-3-yl)thiophen-2-yl)isoindolin-1-one was reacted with 2,4-difluorobenzenesulfonyl chloride according to general procedure E to give the title compound (48) as a pale pink-orange solid (21%), mp ($MeOH/CH_2Cl_2$) 298-302° C. $^1$H NMR [400 MHz, $(CD_3)_2SO$] δ 11.51 (br s, 1H), 8.69 (d, J=2.0 Hz, 1H), 8.60 (br s, 1H), 8.25 (d, J=2.4 Hz, 1H), 7.97-8.05 (m, 1H), 7.93 (br s, 1H), 7.84 (dd, J=7.9, 1.5 Hz, 1H), 7.69-7.74 (m, 3H), 7.65 (d, J=3.9 Hz, 1H), 7.54-7.61 (m, 1H), 7.28-7.34 (m, 1H), 4.43 (s, 2H). LRMS ($APCI^+$) calcd for $C_{23}H_{16}F_2N_3O_3S_2$ 484 ($MH^+$). found 484. Anal. ($C_{23}H_{15}F_2N_3O_3S_2.0.25H_2O$) C, H, N.

Example 77

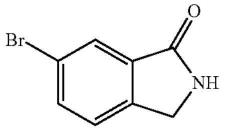 [SMILES: O=C1NCc2ccc(Br)cc21]

6-Bromoisoindolin-1-one

The title compound was prepared from methyl 5-bromo-2-methylbenzoate by bromination with N-bromosuccinimide followed by cyclisation with $NH_3$ according to general procedure A to give a fluffy white solid (89%). $^1$H NMR [400 MHz, $(CD_3)_2SO$] δ 8.71 br s, 1H), 7.75-7.79 (m, 2H), 7.56 (d, J=8.8 Hz, 1H), 4.35 (s, 2H). LRMS ($APCI^+$) calcd for $C_8H_7BrNO$, 212, 214 ($MH^+$). found 212, 214.

Example 78

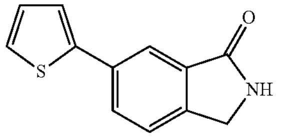 [SMILES: O=C1NCc2ccc(-c3cccs3)cc21]

6-(Thiophen-2-yl)isoindolin-1-one

Reaction of 6-bromoisoindolin-1-one and thiophene-2-boronic acid according to general procedure C gave the title compound as a fluffy white solid (93%). $^1$H NMR [400 MHz, $(CD_3)_2SO$] δ 8.63 (br s, 1H), 7.84 (dd, J=7.9, 1.8 Hz, 1H), 7.82 (br s, 1H), 7.60-7.64 (m, 2H), 7.54 (dd, J=5.1, 1.1 Hz, 1H), 7.16 (dd, J=5.1, 3.6 Hz, 1H), 4.40 (s, 2H). LRMS ($APCI^+$) calcd for $C_{12}H_{10}NOS$, 216 ($MH^+$). found 216.

Example 79

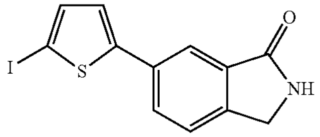 [SMILES: O=C1NCc2ccc(-c3ccc(I)s3)cc21]

6-(5-Iodothiophen-2-yl)isoindolin-1-one

Iodination of 6-(thiophen-2-yl)isoindolin-1-one with N-iodosuccinimide according to general procedure D gave the title compound as a pale grey solid (83%). $^1$H NMR [400

MHz, $(CD_3)_2SO$] δ 8.64 (br s, 1H), 7.78-7.85 (m, 2H), 7.61 (dd, J=7.7, 0.7 Hz, 1H), 7.38 (d, J=3.8 Hz, 1H), 7.36 (d, J=3.8 Hz, 1H), 4.39 (s, 2H). LRMS ($APCI^+$) calcd for $C_{12}H_9INOS$, 342 ($MH^+$). found 342.

Example 80

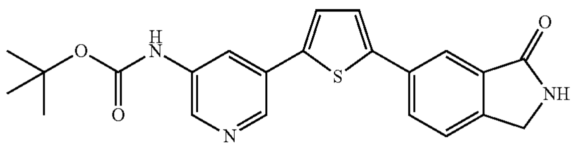 [SMILES: CC(C)(C)OC(=O)Nc1cncc(-c2ccc(-c3ccc4c(c3)C(=O)NC4)s2)c1]

tert-Butyl (5-(5-(3-oxoisoindolin-5-yl)thiophen-2-yl) pyridin-3-yl)carbamate 6-(5-Iodothiophen-2-yl)isoindolin-1-one was reacted with tert-butyl (5-(4,4,5,5-tetramethyl-1,3,2-dioxaborolan-2-yl)pyridin-3-yl)carbamate according to general procedure C to give the title compound as a pale yellow crystalline solid (89%). $^1$H NMR [400 MHz, $(CD_3)_2SO$] δ 9.73 (br s, 1H), 8.66 (br s 1H), 8.60 (d, J=2.1 Hz, 1H), 8.51 (d, J=2.2 Hz, 1H), 8.22 (br s, 1H), 7.92-7.97 (m, 2H), 7.72 (d, J=3.8 Hz, 1H), 7.64 (dd, J=7.8, 0.5 Hz, 1H), 7.62 (d, J=3.8 Hz, 1H), 4.42 (s, 2H), 1.51 (s, 9H). LRMS ($APCI^+$) calcd for $C_{22}H_{22}N_3O_3S$, 408 ($MH^+$). found 408.

Example 81

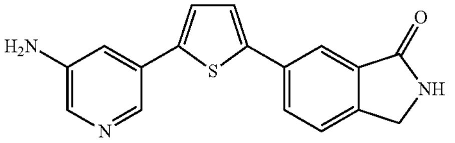 [SMILES: Nc1cncc(-c2ccc(-c3ccc4c(c3)C(=O)NC4)s2)c1]

6-(5-(5-Aminopyridin-3-yl)thiophen-2-yl)isoindolin-1-one

Deprotection of tert-butyl (5-(5-(3-oxoisoindolin-5-yl) thiophen-2-yl)pyridin-3-yl)carbamate according to general procedure J gave the title compound as an off-white solid (98%). $^1$H NMR [400 MHz, $(CD_3)_2SO$] δ 8.65 (s, 1H), 8.12 (d, J=2.0 Hz, 1H), 7.90-7.95 (m, 2H), 7.89 (d, J=2.5 Hz, 1H), 7.67 (d, J=3.8 Hz, 1H), 7.64 (dd, J=7.8, 0.5 Hz, 1H), 7.51 (d, J=3.8 Hz, 1H), 7.16 (t, J=2.3 Hz, 1H), 5.49 (s, 2H), 4.41 (s, 2H). LRMS ($APCI^+$) calcd for $C_{17}H_{14}N_3OS$, 308 ($MH^+$). found 308.

Example 82

(49)

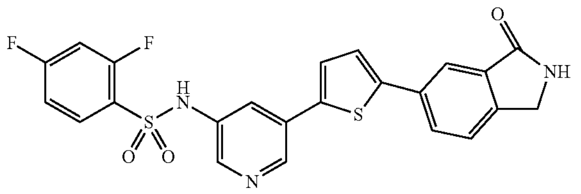

2,4-Difluoro-N-(5-(5-(3-oxoisoindolin-5-yl)thiophen-2-yl)pyridin-3-yl)benzenesulfonamide (49)

6-(5-(5-Aminopyridin-3-yl)thiophen-2-yl)isoindolin-1-one was reacted with 2,4-difluorobenzenesulfonyl chloride according to general procedure E to give the title compound (49) as a pale yellow solid (65%), mp ($MeOH/CH_2Cl_2$) >300° C. $^1$H NMR [400 MHz, $(CD_3)_2SO$] δ 11.14 (br s, 1H), 8.66 (br s, 2H), 8.24 (d, J=2.3 Hz, 1H), 7.98-8.05 (m, 1H), 7.92-8.04 (m, 2H), 7.70-7.73 (m, 2H), 7.65 (dd, J=7.7, 0.7 Hz, 1H), 7.62 (3.8 Hz, 1H), 7.53-7.59 (m, 1H), 7.27-7.33 (m, 1H), 4.42 (s, 2H). LRMS ($APCI^+$) calcd for $C_{23}H_{16}F_2N_3O_3S_2$ 484 ($MH^+$). found 484. Anal. ($C_{23}H_{15}F_2N_3O_3S_2$) C, H, N.

Example 83

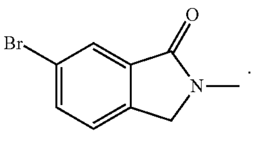

6-Bromo-2-methylisoindolin-1-one

The title compound was prepared by alkylation of 6-bromoisoindolin-1-one with NaI and methyl iodide according to general procedure B to give a pale yellow crystalline solid (85%). $^1$H NMR [400 MHz, $(CD_3)_2SO$] δ7.97 (d, J=1.8 Hz, 1H), 7.64 (dd, J=8.1, 1.9 Hz, 1H), 7.31 (d, J=8.1 Hz, 1H), 4.33 (s, 2H), 3.20 (s, 3H). LRMS ($APCI^+$) calcd for $C_9H_9BrNO$, 226, 228 ($MH^+$). found 226, 228.

Example 84

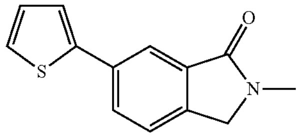 [SMILES: CN1Cc2ccc(-c3cccs3)cc2C1=O]

2-Methyl-6-(thiophen-2-yl)isoindolin-1-one

6-Bromo-2-methylisoindolin-1-one was reacted with thiophene-2-boronic acid according to general procedure C to give the title compound as an off-white solid (97%). $^1$H NMR [400 MHz, $CDCl_3$] δ 8.08 (d, J=1.4 Hz, 1H), 7.77 (dd, J=7.9, 1.8 Hz, 1H), 7.43 (dd, J=7.9, 0.7 Hz, 1H), 7.40 (dd, J=3.6, 1.2 Hz, 1H), 7.31 (dd, J=5.1, 1.1 Hz, 1H), 7.10 (dd, J=5.1, 3.6 Hz, 1H), 4.40 (s, 2H), 3.22 (s, 3H). LRMS ($APCI^+$) calcd for $C_{13}H_{12}NOS$, 230 ($MH^+$). found 230.

Example 85

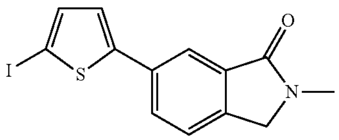 [SMILES: CN1Cc2ccc(-c3ccc(I)s3)cc2C1=O]

6-(5-Iodothiophen-2-yl)-2-methylisoindolin-1-one

Iodination of 2-methyl-6-(thiophen-2-yl)isoindolin-1-one with N-iodosuccinimide according to general procedure D gave the title compound as a pale brown crystalline solid (88%). $^1$H NMR [400 MHz, $CDCl_3$] δ 7.99 (d, J=1.4 Hz, 1H), 7.66 (dd, J=7.9, 1.8 Hz, 1H), 7.43 (dd, J=7.9, 0.7 Hz, 1H), 7.74 (d, J=3.8 Hz, 1H), 7.05 (d, J=3.8 Hz, 1H), 4.39 (s, 2H), 3.22 (s, 3H). LRMS ($APCI^+$) calcd for $C_{13}H_{11}INOS$, 356 ($MH^+$). found 356.

Example 86

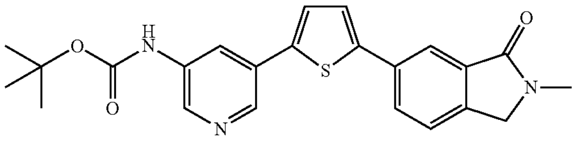 [SMILES: CN1Cc2ccc(-c3ccc(-c4cncc(NC(=O)OC(C)(C)C)c4)s3)cc2C1=O]

tert-Butyl (5-(5-(2-methyl-3-oxoisoindolin-5-yl)thiophen-2-yl)pyridin-3-yl)carbamate 6-(5-Iodothiophen-2-yl)-2-methylisoindolin-1-one was reacted with tert-butyl (5-(4,4,5,5-tetramethyl-1,3,2-dioxaborolan-2-yl)pyridin-3-yl)carbamate according to general procedure C to give the title compound as a pale yellow solid (76%). $^1$H NMR [400 MHz, $(CD_3)_2SO$] δ 9.73 (br s, 1H), 8.60 (d, J=2.0 Hz, 1H), 8.51 (d, J=2.2 Hz, 1H), 8.23 (br s, 1H), 7.91-7.96 (m, 2H), 7.73 (d, J=3.9 Hz, 1H), 7.65 (d, J=8.5 Hz, 1H), 7.61 (d, J=3.8 Hz, 1H), 4.50 (s, 2H), 3.10 (s, 3H), 1.51 (s, 9H). LRMS ($APCI^+$) calcd for $C_{23}H_{24}N_3O_3S$, 422 ($MH^+$). found 422.

Example 87

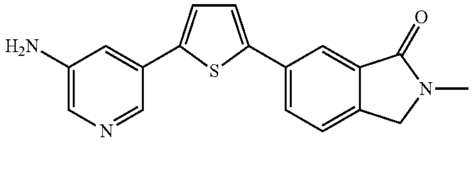 [SMILES: CN1Cc2ccc(-c3ccc(-c4cncc(N)c4)s3)cc2C1=O]

6-(5-(5-Aminopyridin-3-yl)thiophen-2-yl)-2-methylisoindolin-1-one

Deprotection of tert-butyl (5-(5-(2-methyl-3-oxoisoindolin-5-yl)thiophen-2-yl)pyridin-3-yl)carbamate according to general procedure J gave the title compound as a cream solid (100%). $^1$H NMR [400 MHz, $(CD_3)_2SO$] δ 8.12 (d, J=2.0 Hz, 1H), 7.86-7.92 (m, 3H), 7.68 (d, J=3.8 Hz, 1H), 7.64 (d, J=8.4 Hz, 1H), 7.51 (d, J=3.8 Hz, 1H), 7.16 (t, J=2.3 Hz, 1H), 5.49 (br s, 2H), 4.50 (s, 2H), 3.10 (s, 3H). LRMS ($APCI^+$) calcd for $C_{18}H_{16}N_3OS$, 322 ($MH^+$). found 322.

Example 88

(50)

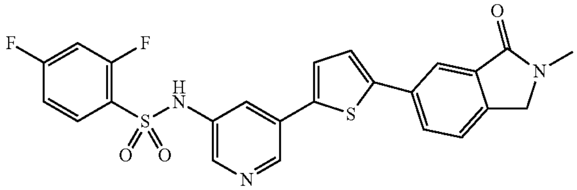

2,4-Difluoro-N-(5-(5-(2-methyl-3-oxoisoindolin-5-yl)thiophen-2-yl)pyridin-3-yl)benzenesulfonamide (50)

6-(5-(5-Aminopyridin-3-yl)thiophen-2-yl)-2-methylisoindolin-1-one was reacted with 2,4-difluorobenzenesulfonyl chloride according to general procedure E to give the title compound (50) as an off-white solid (47%), mp ($MeOH/CH_2Cl_2$) 292-295° C. $^1$H NMR [400 MHz, $(CD_3)_2SO$] δ 11.14 (br s, 1H), 8.68 (d, J=1.9 Hz, 1H), 8.24 (d, J=2.3 Hz, 1H), 7.98-8.05 (m, 1H), 7.91-7.95 (m, 2H), 7.71-7.75 (m, 2H), 7.66 (d, J=8.5 Hz, 1H), 7.62 (d, J=3.8 Hz, 1H), 7.53-7.60 (m, 1H), 7.26-7.32 (m, 1H), 4.51 (s, 2H), 3.10 (s, 3H). LRMS ($APCI^+$) calcd for $C_{24}H_{18}F_2N_3O_3S_2$ 498 ($MH^+$). found 498. Anal. ($C_{24}H_7F_2N_3O_3S_2$) C, H, N.

Example 89

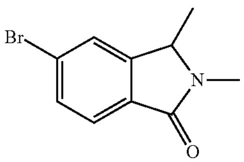

5-Bromo-2,3-dimethylisoindolin-1-one

Methyl 4-Bromo-2-ethylbenzoate was prepared according to a literature procedure (see WO2005040093) then brominated with N-bromosuccinimide and cyclised with methylamine according to general procedure A to give the title compound as a white solid (87% over 2 steps). $^1$H NMR [400 MHz, $CDCl_3$] δ 7.69 (dd, J=7.9, 0.5 Hz, 1H), 7.56-7.60 (m, 2H), 4.42 (q, J=6.8 Hz, 1H), 3.10 (s, 3H), 1.13 (d, J=6.8 Hz, 3H). LRMS ($APCI^+$) calcd for $C_{10}H_{10}BrNO$, 241 ($MH^+$). found 241.

Example 90

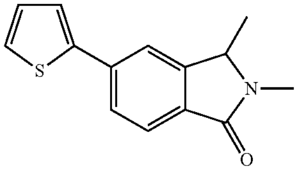 [SMILES: CC1c2cc(-c3cccs3)ccc2C(=O)N1C]

2,3-Dimethyl-5-(thiophen-2-yl)isoindolin-1-one

5-Bromo-2,3-dimethylisoindolin-1-one was reacted with thiophene-2-boronic acid according to general procedure C to give the title compound as a crystalline tan solid (100%). $^1$H NMR [400 MHz, $(CD_3)_2SO$] δ 7.92 (t, J=0.9 Hz, 1H), 7.76 (dd, J=7.9, 1.3 Hz, 1H), 7.65-7.68 (m, 2H), 7.64 (dd, J=5.1, 1.1 Hz, 1H), 7.14 (dd, J=5.1, 3.7 Hz, 1H), 4.59 (q, J=6.7 Hz, 1H), 3.01 (s, 3H), 1.47 (d, J=6.8 Hz, 3H). LRMS ($APCI^+$) calcd for $C_{14}H_{13}NOS$, 244 ($MH^+$). found 244.

Example 91

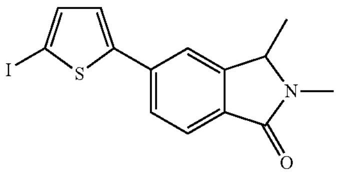 [SMILES: CC1c2cc(-c3ccc(I)s3)ccc2C(=O)N1C]

5-(5-Iodothiophen-2-yl)-2,3-dimethylisoindolin-1-one

Iodination of 2,3-dimethyl-5-(thiophen-2-yl)isoindolin-1-one with N-iodosuccinimide according to general procedure D gave the title compound as a crystalline tan solid (94%). $^1$H NMR [400 MHz, $(CD_3)_2SO$] δ 7.88 (d, J=0.7 Hz, 1H), 7.70 (dd, J=7.9, 1.4 Hz, 1H), 7.65 (dd, J=7.9, 0.3 Hz, 1H), 7.42 (d, J=3.8 Hz, 1H), 7.40 (d, J=3.8 Hz, 1H), 4.58 (q, J=3.7 Hz, 1H), 3.01 (s, 3H), 1.46 (d, J=6.7 Hz, 3H). LRMS ($APCI^+$) calcd for $C_{14}H_{12}INOS$, 370 ($MH^+$). found 370.

Example 92

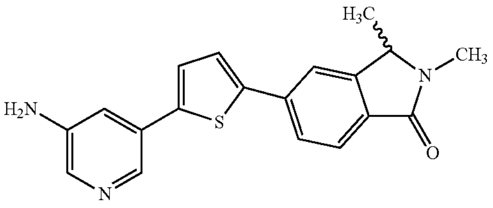 [SMILES: CC1c2cc(-c3ccc(-c4cncc(N)c4)s3)ccc2C(=O)N1C]

5-(5-(5-Aminopyridin-3-yl)thiophen-2-yl)-2,3-dimethylisoindolin-1-one 5-(5-iodothiophen-2-yl)-2,3-dimethylisoindolin-1-one was reacted with 3-aminopyridine-5-boronic acid pinacol ester according to general procedure A. After refluxing for 16 h., the solution was then allowed to cool to room temperature and extracted into 5% $MeOH/CH_2Cl_2$ and washed with $H_2O$. The aqueous layer was further extracted with 5% $MeOH/CH_2Cl_2$ and the organic extracts dried ($Na_2SO_4$), filtered, and concentrated to give a crude solid which was dried onto silica gel. The crude material was chromatographed (1-5% $MeOH/CH_2Cl_2$) to give the title compound as a light-brown solid (86%); mp ($CH_2Cl_2$/MeOH) 239-241° C. $^1$H NMR [400 MHz, $(CD_3)_2SO$] δ 8.13 (d, J=2.0 Hz, 1H), 7.97 (s, 1H), 7.90 (d, J=2.5 Hz, 1H), 7.79 (dd, J=7.9, 1.4 Hz, 1H), 7.70 (t, J=3.8 Hz, 1H), 7.67 (s, 1H), 7.54 (d, J=3.8 Hz, 1H), 7.17 (t, J=2.3 Hz, 1H), 5.50 (br s, 2H), 4.60 (q, J=6.6 Hz, 1H), 3.02 (s, 3H), 1.50 (d, J=6.8 Hz, 3H).

Example 93

(51)

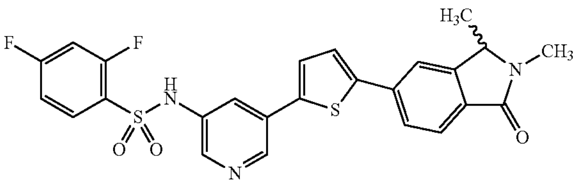

N-(5-(5-(2,3-Dimethyl-1-oxoisoindolin-5-yl)thiophen-2-yl)pyridin-3-yl)-2,4-difluorobenzenesulfonamide (51)

5-(5-(5-Aminopyridin-3-yl)thiophen-2-yl)-2,3-dimethylisoindolin-1-one was reacted with 2,4-difluorobenzenesulphonyl chloride according to general procedure B to give the title compound (51) as a pink solid (19%); mp ($CH_2Cl_2$/MeOH) 229-230° C. $^1$H NMR [400 MHz, $(CD_3)_2SO$] δ 11.15 (br s, 1H), 8.69 (d, J=2.0 Hz, 1H), 8.25 (d, J=2.4 Hz, 1H), 8.00 (m, 2H), 7.82 (dd, J=8.0, 1.4 Hz, 1H), 7.74 (m, 2H), 7.70 (d, J=7.9 Hz, 1H), 7.65 (d, J=3.9 Hz, 1H), 7.56 (dt, J=8.2, 2.4 Hz, 1H), 7.30 (dt, J=8.2, 2.0 Hz, 1H), 4.61 (q, J=6.7 Hz, 1H), 3.02 (s, 3H), 1.50 (d, J=0.2 Hz, 3H). Anal. ($C_{25}H_{19}F_2N_3O_3S_2$) C, H, N.

In this case the product was converted to its sodium salt according to general procedure F to give the desired product as a brown solid (90%). $^1$H NMR [400 MHz, $(CD_3)_2SO$] δ 8.07 (d, J=2.1 Hz, 1H), 7.95 (s, 1H), 7.91 (d, J=2.4 Hz, 1H), 7.81-7.89 (m, 1H), 7.78 (dd, J=7.9, 1.4 Hz, 1H), 7.63-7.70 (m, 2H), 7.40-7.45 (m, 2H), 7.18 (dt, J=8.7, 2.5 Hz, 1H), 7.07 (dt, J=8.4, 2.2 Hz, 1H), 4.60 (q, J=6.6 Hz, 1H), 3.01 (s, 3H), 1.48 (d, J=0.2 Hz, 3H).

Example 94

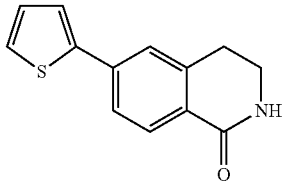 [SMILES: O=C1NCCc2cc(-c3cccs3)ccc21]

6-(Thiophen-2-yl)-3,4-dihydroisoquinolin-1(2H)-one

6-Bromo-3,4-dihydroisoquinolin-1(2H)-one was reacted with thiophene-2-boronic acid according to general procedure C to give the title compound as an off-white solid (100%). $^1$H NMR [400 MHz, $(CD_3)_2SO$] δ 7.92 (br s, 1H), 7.85 (d, J=8.0 Hz, 1H), 7.59-7.65 (m, 4H), 7.17 (t, J=4.3 Hz, 1H), 3.36-3.41 (m, 2H), 2.95 (t, J=6.6 Hz, 2H). LRMS ($APCI^+$) calcd for $C_{13}H_{12}NOS$, 230 ($MH^+$). found 230.

Example 95

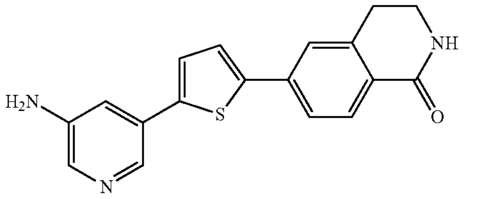 [SMILES: Nc1cncc(-c2ccc(-c3ccc4c(c3)CCNC4=O)s2)c1]

6-(5-(5-Aminopyridin-3-yl)thiophen-2-yl)-3,4-dihydroisoquinolin-1(2H)-one 6-(Thiophen-2-yl)-3,4-dihydroisoquinolin-1(2H)-one was iodinated according to general procedure D to give 6-(5-iodothiophen-2-yl)-3,4-dihydroisoquinolin-1(2H)-one which was then used directly in a reaction with 3-aminopyridine-5-boronic acid pinacol-ester according to general procedure C. After refluxing for 16 h., the solution was allowed to cool to room temperature and extracted into 5% MeOH/$CH_2Cl_2$ and washed with $H_2O$. The aqueous layer was further extracted with 5% MeOH/$CH_2Cl_2$ and the organic extracts dried ($Na_2SO_4$), filtered, and concentrated to give a crude solid which was dried onto silica gel. The crude material was chromatographed (1-5% MeOH/$CH_2Cl_2$) to give the title compound as a green solid (86%); mp ($CH_2Cl_2$/MeOH) 277-280° C. $^1$H NMR [400 MHz, $(CD_3)_2SO$] δ 8.12 (d, J=2.0 Hz, 1H), 7.94 (br s, 1H), 7.89 (d, J=2.5 Hz, 1H), 7.87 (d, J=8.0 Hz, 1H), 7.61 (m, 3H), 7.53 (d, J=3.8 Hz, 1H), 7.15 (t, J=2.2 Hz, 1H), 5.50 (s, 2H), 3.40 (dt, J=6.6, 2.7 Hz, 2H), 2.96 (t, J=6.5 Hz, 2H).

Example 96

(52)

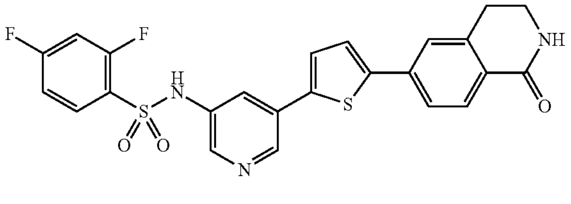

2,4-Difluoro-N-(5-(5-(1-oxo-1,2,3,4-tetrahydroisoquinolin-6-yl)thiophen-2-yl)pyridin-3-yl)benzensulphonamide (52)

6-(5-(5-Aminopyridin-3-yl)thiophen-2-yl)-3,4-dihydroisoquinolin-1(2H)-one was reacted with 2,4-difluorobenzenesulphonyl chloride according to general procedure B to give the title compound (52) as a yellow solid (15%); mp 267-270° C. $^1$H NMR [400 MHz, $(CD_3)_2SO$] δ 11.14 (br s, 1H), 8.69 (d, J=1.6 Hz, 1H), 8.25 (d, J=2.2 Hz, 1H), 7.96-8.06 (m, 1H), 7.95 (br s, 1H), 7.88 (d, J=8.0 Hz, 1H), 7.65-7.76 (m, 4H), 7.64 (d, J=3.8 Hz, 1H), 7.57 (dt, J=8.4, 2.3 Hz, 1H), 7.30 (dt, J=8.4, 2.3 Hz, 1H), 3.40 (dt, J=6.6, 2.4 Hz, 2H), 2.97 (t, J=6.4 Hz, 2H). HRMS (APCI$^+$) calcd for $C_{24}H_{17}F_2N_3O_3S_2$ 498.0752 (MH$^+$). found 498.0753.

In this case the product was converted to its sodium salt according to general procedure F to give the desired product as a light-brown solid (90%). $^1$H NMR [400 MHz, $(CD_3)_2SO$] δ 8.07 (d, J=2.1 Hz, 1H), 7.92 (br s, 1H), 7.90 (d, J=2.4 Hz, 1H), 7.80-7.88 (m, 2H), 7.66 (dd, J=8.0, 1.7 Hz, 1H), 7.63 (s, 1H), 7.62 (d, J=3.8 Hz, 1H), 7.38-7.44 (m, 2H), 7.18 (dt, J=9.7, 2.5 Hz, 1H), 7.07 (dt, J=9.2, 2.7 Hz, 1H), 3.40 (dt, J=6.4, 2.9 Hz, 2H), 2.97 (t, J=6.5 Hz, 2H).

Example 97

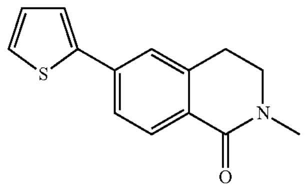 [SMILES: CN1CCc2cc(-c3cccs3)ccc2C1=O]

2-Methyl-6-(thiophen-2-yl)-3,4-dihydroisoquinolin-1(2H)-one 6-(Thiophen-2-yl)-3,4-dihydroisoquinolin-1(2H)-one was alkylated with methyl iodide according to general procedure B to give the title compound as a cream solid (1.35 g, 78%). $^1$H NMR [400 MHz, $(CD_3)_2SO$] δ 7.87 (d, J=8.1 Hz, 1H), 7.61-7.65 (m, 3H), 5.57 (br s, 1H), 7.17 (dd, J=4.9, 3.8 Hz, 1H), 3.56 (t, J=6.7 Hz, 2H), 3.00-3.04 (m, 5H). LRMS (APCI$^+$) calcd for $C_{14}H_{14}NOS$, 244 (MH$^+$). found 244.

Example 98

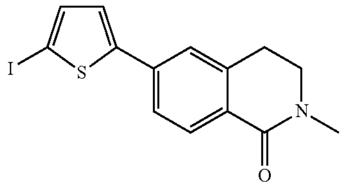 [SMILES: CN1CCc2cc(-c3ccc(I)s3)ccc2C1=O]

6-(5-Iodothiophen-2-yl)-2-methyl-3,4-dihydroisoquinolin-1(2H)-one

Iodination of 2-methyl-6-(thiophen-2-yl)-3,4-dihydroisoquinolin-1(2H)-one with N-iodosuccinimide according to general procedure D gave the title compound as a cream solid (37%). $^1$H NMR [400 MHz, $(CD_3)_2SO$] δ 7.86 (d, J=8.0 Hz, 1H), 7.52-7.60 (m, 2H), 7.40 (d, J=3.8 Hz, 1H), 7.34 (d, J=3.8 Hz, 1H), 3.55 (t, J=6.7 Hz, 2H), 2.97-3.04 (m, 5H). LRMS (APCI$^+$) calcd for $C_{14}H_{13}INOS$, 370 (MH$^+$). found 370.

Example 99

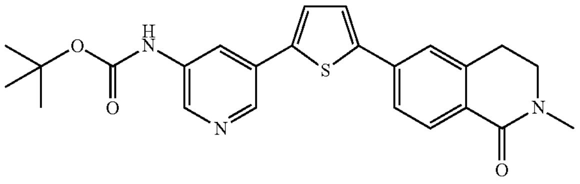 [SMILES: CN1CCc2cc(-c3ccc(-c4cncc(NC(=O)OC(C)(C)C)c4)s3)ccc2C1=O]

tert-Butyl (5-(5-(2-methyl-1-oxo-1,2,3,4-tetrahydroisoquinolin-6-yl)thiophen-2-yl)pyridin-3-yl)carbamate 6-(5-Iodothiophen-2-yl)-2-methyl-3,4-dihydroisoquinolin-1(2H)-one was reacted with tert-butyl (5-(4,4,5,5-tetramethyl-1,3,2-dioxaborolan-2-yl)pyridin-3-yl)carbamate according to general procedure C to give the title compound as a cream solid (55%). $^1$H NMR [400 MHz, $(CD_3)_2SO$] δ 9.74 (br s, 1H), 8.61 (d, J=2.1 Hz, 1H), 8.50 (d, J=2.3 Hz, 1H), 8.26 (br s, 1H), 7.90 (d, J=8.1 Hz, 1H), 7.68-7.72 (m, 2H), 7.63-7.67 (m, 2H), 3.57 (t, J=6.7 Hz, 2H), 3.02-3.07 (m, 5H), 1.51 (s, 9H). LRMS ($APCI^+$) calcd for $C_{24}H_{26}N_3O_3S$, 436 ($MH^+$). found 436.

Example 100

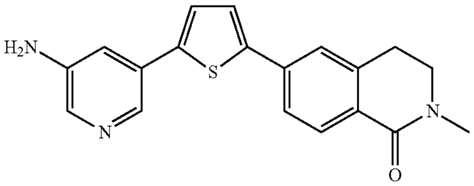 [SMILES: CN1CCc2cc(-c3ccc(-c4cncc(N)c4)s3)ccc2C1=O]

6-(5-(5-Aminopyridin-3-yl)thiophen-2-yl)-2-methyl-3,4-dihydroisoquinolin-1(2H)-one Deprotection of tert-butyl (5-(5-(2-methyl-1-oxo-1,2,3,4-tetrahydroisoquinolin-6-yl)thiophen-2-yl)pyridin-3-yl)carbamate according to general procedure J gave the title compound as a cream solid (92%). $^1$H NMR [400 MHz, $(CD_3)_2SO$] δ 8.12 (d, J=2.0 Hz, 1H), 7.87-7.91 (m, 2H), 7.64-7.68 (m, 2H), 7.62 (br s, 1H), 7.53 (d, J=3.8 Hz, 1H), 7.16 (t, J=2.3 Hz, 1H), 3.57 (t, J=6.7 Hz, 2H), 3.01-3.06 (m, 5H). LRMS ($APCI^+$) calcd for $C_{19}H_{18}N_3OS$, 336 ($MH^+$). found 336.

Example 101

(63)

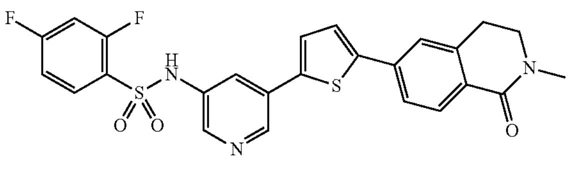

2,4-Difluoro-N-(5-(5-(2-methyl-1-oxo-1,2,3,4-tetrahydroisoquinolin-6-yl)thiophen-2-yl)pyridin-3-yl)benzenesulfonamide (53)

(5-(5-Aminopyridin-3-yl)thiophen-2-yl)-2-methyl-3,4-dihydroisoquinolin-1(2H)-one was reacted with 2,4-difluorobenzenesulfonyl chloride according to general procedure E to give the title compound (53) as an off-white solid (93%), mp ($MeOH/CH_2Cl_2$) 262-265° C. $^1$H NMR [400 MHz, $(CD_3)_2SO$] δ 11.15 (br s, 1H), 8.67 (br s, 1H), 8.24 (d, J=1.9 Hz, 1H), 7.96-8.03 (m, 1H), 7.91 (d, J=8.1 Hz, 1H), 7.62-7.73 (m, 5H), 7.52-7.59 (m, 1H), 7.26-7.33 (m, 1H), 3.57 (t, J=6.7 Hz, 2H), 3.01-3.07 (m, 5H). LRMS ($APCI^+$) calcd for $C_{25}H_{20}F_2N_3O_3S_2$ 512 ($MH^+$). found 512. Anal. ($C_{25}H_{19}F_2N_3O_3S_2$) C, H, N.

Example 102

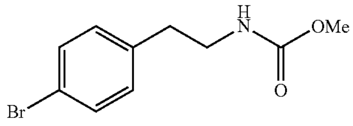 [SMILES: COC(=O)NCCc1ccc(Br)cc1]

Methyl 4-bromophenethylcarbamate

Adaption of a literature procedure (Ortwine, D. F., et al., *J. Med. Chem.* 1992, 35, 1345-70) gave the title compound as a pale yellow oil (94%). $^1$H NMR [400 MHz, $CDCl_3$] δ 7.43 (d, J=8.4 Hz, 2H), 7.06 (d, J=8.3 Hz, 2H), 4.65 (bs, 1H), 3.65 (s, 3H), 3.41 (q, J=6.3 Hz, 2H), 2.77 (t, J=7.0 Hz, 2H). LRMS ($APCI^+$) calcd for $C_{10}H_{13}BrNO_2$ 259 ($MH^+$). found 259.

Example 103

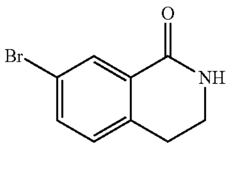 [SMILES: O=C1NCCc2ccc(Br)cc21]

7-Bromo-3,4-dihydroisoquinolin-1(2H)-one

Cyclisation of methyl 4-bromophenethylcarbamate was carried out by adaption of a literature procedure (Wang, X.-J., et al., *Tetrahedron Lett.* 1998, 39, 6609-6612) to give the title compound as a white solid (20%). $^1$H NMR [400 MHz, $CDCl_3$] δ 8.20 (d, J=2.1 Hz, 1H), 7.55 (dd, J=8.1, 2.2 Hz, 1H), 7.09 (d, J=8.1 Hz, 1H), 6.12 (bs, 1H), 3.55 (dt, J=6.2, 2.9 Hz, 2H), 2.94 (t, J=6.6 Hz, 2H). LRMS ($APCI^+$) calcd for $C_9H_9BrNO$, 227 ($MH^+$). found 227.

Example 104

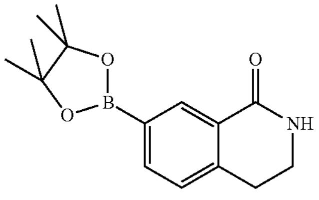 [SMILES: CC1(C)OB(c2ccc3c(c2)C(=O)NCC3)OC1(C)C]

7-(4,4,5,5-Tetramethyl-1,3,2-dioxaborolan-2-yl)-3,4-dihydroisoquinolin-1(2H)-one 7-Bromo-3,4-dihydroisoquinolin-1(2H)-one was converted to the boronate 7-(4,4,5,5-tetramethyl-1,3,2-dioxaborolan-2-yl)-3,4-dihydroisoquinolin-1(2H)-one according to general procedure I to give the title compound as a light brown solid (378 mg, 47%). $^1$H NMR [400 MHz, $CDCl_3$] δ 8.53 (s, 1H), 7.86 (dd, J=7.5, 1.3 Hz, 1H), 7.21 (d, J=7.4 Hz, 1H), 5.88 (br s, 1H), 3.55 (dt, J=6.6, 2.9 Hz, 2H), 3.01 (t, J=6.6 Hz, 2H), 1.33 (s, 12H). LRMS (APCI$^+$) calcd for $C_{15}H_{21}BNO_3$ 274 (MH$^+$). found 274.

Example 105

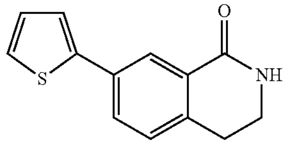 [SMILES: O=C1NCCc2ccc(-c3cccs3)cc21]

7-(Thiophen-2-yl)-3,4-dihydroisoquinolin-1(2H)-one 7-(4,4,5,5-Tetramethyl-1,3,2-dioxaborolan-2-yl)-3,4-dihydroisoquinolin-1(2H)-one was reacted with 2-bromothiophene according to general procedure C to give the title compound as an off-white solid (74%). $^1$H NMR [400 MHz, $CDCl_3$] δ 8.33 (d, J=2.0 Hz, 1H), 7.69 (dd, J=7.9 Hz, 1H), 7.38 (dd, J=3.6, 1.1 Hz, 1H), 7.29 (dd, J=5.1, 1.1 Hz, 1H), 7.24 (d, J=8.0 Hz, 1H), 7.09 (dd, J=5.1, 3.6 Hz, 1H), 6.02 (br s, 1H), 3.56-3.62 (m, 2H), 3.02 (t, J=6.6 Hz, 2H). LRMS (APCI$^+$) calcd for $C_{13}H_{12}NOS$, 230 (MH$^+$). found 230.

Example 106

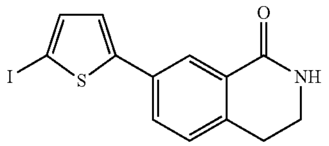 [SMILES: O=C1NCCc2ccc(-c3ccc(I)s3)cc21]

7-(5-Iodothiophen-2-yl)-3,4-dihydroisoquinolin-1(2H)-one

Iodination of 7-(thiophen-2-yl)-3,4-dihydroisoquinolin-1(2H)-one with N-iodosuccinimide according to general procedure D gave the title compound as a pale grey solid (79%). $^1$H NMR [400 MHz, $CDCl_3$] δ 8.04 (br s, 1H), 7.97 (d, J=2.0 Hz, 1H), 7.72 (dd, J=7.9, 2.1 Hz, 1H), 7.34-7.38 (m, 2H), 7.27 (d, J=3.8 Hz, 1H), 3.35-3.40 (m, 2H), 2.91 (t, J=6.6 Hz, 2H). LRMS (APCI$^+$) calcd for $C_{13}H_{11}INOS$, 356 (MH$^+$). found 356.

Example 107

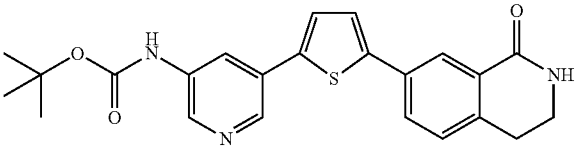 [SMILES: CC(C)(C)OC(=O)Nc1cncc(-c2ccc(-c3ccc4c(c3)C(=O)NCC4)s2)c1]

tert-Butyl (5-(5-(1-oxo-1,2,3,4-tetrahydroisoquinolin-7-yl)thiophen-2-yl)pyridin-3-yl)carbamate 7-(5-Iodothiophen-2-yl)-3,4-dihydroisoquinolin-1(2H)-one was reacted with tert-butyl (5-(4,4,5,5-tetramethyl-1,3,2-dioxaborolan-2-yl)pyridin-3-yl)carbamate according to general procedure C to give the title compound as a dark yellow solid (88%). $^1$H NMR [400 MHz, $(CD_3)_2SO$] δ 9.72 (br s, 1H), 8.59 (d, J=2.0 Hz, 1H), 8.51 (d, J=2.3 Hz, 1H), 8.23 (br s, 1H), 8.10 (d, J=2.0 Hz, 1H), 8.06 (br s, 1H), 7.85 (dd, J=7.9, 2.1 Hz, 1H), 7.62 (d, J=3.8 Hz, 1H), 7.60 (d, J=3.8 Hz, 1H), 7.40 (d, J=8.0 Hz, 1H), 3.37-3.42 (m, 2H), 2.93 (t, J=6.5 Hz, 2H), 1.51 (s, 9H). LRMS (APCI$^+$) calcd for $C_{23}H_{24}N_3O_3S$, 422 (MH$^+$). found 422.

Example 108

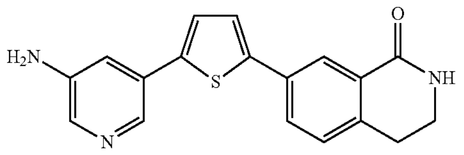 [SMILES: Nc1cncc(-c2ccc(-c3ccc4c(c3)C(=O)NCC4)s2)c1]

7-(5-(5-Aminopyridin-3-yl)thiophen-2-yl)-3,4-dihydroisoquinolin-1(2H)-one

Deprotection of tert-butyl (5-(5-(1-oxo-1,2,3,4-tetrahydroisoquinolin-7-yl)thiophen-2-yl)pyridin-3-yl)carbamate according to general procedure J gave the title compound as a pale yellow solid (98%). $^1$H NMR [400 MHz, $(CD_3)_2SO$] δ 8.12 (d, J=2.0 Hz, 1H), 8.09 (d, J=2.0 Hz, 1H), 8.05 (br s, 1H), 7.89 (d, J=2.4 Hz, 1H), 7.83 (dd, J=7.9, 2.1 Hz, 1H), 7.59 (d, J=3.8 Hz, 1H), 7.50 (d, J=3.9 Hz, 1H), 7.40 (d, J=8.0 Hz, 1H), 7.18 (t, J=2.2 Hz, 1H), 5.49 (br s, 2H), 3.37-3.43 (m, 2H), 2.94 (t, J=6.5 Hz, 2H). LRMS (APCI$^+$) calcd for $C_{18}H_{16}N_3OS$, 322 (MH$^+$). found 322.

Example 109

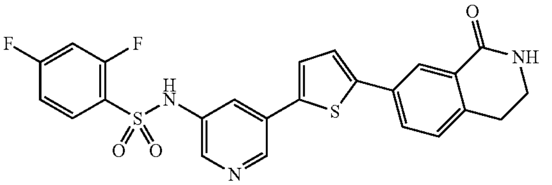

(54)

2,4-Difluoro-N-(5-(5-(1-oxo-1,2,3,4-tetrahydroisoquinolin-7-yl)thiophen-2-yl)pyridin-3-yl)benzenesulfonamide (54)

7-(5-(5-Aminopyridin-3-yl)thiophen-2-yl)-3,4-dihydroisoquinolin-1(2H)-one was reacted with 2,4-difluorobenzenesulfonyl chloride according to general procedure E to give the title compound (54) as a dark yellow solid (74%), mp (MeOH/$CH_2Cl_2$) 252° C. (dec.). $^1$H NMR [400 MHz, $(CD_3)_2SO$] δ 11.14 (br s, 1H), 8.70 (d, J=2.0 Hz, 1H), 8.25 (d, J=2.4 Hz, 1H), 8.10 (d, J=2.1 Hz, 1H), 8.07 (br s, 1H), 7.98-8.05 (m, 1H), 7.84 (dd, J=7.8, 2.1 Hz, 1H), 7.74 (t, J=2.2 Hz, 1H), 7.54-7.64 (m, 3H), 7.41 (d, J=8.0 Hz, 1H), 7.27-7.33 (m, 1H), 3.37-3.43 (m, 2H), 2.94 (t, J=6.5 Hz, 2H). LRMS (APCI$^+$) calcd for $C_{24}H_{18}F_2N_3O_3S_2$ 498 (MH$^+$). found 498. Anal. ($C_{24}H_{17}F_2N_3O_3S_2.H_2O$) C, H, N.

Example 110

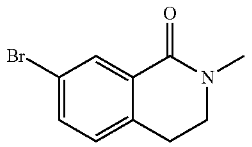

7-Bromo-2-methyl-3,4-dihydroisoquinolin-1(2H)-one

7-Bromo-3,4-dihydroisoquinolin-1(2H)-one was methylated according to general procedure B to give the title compound as a pale yellow waxy solid (95%). $^1$H NMR [400 MHz, $CDCl_3$] δ 8.21 (d, J=2.2 Hz, 1H), 7.52 (dd, J=8.0, 2.1 Hz, 1H), 7.05 (d, J=7.9 Hz, 1H), 3.56 (t, J=6.6 Hz, 2H), 3.15 (s, 3H), 2.96 (t, J=6.8 Hz, 2H). LRMS (APCI$^+$) calcd for $C_{10}H_{11}BrNO$, 240, 242 (MH$^+$). found 240, 242.

Example 111

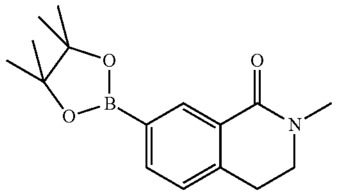

2-Methyl-7-(4,4,5,5-tetramethyl-1,3,2-dioxaborolan-2-yl)-3,4-dihydroisoquinolin-1(2H)-one 7-Bromo-2-methyl-3,4-dihydroisoquinolin-1(2H)-one was reacted with bis(pinacolato)diboron according to general procedure I to give the title compound as a white solid (100%). $^1$H NMR [400 MHz, $CDCl_3$] δ 8.53 (d, J=0.6 Hz, 7.82 (dd, J=7.4, 1.2 Hz, 1H), 7.16 (dd, J=7.4, 0.4 Hz, 1H), 3.55 (t, J=6.7 Hz, 2H), 3.15 (s, 3H), 3.01 (t, J=6.6 Hz, 2H), 1.33 (s, 12H). LRMS (APCI$^+$) calcd for $C_{16}H_{22}BNO_3$ 288 (MH$^+$). found 288.

Example 112

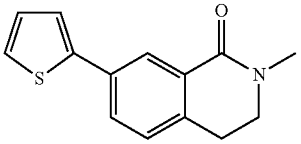 [SMILES: CN1CCc2ccc(-c3cccs3)cc2C1=O]

2-Methyl-7-(thiophen-2-yl)-3,4-dihydroisoquinolin-1(2H)-one

2-Methyl-7-(4,4,5,5-tetramethyl-1,3,2-dioxaborolan-2-yl)-3,4-dihydroisoquinolin-1(2H)-one was reacted with 2-bromothiophene according to general procedure C to give the title compound as a cream solid (73%). $^1$H NMR [400 MHz, $CDCl_3$] δ 8.34 (d, J=2.0 Hz, 1H), 7.64 (dd, J=7.8, 2.1 Hz, 1H), 7.38 (dd, J=3.6, 1.2 Hz, 1H), 7.28 (dd, J=5.1, 1.1 Hz, 1H), 7.18 (d, J=7.7 Hz, 1H), 7.08 (dd, J=5.1, 3.6 Hz, 1H), 3.58 (t, J=6.7 Hz, 2H), 3.18 (s, 3H), 3.01 (t, J=6.7 Hz, 2H). LRMS (APCI$^+$) calcd for $C_{14}H_{14}NOS$, 244 (MH$^+$). found 244.

Example 113

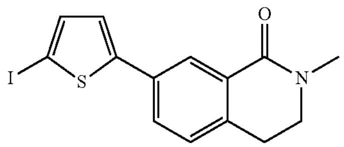 [SMILES: CN1CCc2ccc(-c3ccc(I)s3)cc2C1=O]

7-(5-Iodothiophen-2-yl)-2-methyl-3,4-dihydroisoquinolin-1(2H)-one

Iodination of 2-methyl-7-(thiophen-2-yl)-3,4-dihydroisoquinolin-1(2H)-one with N-iodosuccinimide according to general procedure D gave the title compound as a waxy grey solid (93%). $^1$H NMR [400 MHz, $(CD_3)_2SO$] δ7.99 (d, J=2.0 Hz, 1H), 7.72 (dd, J=7.9, 2.1 Hz, 1H), 7.37 (d, J=3.8 Hz, 1H), 7.34 (d, J=8.0 Hz, 1H), 7.26 (d, J=3.8 Hz, 1H), 3.56 (t, J=6.7 Hz, 2H), 3.04 (s, 3H), 2.98 (t, J=6.6 Hz, 2H). LRMS (APCI$^+$) calcd for $C_{14}H_{13}INOS$, 370 (MH$^+$). found 370.

Example 114

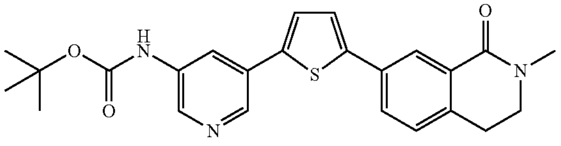 [SMILES: CN1CCc2ccc(-c3ccc(-c4cncc(NC(=O)OC(C)(C)C)c4)s3)cc2C1=O]

tert-Butyl (5-(5-(2-methyl-1-oxo-1,2,3,4-tetrahydroisoquinolin-7-yl)thiophen-2-yl)pyridin-3-yl)carbamate 7-(5-Iodothiophen-2-yl)-2-methyl-3,4-dihydroisoquinolin-1(2H)-one was reacted with tert-butyl (5-(4,4,5,5-tetramethyl-1,3,2-dioxaborolan-2-yl)pyridin-3-yl)carbamate according to general procedure C to give the title compound as a cream solid (92%). $^1$H NMR [400 MHz, $(CD_3)_2SO$] δ 9.72 (br s, 1H), 8.59 (d, J=2.0 Hz, 1H), 8.51 (d, J=2.3 Hz, 1H), 8.22 (br s, 1H), 8.12 (d, J=2.0 Hz, 1H), 7.84 (dd, J=7.9, 2.1 Hz, 1H), 7.59-7.63 (m, 2H), 7.38 (d, J=8.0 Hz, 1H), 3.58 (t, J=6.7 Hz, 2H), 3.06 (s, 3H), 3.01 (t, J=6.6 Hz, 2H), 1.51 (s, 9H). LRMS ($APCI^+$) calcd for $C_{24}H_{26}N_3O_3S$, 436 ($MH^+$). found 436.

Example 115

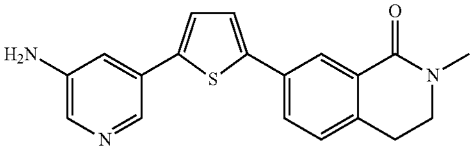 [SMILES: CN1CCc2ccc(-c3ccc(-c4cncc(N)c4)s3)cc2C1=O]

7-(5-(5-Aminopyridin-3-yl)thiophen-2-yl)-2-methyl-3,4-dihydroisoquinolin-1(2H)-one Deprotection of tert-butyl (5-(5-(2-methyl-1-oxo-1,2,3,4-tetrahydroisoquinolin-7-yl)thiophen-2-yl)pyridin-3-yl)carbamate according to general procedure J gave the title compound as a pale yellow solid (100%). $^1$H NMR [400 MHz, $(CD_3)_2SO$] δ 8.12 (d, J=2.0 Hz, 1H), 8.10 (d, J=2.0 Hz, 1H), 7.88 (d, J=2.5 Hz, 1H), 7.81 (dd, J=7.9, 2.1 Hz, 1H), 7.57 (d, J=3.8 Hz, 1H), 7.50 (d, J=3.8 Hz, 1H), 7.37 (d, J=8.0 Hz, 1H), 7.17 (t, J=2.3 Hz, 1H), 3.57 (t, J=6.7 Hz, 2H), 3.05 (s, 3H), 3.00 (t, J=6.6 Hz, 2H). LRMS ($APCI^+$) calcd for $C_{19}H_{18}N_3OS$, 336 ($MH^+$). found 336.

Example 116

(55)

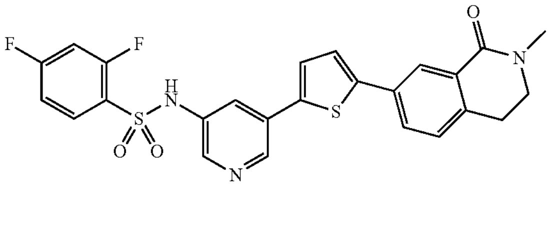

2,4-Difluoro-N-(5-(5-(2-methyl-1-oxo-1,2,3,4-tetrahydroisoquinolin-7-yl)thiophen-2-yl)pyridin-3-yl)benzenesulfonamide (55)

7-(5-(5-Aminopyridin-3-yl)thiophen-2-yl)-2-methyl-3,4-dihydroisoquinolin-1(2H)-one was reacted with 2,4-difluorobenzenesulfonyl chloride according to general procedure E to give the title compound (55) as an off-white solid (80%), mp ($MeOH/CH_2Cl_2$) 280-283° C. $^1$H NMR [400 MHz, $(CD_3)_2SO$] δ 11.12 (br s, 1H), 8.67 (br s, 1H), 8.24 (d, J=2.4 Hz, 1H), 8.11 (d, J=2.0 Hz, 1H), 7.97-8.04 (m, 1H), 7.84 (dd, J=7.8, 2.1 Hz, 1H), 7.72 (t, J=2.2 Hz, 1H), 7.53-7.62 (m, 3H), 7.37 (d, J=8.0 Hz, 1H), 7.26-7.32 (m, 1H), 3.58 (t, J=6.7 Hz, 2H), 3.06 (s, 3H), 3.01 (t, J=6.7 Hz, 2H). LRMS ($APCI^+$) calcd for $C_{25}H_{20}F_2N_3O_3S_2$ 512 ($MH^+$). found 512. Anal. ($C_{25}H_{19}F_2N_3O_3S_2$) C, H, N.

Example 117

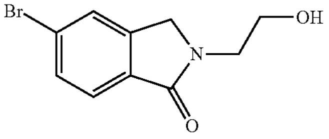 [SMILES: O=C1c2ccc(Br)cc2CN1CCO]

5-Bromo-2-(2-hydroxyethyl)isoindolin-1-one

Methyl 4-bromo-2-methylbenzoate was brominated with N-bromosuccinimide and cyclised with ethanolamine according to general procedure A, to give the title compound as a white crystalline solid (54%). $^1$H NMR [400 MHz, $(CD_3)_2SO$] δ 7.86 (d, J=0.9 Hz, 1H), 7.67 (dd, J=8.0, 1.7 Hz, 1H), 7.60 (d, J=8.0 Hz, 1H), 4.81 (t, J=5.4 Hz, 1H), 4.55 (s, 2H), 3.59-3.64 (m, 2H), 3.53-3.58 (m, 2H). LRMS ($APCI^+$) calcd for $C_{10}H_{11}BrNO_2$ 256, 258 ($MH^+$). found 256, 258.

Example 118

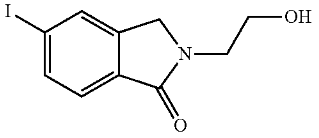 [SMILES: O=C1c2ccc(I)cc2CN1CCO]

2-(2-Hydroxyethyl)-5-iodoisoindolin-1-one

5-Bromo-2-(2-hydroxyethyl)isoindolin-1-one (757 mg, 2.96 mmol), CuI (28 mg, 0.15 mmol), NaI (887 mg, 5.92 mmol) and (±)-trans-N,N'-dimethyl-1,2-cyclohexanediamine (42 mg, 0.30 mmol) were added to an oven-dried pressure tube, 1,4-dioxane (5 mL) added, then the tube sealed under $N_2$ and the entire mixture heated at 130° C. for 24 h. Upon cooling, $c.NH_3$ (25 mL) was added and the mixture stirred until the resulting precipitate achieved a uniform appearance. This suspension was poured into water (100 mL) and extracted with $CH_2Cl_2$ (4×50 mL). The combined $CH_2Cl_2$ fractions were dried ($Na_2SO_4$), filtered, and the solvent removed under reduced pressure to give the crude product. This solid was triturated with $Et_2O$ and collected by filtration to give the title compound as a beige crystalline solid (629 mg, 70%). $^{1}$H NMR [400 MHz, $(CD_3)_2SO$] δ 8.03 (br s, 1H), 7.84 (br d, J=7.9 Hz, 1H), 7.45 (d, J=7.9 Hz, 1H), 4.83 (t, J=5.2 Hz, 1H), 4.52 (s, 2H), 3.58-3.63 (m, 2H), 3.52-3.57 (m, 2H). LRMS (APCI$^+$) calcd for $C_{10}H_{11}INO_2$ 304 (MH$^+$). found 304.

Example 119

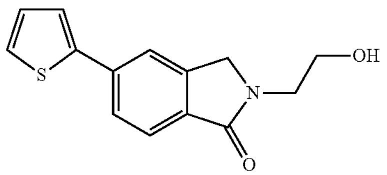 [SMILES: O=C1c2ccc(-c3cccs3)cc2CN1CCO]

2-(2-Hydroxyethyl)-5-(thiophen-2-yl)isoindolin-1-one 2-(2-Hydroxyethyl)-5-iodoisoindolin-1-one was reacted with thiophene-2-boronic acid according to general procedure C to give the title compound as a crystalline brown solid (96%). $^{1}$H NMR [400 MHz, $(CD_3)_2SO$] δ7.88 (br s, 0.7 Hz, 1H), 7.78 (dd, J=7.9, 1.5 Hz, 1H), 7.69 (d, J=7.9 Hz, 1H), 7.62-7.66 (m, 2H), 7.19 (dd, J=5.1, 3.7 Hz, 1H), 4.84 (t, J=5.4 Hz, 1H), 4.58 (s, 2H), 3.55-3.66 (m, 4H). LRMS (APCI$^+$) calcd for $C_{14}H_{14}NO_2S$, 260 (MH$^+$). found 260.

Example 120

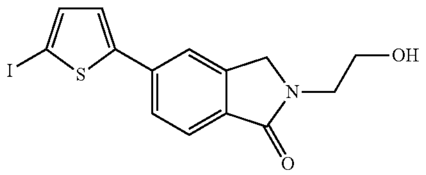 [SMILES: O=C1c2ccc(-c3ccc(I)s3)cc2CN1CCO]

2-(2-Hydroxyethyl)-5-(5-iodothiophen-2-yl)isoindolin-1-one

Iodination of 2-(2-hydroxyethyl)-5-(thiophen-2-yl)isoindolin-1-one with N-iodosuccinimide according to general procedure D gave title compound as a pale brown crystalline solid (74%). $^{1}$H NMR [400 MHz, $(CD_3)_2SO$] δ 7.83 (br d, J=0.7 Hz, 1H), 7.72 (dd, J=8.0, 1.5 Hz, 1H), 7.68 (dd, J=8.0, 0.5 Hz, 1H), 7.41 (d, J=3.4 Hz, 1H), 7.37 (d, J=3.8 Hz, 1H), 4.84 (t, J=5.4 Hz, 1H), 4.57 (s, 2H), 3.54-3.65 (m, 4H). LRMS (APCI$^+$) calcd for $C_{14}H_{13}INO_2S$, 386 (MH$^+$). found 386.

Example 121

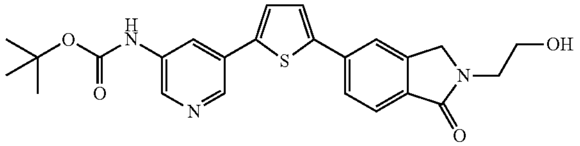 [SMILES: CC(C)(C)OC(=O)Nc1cncc(-c2ccc(-c3ccc4c(c3)CN(CCO)C4=O)s2)c1]

tert-Butyl (5-(5-(2-(2-hydroxyethyl)-1-oxoisoindolin-5-yl)thiophen-2-yl)pyridin-3-yl)carbamate 2-(2-Hydroxyethyl)-5-(5-iodothiophen-2-yl)isoindolin-1-one was reacted with tert-butyl (5-(4,4,5,5-tetramethyl-1,3,2-dioxaborolan-2-yl)pyridin-3-yl)carbamate according to general procedure C to give the title compound as a yellow solid (91%). $^{1}$H NMR [400 MHz, $(CD_3)_2SO$] δ 9.75 (s, 1H), 8.61 (d, J=2.1 Hz, 1H), 8.51 (d, J=2.3 Hz, 1H), 8.26 (br s, 1H), 7.96 (d, J=0.7 Hz, 1H), 7.84 (dd, J=8.0, 1.5 Hz, 1H), 7.69-7.74 (m, 2H), 7.65 (d, J=3.9 Hz, 1H), 4.85 (t, J=5.2 Hz, 1H), 4.60 (s, 2H), 3.56-3.66 (m, 4H), 1.51 (s, 9H). LRMS (APCI$^+$) calcd for $C_{24}H_{26}N_3O_4S$, 452 (MH$^+$). found 452.

Example 122

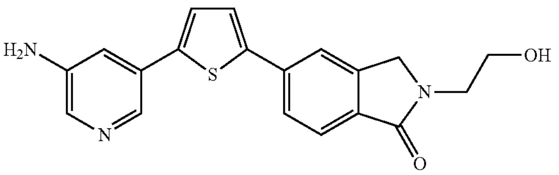 [SMILES: Nc1cncc(-c2ccc(-c3ccc4c(c3)CN(CCO)C4=O)s2)c1]

5-(5-(5-Aminopyridin-3-yl)thiophen-2-yl)-2-(2-hydroxyethyl)isoindolin-1-one

Deprotection of tert-butyl (5-(5-(2-(2-hydroxyethyl)-1-oxoisoindolin-5-yl)thiophen-2-yl)pyridin-3-yl)carbamate according to general procedure J gave the title compound as a pale green solid (100%). $^{1}$H NMR [400 MHz, $(CD_3)_2SO$] δ 8.12 (d, J=2.0 Hz, 1H), 7.93 (d, J=0.7 Hz, 1H), 7.90 (d, J=2.5 Hz, 1H), 7.81 (dd, J=8.0, 1.6 Hz, 1H), 7.71 (d, J=8.0 Hz, 1H), 7.68 (d, J=3.8 Hz, 1H), 7.54 (d, J=3.8 Hz, 1H), 7.16 (t, J=2.3 Hz, 1H), 5.51 (br s, 2H), 4.87 (br s, 1H), 4.60 (s, 2H), 3.56-3.65 (m, 4H). LRMS (APCI$^+$) calcd for $C_{19}H_{18}N_3O_2S$, 352 (MH$^+$). found 352.

Example 123

(56)

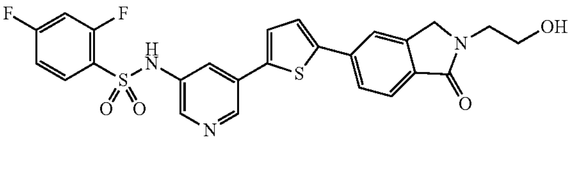

2,4-Difluoro-N-(5-(5-(2-(2-hydroxyethyl)-1-oxoisoindolin-5-yl)thiophen-2-yl)pyridin-3-yl)benzenesulfonamide (56)

5-(5-(5-Aminopyridin-3-yl)thiophen-2-yl)-2-(2-hydroxyethyl)isoindolin-1-one was reacted with 2,4-difluorobenzenesulfonyl chloride according to general procedure E to give the title compound (56) as a mustard-yellow solid (18%), mp ($MeOH/CH_2Cl_2$) 211-216° C. $^{1}$H NMR [400 MHz, $(CD_3)_2SO$] δ 11.14 (br s, 1H), 8.68 (br s, 1H), 8.24 (br s, 1H), 7.94-8.05 (m, 2H), 7.84 (br d, J=7.9 Hz, 1H), 7.70-7.76 (m, 3H), 7.65 (d, J=4.2 Hz, 1H), 7.52-7.60 (m, 1H), 7.27-7.60

(m, 1H), 4.85 (t, J=5.2 Hz, 1H), 4.61 (s, 2H), 3.56-3.66 (m, 4H). HRMS ($ESI^+$) calcd for $C_{25}H_{20}F_2N_3O_4S_2$ 528.0850 ($MH^+$). found 528.0858.

Example 124

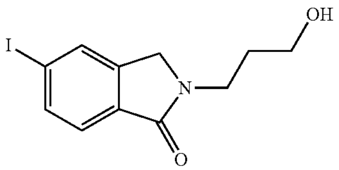 [SMILES: O=C1c2ccc(I)cc2CN1CCCO]

2-(3-Hydroxypropyl)-5-iodoisoindolin-1-one

Methyl 4-iodo-2-methylbenzoate was brominated with N-bromosuccinimide and cyclised with 3-amino-1-propanol according to general procedure A, to give the title compound as a white crystalline solid (54%). $^1$H NMR [400 MHz, $(CD_3)_2SO$] δ 8.02 (d, J=0.7 Hz, 1H), 7.84 (dd, J=7.9, 1.4 Hz, 1H), 7.45 (d, J=7.9 Hz, 1H), 4.48 (t, J=5.1 Hz, 1H), 4.45 (s, 2H), 3.55 (t, J=7.2 Hz, 2H), 3.43 (q, J=5.9 Hz, 2H), 1.70-1.77 (m, 2H). LRMS ($APCI^+$) calcd for $C_{11}H_{13}INO_2$ 318 ($MH^+$). found 318.

Example 125

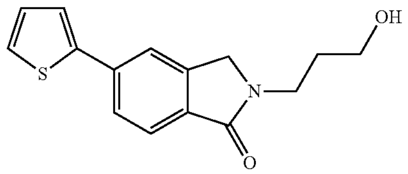 [SMILES: O=C1c2ccc(-c3cccs3)cc2CN1CCCO]

2-(3-Hydroxypropyl)-5-(thiophen-2-yl)isoindolin-1-one 2-(3-Hydroxpropyl)-5-iodoisoindolin-1-one was reacted with thiophene-2-boronic acid according to general procedure C to give the title compound as a pale brown solid (89%). $^1$H NMR [400 MHz, $(CD_3)_2SO$] δ 7.88 (d, J=0.7 Hz, 1H), 7.78 (dd, J=8.0, 1.6 Hz, 1H), 7.68 (dd, J=7.9, 0.3 Hz, 1H), 7.62-7.66 (m, 2H), 7.17 (dd, J=5.1, 4.0 Hz, 1H), 4.50-4.54 (m, 3H), 3.57 (t, J=7.3 Hz, 2H), 3.45 (q, J=5.9 Hz, 2H), 1.76 (pentet, J=6.3 Hz, 2H). LRMS ($APCI^+$) calcd for $C_{15}H_{16}NO_2S$, 274 ($MH^+$). found 274.

Example 126

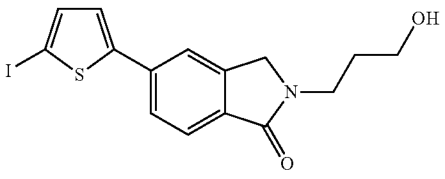 [SMILES: O=C1c2ccc(-c3ccc(I)s3)cc2CN1CCCO]

2-(3-Hydroxypropyl)-5-(5-iodothiophen-2-yl)isoindolin-1-one

Iodination of 2-(3-hydroxypropyl)-5-(thiophen-2-yl) isoindolin-1-one with N-iodosuccinimide according to general procedure D gave the title compound as a pale brown crystalline solid (87%). $^1$H NMR [400 MHz, $(CD_3)_2SO$] δ7.83 (d, J=0.7 Hz, 1H), 7.72 (dd, J=7.9, 1.5 Hz, 1H), 7.67 (d, J=7.9 Hz, 1H), 7.41 (d, J=3.8 Hz, 1H), 7.37 (d, J=3.8 Hz, 1H), 4.50-4.54 (m, 3H), 3.57 (t, J=7.2 Hz, 2H), 3.45 (q, J=5.9 Hz, 2H), 1.75 (pentet, J=6.3 Hz, 2H). LRMS ($APCI^+$) calcd for $C_{15}H_{15}INO_2S$, 400 ($MH^+$). found 400.

Example 127

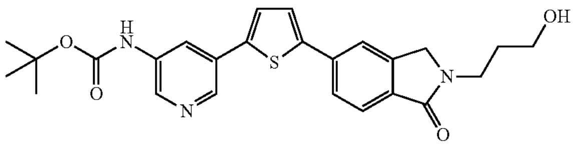 [SMILES: CC(C)(C)OC(=O)Nc1cncc(-c2ccc(-c3ccc4c(c3)CN(CCCO)C4=O)s2)c1]

tert-Butyl (5-(5-(2-(3-hydroxypropyl)-1-oxoisoindolin-5-yl)thiophen-2-yl)pyridin-3-yl)carbamate 2-(3-Hydroxypropyl)-5-(5-iodothiophen-2-yl)isoindolin-1-one was reacted with tert-butyl (5-(4,4,5,5-tetramethyl-1,3,2-dioxaborolan-2-yl)pyridin-3-yl)carbamate according to general procedure C to give the title compound as a yellow solid (83%). $^1$H NMR [400 MHz, $(CD_3)_2SO$] δ 9.74 (br s, 1H), 8.61 (d, J=2.0 Hz, 1H), 8.51 (d, J=2.3 Hz, 1H), 8.26 (br s, 1H), 7.95 (s, 1H), 7.84 (dd, J=8.0, 1.5 Hz, 1H), 7.73 (d, J=3.9 Hz, 1H), 7.70 (d, J=7.9 Hz, 1H), 7.65 (d, J=3.9 Hz, 1H), 4.52-4.54 (m, 3H), 3.58 (t, J=7.1 Hz, 2H), 3.45 (q, J=5.9 Hz, 2H), 1.76 (pentet, J=6.3 Hz, 2H), 1.51 (s, 9H). LRMS ($APCI^+$) calcd for $C_{25}H_{28}N_3O_4S$, 466 ($MH^+$). found 466.

Example 128

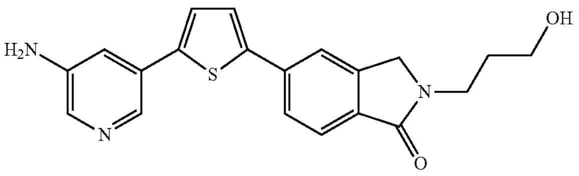 [SMILES: Nc1cncc(-c2ccc(-c3ccc4c(c3)CN(CCCO)C4=O)s2)c1]

5-(5-(5-Aminopyridin-3-yl)thiophen-2-yl)-2-(3-hydroxypropyl)isoindolin-1-one

Deprotection of tert-Butyl (5-(5-(2-(3-hydroxypropyl)-1-oxoisoindolin-5-yl)thiophen-2-yl)pyridin-3-yl)carbamate according to general procedure J gave the title compound as a beige solid (100%). $^1$H NMR [400 MHz, $(CD_3)_2SO$] δ 8.13 (d, J=2.0 Hz, 1H), 7.88-7.93 (m, 2H), 7.81 (dd, J=8.0, 1.4 Hz, 1H), 7.67-7.72 (m, 2H), 7.54 (d, J=3.8 Hz, 1H), 7.18 (t, J=2.2 Hz, 1H), 5.53 (br s, 2H), 4.52-4.56 (m, 3H), 3.58 (t, J=7.2 Hz, 1H), 3.45 (br s, 2H), 1.76 (pentet, J=6.7 Hz, 2H). LRMS ($APCI^+$) calcd for $C_{20}H_{20}N_3O_2S$, 366 ($MH^+$). found 366.

Example 129

(57)

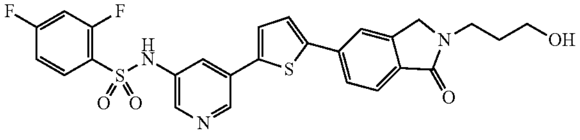

2,4-Difluoro-N-(5-(5-(2-(3-hydroxypropyl)-1-oxoisoindolin-5-yl)thiophen-2-yl)pyridin-3-yl)benzenesulfonamide (57)

5-(5-(5-Aminopyridin-3-yl)thiophen-2-yl)-2-(3-hydroxypropyl)isoindolin-1-one was reacted with 2,4-difluorobenzenesulfonyl chloride according to general procedure E to give the title compound (57) as a pale pink solid (11%), mp ($MeOH/CH_2Cl_2$) 239-241° C. $^1H$ NMR [400 MHz, $(CD_3)_2SO$] δ 11.15 (br s, 1H), 8.69 (d, J=1.8 Hz, 1H), 8.25 (d, J=2.4 Hz, 1H), 7.97-8.04 (m, 1H), 7.94 d, J=0.7 Hz, 1H), 7.84 (dd, J=8.0, 1.5 Hz, 1H), 7.69-7.74 (m, 3H), 7.65 (d, J=3.9 Hz, 1H), 7.53-7.60 (m, 1H), 7.27-7.34 (m, 1H), 4.50-4.56 (m, 3H), 3.59 (t, J=7.2 Hz, 2H), 3.45 (q, J=5.8 Hz, 2H), 1.76 (pentet, J=6.7 Hz, 2H). LRMS ($APCI^+$) calcd for $C_{26}H_{22}F_2N_3O_4S_2$ 542 ($MH^+$). found 542. Anal. ($C_{26}H_{21}F_2N_3O_4S_2$) C, H, N.

Compounds of the invention can also be prepared via general procedures as set out in Scheme 4:

Scheme 4

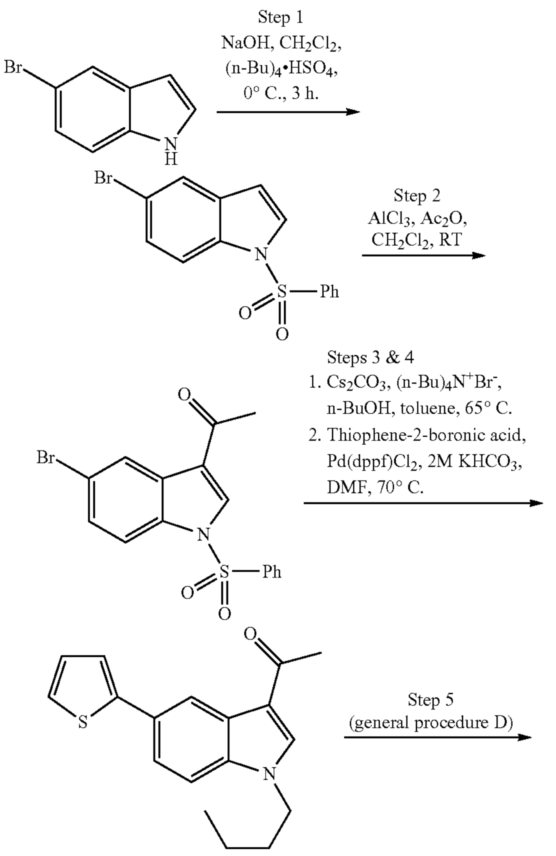

-continued

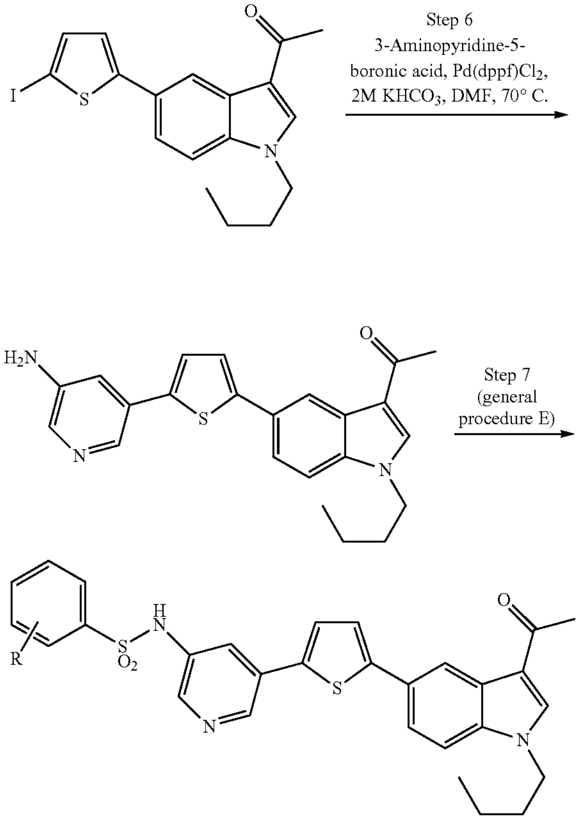

Example 130

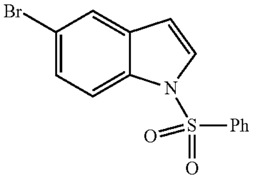 [SMILES: O=S(=O)(c1ccccc1)n1ccc2cc(Br)ccc21]

5-Bromo-1-(phenylsulfonyl)-1H-indole (step 1, Scheme 4)

The title compound was prepared by adaption of a literature procedure (Fraser, H. L. and Gribble, G. W. *Can. J. Chem.,* 2001, 79, 1515-1521). To a stirred suspension of powdered sodium hydroxide (7.18 g, 180 mmol), and $(n\text{-}Bu)_4.HSO_4$ (505 mg, 1.48 mmol) in $CH_2Cl_2$ (180 mL) at 0° C. was added 5-bromoindole (10.0 g, 51.0 mmol). After 3 hours the mixture was filtered through a pad of silica and washed with $CH_2Cl_2$. The eluant was concentrated to give an oil which solidified on standing (17.0 g, 95%). $^1H$ NMR [400 MHz, $CDCl_3$] δ 7.83-7.89 (m, 3H), 7.66 (d, J=1.9 Hz, 1H), 7.53-7.58 (m, 2H), 7.41 (dd, J=8.8, 1.9 Hz, 1H), 7.43-7.48 (m, 2H), 6.60 (dd, J=3.7, 0.7 Hz, 1H). LRMS ($APCI^+$) calcd for $C_{14}H_{11}BrNO_2S$, 336 ($MH^+$). found 336.

Example 131

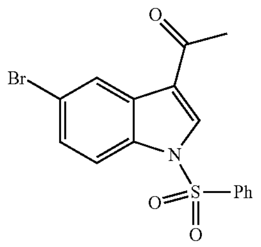 [SMILES: CC(=O)c1cn(S(=O)(=O)c2ccccc2)c2ccc(Br)cc12]

1-(5-Bromo-1-(phenylsulfonyl)-1H-indol-3-yl)ethanone (step 2, Scheme 4)

To a stirred solution of $AlCl_3$ (13.9 g, 105 mmol), and $Ac_2O$ (4.58 g, 44.8 mmol) in $CH_2Cl_2$ (180 mL) at room temperature, was added a dropwise solution of 5-bromo-1-(phenylsulfonyl)-1H-indole (5.03 g, 14.9 mmol). The reaction was stirred for 3 h and then poured onto ice, and extracted with $CH_2Cl_2$. The solvent was dried with $MgSO_4$ and concentrated. The crude material was purified by trituration with $CH_2Cl_2$/hexanes to give the title compound as a brown solid (3.62 g, 64%). $^1H$ NMR [400 MHz, $CDCl_3$] δ 8.88 (s, 1H), 8.32 (d, J=2.0 Hz, 1H), 8.13-8.17 (m, 1H), 7.93 (d, J=8.6 Hz, 1H), 7.75-7.79 (m, 1H), 7.62-7.68 (m, 1H), 7.58 (dd, J=8.9, 2.1 Hz, 1H), 2.59 (s, 3H). LRMS ($APCI^+$) calcd for $C_{16}H_{13}BrNO_3S$, 378 ($MH^+$). found 378.

Example 132

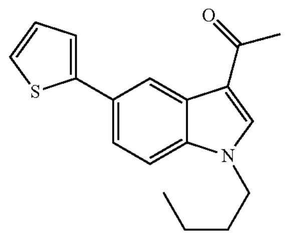 [SMILES: CCCCn1cc(C(C)=O)c2cc(-c3cccs3)ccc21]

1-(1-Butyl-5-(thiophen-2-yl)-1H-indol-3-yl)ethanone (steps 3 and 4, Scheme 4)

A 50 mL round bottom flask was charged with 1-(5-bromo-1-(phenylsulfonyl)-1H-indol-3-yl)ethanone (935 mg, 2.47 mmol), n-BuOH (201 mg, 2.71 mmol), tetra-n-butylammonium bromide (39.0 mg, 120 mol), $CsCO_3$ (886 mg, 2.71 mmol) and toluene (24 mL). The mixture was heated to 65° C. for 24 h before being quenched with saturated $NH_4Cl$ and extracted with $CH_2Cl_2$. The organic extracts were dried with $MgSO_4$ and evaporated giving a crude oil that was used in the following step without purification. The crude material from the previous step was transferred to a 50 mL round bottom flask and mixed with thiophene-2-boronic acid (569 mg, 4.45 mmol) and $PdCl_2$ (dppf) (20.0 mg, 27.3 μmol). The mixture was suspended in DMF (12 mL) and 2 M $KHCO_3$ (3 mL), degassed and then heated to 70° C. for 3 h. The reaction was diluted with saturated $NH_4Cl$, extracted with $CH_2Cl_2$, dried over $MgSO_4$ and concentrated to give a black solid. Flash column chromatography ($CH_2Cl_2$/MeOH 98:2 as eluent) gave the title compound as a yellow solid (600 mg, 86%). $^1H$ NMR [400 MHz, $CDCl_3$] δ 8.65 (dd, J=1.8, 0.6 Hz, 1H), 7.73 (s, 1H), 7.56 (td, J=5.2, 2.6, 2.6 Hz, 1H), 7.36 (dd, J=3.6, 1.2 Hz, 1H), 7.34 (dd, J=8.6, 0.5 Hz, 1H), 7.25 (dd, J=5.2, 1.2 Hz, 1H), 7.09 (dd, J=5.1, 3.6 Hz, 1H), 4.15 (t, J=7.2, 7.2 Hz, 2H), 2.54 (s, 3H) 1.88 (td, J=14.9, 7.5, 7.5 Hz, 2H), 1.39 (qd, J=14.7, 7.4, 7.4, 7.3 Hz, 2H), 0.97 (t, J=7.4, 7.4 Hz, 3H). LRMS ($APCI^+$) calcd for $C_{18}H_{20}NOS$, 298 ($MH^+$). found 298.

Example 133

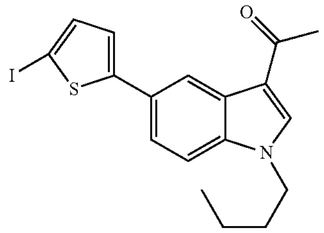 [SMILES: CCCCn1cc(C(C)=O)c2cc(-c3ccc(I)s3)ccc21]

1-(5-(5-Iodothiophen-2-yl)-1-methyl-1H-indol-3-yl) ethanone (step 5, Scheme 4)

Iodination of 1-(1-butyl-5-(thiophen-2-yl)-1H-indol-3-yl) ethanone with N-iodosuccinimide according to general procedure D gave an oil which was further purified by silica gel chromatography (hexanes/EtOAc 2:1 as eluent). The title compound was obtained as a white solid (26%). $^1H$ NMR [400 MHz, $CDCl_3$] δ 8.57 (dd, J=1.7, 0.4 Hz, 1H), 7.73 (s, 1H), 7.46 (dd, J=8.6, 1.8 Hz, 1H), 7.34 (d, J=8.1 Hz, 1H), 7.22 (d, J=3.7 Hz, 1H), 7.03 (d, J=3.7 Hz, 1H), 4.16 (t, J=7.2, 7.2 Hz, 2H), 2.53 (s, 3H), 1.88 (td, J=14.9, 7.4, 7.4 Hz, 2H), 1.38 (qd, J=14.7, 7.4, 7.4, 7.3 Hz, 2H), 0.97 (t, J=7.4, 7.4 Hz, 2H). LRMS ($APCI^-$) calcd for $C_{15}H_{12}INOS$, 381 (M-H). found 381.

Example 134

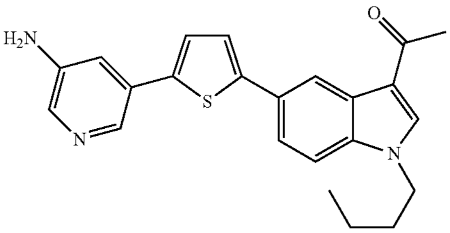 [SMILES: CCCCn1cc(C(C)=O)c2cc(-c3ccc(-c4cncc(N)c4)s3)ccc21]

1-(5-(5-(5-Aminopyridin-3-yl)thiophen-2-yl)-1-butyl-1H-indol-3-yl)ethanone (step 6, Scheme 4)

A 50 mL round bottom flask was charged with 1-(5-(5-iodothiophen-2-yl)-1-methyl-1H-indol-3-yl)ethanone (231 mg, 650 mol), 3-aminopyridine-5-boronic acid (171 mg, 780 μmol), Pd(dppf)$Cl_2$ (25 mg, 34.2 μmol), DMF (12 mL) and 2M $KHCO_3$ (3 mL). The mixture was heated to 70° C. before being quenched with saturated $NH_4Cl$ (20 mL), diluted with water and extracted with $CH_2Cl_2$. The organic extracts were dried over $MgSO_4$ and concentrated to give an oil that was further purified by flash column chromatography ($CH_2Cl_2$/MeOH 98:2 as eluent). The title compound was isolated as an off-white solid (223 mg, 78%). $^1$H NMR [400 MHz, $CDCl_3$] δ 8.67 (d, J=1.3 Hz, 1H), 8.35 (br s, 1H), 8.00 (d, J=1.9 Hz, 1H), 7.74 (s, 1H), 7.58 (dd, J=8.6, 1.8 Hz, 1H), 7.37 (d, J=8.8 Hz, 1H), 7.36 (d, J=3.8 Hz, 1H), 7.31 (d, J=3.8 Hz, 1H), 7.21-7.17 (m, 1H), 4.17 (t, J=7.2, 7.2 Hz, 2H), 3.77 (s, 2H), 2.55 (s, 3H), 1.89 (td, J=14.9, 7.5, 7.5 Hz, 2H), 1.40 (qd, J=14.7, 7.4, 7.4, 7.3 Hz, 2H), 0.98 (t, J=7.4, 7.4 Hz, 3H). LRMS (APCI$^+$) calcd for $C_{23}H_{24}N_3OS$, 390 (MH$^+$). found 390.

Example 135

(58)

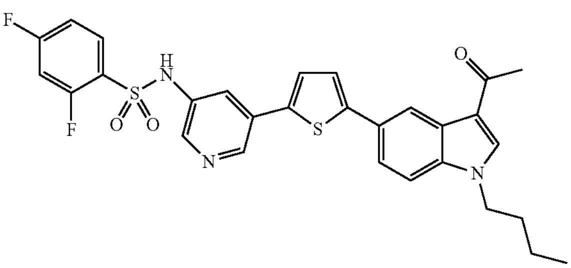

N-(5-(5-(3-Acetyl-1-butyl-1H-indol-5-yl)thiophen-2-yl)pyridin-3-yl)-2,4-difluorobenzenesulfonamide (58) (step 7, Scheme 4)

1-(5-(5-(5-Aminopyridin-3-yl)thiophen-2-yl)-1-butyl-1H-indol-3-yl)ethanone was reacted with 2,4-difluorobenzenesulfonyl chloride according to general procedure E, and purified by flash column chromatography using silica gel (98:2 $CH_2Cl_2$/MeOH as eluant) followed by trituration from $CH_2Cl_2$/hexanes, to give the title compound (58) as a cream coloured solid (68%), mp (MeOH/$CH_2Cl_2$) 188-191° C. $^1$H NMR [400 MHz, $(CD_3)_2SO$] δ 8.68-8.64 (m, 2H), 8.22-8.26 (m, 1H), 7.96-7.87 (m, 1H), 7.57 (dd, J=8.6, 1.8 Hz, 1H), 7.88-7.75 (m, 1H), 7.78-7.75 (m, 2H), 7.38 (d, J=8.3 Hz, 1H), 7.34 (dd, J=0.9.1, 3.8 Hz, 1H), 7.39 (s, 1H), 7.24 (s, 1H), 7.01-6.94 (m, 1H), 4.18 (t, J=7.2, 7.2 Hz, 1H), 2.56 (s, 3H), 1.90 (td, J=14.9, 7.5, 7.5 Hz, 1H), 1.40 (qd, J=14.7, 7.4, 7.36, 7.4 Hz, 1H), 0.99 (t, J=7.4, 7.4 Hz, 1H). Anal. ($C_{29}H_{25}F_2N_3O_3S_2$) C, H, N.

Example 136

(59)

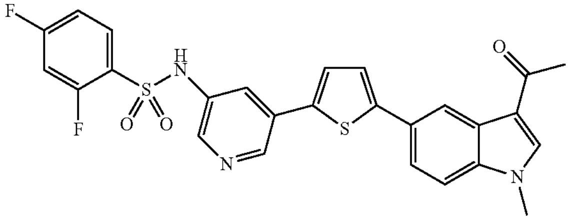

N-(5-(5-(3-Acetyl-1-methyl-1H-indol-5-yl)thiophen-2-yl)-pyridin-3-yl)-2,4-difluorobenzenesulfonamide (59)

The title compound (59) was prepared by substituting butanol for methanol in step 3 of scheme 4 outlined above to give 1-(5-(5-(5-aminopyridin-3-yl)thiophen-2-yl)-1-methyl-1H-indol-3-yl)ethanone. This was reacted with 2,4-difluorobenzenesulfonyl chloride according to general procedure E, affording the title compound (59) as an off-white solid (7.5%), mp (MeOH/$CH_2Cl_2$) 241-244° C. $^1$H NMR [400 MHz, $(CD_3)_2SO$] δ 11.1 (br s, 1H), 8.69 (d, J=2.0 Hz, 1H), 8.48 (d, J=1.4 Hz, 1H), 8.39 Hz (s, 1H), 8.23 (d, J=2.4 Hz, 1H), 7.98-8.05 (m, 1H), 7.72 (t, J=2.2, 2.2 Hz, 1H), 7.52-7.70 (m, 5H), 7.28-7.34 (m, 1H), 3.89 (s, 3H), 2.46 (s, 3H). Anal. ($C_{26}H_{19}F_2N_3O_3S_2$) C, H, N.

Example 137

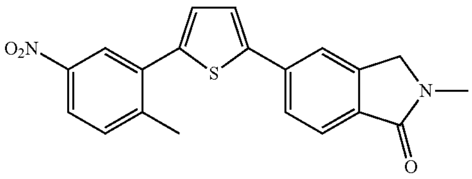 [SMILES: Cc1ccc([N+](=O)[O-])cc1-c1ccc(-c2ccc3c(c2)CN(C)C3=O)s1]

2-Methyl-5-(5-(2-methyl-5-nitrophenyl)thiophen-2-yl)isoindolin-1-one 5-(5-Iodothiophen-2-yl)-2-methylisoindolin-1-one was reacted with (2-methyl-5-nitrophenyl)boronic acid according to general procedure C, followed by flash column chromatography ($CH_2Cl_2$/MeOH 98:2 as eluent) to give the title compound as a yellow solid (80%). $^1$H NMR [400 MHz, $CDCl_3$] δ 8.32 (d, J=2.5 Hz, 1H), 8.11 (dd, J=8.4, 2.5 Hz, 1H), 7.87 (d, J=7.9 Hz, 1H), 7.74 (dd, J=7.9, 1.5 Hz, 1H), 7.69 (dd, J=1.4, 0.7 Hz, 1H), 7.46 (d, J=8.4 Hz, 1H), 7.42 (d, J=3.8 Hz, 1H), 7.16 (d, J=3.8 Hz, 1H), 4.43 (s, 2H), 3.23 (s, 3H), 2.59 (s, 3H). LRMS (APCI$^+$) calcd for $C_{20}H_{17}N_2O_3S$, 365 (MH$^+$). found 365.

Example 138

(60)

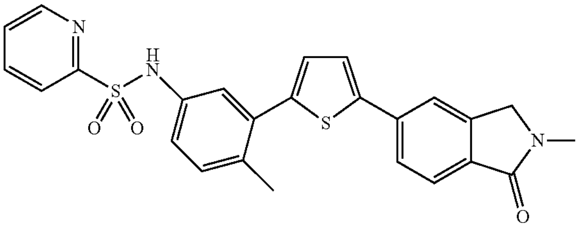

N-(4-Methyl-3-(5-(2-methyl-1-oxoisoindolin-5-yl)thiophen-2-yl)phenyl)pyridine-2-sulfonamide (60)

A 200 mL Parr hydrogenation vessel was charged with 2-methyl-5-(5-(2-methyl-5-nitrophenyl)thiophen-2-yl)isoindolin-1-one (388 mg, 1.06 mmol) which was dissolved in a 1:1:1 mixture of ethanol, EtOAc and THF (90 mL). The mixture was agitated under 60 psi hydrogen at room temperature for 3 h before being filtered through celite. The solvents were evaporated giving 5-(5-(5-amino-2-methylphenyl)thiophen-2-yl)-2-methylisoindolin-1-one (350 mg) which was used in the next step without further purification. The crude aniline (111 mg, 331 mol) was then reacted with pyridine-2-sulfonyl chloride according to general procedure E to give the title compound (60) as a cream solid (66 mg, 42%), mp (MeOH/$CH_2Cl_2$) 274-277° C. $^1$H NMR [400 MHz, $(CD_3)_2SO$] δ 10.58 (s, 1H), 8.74 (ddd, J=4.65, 1.6, 0.8 Hz, 1H), 8.08 (dt, J=7.7, 7.7, 1.7 Hz, 1H), 7.98 (td, J=7.9, 1.0, 1.0 Hz, 1H), 7.90 (s, 1H), 7.80 (dd, J=7.9, 1.6 Hz, 1H), 7.70 (d, J=8.0 Hz, 1H), 7.68-7.64 (m, 2H), 7.26 (d, J=2.3 Hz, 1H), 7.20-7.16 (m, 2H), 7.06 (dd, J=8.2, 2.3 Hz, 1H), 4.51 (s, 2H), 3.09 (s, 3H), 2.32 (s, 3H). Anal. ($C_{25}H_{21}N_3O_3S_2$) C, H, N.

Example 139

(61)

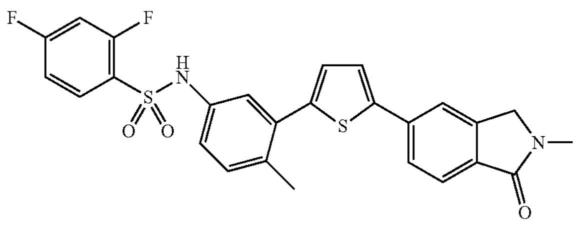

2,4-Difluoro-N-(4-methyl-3-(5-(2-methyl-1-oxoisoindolin-5-yl)thiophen-2-yl)phenyl)benzenesulfonamide (61)

Reaction of 5-(5-(5-amino-2-methylphenyl)thiophen-2-yl)-2-methylisoindolin-1-one with 2,4-difluorobenzenesulfonyl chloride according to general procedure E gave the title compound (61) as a cream solid (30%), mp (MeOH/$CH_2Cl_2$) 268-271° C. $^1$H NMR [400 MHz, $(CD_3)_2SO$] δ 10.68 (s, 1H), 7.88-7.95 (m, 2H), 7.80 (dd, J=8.0, 1.5 Hz, 1H), 7.70 (d, J=8.0 Hz, 1H), 7.67 (d, J=3.8 Hz, 1H), 7.56 (ddd, J=11.4, 9.2, 2.4 Hz, 1H), 7.29 (dt, J=8.5, 8.4, 2.1 Hz, 1H), 7.18-7.24 (m, 2H), 7.03 (dd, J=8.2, 2.4 Hz, 1H), 4.52 (s, 2H), 3.09 (s, 3H), 2.33 (s, 3H). Anal. ($C_{26}H_{20}F_2N_2O_3S_2$).

Example 140

(62)

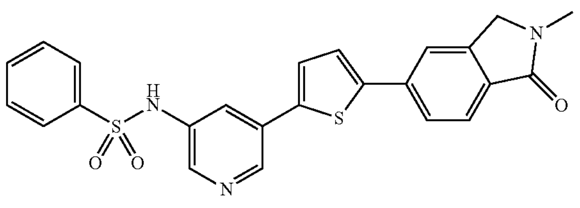

N-(5-(5-(2-Methyl-1-oxoisoindolin-5-yl)thiophen-2-yl)pyridin-3-yl)benzenesulphonamide (62)

5-(5-(5-Aminopyridin-3-yl)thiophen-2-yl)-2-methylisoindolin-1-one was reacted with benzenesulphonyl chloride according to general procedure E, and the desired title compound was given as a yellow solid (64%); mp 300-303° C. $^1$H NMR [400 MHz, $(CD_3)_2SO$] δ 10.77 (br s, 1H), 8.67 (d, J=2.0 Hz, 1H), 8.21 (d, J=2.4 Hz, 1H), 7.94 (s, 1H), 7.75-7.80 (m, 3H), 7.68-7.76 (m, 3H), 7.55-7.67 (m, 4H), 4.52 (s, 2H), 3.09 (s, 3H).

In this case the product was converted to its sodium salt according to general procedure F to give the desired product (62.Na) as a yellow solid (94%). $^1$H NMR [400 MHz, $(CD_3)_2SO$] δ 8.00 (d, J=2.1 Hz, 1H), 7.90 (s, 1H), 7.88 (d, J=2.4, 1H), 7.80 (dd, J=7.9, 1.5 Hz, 1H), 7.71-7.77 (m, J=8.0, 2H), 7.68 (d, J=8.0, 1H), 7.63 (d, J=3.8, 1H), 7.30-7.10 (m, 5H), 4.51 (s, 2H), 3.08 (s, 3H). Anal. ($C_{24}H_{19}N_3O_3S_2$) C, H, N.

Scheme 5

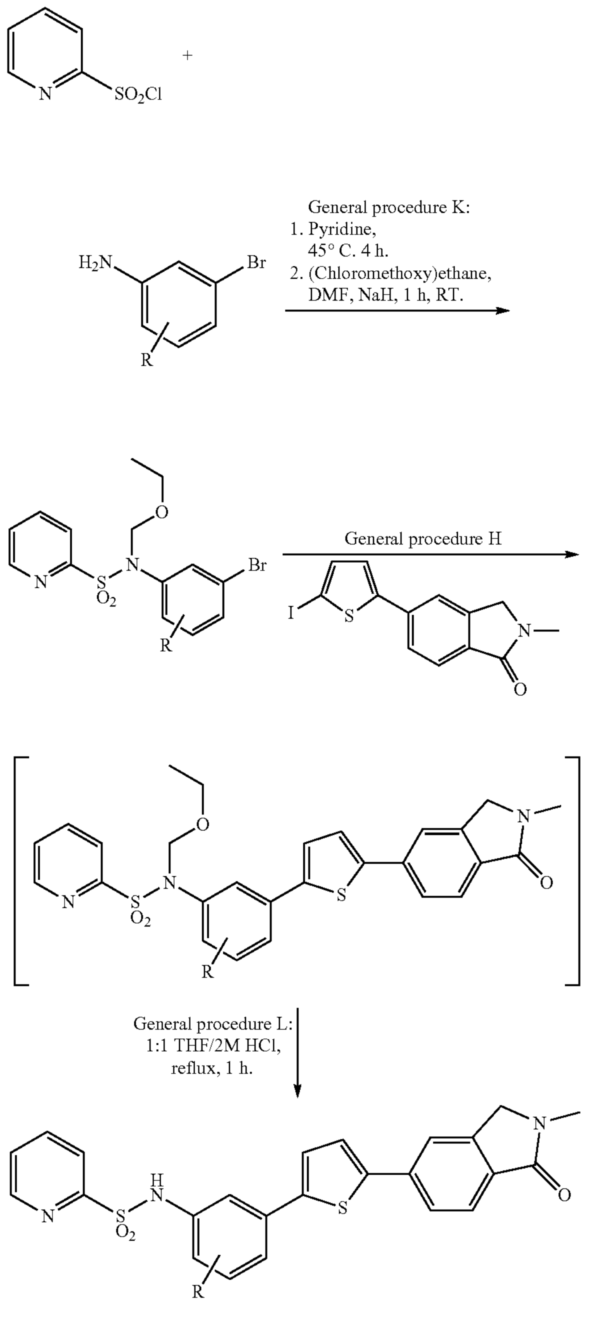

Example 141

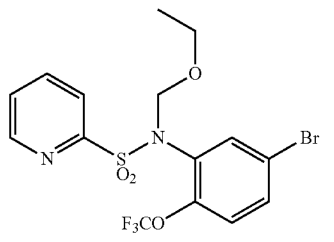 [SMILES: CCOCN(c1cc(Br)ccc1OC)S(=O)(=O)c1ccccn1]

General Procedure K: N-(5-Bromo-2-(trifluoromethoxy)phenyl)-N-(ethoxymethyl)pyridine-2-sulfonamide (Scheme 5)

To a stirred solution of 5-bromo-2-(trifluoromethoxy) aniline (540 mg, 2.11 mmol) in pyridine was added pyridine-2-sulfonyl chloride (410 mg, 2.31 mmol and the mixture was heated to 45° C. for 4 h. After quenching with water the mixture was extracted with $CH_2Cl_2$, dried over $MgSO_4$ and evaporated to give a solid (769 mg) that was used without further purification. To a mixture of the aforementioned crude solid and (chloromethoxy)ethane (329 mg, 3.49 mmol) in DMF at room temperature was added a 60% w/w dispersion of NaH in mineral oil (140 mg, 3.49 mol) and the mixture was stirred for 1 h. After quenching with water the mixture was extracted with $CH_2Cl_2$, dried with $MgSO_4$ and evaporated to give a solid which was purified by column chromatography eluting with hexanes/EtOAc 3:1. The title compound was isolated as a colourless oil (857 mg, 89%, 2 steps). $^1H$ NMR [400 MHz, $CDCl_3$] δ 8.75 (ddd, J=4.8, 1.6, 1.0 Hz, 1H), 7.90-7.82 (m, 2H), 7.54-7.46 (m, 3H), 7.10 (dddd, J=8.9, 1.9, 1.8, 1.8 Hz, 1H), 5.21 (br s, 2H), 3.79 (q, J=7.0 Hz, 2H), 1.20 (t, J=7.0 Hz, 3H). LRMS ($APCI^+$) calcd for $C_{13}H_{10}BrF_3N_2O_3S$, 409 $(M-EtO)^+$. found 409.

Example 142

(63)

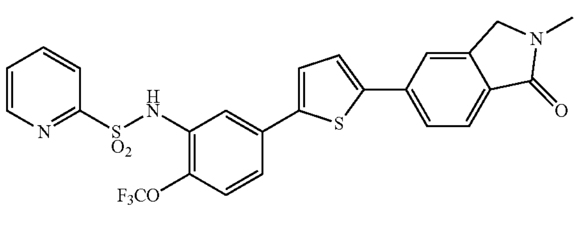

General Procedure L: N-(5-(5-(2-Methyl-1-oxoisoindolin-5-yl)thiophen-2-yl)-2-(trifluoromethoxy)phenyl)pyridine-2-sulfonamide (63) (Scheme 5)

N-(5-Bromo-2-(trifluoromethoxy)phenyl)-N-(ethoxymethyl)pyridine-2-sulfonamide was reacted with bis(pinacolato)diboron, followed by 5-(5-iodothiophen-2-yl)-2-methylisoindolin-1-one, according to general procedure H. The crude material from this step was taken up in a 1:1 solution of THF/2M HCl (60 mL) and heated to reflux for 1 h. After cooling to room temperature the THF was removed in vacuo and the reaction carefully quenched with NaOH to pH 6 buffering by the addition of $K_3PO_4$ (ca. 0.5 g). The resulting solid was washed with $Et_2O$ to give the title compound as a yellow solid (263 mg, 51%, 2 steps), mp ($MeOH/CH_2Cl_2$) 200-201° C. $^1H$ NMR [400 MHz, $(CD_3)_2SO$] δ 10.61 (s, 1H), 8.79 (ddd, J=4.6, 1.6, 0.8 Hz, 1H), 8.11 (ddd, J=7.7, 7.7, 1.7 Hz, 1H), 7.99 (ddd, J=7.9, 0.9, 0.9 Hz, 1H), 7.93 (m, 1H), 7.82 (dd, J=8.0, 1.5 Hz, 1H), 7.79 (d, J=2.3 Hz, 1H), 7.74-6.68 (m, 3H), 7.61 (dd, J=8.6, 2.3 Hz, 1H), 7.53 (d, J=3.4 Hz, 1H), 7.39 (dddd, J=8.5, 1.5, 1.5, 1.5 Hz, 1H), 4.52 (s, 2H), 3.09 (s, 3H). Anal. ($C_{25}H_{18}F_3N_3O_4S_2$) C, H, N.

Example 143

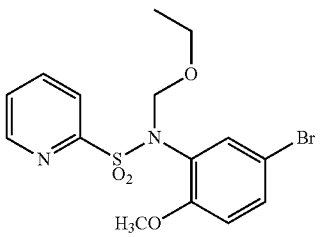

5-Bromo-N-(ethoxymethyl)-2-methoxy-N-(pyridin-2-yl)benzenesulfonamide

The title compound was prepared according to general procedure K and isolated as a colourless oil (99%, 2 steps). $^1H$ NMR [400 MHz, $CDCl_3$] δ 8.76 (ddd, J=4.7, 1.6, 0.8 Hz, 1H), 7.82 (dd, J=7.7, 1.7 Hz, 1H), 7.76 (ddd, J=7.9, 1.1, 1.1 Hz, 1H), 7.48 (ddd, J=7.6, 4.8, 1.3 Hz, 1H), 7.40-7.37 (m, 2H), 6.68-6.64 (m, 1H), 5.19 (br s, 2H), 3.80 (q, J=7.0 Hz, 2H), 3.37 (s, 3H), 1.21 (t, J=7.0 Hz, 3H). LRMS ($APCI^+$) calcd for $C_{13}H_{13}BrN_2O_3S$, 355 $(M-EtO)^+$. found 355.

Example 144

(64.Na)

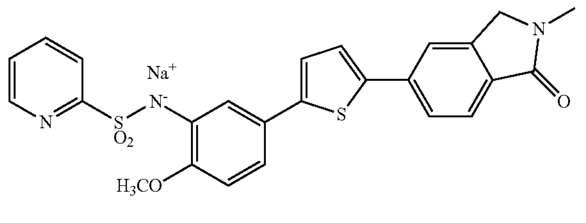

Sodium ((2-Methoxy-5-(5-(2-methyl-1-oxoisoindolin-5-yl)thiophen-2-yl)phenyl)sulfonyl)(pyridin-2-yl) amide (64.Na)

The title compound was prepared according to general procedures H and L, and isolated as a yellow solid. In this case the product was converted to its sodium salt according to general procedure F to give the desired product (64.Na), also as a yellow solid (68%, 3 steps), mp ($MeOH/CH_2Cl_2$) 322-325° C. $^1H$ NMR [400 MHz, $(CD_3)_2SO$] δ 8.10 (br d, J=2.5 Hz, 1H), 7.89 (br s, 1H), 7.86 (ddd, J=4.9, 2.1, 0.8 Hz, 1H), 7.79 (dd, J=8.0, 1.5 Hz, 1H), 7.68-7.63 (m, 3H), 7.36

(d, J=3.8 Hz, 1H), 7.20 (ddd, J=8.4, 7.0, 2.1 Hz, 1H), 7.04 (d, J=8.7 Hz, 1H), 6.71 (br d, J=8.4 Hz, 1H), 6.36 (ddd, J=6.9, 4.8, 1.0 Hz, 1H), 4.50 (s, 2H), 3.74 (s, 3H), 3.08 (s, 3H). Anal. ($C_{25}H_{20}N_3NaO_4S_2$. $2.5H_2O$) C, H, N.

Example 145

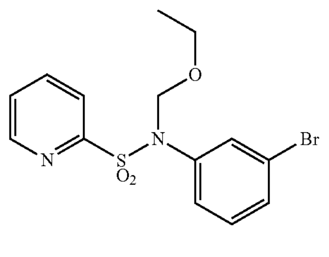 [SMILES: CCOCN(c1cccc(Br)c1)S(=O)(=O)c1ccccn1]

3-Bromo-N-(ethoxymethyl)-N-(pyridin-2-yl)benzenesulfonamide

The title compound was prepared according to general procedure K and isolated as a colourless oil (63%, 2 steps). $^1H$ NMR [400 MHz, $CDCl_3$] δ 8.35 (ddd, J=4.8, 1.9, 0.8 Hz, 1H), 7.98 (dd, J=1.8, 1.8 Hz, 1H), 7.74-7.69 (m, 3H), 7.66 (ddd, J=8.1, 1.9, 1.0 Hz, 1H), 7.48 (ddd, J=8.2, 0.8, 0.8 Hz, 1H), 7.32 (dd, J=8.0, 8.0 Hz, 1H), 7.16 (ddd, J=7.4, 4.9, 1.0 Hz, 1H), 5.38 (s, 2H), 3.68 (q, J=7.1 Hz, 2H), 1.19 (t, J=7.1 Hz, 3H). LRMS ($APCI^+$) calcd for $C_{12}H_{10}BrFN_2O_2S$, 325 $(M-EtO)^+$. found 325.

Example 146

(65.Na)

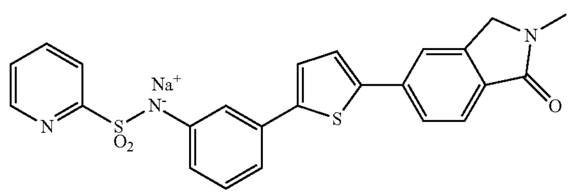

Sodium ((3-(5-(2-Methyl-1-oxoisoindolin-5-yl)thiophen-2-yl)phenyl)sulfonyl)(pyridin-2-yl)amide (65.Na)

The title compound was prepared according to general procedures H and L, and isolated as a yellow solid. In this case the product was converted to its sodium salt according to general procedure F to give the desired product (65.Na), also as a yellow solid (68%, 3 steps), mp ($MeOH/CH_2Cl_2$) 302-306° C. $^1H$ NMR [400 MHz, $(CD_3)_2SO$] δ 8.09 (dd, J=1.6, 1.6 Hz, 1H), 7.94 (br s, 1H), 7.87 (ddd, J=4.9, 2.1, 0.7 Hz, 1H), 7.83 (dd, J=8.0, 1.5 Hz, 1H), 7.72-7.68 (m, 4H), 7.56 (d, J=3.9 Hz, 1H), 7.41 (dd, J=7.8, 7.8 Hz, 1H), 7.19 (ddd, J=8.5, 7.0, 2.2 Hz, 1H), 6.59 (ddd, J=8.6, 0.9, 0.9 Hz, 1H), 6.36 (ddd, J=7.0, 5.0, 1.0 Hz, 1H), 4.51 (s, 2H), 3.08 (s, 3H). Anal. ($C_{24}H_{18}N_3NaO_3S_2$. $0.5H_2O$) C, H, N.

Example 147

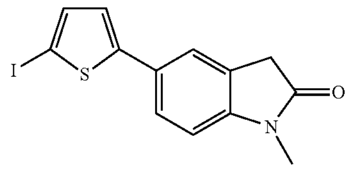 [SMILES: CN1C(=O)Cc2cc(-c3ccc(I)s3)ccc21]

5-(5-Iodothiophen-2-yl)-1-methylindolin-2-one

1-Methyl-5-(thiophen-2-yl)indolin-2-one was prepared according to a literature procedure[1] then iodinated with N-iodosuccinimide according to general procedure D. The title compound was isolated as a pale brown solid (97%). $^1H$ NMR [400 MHz, $(CD_3)_2SO$] δ7.49-7.53 (m, 2H), 7.32 (d, J=3.8 Hz, 1H), 7.14 (d, J=3.8 Hz, 1H), 7.00 (d, J=8.7 Hz, 1H), 3.59 (s, 2H), 3.13 (s, 3H). LRMS ($APCI^+$) calcd for $C_{13}H_{11}IOS$, 356 ($MH^+$). found 356.

Example 148

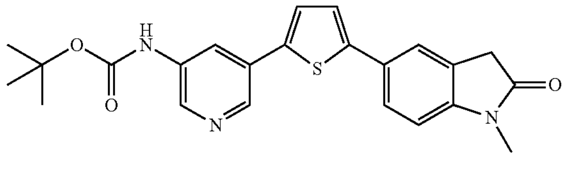 [SMILES: CN1C(=O)Cc2cc(-c3ccc(-c4cncc(NC(=O)OC(C)(C)C)c4)s3)ccc21]

tert-Butyl (5-(5-(1-methyl-2-oxoindolin-5-yl)thiophen-2-yl)pyridin-3-yl)carbamate tert-Butyl (5-(4,4,5,5-tetramethyl-1,3,2-dioxaborolan-2-yl)pyridin-3-yl)carbamate and 5-(5-iodothiophen-2-yl)-1-methylindolin-2-one were reacted according to general procedure C. The title compound was isolated as a pale brown solid (91%). $^1H$ NMR [400 MHz, $(CD_3)_2SO$] δ 9.71 (br s, 1H), 8.56 (d, J=2.1 Hz, 1H), 8.48 (d, J=2.3 Hz, 1H), 8.21 (br s, 1H), 7.62-7.66 (m, 2H), 7.56 (d, J=3.8 Hz, 1H), 7.48 (d, J=3.8 Hz, 1H), 7.04 (d, J=8.7 Hz, 1H), 3.62 (s, 2H), 3.15 (s, 3H), 1.51 (s, 9H). LRMS ($APCI^+$) calcd for $C_{23}H_{24}N_3O_3S$, 422 ($MH^+$). found 422.

Example 149

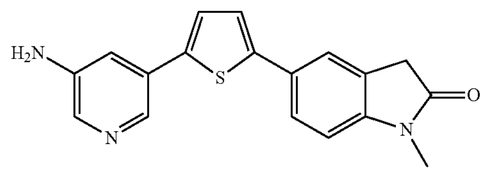 [SMILES: CN1C(=O)Cc2cc(-c3ccc(-c4cncc(N)c4)s3)ccc21]

5-(5-(5-Aminopyridin-3-yl)thiophen-2-yl)-1-methylindolin-2-one

Deprotection of tert-butyl (5-(5-(1-methyl-2-oxoindolin-5-yl)thiophen-2-yl)pyridin-3-yl)carbamate according to general procedure J gave the title compound as a pale yellow solid (78%). $^1$H NMR [400 MHz, $(CD_3)_2SO$] δ 8.09 (d, J=2.0 Hz, 1H), 7.86 (d, J=2.1 Hz, 1H), 7.58-7.62 (m, 2H), 7.44 (d, J=3.8 Hz, 1H), 7.45 (d, J=3.8 Hz, 1H), 7.13 (t, J=2.3 Hz, 1H), 7.03 (d, J=8.7 Hz, 1H), 5.47 (s, 2H), 3.62 (s, 2H), 3.15 (s, 3H). LRMS ($APCI^+$) calcd for $C_{18}H_{16}N_3OS$, 322 ($MH^+$). found 322.

Example 150

(66)

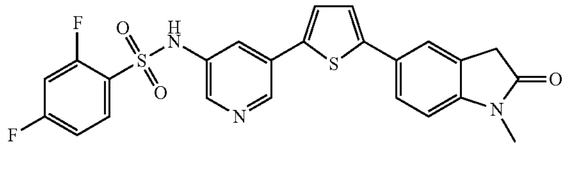

2,4-Difluoro-N-(5-(5-(1-methyl-2-oxoindolin-5-yl) thiophen-2-yl)pyridin-3-yl)benzenesulfonamides (66)

5-(5-(5-Aminopyridin-3-yl)thiophen-2-yl)-1-methylindolin: 2-one was reacted with 2,4-difluorobenzenesulfonyl chloride according to general procedure E, and the resulting crude product purified by flash column chromatography (2% $MeOH/CH_2Cl_2$ as eluant) to give the title compound as a dark yellow solid (93%), mp ($MeOH/CH_2Cl_2$) 268-271° C. $^1$H NMR [400 MHz, $(CD_3)_2SO$] δ 11.11 (br s, 1H), 8.63 (d, J=1.7 Hz, 1H), 8.21 (d, J=2.4 Hz, 1H), 4.96-8.03 (m, 1H), 7.67 (t, J=2.2 Hz, 1H), 7.61-7.66 (m, 2H), 7.52-7.59 (m, 2H), 7.48 (d, J=3.8 Hz, 1H), 7.30 (td, J=8.3, 2.0 Hz, 1H), 7.05 (d, J=8.0 Hz, 1H), 3.62 (s, 2H), 3.15 (s, 3H). LRMS ($APCI^-$) calcd for $C_{24}H_{16}F_2N_3O_3S_2$ 496 (M-H). found 496. Anal. ($C_{24}H_{17}F_2N_3O_3S_2$) C, H, N.

Example 151

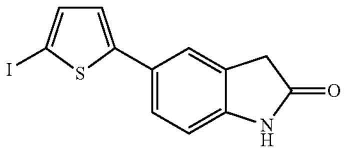 [SMILES: O=C1Cc2cc(-c3ccc(I)s3)ccc2N1]

5-(5-Iodothiophen-2-yl)indolin-2-one 5-(Thiophen-2-yl)indolin-2-one was iodinated with N-iodosuccinimide according to general procedure D. The title compound was isolated as a pale brown solid (100%). $^1$H NMR [400 MHz, $(CD_3)_2SO$] δ 10.49 (br s, 1H), 7.45 (br s, 1H), 7.40 (dd, J=8.1, 1.9 Hz, 1H), 7.30 (d, J=3.7 Hz, 1H), 7.09 (d, J=3.7 Hz, 1H), 6.83 (d, J=8.0 Hz, 1H), 3.52 (s, 2H). LRMS ($APCI^+$) calcd for $C_{12}H_9INOS$, 342 ($MH^+$). found 342.

Example 152

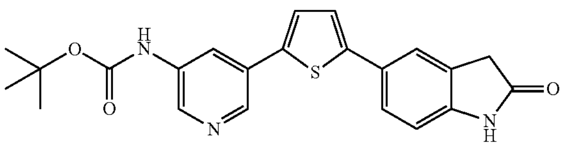 [SMILES: CC(C)(C)OC(=O)Nc1cncc(-c2ccc(-c3ccc4c(c3)CC(=O)N4)s2)c1]

tert-Butyl (5-(5-(2-oxoindolin-5-yl)thiophen-2-yl) pyridin-3-yl)carbamate tert-Butyl (5-(4,4,5,5-tetramethyl-1,3,2-dioxaborolan-2-yl)pyridin-3-yl)carbamate and 5-(5-iodothiophen-2-yl)indolin-2-one were reacted according to general procedure C. The title compound was isolated as a pale yellow solid (56%). $^1$H NMR [400 MHz, $(CD_3)_2SO$] δ 10.52 (br s, 1H), 9.71 (br s, 1H), 8.55 (d, J=2.0, 1H), 8.48 (d, J=2.2 Hz, 1H), 8.19 (br s, 1H), 7.51-7.60 (m, 3H), 7.44 (d, J=3.8 Hz, 1H), 6.86 (d, J=8.1 Hz, 1H), 3.54 (s, 2H), 1.51 (s, 9H). LRMS ($APCI^+$) calcd for $C_{22}H_{22}N_3O_3S$, 408 ($MH^+$). found 408.

Example 153

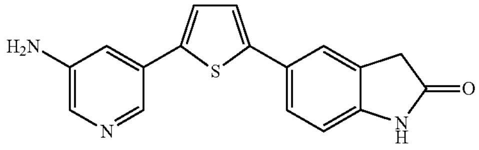 [SMILES: Nc1cncc(-c2ccc(-c3ccc4c(c3)CC(=O)N4)s2)c1]

5-(5-(5-Aminopyridin-3-yl)thiophen-2-yl)indolin-2-one

Deprotection of tert-butyl (5-(5-(2-oxoindolin-5-yl)thiophen-2-yl)pyridin-3-yl)carbamate according to general procedure J gave the title compound as a cream solid (100%). $^1$H NMR [400 MHz, $(CD_3)_2SO$] δ 10.51 (br s, 1H), 8.08 (d, J=1.9 Hz, 1H), 7.86 (d, J=2.4 Hz, 1H), 7.55 (br s, 1H), 7.50 (dd, J=8.1, 1.9 Hz, 1H), 7.44 (d, J=3.8 Hz, 1H), 7.39 (d, J=3.8 Hz, 1H), 7.12 (t, J=2.2 Hz, 1H), 6.86 (d, J=8.1 Hz, 1H), 5.46 (br s, 2H), 3.54 (s, 2H). LRMS ($APCI^+$) calcd for $C_7H_{14}N_3OS$, 308 ($MH^+$). found 308.

Example 154

(67)

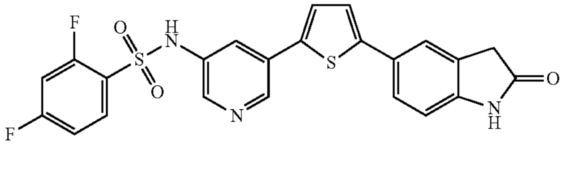

2,4-Difluoro-N-(5-(5-(2-oxoindolin-5-yl)thiophen-2-yl)pyridin-3-yl)benzenesulfonamides (67)

5-(5-(5-Aminopyridin-3-yl)thiophen-2-yl)indolin-2-one was reacted with 2,4-difluorobenzenesulfonyl chloride according to general procedure E, and the resulting crude product purified by flash column chromatography (5% $MeOH/CH_2Cl_2$ as eluant) to give the title compound as a pale yellow solid (52%), mp ($MeOH/CH_2Cl_2$) 301-305° C. $^1H$ NMR [400 MHz, $(CD_3)_2SO$] δ 11.11 (br s, 1H), 10.53 (br s, 1H), 8.64 (d, J=2.0 Hz, 1H), 8.22 (d, J=2.3 Hz, 1H), 7.96-8.04 (m, 1H), 7.68 (t, J=2.2 Hz, 1H), 7.50-7.61 (m, 4H), 7.44 (d, J=3.8 Hz, 1H), 7.30 (td, J=8.3, 2.0 Hz, 1H), 6.87 (d, J=8.1 Hz, 1H), 3.55 (s, 2H). LRMS ($APCI^+$) calcd for $C_{23}H_{16}F_2N_3O_3S_2$ 484 ($MH^+$). found 484. Anal. ($C_{23}H_{15}F_2N_3O_3S_2$) C, H, N.

Example 155

(68)

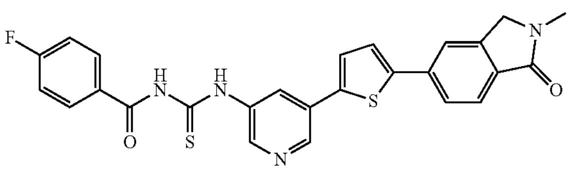

4-Fluoro-N-((5-(5-(2-methyl-1-oxoisoindolin-5-yl)thiophen-2-yl)pyridin-3-yl) carbamothioyl)benzamide (68)

To a stirred solution of potassium isothiocyanate (20 mg, 0.208 mmol) in acetone (2 mL) was added 4-fluorobenzoylchloride (0.02 mL, 0.208 mmol), and the mixture was stirred vigously at 50° C. for 1 h. To the resultant suspension was added a solution of 5-(5-(5-aminopyridin-3-yl)thiophen-2-yl)-2-methylisoindolin-1-one (100 mg, 0.311 mmol) in acetone (2 mL) dropwise, and the mixture was stirred at 50° C. for 4 h. The reaction mixture was quenched with cold water (10 mL) and extracted with 5% $MeOH/CH_2Cl_2$(3×10 mL) and the combined organic extracts were dried ($Na_2SO_4$), filtered, and concentrated to dryness in vacuo. Purification by column chromatography on silica gel (1-5% $MeOH/CH_2Cl_2$) gave the title compound as a yellow solid (11 mg, 7%); mp 225-228° C. $^1H$ NMR [400 MHz, $(CD_3)_2SO$] δ 12.55 (s, 1H), 11.87 (s, 1H), 8.86 (d, J=2.0 Hz, 1H), 8.69 (d, J=2.2 Hz, 1H), 8.52 (s, 1H), 8.05-8.14 (m, 2H), 7.95 (s, 1H), 7.84 (dd, J=7.9, 1.3 Hz, 1H), 7.77 (s, 2H), 7.71 (d, J=7.9 Hz, 1H), 7.40 (dt, J=8.8, 2.0 Hz, 1H), 4.52 (s, 2H), 3.09 (s, 3H). HRMS ($APCI^+$) calcd for $C_{26}H_{20}FN_4O_2S_2$ 503.1006 ($MH^+$). found 503.1016.

Example 156

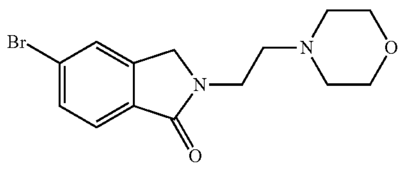 [SMILES: O=C1c2ccc(Br)cc2CN1CCN1CCOCC1]

5-Bromo-2-(2-morpholinoethyl)isoindolin-1-one

Methyl 4-bromo-2-methylbenzoate was brominated with N-bromosuccinimide and cyclised with 4-(2-aminoethyl)morpholine according to general procedure A, to give the title compound as a pale pink solid (62%). $^1H$ NMR [400 MHz, $(CD_3)_2SO$] δ 7.86 (d, J=0.9 Hz, 1H), 7.67 (dd, J=8.0, 1.7 Hz, 1H), 7.60 (d, J=8.1 Hz, 1H), 4.55 (s, 2H), 3.63 (t, J=6.3 Hz, 2H), 3.53 (t, J=4.6 Hz, 4H), 2.54 (t, J=6.3 Hz, 2H), 2.42 (br t, J=4.4 Hz, 4H). LRMS ($APCI^+$) calcd for $C_{14}H_{18}BrN_2O_2$ 325, 327 ($MH^+$). found 325, 327.

Example 157

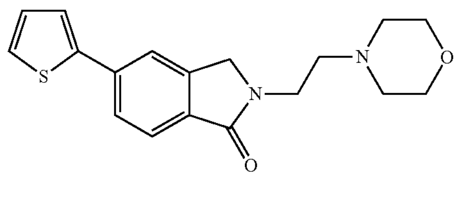 [SMILES: O=C1c2ccc(-c3cccs3)cc2CN1CCN1CCOCC1]

2-(2-Morpholinoethyl)-5-(thiophen-2-yl)isoindolin-1-one

Reaction of 5-bromo-2-(2-morpholinoethyl)isoindolin-1-one with thiophene-2-boronic acid according to general procedure C gave the title compound as a pale brown solid (100%). $^1H$ NMR [400 MHz, $(CD_3)_2SO$] δ 7.88 (d, J=0.7 Hz, 1H), 7.77 (dd, J=7.9, 1.5 Hz, 1H), 7.68 (d, J=8.0 Hz, 1H), 7.62-7.66 (m, 2H), 7.19 (dd, J=5.1, 3.7 Hz, 1H), 4.59 (s, 2H), 3.65 (t, J=6.3 Hz, 2H), 3.55 (t, J=4.6 Hz, 4H), 2.55 (t, J=6.3 Hz, 2H), 2.43 (br s, 4H). LRMS ($APCI^+$) calcd for $C_{28}H_{21}N_2O_2S$, 329 ($MH^+$). found 329.

Example 158

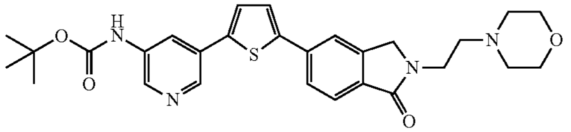 [SMILES: CC(C)(C)OC(=O)Nc1cncc(-c2ccc(-c3ccc4c(c3)CN(CCN3CCOCC3)C4=O)s2)c1]

tert-Butyl (5-(5-(2-(2-morpholinoethyl)-1-oxoisoindolin-5-yl)thiophen-2-yl)pyridin-3-yl)carbamate 2-(2-Morpholinoethyl)-5-(thiophen-2-yl)isoindolin-1-one was brominated with N-bromosuccinimide according to general procedure D. The crude product, 5-(5-bromothiophen-2-yl)-2-(2-morpholinoethyl)isoindolin-1-one, was then reacted directly with tert-butyl (5-(4,4,5,5-tetramethyl-1,3,2-dioxaborolan-2-yl)pyridin-3-yl)carbamate according to general procedure C. The title compound was isolated as a cream solid (34%). $^1H$ NMR [400 MHz, $(CD_3)_2SO$] δ 9.75 (br s, 1H), 8.60 (d, J=2.0 Hz, 1H), 8.50 (d, J=2.2 Hz, 1H), 8.26 (br s, 1H), 7.96 (br s, 1H), 7.84 (dd, J=8.0, 1.4 Hz, 1H), 7.73 (d, J=3.9 Hz, 1H), 7.71 (d, J=8.2 Hz, 1H), 7.65 (d, J=3.9 Hz, 1H), 4.60 (s, 2H), 3.66 (t, J=6.2 Hz, 2H), 3.55 (t, J=4.5 Hz, 4H), 2.56 (t, J=6.2 Hz, 2H), 2.43 (br s, 4H), 1.51 (s, 9H). LRMS ($APCI^+$) calcd for $C_{28}H_{33}N_4O_4S$, 521 ($MH^+$). found 521.

Example 159

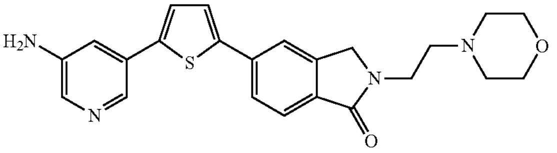 [SMILES: Nc1cncc(-c2ccc(-c3ccc4c(c3)CN(CCN3CCOCC3)C4=O)s2)c1]

5-(5-(5-Aminopyridin-3-yl)thiophen-2-yl)-2-(2-morpholinoethyl)isoindolin-1-one

Deprotection of tert-butyl (5-(5-(2-(2-morpholinoethyl)-1-oxoisoindolin-5-yl)thiophen-2-yl)pyridin-3-yl)carbamate according to general procedure J gave the title compound as a pale yellow solid (93%). $^{1}H$ NMR [400 MHz, $(CD_3)_2SO$] δ 8.12 (d, J=2.0 Hz, 1H), 7.92 (d, J=0.7 Hz, 1H), 7.90 (d, J=2.4 Hz, 1H), 7.81 (dd, J=8.0, 1.5 Hz, 1H), 7.67-7.72 (m, 2H), 7.54 (d, J=3.8 Hz, 1H), 7.16 (t, J=2.2 Hz, 1H), 5.51 (br s, 2H), 4.60 (s, 2H), 3.65 (t, J=6.2 Hz, 2H), 3.55 (t, J=4.5 Hz, 4H), 2.56 (t, J=6.2 Hz, 2H), 2.43 (br s, 4H). LRMS ($APCI^+$) calcd for $C_{23}H_{25}N_4O_2S$, 421 ($MH^+$). found 421.

Example 160

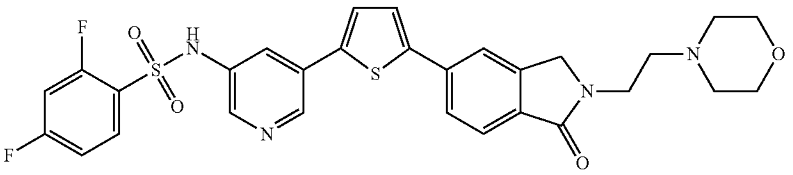

(69)

2,4-Difluoro-N-(5-(5-(2-(2-morpholinoethyl)-1-oxoisoindolin-5-yl)thiophen-2-yl)pyridin-3-yl)benzenesulfonamide (69)

5-(5-(5-Aminopyridin-3-yl)thiophen-2-yl)-2-(2-morpholinoethyl)isoindolin-1-one was reacted with 2,4-difluorobenzenesulfonyl chloride according to general procedure E, and the resulting crude product purified by flash column chromatography (0.1% $NH_4OH$ in 5% $MeOH/CH_2Cl_2$ as eluant) to give the title compound as an off-white solid (11%), mp ($MeOH/CH_2Cl_2$) 249-251° C. $^{1}H$ NMR [400 MHz, $(CD_3)_2SO$] δ 11.11 (br s, 1H), 8.65 (br s, 1H), 8.23 (d, J=2.3 Hz, 1H), 7.94-8.04 (m, 2H), 7.84 (dd, J=8.0, 1.5 Hz, 1H), 7.69-7.74 (m, 3H), 7.64 (d, J=3.8 Hz, 1H), 7.50-7.58 (m, 1H), 7.29 (td, J=8.4, 2.1 Hz, 1H), 4.61 (s, 2H), 3.67 (t, J=6.2 Hz, 2H), 3.56 (t, J=4.5 Hz, 4H), 2.58 (t, J=6.2 Hz, 2H), 2.45 (br s, 4H). LRMS ($APCI^+$) calcd for $C_{29}H_{27}F_2N_4O_4S_2$ 597 ($MH^+$). found 597. Anal. ($C_{29}H_{26}F_2N_4O_4S_2$) C, H, N.

Example 161

(70)

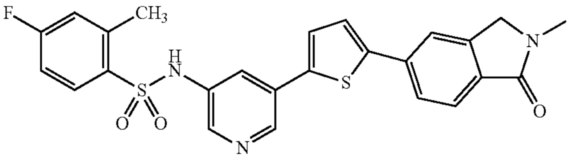

4-Fluoro-2-methyl-N-(5-(5-(2-methyl-1-oxoisoindolin-5-yl)thiophen-2-yl)pyridin-3-yl)benzenesulphonamide (70)

5-(5-(5-Aminopyridin-3-yl)thiophen-2-yl)-2-methylisoindolin-1-one was reacted with 4-fluoro-2-methylbenzene-1-sulphonyl chloride according to general procedure E, and the desired title compound was given as a light-brown solid (50%), mp 280-283° C. $^{1}H$ NMR [400 MHz, $(CD_3)_2SO$] δ 10.95 (br s, 1H), 8.65 (d, J=2.0 Hz, 1H), 8.23 (d, J=2.4 Hz, 1H), 8.05 (dd, J=5.8, 3.1 Hz, 1H), 7.95 (s, 1H), 7.83 (dd, J=7.9, 1.4 Hz, 1H), 7.68-7.75 (m, 2H), 7.66 (t, J=2.2 Hz, 1H), 7.63 (d, J=3.9 Hz, 1H), 7.33 (dd, J=9.9, 2.5 Hz, 1H), 7.27 (dt, J=8.4, 2.6 Hz, 1H), 4.52 (s, 2H), 3.09 (s, 3H). Anal. ($C_{25}H_{20}FN_3O_3S_2$) C, H, N.

Example 162

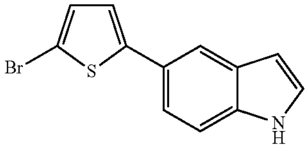 [SMILES: Brc1ccc(-c2ccc3[nH]ccc3c2)s1]

5-(5-Bromothiophen-2-yl)-1H-indole

Reaction of 2,5-dibromothiophene and indole-5-boronic acid according to general procedure C gave the title compound as a crystalline yellow solid (51%). $^1$H NMR [400 MHz, $(CD_3)_2SO$] δ 11.22 (br s, 1H), 7.77 (d, J=1.7 Hz, 1H), 7.42 (dd, J=8.5, 0.7 Hz, 1H), 7.39 (t, J=2.7 Hz, 1H), 7.33 (dd, J=8.5, 1.8 Hz, 1H), 7.22 (d, J=3.8, 1H), 7.20 (d, J=3.8 Hz, 1H), 6.45-6.48 (m, 1H). LRMS ($APCI^+$) calcd for $C_{12}H_9BrNS$, 278, 280 ($MH^+$). found 278, 280.

Example 163

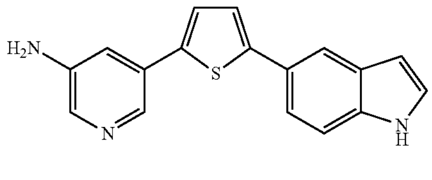 [SMILES: Nc1cncc(-c2ccc(-c3ccc4[nH]ccc4c3)s2)c1]

5-(5-(1H-Indol-5-yl)thiophen-2-yl)pyridin-3-amine

Reaction of 5-(5-bromothiophen-2-yl)-1H-indole and 3-aminopyridine-5-boronic acid according to general procedure C gave the title compound as an olive-green powder (63%). $^1$H NMR [400 MHz, $(CD_3)_2SO$] δ 11.22 (br s, 1H), 8.10 (d, J=2.0 Hz, 1H), 7.85 (d, J=2.3 Hz, 2H), 7.42-7.47 (m, 3H), 7.41 (d, J=3.8 Hz, 1H), 7.39 (t, J=2.7 Hz, 1H), 7.14 (t, J=2.2 Hz, 1H), 6.48 (d, J=2.4 Hz, 1H), 5.46 (br s, 2H). LRMS ($APCI^+$) calcd for $C_{17}H_{14}N_3S$, 292 ($MH^+$). found 292.

Example 164

(71)

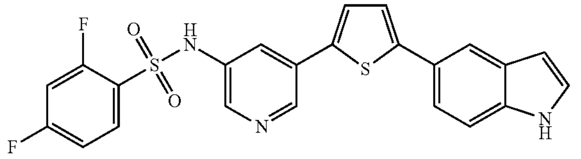

N-(5-(5-(1H-indol-5-yl)thiophen-2-yl)pyridin-3-yl)-2,4-difluorobenzenesulfonamide (71)

5-(5-(1H-Indol-5-yl)thiophen-2-yl)pyridin-3-amine was reacted with 2,4-difluorobenzenesulfonyl chloride according to general procedure E, and the resulting crude product purified by flash column chromatography (2% MeOH/$CH_2Cl_2$ as eluant) to give the title compound as a dark yellow solid (80%), mp ($CH_2Cl_2/Et_2O$) 228-231° C. $^1$H NMR [400 MHz, $(CD_3)_2SO$] δ 11.23 (br s, 1H), 11.10 (br s, 1H), 8.64 (br s, 1H), 8.21 (br s, 1H), 7.97-8.04 (m, 1H), 7.89 (s, 1H), 7.68 (br s, 1H), 7.53-7.60 (m, 2H), 7.43-7.47 (m, 3H), 7.40 (t, J=2.7 Hz, 1H), 7.28-7.34 (m, 1H), 6.48-6.51 (m, 1H). LRMS ($APCI^+$) calcd for $C_{23}H_{16}F_2N_3O_2S_2$ 468 ($MH^+$). found 468. Anal. ($C_{23}H_{15}F_2N_3O_2S_2$) C, H, N.

Example 165

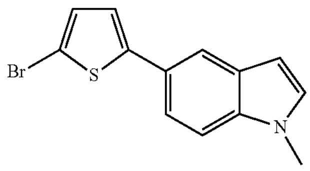 [SMILES: Cn1ccc2cc(-c3ccc(Br)s3)ccc21]

5-(5-Bromothiophen-2-yl)-1-methyl-1H-indole

Reaction of 2,5-dibromothiophene and 1-methylindole-5-boronic acid according to general procedure C gave the title compound as a pale yellow solid (57%). $^1$H NMR [400 MHz, $(CD_3)_2SO$] δ 7.77 (d, J=1.2 Hz, 1H), 7.48 (d, J=8.6 Hz, 1H), 7.40 (dd, J=8.6, 1.8 Hz, 1H), 7.37 (d, J=3.0 Hz, 1H), 7.25 (d, J=3.9, 1H), 7.20 (d, J=3.9 Hz, 1H), 6.46 (dd, J=3.1, 0.7 Hz, 1H), 3.80 (s, 3H). LRMS ($APCI^+$) calcd for $C_{13}H_{11}BrNS$, 292, 294 ($MH^+$). found 292, 294.

Example 166

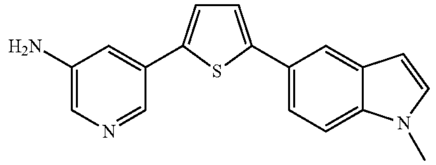 [SMILES: Cn1ccc2cc(-c3ccc(-c4cncc(N)c4)s3)ccc21]

5-(5-(1-Methyl-1H-indol-5-yl)thiophen-2-yl)pyridin-3-amine

Reaction of 5-(5-bromothiophen-2-yl)-1-methyl-1H-indole and 3-aminopyridine-5-boronic acid according to general procedure C gave the title compound as a dark yellow solid (65%). $^1$H NMR [400 MHz, $(CD_3)_2SO$] δ 8.10 (d, J=2.0 Hz, 1H), 7.84-7.87 (m, 2H), 7.48-7.51 (m, 2H), 7.42-7.47 (m, 2H), 7.37 (d, J=3.0 Hz, 1H), 7.14 (t, J=2.2 Hz, 1H), 6.48 (d, J=3.0 Hz, 1H), 5.49 (br s, 2H), 3.81 (s, 3H). LRMS ($APCI^+$) calcd for $C_{18}H_{16}N_3S$, 306 ($MH^+$). found 306.

Example 167

(72)

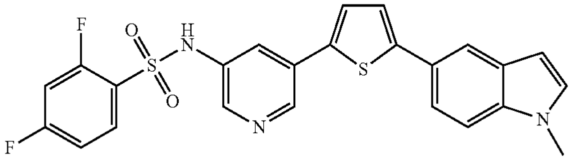

2,4-Difluoro-N-(5-(5-(1-methyl-1H-indol-5-yl)thiophen-2-yl)pyridin-3-yl)benzenesulfonamide (72)

5-(5-(1-Methyl-1H-indol-5-yl)thiophen-2-yl)pyridin-3-amine was reacted with 2,4-difluorobenzenesulfonyl chloride according to general procedure E, and the resulting crude product purified by flash column chromatography (2% $MeOH/CH_2Cl_2$ as eluant) to give the title compound as a pale yellow solid (83%), mp ($MeOH/CH_2Cl_2$) 235-238° C. $^1H$ NMR [400 MHz, $(CD_3)_2SO$] δ 11.10 (br s, 1H), 8.66 (d, J=1.8 Hz, 1H), 8.22 (d, J=2.3 Hz, 1H), 7.97-8.05 (m, 1H), 7.89 (t, J=1.1 Hz, 1H), 7.69 (t, J=2.2 Hz, 1H), 7.53-7.61 (m, 2H), 7.50-7.52 (m, 2H), 7.48 (d, J=3.8 Hz, 1H), 7.38 (d, J=3.0 Hz, 1H), 7.28-7.34 (m, 1H), 6.49 (d, J=3.0 Hz, 1H), 3.82 (s, 3H). LRMS ($APCI^+$) calcd for $C_{24}H_{18}F_2N_3O_2S_2$ 482 ($MH^+$). found 482. Anal. ($C_{24}H_{17}F_2N_3O_2S_2$) C, H, N.

Example 168

(73)

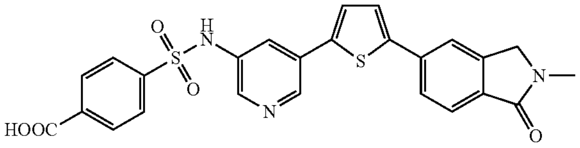

4-(N-(5-(5-(2-Methyl-1-oxoisoindolin-5-yl)thiophen-2-yl)pyridin-3-yl)sulfamoyl)benzoic acid (73)

5-(5-(5-Aminopyridin-3-yl)thiophen-2-yl)-2-methylisoindolin-1-one was reacted with 4-chlorosulphonyl benzoic acid according to general procedure E. The resulting crude product was collected by filtration over celite and dried. Extraction of the celite with 50% $MeOH/CH_2Cl_2$ gave a pale yellow solid which was purified by flash column chromatography (10% $MeOH/CH_2Cl_2$ as eluant) to give the title compound as a pale pink solid (6%), mp ($MeOH/CH_2Cl_2$) >310° C. $^1H$ NMR [400 MHz, $(CD_3)_2SO$] δ 13.46 (v br s, 1H), 10.91 (v br s, 1H), 8.68 (d, J=1.9 Hz, 1H), 8.21 (d, J=2.3 Hz, 1H), 8.11 (d, J=8.6 Hz, 2H), 7.91-7.95 (m, 3H), 7.83 (dd, J=8.0, 1.5 Hz, 1H), 7.69-7.73 (m, 3H), 7.65 (d, J=3.9 Hz, 1H), 4.52 (s, 2H), 3.09 (s, 3H). LRMS ($APCI^-$) calcd for $C_{25}H_{19}N_3O_5S_2$ 505 (M). found 505. Anal. ($C_{25}H_{19}N_3O_5S_2$) C, H, N.

Example 169

(74)

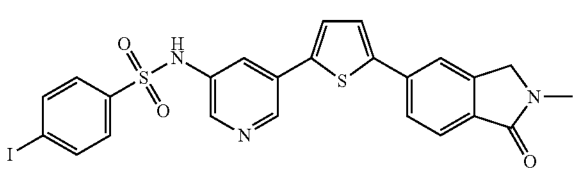

4-Iodo-N-(5-(5-(2-methyl-1-oxoisoindolin-5-yl)thiophen-2-yl)pyridin-3-yl)benzenesulfonamides (74)

5-(5-(5-Aminopyridin-3-yl)thiophen-2-yl)-2-methylisoindolin-1-one was reacted with 4-iodobenzenesulfonyl chloride according to general procedure E, and the resulting crude product purified by flash column chromatography (5% $MeOH/CH_2Cl_2$ as eluant) to give the title compound as a pale yellow solid (59%), mp ($CH_2Cl_2/Et_2O$) 295-298° C. $^1H$ NMR [400 MHz, $(CD_3)_2SO$] δ 10.80 (br s, 1H), 8.70 (d, J=2.0 Hz, 1H), 8.20 (d, J=2.4 Hz, 1H), 7.99 (d, J=8.6 Hz, 2H), 7.95 (d, J=0.70 Hz, 1H), 7.84 (dd, J=8.0, 1.5 Hz, 1H), 7.70-7.74 (m, 2H), 7.68 (t, J=2.2 Hz, 1H), 7.66 (d, J=3.9 Hz, 1H), 7.56 (d, J=8.6 Hz, 2H), 4.52 (s, 2H), 3.09 (s, 3H). LRMS ($APCI^-$) calcd for $C_{24}H_{18}IN_3O_3S_2$ 587 (M). found 587. Anal. ($C_{24}H_{18}IN_3O_3S_2$) C, H, N.

Example 170

(75)

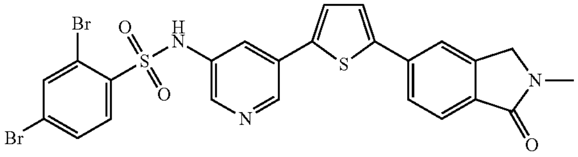

2,4-Dibromo-N-(5-(5-(2-methyl-1-oxoisoindolin-5-yl)thiophen-2-yl)pyridin-3-yl)benzenesulfonamides (75)

5-(5-(5-Aminopyridin-3-yl)thiophen-2-yl)-2-methylisoindolin-1-one was reacted with 2,4-dibromobenzenesulfonyl chloride according to general procedure E, and the resulting crude product purified by trituration with 10% $MeOH/CH_2Cl_2$ to give the title compound as a cream solid (81%), mp ($MeOH/CH_2Cl_2$) 276-279° C. $^1H$ NMR [400 MHz, $(CD_3)_2SO$] δ 11.23 (br s, 1H), 8.66 (d, J=1.9 Hz, 1H), 8.25 (d, J=2.4 Hz, 1H), 8.16 (d, J=1.9 Hz, 1H), 8.08 (d, J=8.5 Hz, 1H), 7.94 (d, J=0.7 Hz, 1H), 7.81-7.87 (m, 2H), 7.67-7.74 (m, 2H), 7.65 (t, J=2.2 Hz, 1H), 7.63 (d, J=3.8 Hz, 1H), 4.52 (s, 2H), 3.09 (s, 3H). LRMS ($APCI^-$) calcd for $C_{24}H_{17}Br_2N_3O_3S_2$ 617, 619, 621 (M). found 617, 619, 621. Anal. ($C_{24}H_{17}Br_2N_3O_3S_2$) C, H, N.

Example 171

(76)

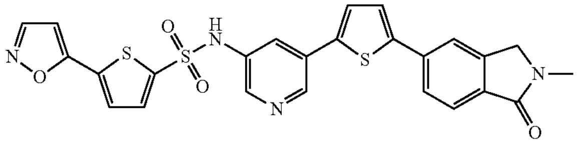

5-(Isoxazol-5-yl)-N-(5-(5-(2-methyl-1-oxoisoindolin-5-yl)thiophen-2-yl)pyridin-3-yl)thiophene-2-sulfonamide (76)

5-(5-(5-Aminopyridin-3-yl)thiophen-2-yl)-2-methylisoindolin-1-one was reacted with 5-(5-isoxazyl)thiophene-2-sulfonyl chloride according to general procedure E, and the resulting crude product purified by flash column chromatography (5% $MeOH/CH_2Cl_2$ as eluant), followed by trituration with warm 10% MeOH/1,4-dioxane to give the title compound as a pale pink solid (20%), mp (MeOH/1,4-dioxane) 245-249° C. $^1H$ NMR [400 MHz, $(CD_3)_2SO$] δ 11.15 (br s, 1H), 8.76 (br s, 1H), 8.72 (d, J=2.0 Hz, 1H), 8.29 (d, J=2.3 Hz, 1H), 7.93 (d, J=0.7 Hz, 1H), 7.82 (dd, J=7.9, 1.5 Hz, 1H), 7.79 (t, J=2.2 Hz, 1H), 7.71-7.75 (m, 4H), 7.70 (d, J=3.6 Hz, 1H), 7.11 (d, J=1.9 Hz, 1H), 4.52 (s, 2H), 3.09 (s, 3H). LRMS (APCI⁻) calcd for $C_{25}H_{18}N_4O_4S_3$ 534 (M). found 534. Anal. ($C_{25}H_{18}N_4O_4S_3$) C, H, N.

Example 172

(77)

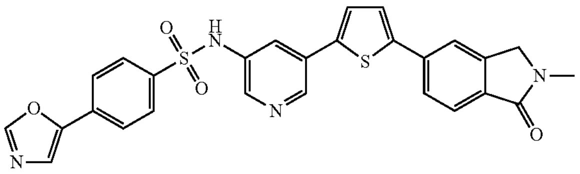

N-(5-(5-(2-Methyl-1-oxoisoindolin-5-yl)thiophen-2-yl)pyridin-3-yl)-4-(oxazol-5-yl)benzenesulfonamides (77)

5-(5-(5-Aminopyridin-3-yl)thiophen-2-yl)-2-methylisoindolin-1-one was reacted with 4-(1,3-oxazol-5-yl)benzenesulfonyl chloride according to general procedure E, and the resulting crude product purified by trituration with 10% $MeOH/CH_2Cl_2$ to give the title compound as a pale yellow solid (81%), mp ($MeOH/CH_2Cl_2$) 278-281° C. $^1H$ NMR [400 MHz, $(CD_3)_2SO$] δ 10.80 (br s, 1H), 8.69 (d, J=2.0 Hz, 1H), 8.53 (s, 1H), 8.23 (d, J=2.3 Hz, 1H), 7.86-7.96 (m, 6H), 7.80 (dd, J=7.9, 1.4 Hz, 1H), 7.68-7.73 (m, 3H), 7.66 (d, J=3.9 Hz, 1H), 4.52 (s, 2H), 3.09 (s, 3H). LRMS (APCI⁻) calcd for $C_{27}H_{20}N_4O_4S_2$ 528 (M). found 528. Anal. ($C_{27}H_{20}N_4O_4S_2$) C, H, N.

Example 173

(78)

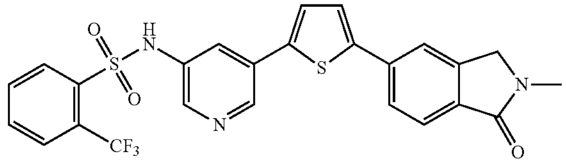

N-(5-(5-(2-Methyl-1-oxoisoindolin-5-yl)thiophen-2-yl)pyridin-3-yl)-2-(trifluoromethyl)benzenesulfonamide (78)

5-(5-(5-Aminopyridin-3-yl)thiophen-2-yl)-2-methylisoindolin-1-one was reacted with 2-(trifluoromethyl)benzenesulfonyl chloride according to general procedure E, and the resulting crude product purified by flash column chromatography (2% $MeOH/CH_2Cl_2$ as eluant) to give the title compound as a pale yellow solid (67%), mp ($CH_2Cl_2/Et_2O$) 271-275° C. $^1H$ NMR [400 MHz, $(CD_3)_2SO$] δ 11.15 (br s, 1H), 8.68 (d, J=1.8 Hz, 1H), 8.25 (d, J=2.3 Hz, 1H), 8.21 (d, J=7.7 Hz, 1H), 8.03 (d, J=7.4 Hz, 1H), 7.84-7.96 (m, 3H), 7.82 (dd, J=8.0, 1.4 Hz, 1H), 7.68-7.74 (m, 3H), 7.63 (d, J=3.8 Hz, 1H), 4.52 (s, 2H), 3.09 (s, 3H). LRMS (APCI⁻) calcd for $C_{25}H_{18}F_3N_3O_3S_2$ 529 (M). found 529. Anal. ($C_{25}H_{18}F_3N_3O_3S_2$) C, H, N.

Example 174

(79)

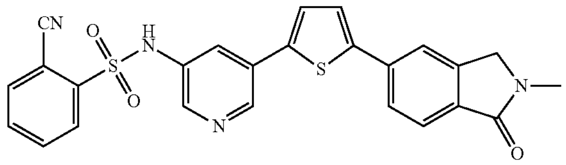

2-Cyano-N-(5-(5-(2-methyl-1-oxoisoindolin-5-yl)thiophen-2-yl)pyridin-3-yl)benzenesulfonamides (79)

5-(5-(5-Aminopyridin-3-yl)thiophen-2-yl)-2-methylisoindolin-1-one was reacted with 2-cyanobenzenesulfonyl chloride according to general procedure E, and the resulting crude product purified by flash column chromatography (5% $MeOH/CH_2Cl_2$ as eluant) to give the title compound as a pale mustard-yellow solid (43%), mp ($MeOH/CH_2Cl_2$) >310° C. $^1H$ NMR [400 MHz, $(CD_3)_2SO$] δ 11.16 (br s, 1H), 8.95 (d, J=1.8 Hz, 1H), 8.89 (d, J=1.5 Hz, 1H), 8.57 (t, J=2.1 Hz, 1H), 8.47 (d, J=7.4 Hz, 1H), 8.13 (d, J=7.0 Hz, 1H), 7.90-8.00 (m, 3H), 7.85 (dd, J=7.9, 1.3 Hz, 1H), 7.79 (d, J=3.9 Hz, 1H), 7.76 (d, J=3.9 Hz, 1H), 7.72 (d, J=8.0 Hz, 1H), 4.53 (s, 2H), 3.09 (s, 3H). LRMS (APCI⁻) calcd for $C_{25}H_{18}N_4O_3S_2$ 486 (M). found 486. Anal. ($C_{25}H_{18}N_4O_3S_2$) C, H, N.

In this case the product was converted to its sodium salt according to general procedure F to give the desired product (79.Na) as a pale yellow solid (100%). $^1H$ NMR [400 MHz, $(CD_3)_2SO$] δ 8.47 (t, J=2.5 Hz, 2H), 8.32 (t, J=2.2 Hz, 1H), 7.91-7.96 (m, 2H), 7.85 (dd, J=8.0, 1.4 Hz, 1H), 7.67-7.73 (m, 3H), 7.68 (d, J=3.9 Hz, 1H), 7.55-7.61 (m, 2H), 4.52 (s, 2H), 3.09 (s, 3H).

Example 175

(80)

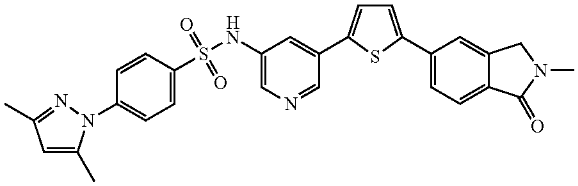

4-(3,5-Dimethyl-1H-pyrazol-1-yl)-N-(5-(5-(2-methyl-1-oxoisoindolin-5-yl)thiophen-2-yl)pyridin-3-yl)benzenesulfonamides (80)

5-(5-(5-Aminopyridin-3-yl)thiophen-2-yl)-2-methylisoindolin-1-one was reacted with 4-(3,5-dimethyl-1H-pyrazol-1-yl)benzenesulfonyl chloride according to general procedure E, and the resulting crude product purified by flash column chromatography (2% $MeOH/CH_2Cl_2$ as eluant) to give the title compound as a beige solid (14%), mp ($Et_2O/CH_2Cl_2$) 265-268° C. $^1H$ NMR [400 MHz, $(CD_3)_2SO$] δ 10.81 (br s, 1H), 8.70 (s, 1H), 8.25 (d, J=2.2 Hz, 1H), 7.94

(br s, 1H), 7.91 (d, J=8.7 Hz, 2H), 7.82 (dd, J=8.0, 1.3 Hz, 1H), 7.77 (d, J=8.7 Hz, 2H), 7.68-7.74 (m, 3H), 7.61 (d, J=3.9 Hz, 1H), 6.12 (s, 1H), 4.51 (s, 2H), 3.09 (s, 3H), 2.34 (s, 3H), 2.15 (s, 3H). LRMS ($APCI^-$) calcd for $C_{29}H_{25}N_5O_3S_2$ 555 (M). found 555. Anal. ($C_{29}H_{25}N_5O_3S_2$) C, H, N.

Example 176

(81)

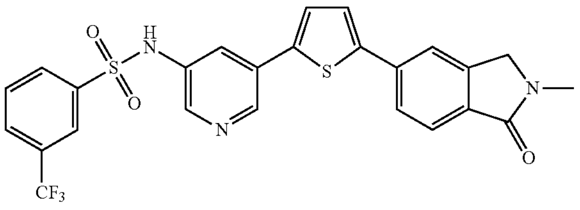

N-(5-(5-(2-Methyl-1-oxoisoindolin-5-yl)thiophen-2-yl)pyridin-3-yl)-3-(trifluoromethyl)benzenesulfonamides (81)

5-(5-(5-Aminopyridin-3-yl)thiophen-2-yl)-2-methylisoindolin-1-one was reacted with 3-(trifluoromethyl)benzenesulfonyl chloride according to general procedure E, and the resulting crude product purified by flash column chromatography (2% MeOH/$CH_2Cl_2$ as eluant) to give the title compound as a pale yellow solid (65%), mp (1,4-dioxane) 262-265° C. $^1H$ NMR [400 MHz, $(CD_3)_2SO$] δ 10.92 (br s, 1H), 8.71 (d, J=2.0 Hz, 1H), 8.20 (d, J=2.3 Hz, 1H), 8.05-8.12 (m, 3H), 7.93 (d, J=0.7 Hz, 1H), 7.86 (d, J=7.9 Hz, 1H), 7.82 (dd, J=7.9, 1.6 Hz, 1H), 7.68-7.74 (m, 3H), 7.66 (d, J=3.8 Hz, 1H), 4.52 (s, 2H), 3.09 (s, 3H). LRMS ($APCI^-$) calcd for $C_{25}H_{18}F_3N_3O_3S_2$ 529 (M). found 529. Anal. ($C_{25}H_{18}F_3N_3O_3S_2$) C, H, N.

Example 177

(82)

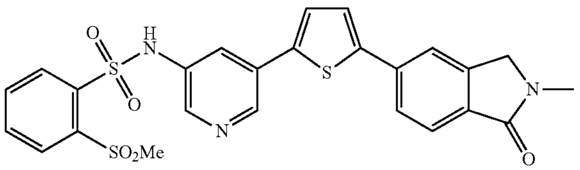

N-(5-(5-(2-Methyl-1-oxoisoindolin-5-yl)thiophen-2-yl)pyridin-3-yl)-2-(methylsulfonyl)benzenesulfonamides (82)

5-(5-(5-Aminopyridin-3-yl)thiophen-2-yl)-2-methylisoindolin-1-one was reacted with 2-(methanesulfonyl)benzenesulfonyl chloride according to general procedure E, and the resulting crude product purified by flash column chromatography (2% MeOH/$CH_2Cl_2$ as eluant) to give the title compound as a pale orange solid (77%), mp ($Et_2O/CH_2Cl_2$) 269-272° C. $^1H$ NMR [400 MHz, $(CD_3)_2SO$] δ 10.22 (br s, 1H), 8.68 (d, J=1.5 Hz, 1H), 8.22-8.27 (m, 2H), 8.14-8.18

(m, 1H), 7.89-7.97 (m, 3H), 7.82 (dd, J=8.0, 1.5 Hz, 1H), 7.76 (t, J=2.2 Hz, 1H), 7.68-7.73 (m, 2H), 7.65 (d, J=3.9 Hz, 1H), 4.52 (s, 2H), 3.53 (s, 3H), 3.09 (s, 3H). LRMS ($APCI^-$) calcd for $C_{25}H_{21}N_3O_5S_3$ 539 (M). found 539. Anal. ($C_{25}H_{21}N_3O_5S_3$) C, H, N.

Example 178

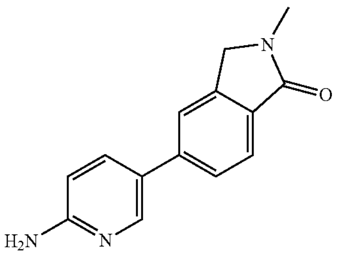 [SMILES: CN1Cc2cc(-c3ccc(N)nc3)ccc2C1=O]

5-(6-Aminopyridin-3-yl)-2-methylisoindolin-1-one

5-Bromo-2-methylisoindolin-1-one was reacted with 5-(4,4,5,5-tetramethyl-1,3,2-dioxaborolan-2-yl)pyridin-2-amine according to general procedure C. Purification by column chromatography on silica gel (1-3% MeOH/$CH_2Cl_2$) gave the title compound as a brown solid (68%). $^1H$ NMR [400 MHz, $(CD_3)_2SO$] δ 8.30 (s, 1H), 7.80 (s, 2H), 7.60 (s, 2H), 6.54 (d, J=8.4 Hz, 1H), 6.17 (s, 2H), 4.47 (s, 2H), 3.08 (s, 3H). LRMS ($APCI^+$) calcd for $C_{14}H_{13}N_3O$, 240 ($MH^+$). found 240.

Example 179

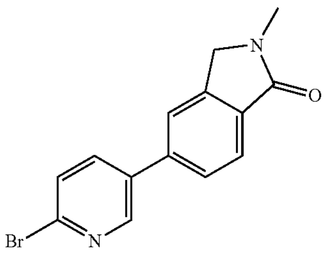 [SMILES: CN1Cc2cc(-c3ccc(Br)nc3)ccc2C1=O]

5-(6-Bromopyridin-3-yl)-2-methylisoindolin-1-one 5-(6-Aminopyridin-3-yl)-2-methyl isoindolin-1-one (300 mg, 1.26 mmol) was dissolved slowly with constant stirring in 47% HBr solution (5 mL) and cooled to −10° C. A solution of $NaNO_2$ (277 mg, 3.26 mmol) in $H_2O$ (3 mL) was added slowly to the reaction mixture followed by drop-wise addition of bromine (0.2 mL, 3.77 mmol). The reaction mixture was allowed to warm to RT and left to stir until 5-(6-aminopyridin-3-yl)-2-methylisoindolin-1-one had been consumed (TLC). The reaction mixture was neutralised with cold aqueous $Na_2CO_3$ and extracted in $CH_2Cl_2$ (3×50 mL). The combined organic extracts were washed with brine (1×50 mL), dried ($Na_2SO_4$), filtered through a plug of silica gel, and concentrated in vacuo to give the title compound as a dark-brown solid (133 mg, 35%). This was used directly in the next step without further purification. LRMS ($APCI^+$) calcd for $C_{14}H_{11}BrN_2O$, 304 ($MH^+$). found 304.

Example 180

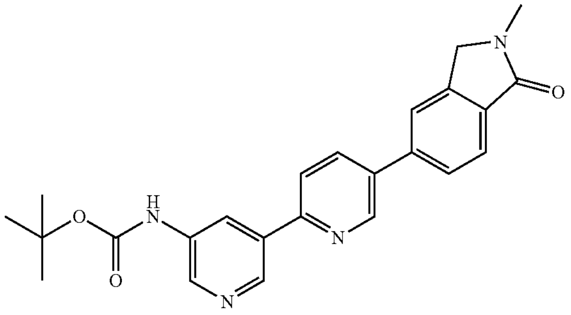 [SMILES: CN1Cc2cc(-c3ccc(-c4cncc(NC(=O)OC(C)(C)C)c4)nc3)ccc2C1=O]

tert-Butyl (5-(2-methyl-1-oxoisoindolin-5-yl)-[2,3'-bipyridin]-5'-yl)carbamate 5-(6-Bromopyridin-3-yl)-2-methylisoindolin-1-one was reacted with tert-butyl (5-(4,4,5,5-tetramethyl-1,3,2-dioxaborolan-2-yl)pyridin-3-yl)carbamate according to general procedure C. Purification by column chromatography on silica gel (1-5% $MeOH/CH_2Cl_2$) gave the title compound as an off-white solid (55%). $^1H$ NMR [400 MHz, $(CD_3)_2SO$] δ 9.75 (br s, 1H), 9.11 (d, J=1.9 Hz, 1H), 8.93 (d, J=1.9 Hz, 1H), 8.72 (s, 1H), 8.65 (d, J=2.4 Hz, 1H), 8.30 (dd, J=8.4, 2.4 Hz, 1H), 8.13 (d, J=8.1 Hz, 1H), 8.03 (s, 1H), 7.91 (dd, J=8.0, 1.2 Hz, 1H), 7.80 (d, J=7.9 Hz, 1H), 4.56 (s, 2H), 3.11 (s, 3H), 1.52 (s, 9H). LRMS ($APCI^+$) calcd for $C_{24}H_{24}N_4O_3$ 418 ($MH^+$). found 418.

Example 181

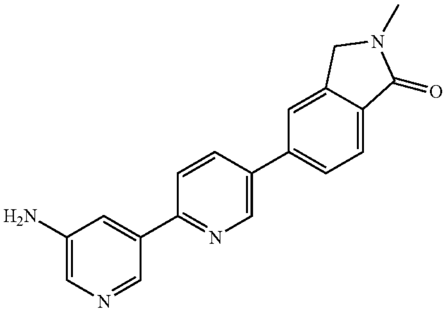 [SMILES: CN1Cc2cc(-c3ccc(-c4cncc(N)c4)nc3)ccc2C1=O]

5-(5'-Amino-[2,3'-bipyridin]-5-yl)-2-methylisoindolin-1-one

Deprotection of tert-butyl (5-(2-methyl-1-oxoisoindolin-5-yl)-[2,3'-bipyridin]-5'-yl)carbamate according to general procedure J gave the title compound as an off-white solid (86%). $^1H$ NMR [400 MHz, $(CD_3)_2SO$] δ 9.05 (dd, J=2.4, 0.6 Hz, 1H), 8.48 (d, J=1.9 Hz, 1H), 8.25 (dd, J=8.4, 2.5 Hz, 1H), 8.01-8.06 (m, 2H), 8.00 (d, J=2.6 Hz, 1H), 7.90 (dd, J=7.9, 1.5 Hz, 1H), 7.79 (d, J=7.9 Hz, 1H), 7.69 (t, J=2.3 Hz, 1H), 5.48 (br s, 2H), 4.55 (s, 2H), 3.11 (s, 3H). LRMS ($APCI^+$) calcd for $C_{19}H_{16}N_4O$, 317 ($MH^+$). found 317.

Example 182

(83)

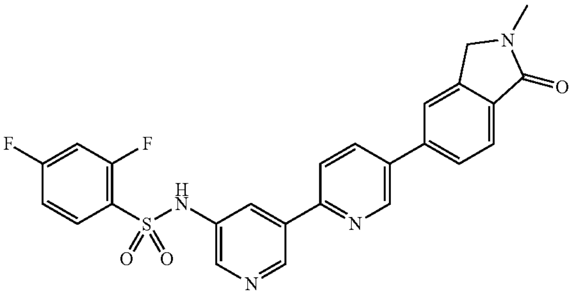

2,4-Difluoro-N-(5-(2-methyl-1-oxoisoindolin-5-yl)-[2,3'-bipyridin]-5'-yl)benzenesulphonamide (83)

5-(5'-Amino-[2,3'-bipyridin]-5-yl)-2-methylisoindolin-1-one was reacted with 2,4-difluorobenzenesulphonyl chloride according to general procedure E, and the desired title compound was given as a pink solid (62%), mp 278-282° C. $^1H$ NMR [400 MHz, $(CD_3)_2SO$] δ 11.12 (br s, 1H), 9.10 (d, J=2.1 Hz, 1H), 9.05 (d, J=1.7 Hz, 1H), 8.41 (d, J=2.4 Hz, 1H), 8.25-8.34 (m, 2H), 8.13 (d, J=8.3 Hz, 1H), 8.04 (s, 1H), 7.93-8.01 (m, 1H), 7.90 (d, J=8.6 Hz, 1H), 7.79 (d, J=7.9 Hz, 1H), 7.56 (dt, J=8.4, 2.4 Hz, 1H), 7.29 (dt, J=8.4, 2.1 Hz, 1H), 4.55 (s, 2H), 3.11 (s, 3H). Anal. ($C_{25}H_{18}F_2N_4O_3S.0.75H_2O$) C, H, N.

Example 183

(84)

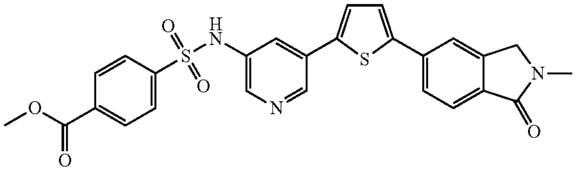

Methyl 4-(N-(5-(5-(2-methyl-1-oxoisoindolin-5-yl)thiophen-2-yl)pyridin-3-yl)sulfamoyl)benzoate (84)

5-(5-(5-Aminopyridin-3-yl)thiophen-2-yl)-2-methylisoindolin-1-one was reacted with methyl 4-(chlorosulfonyl)benzoate according to general procedure E, and the resulting crude product purified by flash column chromatography (5% $MeOH/CH_2Cl_2$ as eluant) to give the title compound as a pale yellow solid (60%), mp ($CH_2Cl_2/Et_2O$) 269-272° C. $^1H$ NMR [400 MHz, $(CD_3)_2SO$] δ 10.95 (br s, 1H), 8.67 (d, J=1.9 Hz, 1H), 8.19 (d, J=2.3 Hz, 1H), 8.13 (d, J=8.6 Hz, 2H), 7.92-7.97 (m, 3H), 7.82 (dd, J=8.0, 1.6 Hz, 1H), 7.68-7.73 (m, 3H), 7.65 (d, J=3.9 Hz, 1H), 4.52 (s, 2H), 3.85 (s, 3H), 3.09 (s, 3H). LRMS ($APCI^+$) calcd for $C_{26}H_{22}N_3O_5S_2$ 520 ($MH^+$). found 520. Anal. ($C_{26}H_{21}N_3O_5S_2$) C, H, N.

Example 184

(85)

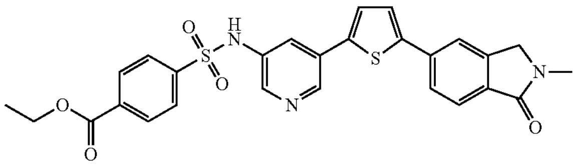

Ethyl 4-(N-(5-(5-(2-methyl-1-oxoisoindolin-5-yl) thiophen-2-yl)pyridin-3-yl)sulfamoyl)benzoate (85)

5-(5-(5-Aminopyridin-3-yl)thiophen-2-yl)-2-methylisoindolin-1-one was reacted with ethyl 4-(chlorosulfonyl) benzoate according to general procedure E, and the resulting crude product purified by flash column chromatography (5% $MeOH/CH_2Cl_2$ as eluant) to give the title compound as a pale yellow solid (52%), mp ($CH_2Cl_2/Et_2O$) 272-275° C. $^1$H NMR [400 MHz, $(CD_3)_2SO$] δ 10.93 (br s, 1H), 8.69 (d, J=2.0 Hz, 1H), 8.20 (d, J=2.4 Hz, 1H), 8.13 (d, J=8.6 Hz, 2H), 7.93-7.98 (m, 3H), 7.83 (dd, J=8.0, 1.6 Hz, 1H), 7.69-7.74 (m, 3H), 7.66 (d, J=3.9 Hz, 1H), 4.52 (s, 2H), 4.31 (q, J=7.1 Hz, 2H), 3.09 (s, 3H), 1.29 (t, J=7.1 Hz, 3H). LRMS ($APCI^+$) calcd for $C_{27}H_{24}N_3O_5S_2$ 534 ($MH^+$). found 534. Anal. ($C_{27}H_{23}N_3O_5S_2$) C, H, N.

Example 185

(86)

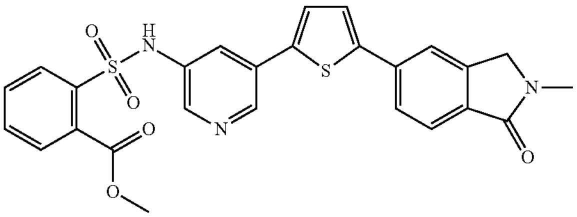

Methyl 2-(N-(5-(5-(2-methyl-1-oxoisoindolin-5-yl) thiophen-2-yl)pyridin-3-yl)sulfamoyl)benzoate (86)

5-(5-(5-Aminopyridin-3-yl)thiophen-2-yl)-2-methylisoindolin-1-one was reacted with methyl 2-(chlorosulfonyl) benzoate according to general procedure E, and the resulting crude product purified by flash column chromatography (2% $MeOH/CH_2Cl_2$ as eluant) to give the title compound as a pale orange solid (23%), mp ($CH_2Cl_2/Et_2O$) 209-212° C. $^1$H NMR [400 MHz, $(CD_3)_2SO$] δ 10.74 (br s, 1H), 8.66 (d, J=2.0 Hz, 1H), 8.22 (d, J=2.4 Hz, 1H), 7.95-7.99 (m, 1H), 7.93 (br d, J=0.7 Hz, 1H), 7.82 (dd, J=8.0, 1.6 Hz, 1H), 7.68-7.76 (m, 5H), 7.63-7.67 (m, 2H), 4.52 (s, 2H), 3.85 (s, 3H), 3.09 (s, 3H). LRMS ($APCI^+$) calcd for $C_{26}H_{22}N_3O_5S_2$ 520 ($MH^+$). found 520. Anal. ($C_{26}H_{21}N_3O_5S_2$) C, H, N.

Example 186

(87)

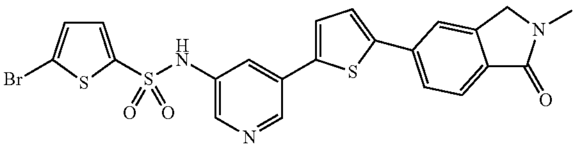

5-Bromo-N-(5-(5-(2-methyl-1-oxoisoindolin-5-yl) thiophen-2-yl)pyridin-3-yl)thiophene-2-sulphonamide (87)

5-(5-(5-Aminopyridin-3-yl)thiophen-2-yl)-2-methylisoindolin-1-one was reacted with 5-bromothiophene-2-sulphonyl chloride according to general procedure E, and the desired title compound was given as a pink solid (14%); mp 269-272° C. $^1$H NMR [400 MHz, $(CD_3)_2SO$] δ 11.05 (br s, 1H), 8.77 (d, J=2.0, Hz, 1H), 8.27 (d, J=2.4 Hz, 1H), 7.96 (d, J=0.7 Hz, 1H), 7.84 (dd, J=7.9, 1.5 Hz, 1H), 7.77 (t, J=2.2 Hz, 1H), 7.75 (d, J=3.9 Hz, 1H), 7.71 (d, J=7.9 Hz, 1H), 7.70 (d, J=3.8 Hz, 1H), 7.50 (d, J=4.1 Hz, 1H), 7.34 (d, J=4.1 Hz, 1H), 4.52 (s, 2H), 3.09 (s, 3H). Anal. ($C_{22}H_{16}BrN_3O_3S_3$) C, H, N.

Example 187

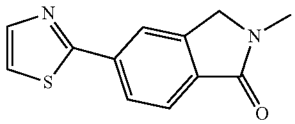 [SMILES: CN1Cc2cc(-c3nccs3)ccc2C1=O]

2-Methyl-5-(thiazol-2-yl)isoindolin-1-one

2-Bromothiazole was reacted with 2-methyl-5-(4,4,5,5-tetramethyl-1,3,2-dioxaborolan-2-yl)isoindolin-1-one according to general procedure C, to give the desired title compound as a light-brown solid (64%). $^1$H NMR [400 MHz, $(CD_3)_2SO$] δ 8.18 (d, J=0.7 Hz, 1H), 8.07 (dd, J=7.9, 1.5 Hz, 1H), 8.00 (d, J=3.2 Hz, 1H), 7.88 (d, J=3.2 Hz, 1H), 7.77 (d, J=7.9 Hz, 1H), 4.54 (s, 2H), 3.09 (s, 3H). LRMS ($APCI^+$) calcd for $C_{22}H_{10}N_2OS$, 231 ($MH^+$). found 231.

Example 188

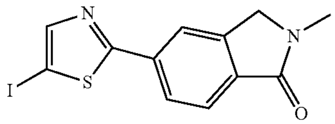 [SMILES: CN1Cc2cc(-c3ncc(I)s3)ccc2C1=O]

5-(5-Iodothiazol-2-yl)-2-methylisoindolin-1-one

2-Methyl-5-(thiazol-2-yl)isoindolin-1-one was iodinated with N-iodosuccinimide according to general procedure D. After workup, the crude solid was filtered through a plug of silica gel (1% MeOH/$CH_2Cl_2$), concentrated in vacuo, and recrystallised from 5% MeOH/$CH_2Cl_2$ and hexanes to give the title compound as a light-brown solid (12%). This was used directly in the next step without further purification. $^1H$ NMR [400 MHz, $(CD_3)_2SO$] δ 8.13 (s, 1H), 8.10 (s, 1H), 8.00 (dd, J=8.0, 1.5 Hz, 1H), 7.76 (d, J=7.9, 1H), 4.54 (s, 2H), 3.09 (s, 3H). LRMS ($APCI^+$) calcd for $Cl_2H_9IN_2OS$, 357 ($MH^+$). found 357.

Example 189

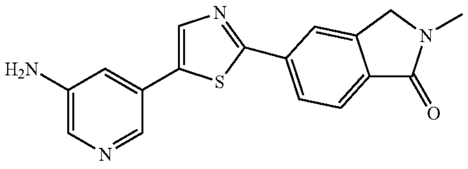 [SMILES: CN1Cc2cc(-c3ncc(-c4cncc(N)c4)s3)ccc2C1=O]

5-(5-(5-Aminopyridin-3-yl)thiazol-2-yl)-2-methylisoindolin-1-one 5-(5-Iodothiazol-2-yl)-2-methylisoindolin-1-one was reacted with 5-(4,4,5,5-tetramethyl-1,3,2-dioxaborolan-2-yl)pyridin-3-amine according to general procedure C. Purification by column chromatography on silica gel (1-5% MeOH/$CH_2Cl_2$) gave the title compound as a brown solid (41%). $^1H$ NMR [400 MHz, $(CD_3)_2SO$] δ 8.34 (s, 1H), 8.20 (s, 1H), 8.14 (s, 1H), 8.09 (d, J=7.4 Hz, 1H), 7.95 (s, 1H), 7.80 (d, J=8.04 Hz, 1H), 7.18 (s, 1H), 4.56 (s, 2H), 3.10 (s, 3H). LRMS ($APCI^+$) calcd for $C_{17}H_{14}N_4OS$, 323 ($MH^+$). found 323.

Example 190

(88)

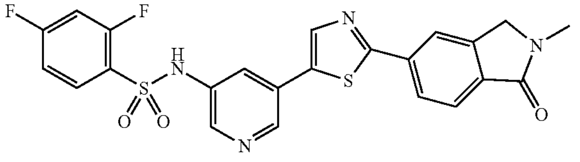

2,4-Difluoro-N-(5-(2-(2-methyl-1-oxoisoindolin-5-yl)thiazol-5-yl)pyridin-3-yl)benzenesulphonamide (88)

5-(5-(5-Aminopyridin-3-yl)thiazol-2-yl)-2-methylisoindolin-1-one was reacted with 2,4-difluorobenzenesulphonyl chloride according to general procedure E, and the desired title compound was given as a beige solid (16%), mp>300° C. $^1H$ NMR [400 MHz, $(CD_3)_2SO$] δ 11.21 (br s, 1H), 8.74 (d, J=2.0 Hz, 1H), 8.46 (s, 1H), 8.31 (d, J=2.4 Hz, 1H), 8.22 (d, J=0.7 Hz, 1H), 8.11 (dd, J=7.9, 1.4 Hz, 1H), 7.98-8.07 (m, 1H), 7.80 (d, J=7.9 Hz, 1H), 7.76 (t, J=2.2 Hz, 1H), 7.53-7.62 (m, 1H), 7.31 (dt, J=8.2, 2.2 Hz, 1H), 4.56 (s, 2H), 3.11 (s, 3H). HRMS ($APCI^+$) calcd for $C_{23}H_{17}F_2N_4O_3S_2$ 499.0705 ($MH^+$). found 499.0710.

Example 191

(89)

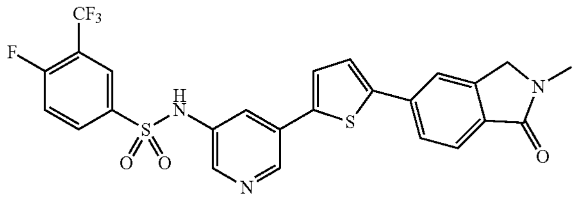

4-Fluoro-N-(5-(5-(2-methyl-1-oxoisoindolin-5-yl)thiophen-2-yl)pyridin-3-yl)-3-(trifluoromethyl)benzenesulphonamide (89)

5-(5-(5-Aminopyridin-3-yl)thiophen-2-yl)-2-methylisoindolin-1-one was reacted with 4-fluoro-3-(trifluoromethyl)benzene-1-sulphonyl chloride according to general procedure E, and the desired title compound was given as a yellow solid (40%), mp 250-252° C. $^1H$ NMR [400 MHz, $(CD_3)_2SO$] δ 10.93 (br s, 1H), 8.20 (d, J=2.4 Hz, 1H), 8.11-8.19 (m, 2H), 7.93 (d, J=0.6 Hz, 1H), 7.82 (dd, J=8.4, 1.6 Hz, 1H), 7.77 (d, J=9.9 Hz, 1H), 7.68-7.75 (m, 2H), 7.70 (d, J=7.9 Hz, 1H), 7.66 (d, J=3.9 Hz, 1H), 4.52 (s, 2H), 3.09 (s, 3H). HRMS ($APCI^+$) calcd for $C_{25}H_{18}F_4N_3O_3S_2$ 548.0720 ($MH^+$). found 548.0743.

Example 192

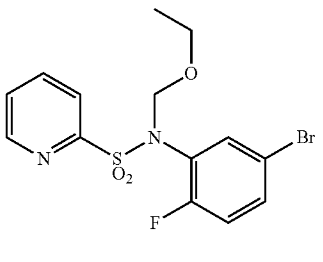 [SMILES: CCOCN(c1cc(Br)ccc1F)S(=O)(=O)c1ccccn1]

N-(5-Bromo-2-fluoropyridin-3-yl)-N-(ethoxymethyl)pyridine-2-sulfonamide

The title compound was prepared according to general procedure K and isolated as a colourless oil (32%, 2 steps). $^1H$ NMR [400 MHz, $(CD_3)_2SO$] δ 8.75 (ddd, J=4.7, 1.6, 0.9 Hz, 1H), 8.22 (dd, J=2.4, 1.5 Hz, 1H), 8.01 (dd, J=8.1, 2.4 Hz, 1H), 7.92-7.84 (m, 2H), 7.54 (ddd, J=7.4, 4.7, 1.4 Hz, 1H), 5.21 (s, 2H), 3.76 (q, J=7.1 Hz, 2H), 1.20 (t, J=7.0 Hz, 3H). LRMS ($APCI^+$) calcd for $C_{11}H_8BrFN_3O_2S$, 346 $(M-EtO)^+$. found 346.

Example 193

(90)

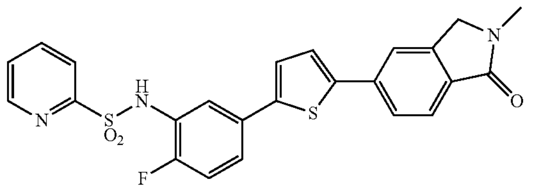

N-(2-Fluoro-5-(5-(2-methyl-1-oxoisoindolin-5-yl)thiophen-2-yl)pyridin-3-yl)pyridine-2-sulfonamide (90)

The title compound was prepared according to general procedures K and L, and isolated as a white solid (63%, 17%). $^1$H NMR [400 MHz, $(CD_3)_2SO$] δ 10.9 (br s, 1H), 8.76 (ddd, J=4.7, 1.6, 0.9 Hz, 1H), 8.39 (dd, J=2.0, 1.3 Hz, 1H), 8.21 (dd, J=9.2, 2.4 Hz, 1H), 8.13 (dd, J=9.2, 2.4 Hz, 1H), 8.02 (ddd, J=7.9, 1.0, 1.0 Hz, 1H), 7.95 (br s, 1H), 7.84 (dd, J=7.9, 1.6 Hz, 1H), 7.74-7.70 (m, 3H), 7.65 (J=3.9 Hz, 1H), 4.52 (s, 2H), 3.09 (s, 3H). Anal. ($C_{23}H_{17}FN_4O_3S_2$) C, H, N.

Example 194

(91)

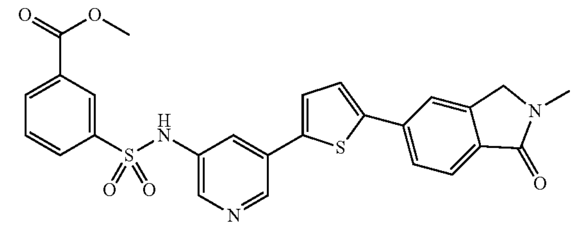

Methyl 3-(N-(5-(5-(2-methyl-1-oxoisoindolin-5-yl)thiophen-2-yl)pyridin-3-yl)sulfamoyl)benzoate (91)

5-(5-(5-Aminopyridin-3-yl)thiophen-2-yl)-2-methylisoindolin-1-one was reacted with methyl 3-(chlorosulfonyl)benzoate according to general procedure E, and the desired title compound was isolated as a beige solid (24%). $^1$H NMR [400 MHz, $(CD_3)_2SO$] δ 10.92 (s, 1H), 8.70 (d, J=8.7 Hz, 1H), 8.38 (dd, J=1.6, 1.6 Hz, 1H), 8.21-8.19 (m, 2H), 8.07 (ddd, J=7.9, 1.9, 1.1 Hz, 1H), 7.94 (br s, 1H), 7.77 (d, J=7.9 Hz, 1H), 7.75-7.70 (m, 3H), 7.66 (d, J=3.4 Hz, 1H), 4.52 (s, 2H), 3.87 (s, 3H), 3.09 (s, 3H). HRMS (ESI$^+$) calcd for $C_{26}H_{22}N_3O_5S_2$ 520.0995 (MH$^+$). found 520.1004.

TABLE 1

Elemental Analyses for Selected Final Products

| Cmpd | Chemical Formula | Calcd C | Calcd H | Calcd N | Found C | Found H | Found N |
|---|---|---|---|---|---|---|---|
| 1 | $C_{24}H_{17}F_2N_3O_3S$ | 57.9 | 3.4 | 8.5 | 58.1 | 3.4 | 8.3 |
| 1.Na | $C_{24}H_{16}F_2N_3NaO_3S_2$•$H_2O$ | 53.6 | 3.4 | 7.8 | 53.7 | 3.4 | 7.7 |
| 2 | $C_{25}H_{21}N_3O_3S_2$ | 63.1 | 4.5 | 8.8 | 63.3 | 4.4 | 8.8 |
| 3 | $C_{28}H_{27}N_3O_3S_2$•0.1$H_2O$ | 64.7 | 5.3 | 8.1 | 64.4 | 5.4 | 7.9 |
| 4 | $C_{24}H_{18}FN_3O_3S_2$ | 60.1 | 3.8 | 8.8 | 60.4 | 3.7 | 8.8 |
| 5 | $C_{24}H_{18}FN_3O_3S_2$ | 60.1 | 3.8 | 8.8 | 60.1 | 3.7 | 8.7 |
| 6.Na | $C_{24}H_{17}FN_3NaO_3S_2$•3$H_2O$ | 51.9 | 4.2 | 7.6 | 51.9 | 3.8 | 7.5 |
| 7 | $C_{24}H_{17}F_2N_3O_3S_2$ | 57.9 | 3.4 | 8.5 | 58.2 | 3.3 | 8.5 |
| 8 | $C_{24}H_{16}F_3N_3O_3S_2$ | 55.9 | 3.1 | 8.2 | 56.3 | 3.1 | 8.2 |
| 9 | $C_{24}H_{18}ClN_3O_3S_2$•0.1$CH_2Cl_2$ | 57.4 | 3.6 | 8.3 | 57.2 | 3.6 | 8.3 |
| 10 | $C_{24}H_{18}ClN_3O_3S_2$•0.2$H_2O$ | 57.7 | 3.7 | 8.4 | 57.4 | 3.7 | 8.2 |
| 11 | $C_{24}H_{18}ClN_3O_3S_2$ | 58.1 | 3.7 | 8.5 | 57.9 | 3.6 | 8.3 |
| 11.Na | $C_{24}H_{17}ClN_3O_3S_2Na$•2$H_2O$ | 52.0 | 3.7 | 7.5 | 52.0 | 3.8 | 7.6 |
| 13.Na | $C_{24}H_{16}Cl_2N_3NaO_3S_2$0.9$CH_2Cl_2$ | 47.6 | 2.7 | 6.7 | 47.5 | 3.1 | 6.5 |
| 14 | $C_{24}H_{17}ClFN_3O_3S_2$•0.1$H_2O$ | 55.9 | 3.4 | 8.2 | 55.6 | 3.3 | 7.9 |
| 15 | $C_{24}H_{18}N_3O_3S_2Br$•0.3$CH_2Cl_2$ | 51.6 | 3.3 | 7.4 | 51.6 | 3.2 | 7.4 |
| 16 | $C_{24}H_{18}BrN_3O_3S_2$ | 53.3 | 3.4 | 7.8 | 53.2 | 3.3 | 7.6 |
| 17 | $C_{24}H_{18}N_3O_3S_2Br$•0.1$C_3H_6O$ | 54.0 | 3.9 | 7.2 | 54.3 | 3.4 | 7.4 |
| 18 | $C_{25}H_{21}N_3O_4S_2$ | 61.1 | 4.3 | 8.6 | 61.1 | 4.2 | 8.5 |
| 19 | $C_{25}H_{21}N_3O_4S_2$ | 61.1 | 4.3 | 8.6 | 60.9 | 4.1 | 8.4 |
| 21.Na | $C_{26}H_{22}N_3O_5S_2Na$•1.2$H_2O$ | 55.3 | 4.4 | 7.4 | 54.9 | 4.4 | 7.4 |
| 22 | $C_{25}H_{18}F_3N_3O_4S_2$•0.2$H_2O$ | 55.0 | 3.3 | 7.7 | 54.3 | 3.3 | 7.6 |
| 24 | $C_{25}H_{18}F_3N_3O_4S_2$ | 55.0 | 3.3 | 7.7 | 55.1 | 3.3 | 7.7 |
| 25 | $C_{25}H_{18}F_3N_3O_3S_2$ | 56.7 | 3.4 | 7.9 | 56.7 | 3.4 | 8.0 |
| 26 | $C_{25}H_{17}ClF_3N_3O_3S_2$ | 53.2 | 3.0 | 7.5 | 53.4 | 3.0 | 7.3 |
| 27 | $C_{25}H_{20}ClN_3O_3S_2$ | 58.9 | 4.0 | 8.2 | 58.8 | 3.9 | 8.2 |
| 28 | $C_{24}H_{18}N_4O_5S_2$ | 56.9 | 3.6 | 11.1 | 56.9 | 3.6 | 11.2 |
| 30 | $C_{25}H_{18}N_4O_3S_2$•0.1$H_2O$ | 61.5 | 3.8 | 11.5 | 61.2 | 3.8 | 11.1 |
| 33 | $C_{23}H_{17}ClN_4O_3S_2$ | 55.6 | 3.5 | 11.3 | 55.3 | 3.3 | 11.0 |
| 34.Na | $C_{22}H_{16}N_3NaO_3S_3$•2.1$H_2O$ | 50.1 | 3.9 | 8.0 | 49.7 | 3.8 | 7.8 |
| 35 | $C_{22}H_{17}N_3O_3S_3$ | 56.5 | 3.7 | 9.0 | 56.5 | 3.5 | 8.9 |
| 36 | $C_{25}H_{21}N_3O_4S_2$ | 61.1 | 4.3 | 8.6 | 61.2 | 4.3 | 8.6 |
| 37 | $C_{25}H_{19}F_2N_3O_4S_2$ | 56.9 | 3.6 | 8.0 | 57.0 | 3.6 | 7.9 |
| 39.Na | $C_{24}H_{15}F_3N_3NaO_3S_2$•1.9$H_2O$ | 50.4 | 3.3 | 7.4 | 50.8 | 3.3 | 7.0 |
| 40 | $C_{24}H_{16}ClF_2N_3O_3S_2$ | 54.2 | 3.0 | 7.9 | 54.2 | 3.0 | 7.8 |
| 41 | $C_{24}H_{17}N_3O_3S_2F_2$•0.2$H_2O$ | 57.5 | 3.5 | 8.4 | 57.4 | 3.4 | 8.3 |
| 42 | $C_{24}H_{17}N_3O_3S_2F_2$•0.1$C_5H_5N$ | 58.2 | 3.5 | 8.6 | 58.6 | 3.4 | 8.4 |
| 43 | $C_{25}H_{18}F_2N_2O_3S_2$•0.2$C_6H_{14}$ | 61.3 | 4.1 | 5.5 | 61.6 | 3.7 | 5.6 |

TABLE 1-continued

| Elemental Analyses for Selected Final Products | | | | | | | |
|---|---|---|---|---|---|---|---|
| | | Calcd | | | Found | | |
| Cmpd | Chemical Formula | C | H | N | C | H | N |
| 44 | $C_{24}H_{17}F_2N_3O_3S_2$•0.1$H_2O$ | 57.7 | 3.5 | 8.4 | 57.4 | 3.5 | 8.2 |
| 45 | $C_{24}H_{18}F_2N_4O_3S_2$•0.1$H_2O$ | 56.0 | 3.6 | 10.9 | 55.7 | 3.5 | 10.9 |
| 46 | $C_{25}H_{19}F_2N_3O_3S_2$ | 58.7 | 3.7 | 8.2 | 58.9 | 3.8 | 8.0 |
| 47 | $C_{25}H_{17}F_2N_3O_2S$•0.5$H_2O$ | 63.8 | 3.9 | 8.9 | 63.6 | 3.8 | 8.8 |
| 48 | $C_{23}H_{15}F_2N_3O_3S_2$•0.25$H_2O$ | 56.6 | 3.2 | 8.6 | 56.8 | 3.1 | 8.5 |
| 49 | $C_{23}H_{15}F_2N_3O_3S_2$ | 57.1 | 3.1 | 8.7 | 56.9 | 3.3 | 8.5 |
| 50 | $C_{24}H_{17}F_2N_3O_3S_2$ | 57.9 | 3.4 | 8.5 | 58.1 | 3.5 | 8.5 |
| 51 | $C_{25}H_{19}F_2N_3O_3S_2$ | 58.7 | 3.7 | 8.2 | 59.0 | 3.7 | 8.2 |
| 53 | $C_{25}H_{19}F_2N_3O_3S_2$ | 58.7 | 3.7 | 8.2 | 58.9 | 3.7 | 8.2 |
| 54 | $C_{24}H_{17}F_2N_3O_3S_2$•$H_2O$ | 55.9 | 3.7 | 8.2 | 55.9 | 3.4 | 8.0 |
| 55 | $C_{25}H_{19}F_2N_3O_3S_2$ | 58.7 | 3.7 | 8.2 | 59.0 | 3.7 | 8.1 |
| 57 | $C_{26}H_{21}F_2N_3O_4S_2$ | 57.7 | 3.9 | 7.8 | 57.8 | 3.9 | 7.7 |
| 58 | $C_{29}H_{25}F_2N_3O_3S_2$ | 61.6 | 4.5 | 7.4 | 61.9 | 4.5 | 7.4 |
| 59 | $C_{26}H_{19}F_2N_3O_3S_2$ | 59.6 | 3.7 | 8.0 | 59.5 | 3.7 | 7.9 |
| 60 | $C_{25}H_{21}N_3O_3S_2$ | 63.1 | 4.5 | 8.8 | 63.3 | 4.3 | 8.8 |
| 61 | $C_{26}H_{20}F_2N_2O_3S_2$ | 61.2 | 4.0 | 5.5 | 61.1 | 3.9 | 5.5 |
| 62 | $C_{24}H_{19}N_3O_3S_2$ | 62.5 | 4.2 | 9.1 | 62.6 | 4.2 | 9.1 |
| 63 | $C_{25}H_{18}F_3N_3O_4S_2$ | 55.0 | 3.3 | 7.7 | 55.0 | 3.2 | 7.6 |
| 64.Na | $C_{25}H_{20}N_3NaO_4S_2$•2.5$H_2O$ | 53.8 | 4.5 | 7.5 | 53.9 | 4.5 | 7.6 |
| 65.Na | $C_{24}H_{18}N_3NaO_3S_2$•0.5$H_2O$ | 58.5 | 3.9 | 8.5 | 58.2 | 4.0 | 8.3 |
| 66 | $C_{24}H_{17}F_2N_3O_3S_2$ | 57.9 | 3.4 | 8.5 | 57.9 | 3.3 | 8.4 |
| 67 | $C_{23}H_{15}F_2N_3O_3S_2$•0.25$H_2O$ | 56.6 | 3.2 | 8.6 | 56.5 | 3.0 | 8.5 |
| 69 | $C_{29}H_{26}F_2N_4O_4S_2$•0.25$H_2O$ | 57.9 | 4.4 | 9.3 | 57.9 | 4.2 | 9.2 |
| 70 | $C_{25}H_{20}FN_3O_3S_2$ | 60.8 | 4.1 | 8.5 | 60.7 | 4.0 | 8.4 |
| 71 | $C_{23}H_{15}F_2N_3O_2S_2$ | 59.1 | 3.2 | 9.0 | 59.2 | 3.2 | 8.8 |
| 72 | $C_{24}H_{17}F_2N_3O_2S_2$ | 59.9 | 3.6 | 8.7 | 60.0 | 3.5 | 8.6 |
| 73 | $C_{25}H_{19}N_3O_5S_2$•0.5$H_2O$ | 58.4 | 3.9 | 8.2 | 58.5 | 3.8 | 8.1 |
| 74 | $C_{24}H_{18}IN_3O_3S_2$ | 49.1 | 3.1 | 7.2 | 48.8 | 3.0 | 6.9 |
| 75 | $C_{24}H_{17}Br_2N_3O_3S_2$•0.25$Et_2O$ | 47.1 | 3.1 | 6.6 | 47.1 | 2.8 | 6.7 |
| 76 | $C_{25}H_{18}N_4O_4S_3$ | 56.2 | 3.4 | 10.5 | 56.1 | 3.4 | 10.3 |
| 77 | $C_{27}H_{20}N_4O_4S_2$ | 61.4 | 3.8 | 10.6 | 61.2 | 4.0 | 10.6 |
| 78 | $C_{25}H_{18}F_3N_3O_3S_2$ | 56.7 | 3.4 | 7.9 | 56.8 | 3.5 | 7.9 |
| 79 | $C_{25}H_{18}N_4O_3S_2$•0.75$H_2O$ | 60.0 | 3.9 | 11.2 | 60.0 | 3.7 | 11.1 |
| 80 | $C_{29}H_{25}N_5O_3S_2$•0.25$H_2O$ | 62.2 | 4.6 | 12.5 | 62.2 | 4.4 | 12.4 |
| 81 | $C_{25}H_{18}F_3N_3O_3S_2$ | 56.7 | 3.4 | 7.9 | 57.0 | 3.4 | 8.0 |
| 82 | $C_{25}H_{21}N_3O_5S_3$•0.5$H_2O$ | 54.4 | 3.8 | 7.5 | 54.7 | 4.0 | 7.7 |
| 83 | $C_{25}H_{18}F_2N_4O_3S$•0.75$H_2O$ | 59.3 | 3.9 | 11.1 | 59.5 | 3.8 | 10.9 |
| 84 | $C_{26}H_{21}N_3O_5S_2$ | 60.1 | 4.1 | 8.1 | 60.0 | 4.1 | 8.1 |
| 85 | $C_{27}H_{23}N_3O_5S_2$ | 60.8 | 4.3 | 7.9 | 60.8 | 4.3 | 7.9 |
| 86 | $C_{26}H_{21}N_3O_5S_2$ | 60.1 | 4.1 | 8.1 | 60.1 | 4.1 | 8.0 |
| 87 | $C_{22}H_{16}BrN_3O_3S_3$ | 48.4 | 3.0 | 7.7 | 48.4 | 2.9 | 7.6 |
| 90 | $C_{23}H_{17}FN_4O_3S_2$ | 57.5 | 3.6 | 11.7 | 57.1 | 3.7 | 11.4 |

TABLE 2

| HRMS and HPLC for Selected Compounds | | | | |
|---|---|---|---|---|
| Cmpd | HRMS Formula | Calcd. | Found | HPLC |
| 12 | $C_{24}H_{17}N_3O_3S_2Cl_2$ (M-H) | 528.0016 | 528.0048 | 95.0% |
| 20 | $C_{25}H_{22}N_3O_4S_2$ ($MH^+$) | 492.1046 | 492.1033 | 96.5% |
| 23 | $C_{25}H_{18}F_3N_3O_4S_2$ ($MH^+$) | 546.0764 | 546.0747 | 95.8% |
| 29 | $C_{24}H_{18}N_4O_5S_2$ ($MH^+$) | 507.0791 | 507.0792 | 95.1% |
| 31.Na | $C_{23}H_{17}N_4NaO_3S_2$ ($MH^+$) | 485.0713 | 485.0710 | 99.7% |
| 32 | $C_{23}H_{18}N_4O_3S_2$ ($MH^+$) | 463.0893 | 463.0891 | 99.4% |
| 38 | $C_{24}H_{17}F_2N_3O_4S_2$ ($MH^+$) | 514.0701 | 514.0710 | 96.0% |
| 52 | $C_{24}H_{17}F_2N_3O_3S_2$ ($MH^+$) | 498.0752 | 498.0753 | 99.7% |
| 56 | $C_{25}H_{20}F_2N_2N_3O_4S_2$ ($MH^+$) | 528.0850 | 528.0858 | 87.0% |
| 68 | $C_{26}H_{20}FN_4O_2S_2$ ($MH^+$) | 503.1006 | 503.1016 | 99.3% |
| 88 | $C_{23}H_{17}F_2N_4O_3S_2$ ($MH^+$) | 499.0705 | 499.0710 | 99.5% |
| 89 | $C_{25}H_{18}F_4N_3O_3S_2$ ($MH^+$) | 548.0720 | 548.0743 | 96.9% |
| 91 | $C_{26}H_{22}N_3O_5S_2$ ($MH^+$) | 520.0995 | 520.1004 | 96.3% |

Example 195

Biological Activity of Exemplary Compounds of the Invention

Inhibition of perforin-mediated lysis of Jurkat cells.

The ability of the compounds to inhibit the lysis of nucleated (Jurkat T lymphoma) cells in the presence of 0.1% BSA, as measured by release of $^{51}Cr$ was measured. Jurkat target cells were labelled by incubation in medium with 100 μCi $^{51}Cr$ for one hour. The cells were then washed three times to remove unincorporated isotope and re-suspended at $1\times10^5$ cells per mL in RPMI buffer supplemented with 0.1% BSA. Each test compound was pre-incubated to concentrations of 20 μM, 10 μM, 5 μM, 2.5 μM and 1.25 μM with recombinant perforin for 30 minutes with DMSO as a negative control. $^{51}Cr$ labelled Jurkat cells were then added and cells were incubated at 37° C. for 4 hours. The supernatant was collected and assessed for its radioactive content on a gamma counter (Wallac Wizard 1470 automatic gamma counter). Each data point was performed in triplicate and an $IC_{50}$ was calculated from the range of concentrations described to above. Compounds with an $IC_{50}$<1 μM were titrated down to lower concentrations in the same manner as above, to determine an accurate $IC_{50}$.

Inhibition of KHYG-1 NK Cell-Mediated Lysis of K562 Cells.

KHYG-1 cells were washed and resuspended in RPMI+ 0.1% BSA at $4\times10^5$ cells/ml and 50 µl of KHYG-1 cells were dispensed to each well of a 96-well V-bottom plate. Test compounds were added to KHYG-1 cells at various concentrations up to 20 M and incubated at RT for 20 minutes. $1\times10^6$ K562 target cells were labelled with 75 µCi $^{51}$Cr in 200 µl RPMI for 90 mins at 37° C., cells were washed as described above and resuspended in 5 ml RPMI+0.1% BSA. 50 µl of $^{51}$Cr labelled K562 leukemia target cells were added to each well of the KHYG-1 plate (Effector:Target 2:1) and incubated at 37° C. for 4 hours. $^{51}$Cr release was assayed using a Skatron Harvesting Press and radioactivity estimated on a Wallac Wizard 1470 Automatic Gamma counter (Turku, Finland). The percentage of specific cytotoxicity was calculated by the formula:

$$\%\text{ specific lysis} = \frac{(\text{experimental release} - \text{spontaneous release})}{(\text{maximum release} - \text{spontaneous release})} \times 100$$

and expressed as the mean of triplicate assays+/− standard error of the mean.

Toxicity to KHYG-1 NK Cells.

KHYG-1 cells were washed and resuspended in RPMI+ 0.1% BSA at $4\times10^5$ cells/ml and 50 µl of KHYG-1 cells were dispensed to each well of a 96-well V-bottom plate. Test compounds were added to KHYG-1 cells at a concentration of 20 µM and incubated at RT for 20 minutes. 100 µl of RPMI 0.1% BSA was added and the cells were incubated for 4 hours at 37° C. then washed ×3 in RPMI+0.1% BSA. Cells were then resuspended in 200 µl of complete medium and incubated for 18 to 24 hours at 37° C. Trypan blue was added to each well and viable (clear) cells counted as a percentage of total (clear+blue) cell number (% viability).

TABLE 3

Biological Activity of Selected Compounds

| Cmpd | Jurkat $IC_{50}$ (µM) | Inhibition of KHYG-1 at 20 µM (%) | Toxicity to KHYG-1 left for 24 h at 20 µM (%) |
|---|---|---|---|
| 1 | 1.17 | 46 | 93 |
| 1.Na | 1.59 | 48 | 93 |
| 2 | 7.33 | 27 | 78 |
| 4 | 2.03 | 40 | 66 |
| 6 | 9.65 | 10 | 96 |
| 8 | 1.76 | 52 | 93 |
| 9 | 4.01 | 47 | 63 |
| 10 | 2.42 | 31 | 74 |
| 11 | 5.39 | 17 | 94 |
| 11.Na | 8.28 | 14 | 87 |
| 12 | 1.32 | 45 | 63 |
| 13 | 14.98 | | |
| 14 | 12.97 | | |
| 15 | 2.66 | 42 | 79 |
| 16 | 2.11 | 20 | 84 |
| 17 | 8.77 | 6 | 98 |
| 18 | 14.81 | | |
| 19 | 2.56 | 17 | 88 |
| 20 | 6.27 | 24 | 75 |
| 21.Na | 13.76 | 31 | 69 |
| 22 | 17.67 | | |
| 23 | 1.42 | 38 | 78 |
| 27 | | 52 | 70 |
| 28 | 6.65 | 71 | 77 |
| 29 | 2.74 | 48 | 85 |
| 29.Na | 3.34 | 49 | 73 |

TABLE 3-continued

Biological Activity of Selected Compounds

| Cmpd | Jurkat $IC_{50}$ (µM) | Inhibition of KHYG-1 at 20 µM (%) | Toxicity to KHYG-1 left for 24 h at 20 µM (%) |
|---|---|---|---|
| 30 | 5.17 | 49 | 95 |
| 31 | 0.74# | 19 | 97 |
| 32 | 15.13 | | |
| 34 | 1.07 | 45 | 86 |
| 37 | 3.56 | 36 | 90 |
| 38 | 5.41 | | |
| 39 | 1.99 | 56 | 92 |
| 39.Na | 0.75 | 48 | 98 |
| 40 | 1.03 | 85 | 94 |
| 41 | 4.70 | 14 | 66 |
| 43 | 5.74 | 18 | 91 |
| 44 | 2.24 | 57 | 97 |
| 45 | 4.63 | 14 | 84 |
| 46 | 9.13 | 28 | 99 |
| 48 | 6.87 | 35 | 94 |
| 49 | 13.15 | 49 | 96 |
| 50 | 10.39 | 27 | 87 |
| 55 | 13.6 | 0 | 95 |
| 56 | 1.33 | 32 | 93 |
| 58 | 5.50 | 64 | 84 |
| 59 | 11.23 | 72 | 99 |
| 60 | 15.4 | 17 | 99 |
| 62 | 8.46 | 9.71 ± 2 | 95 ± 5.74 |
| 63 | >20 | 56.14 ± 9 | 97 ± 2 |
| 63.Na | 19.57 | 77.07 ± 5 | 90 ± 5 |
| 64.Na | 10.97 | 29 ± 7 | 84 ± 9.18 |
| 65.Na | 10.09 | 18.26 ± 6 | 90 ± 10.32 |
| 66 | 10.20 | 34.3 ± 9 | 90 ± 8.08 |
| 67 | 5.04 | 42.83 ± 10 | 96 ± 1.12 |
| 68 | 15.94 | | |
| 69 | 16.97 | | |
| 70 | 5.53 | 17.59 ± 13 | 94 ± 2.25 |
| 71 | 5.80 | 87.66 ± 9 | 96 |
| 72 | 8.63 | 19 ± 17 | 97 ± 2.47 |
| 73 | 0.75 | 56.92 ± 29.62 | 57.59 ± 16.83 |
| 74 | 5.00 | 15.61 ± 5 | 85.10 |
| 75 | 2.52 | 49.25 ± 15 | 97 ± 2.47 |
| 76 | 7.10 | 47.53 ± 10 | 89 |
| 77 | 3.05 | 38.26 ± 5 | 99 ± 0.91 |
| 78 | 1.45 | 56 ± 9 | 100 |
| 79.Na | 9.17 | | |
| 80 | 19.13 | | |
| 81 | 0.91 | 37.83 ± 19 | 98 ± 3.75 |
| 82 | 6.80 | 30.52 ± 11 | 97 ± 4.59 |
| 83 | 8.17 | | |
| 84 | 8.16 | 8.84 | 93 |
| 85 | 19.38 | | |
| 86 | 2.90 | 2.3 ± 3 | 94 |
| 87 | 1.80 | 31.62 ± 6 | 80 ± 8.34 |
| 88 | 18.80 | 40.47 ± 23 | 98 ± 2.38 |
| 89 | 3.75 | 59.94 ± 13 | 98 ± 1.27 |
| 90 | 4.10 | | |
| 91 | 7.77 | | |

In Vivo Inhibition of Perforin-Mediated Bone Marrow Rejection.

Figure 2:
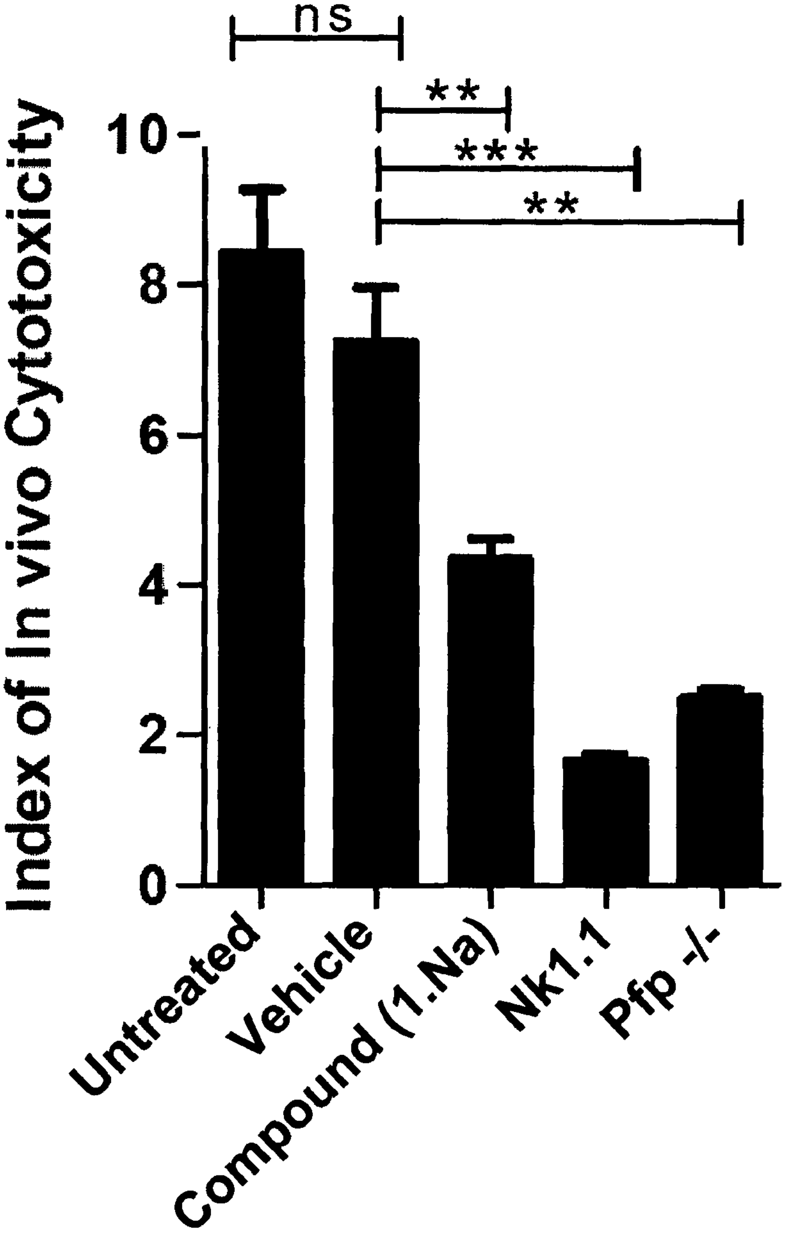
FIG. 2: Graphical representation of in vivo cytotoxicity in C57BI/6 mice treated untreated, or treated with vehicle, compound (1.Na) or Nk1.1 as well as untreated B6.Perforin$^{-/-}$ mice (Pfp−/−) following administration of Balb/c (CD45.2+) CFSE labeled bone marrow and B6.PTP (CD45.1+) bone marrow.

C57Bl/6 mice were untreated or treated with vehicle (20% hydroxypropylcyclodextrin), compound (1) in the form of its sodium salt (1.Na) (120 mg/kg diluted in vehicle solution) or NK1.1 (1 mg), untreated B6.Perforin−/− mice were also tested. Vehicle and compound (1.Na) was administered via intra-peritoneal injection once daily from day −2 through to day +1 post bone marrow transplant. On day 0 mice received 12×106 Balb/c (CD45.2+) CFSE labelled bone marrow as well as 12×106 B6.PTP (CD45.1+) bone marrow. On day +1 blood was collected for in vivo cytotoxicity assays looking at the ratio of recipient (CD45.1+) versus donor cells (CFSE+) (FIG. 1). Results are illustrated in FIG. 2 as two experiments combined with n=6, 10, 10, 4 and 3/group. As is evident, compound (1.Na) is able to inhibit NK and perforin-mediated bone marrow rejection. Statistically significant differences were calculated using two-tailed t tests between groups.

REFERENCES

1. Prandi, C.; Occhiato, E. G.; Tabasso, S.; Bonfante, P.; Novero, M.; Scarpi, D.; Bova, M. E.; Miletto, I. "New Potent Fluorescent Analogues of Strigolactones: Synthesis and Biological Activity in Parasitic Weed Germination and Fungal Branching". *Eur. J. Org. Chem.,* 2011, 3781-3793.

The claims defining the invention are as follows:

1. A compound of formula (Ia):

formula (Ia)

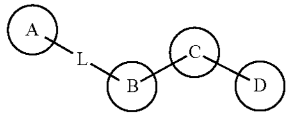

wherein

Ring A is phenyl optionally substituted with 1 to 3 substituents selected from halo, nitro, cyano, —$C_1$-$C_6$alkyl, —$C_1$-$C_6$aminoalkyl, —$C_1$-$C_6$hydroxyalkyl, -halo$C_1$-$C_6$alkyl, —$C_1$-$C_6$alkoxyl, -halo$C_1$-$C_6$alkoxyl, hydroxyl, —C(O)$C_1$-$C_6$alkyl, —OC(O)$C_1$-$C_6$alkyl, —$CH_2$OC(O)$C_1$-$C_6$alkyl, —C(O)O$C_1$-$C_6$alkyl, —NHC(O)$C_1$-$C_6$alkyl, —NHS$(O)_2C_1$-$C_6$alkyl, —$S(O)_2C_1O_6$, —$S(O)_2NH_2$, and —C(O)NJJ;

Ring B is pyridyl optionally substituted at a C atom with Cl, F, $CF_3$, $OCF_3$, $C_1$-$C_3$alkyl, $C_1$-$C_3$alkoxy, or NJJ;

Ring C is thiophenylene;

Ring D is:

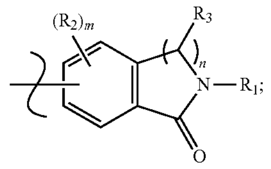

$R_1$ is H or $C_1$-$C_6$ alkyl optionally substituted with hydroxyl, or halo;

$R_2$ is halo, nitro, —$C_1$-$C_6$alkyl, —$C_1$-$C_6$aminoalkyl, —$C_1$-$C_6$hydroxyalkyl, —$C_1$-$C_6$haloalkyl, —$C_1$-$C_6$alkoxyl, -halo-$C_1$-$C_6$alkoxyl, hydroxyl, —C(O)$C_1$-$C_6$alkyl, —OC(O)$C_1$-$C_6$alkyl, —$CH_2$OC(O)$C_1$-$C_6$alkyl, —C(O)O$C_1$-$C_3$alkyl, —NHC(O)$C_1$-$C_6$alkyl, —NHS$(O)_2C_1$-$C_6$alkyl, —$S(O)_2C_1$-$C_6$alkyl, —S(O)$_2NH_2$, or —C(O)NJJ;

$R_3$ in each occurrence is independently H or $C_1$-$C_6$ alkyl;

n is 1;

m is 0-2;

L is a linker selected from branched or unbranched $C_1$-$C_4$ alkylene, —$S(O)_2$—NH—, —C(O)—NH—, —NH—C(O)—NH—, —$S(O)_2$—NH—C(O)—NH—, —$S(O)_2$ —NH—C(O)—, —C(O)—NH—C(S)—NH— and —CH═CH—;

wherein Rings B and C, and Rings C and D, are connected to each other via a C—C bond at any of the available C atoms on each respective ring; and J in each occurrence is independently selected from H, or $C_1$-$C_6$alkyl;

or a pharmaceutically acceptable salt-thereof.

2. A compound of formula (II):

(II)

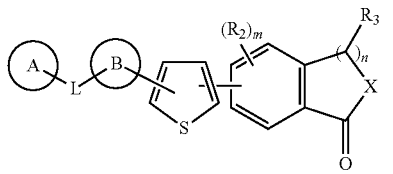

where Ring A, L and Ring B are as defined in claim 1;

X is N—$R_1$;

$R_1$ is H or $C_1$-$C_6$ alkyl optionally substituted with hydroxyl or halo;

$R_2$ is halo, nitro, —$C_1$-$C_6$alkyl, —$C_1$-$C_6$aminoalkyl, —$C_1$-$C_6$hydroxyalkyl, —$C_1$-$C_6$haloalkyl, —$C_1$-$C_6$alkoxyl, -halo-$C_1$-$C_6$alkoxyl, hydroxyl, —C(O)$C_1$-$C_6$alkyl, —OC(O)$C_1$-$C_6$alkyl, —$CH_2$OC(O)$C_1$-$C_6$alkyl, —C(O)O$C_1$-$C_3$alkyl, —NHC(O)$C_1$-$C_6$alkyl, —NHS$(O)_2C_1$-$C_6$alkyl, —$S(O)_2C_1$-$C_6$alkyl, —$S(O)_2$ $NH_2$, or —C(O)NJJ, wherein each J is independently hydrogen or $C_1$-$C_3$ alkyl;

$R_3$ in each occurrence is independently H or $C_1$-$C_6$ alkyl;

n is 1;

m is 0-2; and o is 0-2.

3. The compound of claim 2 of formula (IIa):

(IIa)

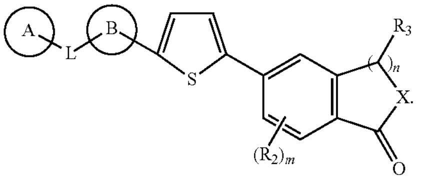

(IIIa)

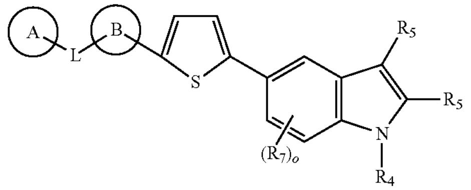

4. A compound of formula (II'):

(II')

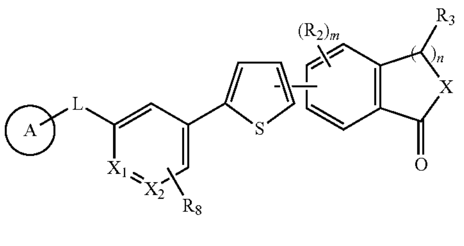

-continued (III')

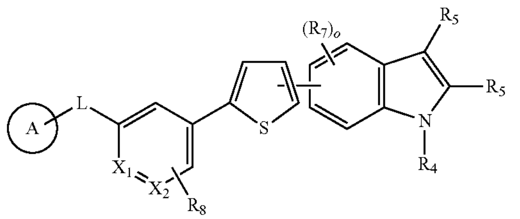

wherein Ring A, L, and variables X, $R_2$, $R_3$, m and n are as defined in claim 2;

$X_1$ and $X_2$ are independently CH or N, and when $X_1$ is CH, $X_2$ is N; or when $X_1$ is N, $X_2$ is CH; and $R_8$ is an optional substituent attached to a C atom selected from Cl, F, $CF_3$, $OCF_3$, $C_1$-$C_3$alkyl, $C_1$-$C_3$alkoxy, or NJJ, wherein each J is independently selected from hydrogen or $C_1$-$C_3$alkyl.

5. The compound of claim 4 of formula (IIa')

(IIa')

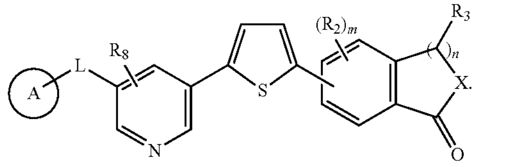

(IIIa')

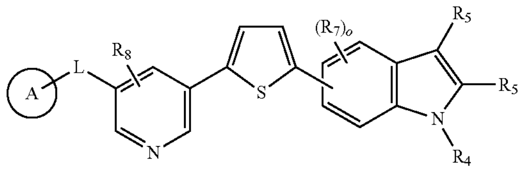

6. The compound of claim 4 of formula (IIb') or (IIc'):

(IIb')

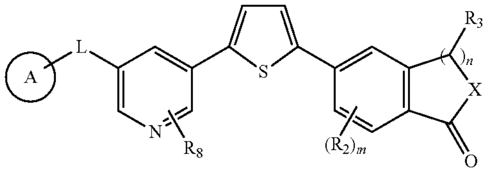

(IIc')

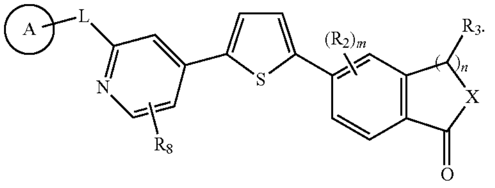

7. A compound selected from:

2,4-Difluoro-N-(5-(5-(2-methyl-1-oxoisoindolin-5-yl) thiophen-2-yl)pyridin-3-yl)benzenesulfonamide (1);

3-Methyl-N-(5-(5-(2-methyl-1-oxoisoindolin-5-yl)thiophen-2-yl)pyridin-3-yl)benzenesulfonamide (2);

4-(tert-Butyl)-N-(5-(5-(2-methyl-1-oxoisoindolin-5-yl) thiophen-2-yl)pyridin-3-yl)benzenesulfonamide (3);

2-Fluoro-N-(5-(5-(2-methyl-1-oxoisoindolin-5-yl)thiophen-2-yl)pyridin-3-yl)benzene-sulfonamide (4);

3-Fluoro-N-(5-(5-(2-methyl-1-oxoisoindolin-5-yl)thiophen-2-yl)pyridin-3-yl)benzene-sulfonamide (5);

4-Fluoro-N-(5-(5-(2-methyl-1-oxoisoindolin-5-yl)thiophen-2-yl)pyridin-3-yl)benzene-sulfonamide (6);

3,4-Difluoro-N-(5-(5-(2-methyl-1-oxoisoindolin-5-yl) thiophen-2-yl)pyridin-3-yl)benzene-sulfonamide (7);

2,4,6-Trifluoro-N-(5-(5-(2-methyl-1-oxoisoindolin-5-yl) thiophen-2-yl)pyridin-3-yl)benzene-sulfonamide (8);

2-Chloro-N-(5-(5-(2-methyl-1-oxoisoindolin-5-yl)thiophen-2-yl)pyridin-3-yl)benzenesulfonamide (9);

3-Chloro-N-(5-(5-(2-methyl-1-oxoisoindolin-5-yl)thiophen-2-yl)pyridin-3-yl)benzenesulfonamide (10);

4-Chloro-N-(5-(5-(2-methyl-1-oxoisoindolin-5-yl)thiophen-2-yl)pyridin-3-yl)benzenesulfonamide (11);

3,4-Dichloro-N-(5-(5-(2-methyl-1-oxoisoindolin-5-yl) thiophen-2-yl)pyridin-3-yl)benzenesulfonamide (12);

2,4-Dichloro-N-(5-(5-(2-methyl-1-oxoisoindolin-5-yl) thiophen-2-yl)pyridin-3-yl)benzene-sulfonamide (13);

3-Chloro-2-fluoro-N-(5-(5-(2-methyl-1-oxoisoindolin-5-yl)thiophen-2-yl)pyridin-3-yl) benzenesulfonamide (14);

2-Bromo-N-(5-(5-(2-methyl-1-oxoisoindolin-5-yl)thiophen-2-yl)pyridin-3-yl)benzenesulfonamide (15);

3-Bromo-N-(5-(5-(2-methyl-1-oxoisoindolin-5-yl)thiophen-2-yl)pyridin-3-yl)benzenesulfonamide (16);

4-Bromo-N-(5-(5-(2-methyl-1-oxoisoindolin-5-yl)thiophen-2-yl)pyridin-3-yl)benzenesulfonamide (17);

2-Methoxy-N-(5-(5-(2-methyl-1-oxoisoindolin-5-yl)thiophen-2-yl)pyridin-3-yl)benzenesulfonamide (18);

3-Methoxy-N-(5-(5-(2-methyl-1-oxoisoindolin-5-yl)thiophen-2-yl)pyridin-3-yl)benzenesulfonamide (19);

4-Methoxy-N-(5-(5-(2-methyl-1-oxoisoindolin-5-yl)thiophen-2-yl)pyridin-3-yl)benzenesulfonamide (20);

3,4-Dimethoxy-N-(5-(5-(2-methyl-1-oxoisoindolin-5-yl) thiophen-2-yl)pyridin-3-yl)benzenesulfonamide (21);

N-(5-(5-(2-Methyl-1-oxoisoindolin-5-yl)thiophen-2-yl) pyridin-3-yl)-2-(trifluoromethoxy)-benzenesulfonamide (22);

N-(5-(5-(2-Methyl-1-oxoisoindolin-5-yl)thiophen-2-yl) pyridin-3-yl)-3-(trifluoromethoxy)-benzenesulfonamide (23);

N-(5-(5-(2-Methyl-1-oxoisoindolin-5-yl)thiophen-2-yl) pyridin-3-yl)-4-(trifluoromethoxy)-benzenesulfonamide (24);

N-(5-(5-(2-Methyl-1-oxoisoindolin-5-yl)thiophen-2-yl) pyridin-3-yl)-4-(trifluoromethyl)-benzenesulfonamide (25);

2-Chloro-N-(5-(5-(2-methyl-1-oxoisoindolin-5-yl)thiophen-2-yl)pyridin-3-yl)-4-(trifluoromethyl)benzenesulfonamide (26);

3-Chloro-4-methyl-N-(5-(5-(2-methyl-1-oxoisoindolin-5-yl)thiophen-2-yl)pyridin-3-yl)benzenesulfonamide (27);

N-(5-(5-(2-Methyl-1-oxoisoindolin-5-yl)thiophen-2-yl) pyridin-3-yl)-2-nitrobenzenesulfonamide (28);

N-(5-(5-(2-Methyl-1-oxoisoindolin-5-yl)thiophen-2-yl) pyridin-3-yl)-4-nitrobenzenesulfonamide (29);

4-Cyano-N-(5-(5-(2-methyl-1-oxoisoindolin-5-yl)thiophen-2-yl)pyridin-3-yl)benzenesulfonamide (30);

N-(2-Methoxy-5-(5-(2-methyl-1-oxoisoindolin-5-yl)thiophen-2-yl)pyridin-3-yl)benzene sulphonamide (36);

2,4-Difluoro-N-(2-methoxy-5-(5-(2-methyl-1-oxoisoindolin-5-yl) thiophen-2-yl)pyridin-3-yl)benzenesulphonamide (37);

2,4-Difluoro-N-(2-methoxy-5-(5-(1-oxoisoindolin-5-yl) thiophen-2-yl)pyridin-3-yl)benzene sulphonamide (38);

2,4-Difluoro-N-(2-fluoro-5-(5-(2-methyl-1-oxoisoindolin-5-yl)thiophen-2-yl)pyridin-3-yl)benzenesulphonamide (39);

2,4-Difluoro-N-(2-chloro-5-(5-(2-methyl-1-oxoisoindolin-5-yl)thiophen-2-yl)pyridin-3-yl)benzenesulphonamide (40);

2,4-Difluoro-N-(4-(5-(2-methyl-1-oxoisoindolin-5-yl) thiophen-2-yl)pyridin-2-yl)benzenesulfonamide (41);

2,4-Difluoro-N-(5-(5-(2-methyl-1-oxoisoindolin-5-yl) thiophen-2-yl)pyridin-2-yl)benzenesulfonamide (42);

N-(2,4-Difluorophenyl)-5-(5-(2-methyl-1-oxoisoindolin-5-yl)thiophen-2-yl)pyridine-3-sulphonamide (44);

2-Amino-N-(2,4-difluorophenyl)-5-(5-(2-methyl-1-oxoisoindolin-5-yl)thiophen-2-yl)pyridine-3-sulphonamide (45);

2,4-Difluoro-N-methyl-N-(5-(5-(2-methyl-1-oxoisoindolin-5-yl)thiophen-2-yl)pyridin-3-yl) benzenesulphonamide (46);

2,4-Difluoro-N-(5-(5-(2-methyl-1-oxoisoindolin-5-yl) thiophen-2-yl)pyridin-3-yl)benzamide (47);

2,4-Difluoro-N-(5-(5-(1-oxoisoindolin-5-yl)thiophen-2-yl)pyridin-3-yl)benzenesulfonamide (48);

2,4-Difluoro-N-(5-(5-(3-oxoisoindolin-5-yl)thiophen-2-yl)pyridin-3-yl)benzenesulfonamide (49);

2,4-Difluoro-N-(5-(5-(2-methyl-3-oxoisoindolin-5-yl) thiophen-2-yl)pyridin-3-yl)benzenesulfonamide (50);

N-(5-(5-(2,3-Dimethyl-1-oxoisoindolin-5-yl)thiophen-2-yl)pyridin-3-yl)-2,4-difluorobenzenesulfonamide (51);

2,4-Difluoro-N-(5-(5-(2-(2-hydroxyethyl)-1-oxoisoindolin-5-yl)thiophen-2-yl)pyridin-3-yl)benzenesulfonamide (56);

2,4-Difluoro-N-(5-(5-(2-(3-hydroxypropyl)-1-oxoisoindolin-5-yl)thiophen-2-yl)pyridin-3-yl)benzenesulfonamide (57);

N-(5-(5-(2-Methyl-1-oxoisoindolin-5-yl)thiophen-2-yl) pyridin-3-yl)benzenesulphonamide (62);

4-Fluoro-N-((5-(5-(2-methyl-1-oxoisoindolin-5-yl)thiophen-2-yl)pyridin-3-yl) carbamothioyl)benzamide (68);

4-Fluoro-2-methyl-N-(5-(5-(2-methyl-1-oxoisoindolin-5-yl)thiophen-2-yl)pyridin-3-yl) benzenesulphonamide (70);

4-(N-(5-(5-(2-Methyl-1-oxoisoindolin-5-yl)thiophen-2-yl)pyridin-3-yl)sulfamoyl)benzoic acid (73);

4-Iodo-N-(5-(5-(2-methyl-1-oxoisoindolin-5-yl)thiophen-2-yl)pyridin-3-yl)benzenesulfonamide (74);

2,4-Dibromo-N-(5-(5-(2-methyl-1-oxoisoindolin-5-yl) thiophen-2-yl)pyridin-3-yl)benzenesulfonamide (75);

N-(5-(5-(2-Methyl-1-oxoisoindolin-5-yl)thiophen-2-yl) pyridin-3-yl)-2-(trifluoromethyl)benzenesulfonamide (78);

2-Cyano-N-(5-(5-(2-methyl-1-oxoisoindolin-5-yl)thiophen-2-yl)pyridin-3-yl)benzenesulfonamide (79);

4-(3,5-Dimethyl-1H-pyrazol-1-yl)-N-(5-(5-(2-methyl-1-oxoisoindolin-5-yl)thiophen-2-yl)pyridin-3-yl)benzenesulfonamide (80);

N-(5-(5-(2-Methyl-1-oxoisoindolin-5-yl)thiophen-2-yl) pyridin-3-yl)-3-(trifluoromethyl)benzenesulfonamide (81);

N-(5-(5-(2-Methyl-1-oxoisoindolin-5-yl)thiophen-2-yl) pyridin-3-yl)-2-(methylsulfonyl)benzenesulfonamide (82);

Methyl 4-(N-(5-(5-(2-methyl-1-oxoisoindolin-5-yl)thiophen-2-yl)pyridin-3-yl)sulfamoyl)benzoate (84);

Ethyl 4-(N-(5-(5-(2-methyl-1-oxoisoindolin-5-yl)thiophen-2-yl)pyridin-3-yl)sulfamoyl)benzoate (85);

Methyl 2-(N-(5-(5-(2-methyl-1-oxoisoindolin-5-yl)thiophen-2-yl)pyridin-3-yl)sulfamoyl)benzoate (86);

4-Fluoro-N-(5-(5-(2-methyl-1-oxoisoindolin-5-yl)thiophen-2-yl)pyridin-3-yl)-3-(trifluoromethyl)benzenesulphonamide (89);

Methyl 3-(N-(5-(5-(2-methyl-1-oxoisoindolin-5-yl)thiophen-2-yl)pyridin-3-yl)sulfamoyl)benzoate (91);

and pharmaceutically acceptable salts thereof.

8. A pharmaceutical composition comprising a compound according to claim 1 together with a pharmaceutically acceptable carrier, excipient, diluent or adjuvant, or combinations thereof.

* * * * *